US011649265B2

(12) United States Patent
Shakeel et al.

(10) Patent No.: US 11,649,265 B2
(45) Date of Patent: May 16, 2023

(54) COMPOSITIONS AND METHODS FOR THE ENCAPSULATION AND SCALABLE DELIVERY OF AGROCHEMICALS

(71) Applicant: AgroSpheres, Inc., Charlottesville, VA (US)

(72) Inventors: Ameer Hamza Shakeel, Leesburg, VA (US); Sepehr Zomorodi, Charlottesville, VA (US); Joseph Thomas Frank, Charlottesville, VA (US); Zachery George Davis, Charlottesville, VA (US); Payam Pourtaheri, Charlottesville, VA (US)

(73) Assignee: AgroSpheres, Inc., Charlottesville, VA (US)

(*) Notice: Subject to any disclaimer, the term of this patent is extended or adjusted under 35 U.S.C. 154(b) by 152 days.

(21) Appl. No.: 16/606,601

(22) PCT Filed: Apr. 30, 2018

(86) PCT No.: PCT/US2018/030329
§ 371 (c)(1),
(2) Date: Oct. 18, 2019

(87) PCT Pub. No.: WO2018/201161
PCT Pub. Date: Nov. 1, 2018

(65) Prior Publication Data

US 2020/0113177 A1 Apr. 16, 2020

Related U.S. Application Data

(60) Provisional application No. 62/570,368, filed on Oct. 10, 2017, provisional application No. 62/491,608, filed on Apr. 28, 2017.

(51) Int. Cl.

| | |
|---|---|
| ***A01N 25/26*** | (2006.01) |
| ***A01N 25/28*** | (2006.01) |
| ***C07K 14/195*** | (2006.01) |
| ***A01N 63/22*** | (2020.01) |
| ***C07K 14/32*** | (2006.01) |
| ***C07K 14/335*** | (2006.01) |
| ***C07K 14/34*** | (2006.01) |
| ***C12N 1/08*** | (2006.01) |
| ***C12N 9/54*** | (2006.01) |
| ***A01N 63/50*** | (2020.01) |
| ***C12N 15/62*** | (2006.01) |
| ***C12N 9/52*** | (2006.01) |
| *A61K 39/108* | (2006.01) |
| *B01F 101/04* | (2022.01) |

(52) U.S. Cl.
CPC ............ *C07K 14/195* (2013.01); *A01N 25/28* (2013.01); *A01N 63/22* (2020.01); *A01N 63/50* (2020.01); *C07K 14/32* (2013.01); *C07K 14/335* (2013.01); *C07K 14/34* (2013.01); *C12N 1/08* (2013.01); *C12N 9/52* (2013.01); *C12N 9/54* (2013.01); *C12N 15/62* (2013.01); *A61K 39/0258* (2013.01); *B01F 2101/04* (2022.01); *C07K 2319/705* (2013.01)

(58) Field of Classification Search
CPC ........... C07K 14/195; C07K 2319/705; C07K 14/32; C07K 14/335; C07K 14/34; A01N 25/28; A01N 63/22; A01N 25/26; C12N 9/52; C12N 15/62; C12N 9/54; A61K 39/0258; B01F 2101/04
See application file for complete search history.

(56) References Cited

U.S. PATENT DOCUMENTS

| | | | |
|---|---|---|---|
| 4,613,355 | A | 9/1986 | Omura et al. |
| 6,071,725 | A | 6/2000 | Pan et al. |
| 7,183,105 | B2 | 2/2007 | Sabbadini et al. |
| 7,396,822 | B2 | 7/2008 | Sabbadini et al. |
| 7,871,815 | B2 | 1/2011 | Sabbadini et al. |
| 8,101,396 | B2 | 1/2012 | Sabbadini et al. |
| 8,129,166 | B2 | 3/2012 | Sabbadini et al. |
| 8,524,484 | B2 | 9/2013 | Sabbadini et al. |
| 9,017,986 | B2 | 4/2015 | Sabbadini et al. |
| 9,045,761 | B2 | 6/2015 | Giacalone et al. |
| 9,267,108 | B2 | 2/2016 | Giacalone |
| 9,566,321 | B2 | 2/2017 | Giacalone |
| 9,670,270 | B2 | 6/2017 | Sabbadini et al. |
| 10,005,820 | B2 | 6/2018 | Giacalone et al. |
| 10,039,817 | B2 | 8/2018 | Giacalone |

(Continued)

FOREIGN PATENT DOCUMENTS

| | | | |
|---|---|---|---|
| CA | 3056801 | A1 | 11/2018 |
| CN | 101935669 | A | 1/2011 |

(Continued)

OTHER PUBLICATIONS

Extended European Search Report dated Jun. 14, 2021, in European Application No. 18859413.9, 10 pages.

(Continued)

*Primary Examiner* — Lynn Y Fan
(74) *Attorney, Agent, or Firm* — Cooley LLP

(57) ABSTRACT

The present disclosure is generally directed to an anucleated cell-based platforms for encapsulation and delivery of agricultural compounds. Disclosed herein are compositions for the stable and targeted delivery of agricultural compounds within achromosomal and/or anucleated cells. The present disclosure also provides methods of improving encapsulation and retention of agricultural compounds in achromosomal and/or anucleated cells.

56 Claims, 29 Drawing Sheets

Specification includes a Sequence Listing.

(56) References Cited

U.S. PATENT DOCUMENTS

| | | | |
|---|---|---|---|
| 10,124,024 B2 | 11/2018 | Giacalone et al. | |
| 10,913,940 B2 | 2/2021 | Pourtaheri et al. | |
| 11,219,679 B2 | 1/2022 | Giacalone | |
| 11,312,954 B2 | 4/2022 | Linke et al. | |
| 2003/0166099 A1 | 9/2003 | Sabbadini et al. | |
| 2003/0166279 A1 | 9/2003 | Sabbadini et al. | |
| 2003/0203481 A1 | 10/2003 | Surber et al. | |
| 2004/0109853 A1 | 6/2004 | McDaniel | |
| 2005/0176117 A1 | 8/2005 | Russell et al. | |
| 2005/0222057 A1 | 10/2005 | Brahmbhatt et al. | |
| 2006/0014291 A1 | 1/2006 | Kebeler et al. | |
| 2006/0039870 A1 | 2/2006 | Turner | |
| 2006/0084136 A1 | 4/2006 | Kudlicki et al. | |
| 2006/0225154 A1 | 10/2006 | Kasukabe et al. | |
| 2006/0270040 A1 | 11/2006 | Filutowicz et al. | |
| 2007/0048852 A1 | 3/2007 | Holker et al. | |
| 2011/0045975 A1 | 2/2011 | Ehr et al. | |
| 2011/0104786 A1 | 5/2011 | Van Kimmenade et al. | |
| 2012/0107875 A1 | 5/2012 | Liu et al. | |
| 2012/0207754 A1 | 8/2012 | Giacalone et al. | |
| 2013/0084559 A1 | 4/2013 | Simpson et al. | |
| 2013/0316007 A1 | 11/2013 | Ma et al. | |
| 2013/0337545 A1 | 12/2013 | Sabbadini et al. | |
| 2014/0045692 A1 | 2/2014 | Rossines et al. | |
| 2014/0051571 A1 | 2/2014 | Asolkar et al. | |
| 2014/0147873 A1 | 5/2014 | Clubb et al. | |
| 2015/0087029 A1 | 3/2015 | Tan et al. | |
| 2015/0140037 A1 | 5/2015 | Galan et al. | |
| 2015/0218254 A1* | 8/2015 | Sabbadini .......... | G01N 33/5005 435/252.3 |
| 2015/0264938 A1 | 9/2015 | Gage et al. | |
| 2017/0268002 A1 | 9/2017 | Esau et al. | |
| 2019/0169582 A1 | 6/2019 | Pourtaheri et al. | |
| 2020/0123527 A1 | 4/2020 | Shakeel et al. | |
| 2020/0267971 A1 | 8/2020 | Shakeel et al. | |
| 2020/0399618 A1 | 12/2020 | Pourtaheri et al. | |
| 2022/0008557 A1 | 1/2022 | Von Maltzahn et al. | |
| 2022/0031862 A1 | 2/2022 | Fisher et al. | |
| 2022/0042042 A1 | 2/2022 | Weinstein et al. | |
| 2022/0064661 A1 | 3/2022 | Van Rooijen et al. | |
| 2022/0073950 A1 | 3/2022 | Weinstein et al. | |
| 2022/0105166 A1 | 4/2022 | Sharei et al. | |
| 2022/0152139 A1 | 5/2022 | Van Rooijen et al. | |
| 2022/0192201 A1 | 6/2022 | Van Rooijen et al. | |
| 2022/0195364 A1 | 6/2022 | Sharei et al. | |
| 2022/0202950 A1 | 6/2022 | Brahmbhatt et al. | |

FOREIGN PATENT DOCUMENTS

| | | |
|---|---|---|
| CN | 102021185 A | 4/2011 |
| CN | 111328803 A | 6/2020 |
| EP | 2865755 T3 | 5/2017 |
| WO | WO 03/106490 A1 | 12/2003 |
| WO | WO 2016/198852 A1 | 12/2016 |
| WO | WO 2017/180650 A1 | 10/2017 |
| WO | WO 2018/201160 A1 | 11/2018 |
| WO | WO 2018/201161 A1 | 11/2018 |
| WO | WO 2019/060903 A1 | 3/2019 |
| WO | WO-2019222379 A1 | 11/2019 |
| WO | WO 2021/133846 A2 | 7/2021 |
| WO | WO 2021/236799 A2 | 11/2021 |
| WO | WO-2021257788 A1 | 12/2021 |
| WO | WO-2021257803 A1 | 12/2021 |
| WO | WO-2022010889 A1 | 1/2022 |
| WO | WO-2022076877 A1 | 4/2022 |
| WO | WO-2022108944 A1 | 5/2022 |
| WO | WO-2022125996 A1 | 6/2022 |
| WO | WO-2022140638 A1 | 6/2022 |
| WO | WO-2022140639 A1 | 6/2022 |

OTHER PUBLICATIONS

International Search Report dated Jul. 10, 2017, issued in PCT Application No. PCT/US2017/027048, 3 pages.

International Search Report and Written Opinion dated Jan. 16, 2019, for International Application No. PCT/US2018/052690, 16 pages.

International Search Report and Written Opinion dated Feb. 18, 2022, for International Application No. PCT/US2021/054259, 24 pages.

International Search Report and Written Opinion dated Mar. 16, 2022, for International Application No. PCT/US2021/065009, 13 pages.

International Search Report, dated Aug. 31, 2021, for International Application No. PCT/US2020/066706, 4 pages.

International Search Report, dated Nov. 10, 2021, for International Application No. PCT/US2021/033208, 6 pages.

International Search Report, dated Mar. 15, 2022, for International Application No. PCT/US2021/059571, 5 pages.

Written Opinion dated Jul. 10, 2017, issued in PCT Application No. PCT/US2017/027048, 7 pages.

Written Opinion dated Aug. 31, 2021, issued in PCT Application No. PCT/US2020/066706, 8 pages.

Written Opinion dated Nov. 10, 2021, issued in PCT Application No. PCT/US2021/033208, 9 pages.

Aislabie et al., "A review of bacterial degradation of pesticides", Aust. J. Soil. Res., 1995; 33: 925-942.

Beys da Silva et al., "Metarhizium anisopliae lipolytic activity plays a pivotal role in Rhipicephalus (Boophilus) microplus infection," Fungal Biology, 2010, 114(1), 10-15.

Burwood-Taylor, "Brief: AgroSpheres raises $4m Series A with Ospraie, Wilbur Ellis, for 'Minicell' pesticide tech," AgFunder Network Partners (Aug. 28, 2019) <https://agfundernews.com/agrospheres-raises-4m-series-a-with-ospraie-wilbur-ellis-forminicell-pesticide-tech>: pp. 1-2.

Colla et al., "Biostimulant Action of Protein Hydrolysates: Unraveling Their Effects on Plant Physiology and Microbiome," Frontiers in Plant Science, Dec. 2017, vol. 8, Article 2202.

Crowet et al., "Modeling of non-covalent complexes of the cell-penetrating peptide CADY and its siRNA cargo," Biochemica et Biophysica Acta, Feb. 2013, vol. 1828, No. 2; pp. 499-509.

Garcia-Sosa et al., "Peptide-Ligand Binding Modeling of siRNA with Cell-Penetrating Peptides," BioMed Research International, Jul. 24, 2014, vol. 2014, Article ID 257040.

Hallmann, et al., Bacterial endophytes in agricultural crops. Canadian Journal of 4 Microbiology. 1997, vol. 43, No. 10; pp. 895-914.

Huang et al., "A super long-acting and anti-photolysis pesticide release platform through self-assembled natural polymer-based polyelectrolyte", Reactive and Functional Polymers, Jan. 2020, vol. 146, No. 104429, pp. 1-8.

Huang et al., "Structural Investigation of a Self-Cross-Linked Chitosan/Alginate Dialdehyde Multilayered Film within Situ QCM.D and Spectroscopic Ellipsometry", ACS Omega, 2019, vol. 4, pp. 2019-2029.

Islam et al., "Minicell-based fungal RNAi delivery for sustainable crop protection," Microbial Technology, vol. 14, Issue 4; (Feb. 24, 2021); pp. 1847-1856.

Islam et al., "RNAi-Based Biofungicides as a Promising Next-Generation Strategy for Controlling Devastating Gray Mold Diseases," International Journal of Molecular Sciences, vol. 21, Issue 6, (Mar. 18, 2020); pp. 1-10.

Jog et al., "Plant growth promoting potential and soil enzyme production of the most abundant *Streptomyces* spp. from wheat rhizosphere," Journal of Applied Microbiology, 2012, 113(5), 1154-1164.

Kanchiswamy et al., "Bioprospecting bacterial and fungal volatiles for sustainable agriculture," Trends in Plant Science, 2015, 20(4), 206-211.

Kiernan, "Ospraie Ag Science Leads Rounds Totaling $49M for Two Separate Crop Protection Startups," Global AgInvesting (Sep. 10, 2019) <https://www.globalaginvesting.com/ospraie-ag-science-leads-rounds-totaling-49m-two-separate-crop-protection-startups/>: pp. 1-3. (A, used:2, 10,20).

Kourti et al., "In Search of New Methodologies for Efficient Insect Pest Control: "The RNAi Movement"", Biological Control of Pest and Vector Insects, Apr. 5, 2017, InTech, XP055810178, ISBN: 978-953-51-3036-9 pp. 71-96, DOI: 10.5772/66633.

(56) References Cited

OTHER PUBLICATIONS

Li et al., "Preparation of antifogging and enhanced antimicrobial biopolymer coating and its applications in lettuce preservation", LWT. Jul. 30, 2020, vol. 133, No. 109941, pp. 1-7.
Nguyen et al., "Nanosized Minicells Generated by Lactic Acid Bacteria for Drug Delivery", Journal of Nanomaterials, vol. 2017, Article 6847297 (Sep. 7, 2017): pp. 1-11.
Pichyangkura et al., "Biostimulant activity of chitosan in horticulture," Scientia Horticulturae, 2015, 196, 49-65.
Ryu et al., "Bacterial volatiles promote growth in *Arabidopsis*," Proceedings of the National Academy of Sciences, Apr. 2003, 100(8), 4927-4932.
Ryu, et al., "Bacterial Volatiles Induce Systemic Resistance in *Arabidopsis*," Plant Physiology, 2004, 134(3), 1017-1026.
Sathya et al., Plant growth-promoting actinobacteria: a new strategy for enhancing sustainable production and protection of grain legumes, 3 Biotech, Apr. 2017,7(2).
Singh et al., "Microbial degradation of organophosphorus compounds", FEMS Microbiol. Rev. 30, Apr. 2006, 428-471.
Souza et al., "Plant growth-promoting bacteria as inoculants in agricultural soils," Genetics and Molecular Biology, 2015, 38(4), 401-419.
St. Leger et al., "New perspectives on insect pathogens," Fungal Biology Reviews, Apr. 2011, 25(2), 84-88.
Witzgall et al., "Sex Pheromones and Their Impact on Pest Management," Journal of Chemical Ecology, Jan. 2010, 36(1), 80-100.
Extended European Search Report for Application No. 18791775.2, dated Apr. 28, 2021, 10 pages.
Extended European Search Report for Application No. 18791868.5, dated Dec. 7, 2020, 7 pages.
Nakatani et al., "Cell surface protein engineering for high-performance whole-cell catalysts," Front. Chem. Sci. Eng. 2017, 11(1): 46-57.
Ota et al., "Display of Clostridium cellulovorans Xylose Isomerase on the Cell Surface of *Saccharomyces cerevisiae* and its Direct Application to Xylose Fermentation," Biotechnology Progress, vol. 29, No. 2, Mar. 1, 2013, pp. 346-351.
Schüürmann et al., "Bacterial whole-cell biocatalysts by surface display of enzymes: toward industrial application," Appl Microbiol Biotechnol (2014) 98:8031-8046.
Supplemental European Search Report for European Application No. 18791775.2, dated Jan. 25, 2021, 15 pages.
International Search Report and Written Opinion, dated Apr. 15, 2022, for International Application No. PCT/US2021/062964, 16 pages.
International Preliminary Report on Patentability for Application No. PCT/US2020/066706, dated Jul. 7, 2022, 10 pages.
International Search Report and Written Opinion dated Mar. 28, 2022, for International Application No. PCT/US2021/065010, 9 pages.
Lasko et al., "On-Line Monitoring of Intracellular ATP Concentration in *Escherichia coli* Fermentations," Biotechnology and Bioengineering, Nov. 1996, vol. 52, pp. 364-372.
Manwaring et al., "Nucleoside Triphosphate Pools in Minicells of *Escherichia coli*," Journal of Bacteriology, May 1977, pp. 960-962.
Mathis et al., "ATP concentration in *Escherichia coli* during oxygen toxicity," Biochimica et Biophysica Act, Sep. 1976, 440(3), pp. 723-732.
Mempin et al., "Release of extracellular ATP by bacteria during growth," BMC Microbiology, Dec. 2013, 13:301, 13 pages.
Mendelson et al., "Physiological Studies of Bacillus subtilis Minicells," Journal of Bacteriology, Mar. 1974, vol. 117, No. 3, pp. 1312-1319.
Rampley et al., "Development of SimCells as a novel chassis for functional biosensors," Scientific Reports, Aug. 2017, 7(1):7261, 10 pages.
Sauerbrei, B. et al., "Lon Protease Removes Excess Signal Recognition Particle Protein in *Escherichia coli*", J. Bacteriology, 2020, 202 (14):e00161-20. 15 pages.
Schneider et al., "Relationship between Growth Rate and ATP Concentration in *Escherichia coli*," The Journal of Biological Chemistry, Feb. 27, 2004, vol. 279, No. 9, pp. 8262-8268.
Soini et al., "Transient increase of ATP as a response to temperature up-shift in *Escherichia coli*," Microbial Cell Factories, Apr. 2005, 4:9 doi:10.1186/1475-2859-4-9, 8 pages.
Thomassin, J.L. et al., "OmpT Outer Membrane Proteases of Enterohemorrhagic and Enteropathogenic *Escherichia coli* Contribute Differently to the Degradation of Human LL-37", Infection and Immunity, Feb. 2012, 80(2):483-492.
Yaginuma et al., "Diversity in ATP concentrations in a single bacterial cell population revealed by quantitative single-cell imaging," Scientific Reports, Oct. 6, 2014, 4:6522, 7 pages.
Zhang et al., "*E. coli* Nissle 1917-Derived Minicells for Targeted Delivery of Chemotherapeutic Drug to Hypoxic Regions for Cancer Therapy," Theranostics, Feb. 2018, vol. 8 Issue 6, pp. 1690-1705.
Elish et al, "Biochemical analysis of spontaneous fepA mutants in *Escherichia coli*," Journal of General Microbiology, May 1988, 134(5), pp. 1355-1364.
Ha et al., "The minicell generation in *Escherichia coli* harboring minD of Lactobacillus," J. Chemical and Pharmaceutical Research, 2016, 8(7):328-331.
Jeong et al., "Complete Genome Sequence of *Escherichia coli* strain BL21," Genome Announcement, Mar. 2015, 3(2):e00134-15.
Andrews et al., "Protective efficacy of recombinant Yersinia outer proteins against bubonic plague caused by encapsulated and nonencapsulated Yersinia pestis," Infection and Immunity, Mar. 1, 1999 (Mar. 1, 1999), vol. 67, pp. 1533-1537.
Bhosale et al., "Molecular and Industrial Aspects of Glucose Isomerase," Microbiological Reviews, Jun. 1996, p. 280-300, vol. 60, No. 2.
Cid et al., "Recognition of the helical structure of beta-1,4-galactan by a new family of carbohydrate-binding modules," J Biol Chem. Nov. 12, 2010;285(46):35999-6009.
Datta et al., "Enzyme immobilization: an overview on techniques and support materials," 3 Biotech. Feb. 2013;3(1):1-9.
Farley et al., "Minicells, Back in Fashion," J Bacteriol. Mar. 31, 2016;198(8):1186-95.
Giacalone et al., "Toxic protein expression in *Escherichia coli* using a rhamnose-based tightly regulated and tunable promoter system," Biotechniques, (2006) 40, 355-364.
Giacalone et al., "The use of bacterial minicells to transfer plasmid DNA to eukaryotic cells," Cellular Microbiology (2006), 8(10), 1624-1633.
Giacalone et al., "Immune responses elicited by bacterial minicells capable of simultaneous DNA and protein antigen delivery," Vaccine, 24 (2006), 6009-6017.
Giacalone et al., "Immunization with non-replicating *E. coli* minicells delivering both protein antigen and DNA protects mice from lethal challenge with lymphocytic choriomeningitis virus," Vaccine,25;12 (2007), 2279-2287.
International Search Report and Written Opinion dated Jul. 19, 2018, for International Application No. PCT/US2018/030328, 20 pages.
International Search Report and Written Opinion dated Jul. 10, 2018, for International Application No. PCT/US2018/030329, 18 pages.
Jarmander et al., "A dual tag system for facilitated detection of surface expressed proteins in *Escherichia coli*," Microb Cell Fact. Sep. 3, 2012;11:118.
Jose et al., "Autodisplay of enzymes—molecular basis and perspectives," J Biotechnol. Oct. 15, 2012;161(2):92-103.
Kirk et al., "Industrial enzyme applications," Curr Opin Biotechnol. Aug. 2002;13(4):345-351.
Linder et al., "The roles and function of cellulose-binding domains," Journal of Biotechnology, 57(1), 15-28.
MacDiarmid et al., "Bacterially derived 400 nm particles for encapsulation and cancer cell targeting of chemotherapeutics," Cancer Cell. May 2007;11(5):431-445.
Madhavi et al., "A Scrupulous Overview on Controlled Release Fertilizers," Research Reviews: Journal of Agriculture and Alfred Sciences, Mar. 17, 2016 (Mar. 17, 2016), vol. 5, Issue.1, pp. 1-8.

(56) References Cited

OTHER PUBLICATIONS

Maurer et al., "Autodisplay: One-Component System for Efficient Surface Display and Release of Soluble Recombinant Proteins from *Escherichia coli*," Journal of Bacteriology, Feb. 1997, p. 794-804, vol. 179, No. 3.
Mayne et al., "The cellular membrane as a mediator for small molecule interaction with membrane proteins," Biochimica et Biophysics Acta, May 6, 2016 (May 6, 2016), vol. 1858, pp. 2290-2304.
Mitra et al., "Right Place, Right Time: Focalization of Membrane Proteins in Gram-Positive Bacteria," Trends in Microbiology, 2016, 24(8), 611-621.
Nuruzzaman et al., "Nanoencapsulation, Nano-guard for Pesticides: A New Window for Safe Application," J Agric Food Chem. Feb. 24, 2016;64(7):1447-83.
Parker et al., "High fructose corn syrup: Production, uses and public health concerns," Biotechnology and Molecular Biology Reviews, Sep. 30, 2010 (30.092(J10), vol. 5, No. 5, pp. 71-78.
Shoseyov et al., "Carbohydrate binding modules: biochemical properties and novel applications," Microbiol Mol Biol Rev. Jun. 2006;70(2):283-95.
Sun et al., "BrkAutoDisplay: functional display of multiple exogenous proteins on the surface of *Escherichia coli* by using BrkA autotransporter," Microb Cell Fact. Sep. 4, 2015;14:129.
Tsuji et al., "An Efficient Thermo inducible Bacterial Suicide System—Elimination of Viable Parental Bacteria from Minicells," (2010) BioProcess International, vol. 8, No. 4, 28-40.
Ulmanen et al., "Transcription and Translation of Foreign Genes in Bacillus subtilis by the Aid of a Secretion Vector," Journal of Bacteriology, Apr. 30, 1985 (Apr. 30, 1985), vol. 162, No. 1, pp. 176-182.
Varley et al., "The divIVB region of the Bacillus subtilis chromosome encodes homologs of *Escherichia coli* septum placement (minCD) and cell shape (mreBCD) determinants," Journal of Bacteriology, Nov. 1, 1992 (Nov. 1, 1992), vol. 174, pp. 6729-6742.
Yamamoto et al., "Localization of the Vegetative Cell Wall Hydrolases LytC, LytE, and LytF on the Bacillus subtilis Cell Surface and Stability of These Enzymes to Cell Wall-Bound or Extracellular Proteases," Journal of Bacteriology, Nov. 30, 2003 (Nov. 30, 2003), vol. 185, No. 22, pp. 6666-6677.
Yang et al., "Comparison of Autotransporter and Ice Nucleation Protein as Carrier Proteins for Antibody Display on The Cell Surface of *Escherichia coli*," Progress in Biochemistry and Biophysics 40(12):1209-1219.
Zeigler D.R. "New! Protease-free Bacillus subtilis host," Bacillus Genetic Stock Center News, Jun. 30, 2016 (Jun. 30, 2016), pp. 1-3. Retrieved from the Internet:<http:/www.bgsc.org/new.php?page=2> on Jul. 4, 2018 (Jul. 4, 2018).
Zhang et al., "Surface Immobilization of Human Arginase-1 with an Engineered Ice Nucleation Protein Display System in *E. coli*," PLoS One. Aug. 1, 2016;11(8).

* cited by examiner pGEX-6P-1_Inak-CBM_Expression Cassette
2067 bp

Clothianidin Encapsulation and Mass Fraction (%)

| | Encapsulation Fraction (%) | Mass Fraction (%) |
|---|---|---|
| Exp 1 (10 ug/mL) | 3.51 | 5.69 |
| Exp 2 (10 ug/mL) | 2.76 | 4.53 |
| Exp 3 (10 ug/mL) | 2.64 | 4.34 |

Percentage

SEQUENCE LISTING

```
<160> NUMBER OF SEQ ID NOS: 37

<210> SEQ ID NO 1
<211> LENGTH: 50
<212> TYPE: DNA
<213> ORGANISM: Escherichia coli

<400> SEQUENCE: 1

cgaagtaaca acaataatgc gtgccataga aattccttgt taaaaaggga              50


<210> SEQ ID NO 2
<211> LENGTH: 50
<212> TYPE: DNA
<213> ORGANISM: Escherichia coli

<400> SEQUENCE: 2

cctggcctta ctcaattagc tattaatcat cgccagcgcg cgatgatgtt              50


<210> SEQ ID NO 3
<211> LENGTH: 50
<212> TYPE: DNA
```

<213> ORGANISM: Escherichia coli

<400> SEQUENCE: 3
ttggctgtgt ttttcttccg cgagagaaag aaatcgagta atgccataac 50

<210> SEQ ID NO 4
<211> LENGTH: 50
<212> TYPE: DNA
<213> ORGANISM: Escherichia coli

<400> SEQUENCE: 4
agaaattcct tgttaaaaag ggatcaattt aacggttgaa cggtcaaagc 50

<210> SEQ ID NO 5
<211> LENGTH: 1773
<212> TYPE: DNA
<213> ORGANISM: Artificial Sequence
<220> FEATURE:
<223> OTHER INFORMATION: AIDA-1 annotated

<400> SEQUENCE: 5
atgaataagg cctacagtat catttggagc cactccagac aggcctggat tgtggcctca 60
gagttagcca gaggacatgg ttttgtcctt gcaaaaaata cactgctggt attggcggtt 120
gtttccacaa tcggaaatgc atttgcagtc gaccaccatc accatcacca tctggaagcg 180
ctgttccagg gtccgggtac ccagaaacag cgtaccgagc tcgaaaacct gtacttccag 240
ggtgaacaga aactgattag cgaagaagat ctgtctagag tgaataacaa tggaagcatt 300
gtcattaata acagcattat aaacgggaat attacgaatg atgctgactt aagttttggt 360
acagcaaagc tgctctctgc tacagtgaat ggtagtcttg ttaataacaa aaatatcatt 420
cttaatccta caaaagaaag tgcggccgct ataggtaata ctcttaccgt gtcaaattat 480
actgggacac cgggaagtgt tatttctctt ggtggtgtgc ttgaaggaga taattcactt 540
acggaccgtc tggtggtgaa aggtaatacc tctggtcaaa gtgacatcgt ttatgtcaat 600
gaagatggca gtggtggtca gacgagagat ggtattaata ttatttctgt agagggaaat 660
tctgatgcag aattctctct gaagaaccgc gtagttgccg gagcttatga ttacacactg 720
cagaaaggaa acgagagtgg gacagataat aagggatggt atttaaccag tcatcttccc 780
acatctgata cccggcaata cagaccggag aacggaagtt atgctaccaa tatggcactg 840
gctaactcac tgttcctcat ggatttgaat gagcgtaagc aattcagggc catgagtgat 900
aatacacagc ctgagtctgc atccgtgtgg atgaagatca ctggaggaat aagctctggt 960
aagctgaatg acgggcaaaa taaaacaaca accaatcagt ttatcaatca gctcgggggg 1020
gatatttata aattccatgc tgaacaactg ggtgatttta ccttagggat tatgggagga 1080
tacgcgaatg caaaaggtaa aacgataaat tacacgagca acaaagctgc cagaaacaca 1140
ctggatggtt attctgtcgg ggtatacggt acgtggtatc agaatgggga aaatgcaaca 1200
gggctctttg ctgaaacttg gatgcaatat aactggttta atgcatcagt gaaaggtgac 1260
ggactggaag aagaaaaata taatctgaat ggtttaaccg cttctgcagg tgggggatat 1320
aacctgaatg tgcacacatg gacatcacct gaaggaataa caggtgaatt ctggttacag 1380
cctcatttgc aggctgtctg gatgggggtt acaccggata cacatcagga ggataacgga 1440
acggtggtgc agggagcagg gaaaaataat attcagacaa aagcaggtat tcgtgcatcc 1500
tggaaggtga aaagcaccct ggataaggat accgggcgga ggttccgtcc gtatatagag 1560
gcaaactgga tccataacac tcatgaattt ggtgttaaaa tgagtgatga cagccagttg 1620
ttgtcaggta gccgaaatca gggagagata aagacaggta ttgaaggggt gattactcaa 1680
aacttgtcag tgaatggcgg agtcgcatat caggcaggag gtcacgggag caatgccatc 1740
tccggagcac tggggataaa atacagcttc tga 1773

<210> SEQ ID NO 6
<211> LENGTH: 3033
<212> TYPE: DNA
<213> ORGANISM: Artificial Sequence
<220> FEATURE:
<223> OTHER INFORMATION: BrkAutoTransporter_Annotated

<400> SEQUENCE: 6
atgtatctgg atcgctttcg ccagtgcccg agcagcctgc agattccgcg cagcgcgtgg 60
cgcctgcatg cgctggcggc ggcgctggcg ctggcgggca tggcgcgcct ggcgccggcg 120
gcggcgcagg cgccgcagcc gccggtggcg ggcgcgccgc atgcgcagga tgcgggccag 180
gaaggcgaat ttgatcatcg cgataacacc ctgattgcgg tgtttgatga tggcgtgggc 240
attaacctgg atgatgatcc ggatgaactg ggcgaaaccg cgccgccgac cctgaaagat 300
attcatatta gcgtggaaca taaaaacccg atgagcaaac cggcgattgg cgtgcgcgtg 360
agcggcgcgg gccgcgcgct gaccctggcg ggcagcacca ttgatgcgac cgaaggcggc 420
attccggcgg tggtgcgccg cggcggcacc ctggaactgg atggcgtgac cgtggcgggc 480
ggcgaaggca tggaaccgat gaccgtgagc gatgcgggca gccgcctgag cgtgcgcggc 540
ggcgtgctgg gcggcgaagc gccgggcgtg ggcctggtgc gcgcggcgca gggcggccag 600
gcgagcatta ttgatgcgac cctgcagagc attctgggcc cggcgctgat tgcggatggc 660
ggcagcatta gcgtggcggg cggcagcatt gatatggata tgggcccggg ctttccgccg 720
ccgccgccgc cgctgccggg cgcgccgctg gcggcgcatc cgccgctgga tcgcgtggcg 780
gcggtgcatg cgggccagga tggcaaagtg accctgcgcg aagtggcgct gcgcgcgcat 840
ggcccgcagg cgaccggcgt gtatgcgtat atgccgggca gcgaaattac cctgcagggc 900
ggcaccgtga gcgtgcaggg cgatgatggc gcgggcgtgg tggcgggcgc gggcctgctg 960
gatgcgctgc cgccgggcgg caccgtgcgc ctggatggca ccaccgtgag caccgatggc 1020
gcgaacaccg atgcggtgct ggtgcgcggc gatgcggcgc gcgcggaagt ggtgaacacc 1080
gtgctgcgca ccgcgaaaag cctggcggcg ggcgtgagcg cgcagcatgg cggccgcgtg 1140
accctgcgcc agacccgcat tgaaaccgcg ggcgcgggcg cggaaggcat tagcgtgctg 1200
ggctttgaac cgcagagcgg cagcggcccg gcgagcgtgg atatgcaggg cggcagcatt 1260
accaccaccg gcaaccgcgc ggcgggcatt gcgctgaccc atggcagcgc gcgcctggaa 1320
ggcgtggcgg tgcgcgcgga aggcagcggc agcagcgcgg cgcagctggc gaacggcacc 1380
ctggtggtga gcgcgggcag cctggcgagc gcgcagagcg gcgcgattag cgtgaccgat 1440
accccgctga aactgatgcc gggcgcgctg gcgagcagca ccgtgagcgt gcgcctgacc 1500
gatggcgcga ccgcgcaggg cggcaacggc gtgtttctgc agcagcatag caccattccg 1560
gtggcggtgg cgctggaaag cggcgcgctg gcgcgcggcg atattgtggc ggatggcaac 1620
aaaccgctgg atgcgggcat tagcctgagc gtggcgagcg gcgcggcgtg gcatggcgcg 1680
acccaggtgc tgcagagcgc gaccctgggc aaaggcggca cctgggtggt gaacgcggat 1740
agccgcgtgc aggatatgag catgcgcggc ggccgcgtgg aatttcaggc gccggcgccg 1800
gaagcgagct ataaaaccct gaccctgcag accctggatg gcaacggcgt gtttgtgctg 1860
aacaccaacg tggcggcggg ccagaacgat cagctgcgcg tgaccggccg cgcggatggc 1920
cagcatcgcg tgctggtgcg caacgcgggc ggcgaagcgg atagccgcgg cgcgcgcctg 1980
ggcctggtgc atacccaggg ccagggcaac gcgacctttc gcctggcgaa cgtgggcaaa 2040
gcggtggatc tgggcacctg gcgctatagc ctggcggaag atccgaaaac ccatgtgtgg 2100
agcctgcagc gcgcgggcca ggcgctgagc ggcgcggcga acgcggcggt gaacgcggcg 2160
gatctgagca gcattgcgct ggcggaaagc aacgcgctgg ataaacgcct gggcgaactg 2220
cgcctgcgcg cggatgcggg cggcccgtgg gcgcgcacct ttagcgaacg ccagcagatt 2280
agcaaccgcc atgcgcgcgc gtatgatcag accgtgagcg gcctggaaat tggcctggat 2340
cgcggctgga gcgcgagcgg cggccgctgg tatgcgggcg gcctgctggg ctatacctat 2400
gcggatcgca cctatccggg cgatggcggc ggcaaagtga aaggcctgca tgtgggcggc 2460
tatgcggcgt atgtgggcga tggcggctat tatctggata ccgtgctgcg cctgggccgc 2520
tatgatcagc agtataacat tgcgggcacc gatggcggcc gcgtgaccgc ggattatcgc 2580
accagcggcg cggcgtggag cctggaaggc ggccgccgct ttgaactgcc gaacgattgg 2640
tttgcggaac cgcaggcgga agtgatgctg tggcgcacca gcggcaaacg ctatcgcgcg 2700
agcaacggcc tgcgcgtgaa agtggatgcg aacaccgcga ccctgggccg cctgggcctg 2760
cgctttggcc gccgcattgc gctggcgggc ggcaacattg tgcagccgta tgcgcgcctg 2820
ggctggaccc aggaatttaa aagcaccggc gatgtgcgca ccaacggcat tggccatgcg 2880
ggcgcgggcc gccatggccg cgtggaactg ggcgcgggcg tggatgcggc gctgggcaaa 2940
ggccataacc tgtatgcgag ctatgaatat gcggcgggcg atcgcattaa cattccgtgg 3000
agctttcatg cgggctatcg ctatagcttt tga 3033

<210> SEQ ID NO 7
<211> LENGTH: 2343
<212> TYPE: DNA
<213> ORGANISM: Artificial Sequence
<220> FEATURE:
<223> OTHER INFORMATION: BrkAutoTransporter_CBM

<400> SEQUENCE: 7
atgtatctgg atcgctttcg ccagtgcccg agcagcctgc agattccgcg cagcgcgtgg 60
cgcctgcatg cgctggcggc ggcgctggcg ctggcgggca tggcgcgcct ggcgccggcg 120
gcggcgcagg cgccgcagcc gccggtggcg ggcgcgccgc atgcgcagga tgcgggccac 180
catcaccatc accatgttca gctggttgaa agcggtggtg cactggttca gcctggtggt 240
agcctgcgtc tgagctgtgc agcaagcggt tttccggtta atcgttatag catgcgttgg 300
tatcgtcagg caccgggtaa agaacgtgaa tgggttgcag gtatgagcag tgccggtgat 360
cgtagcagct acgaagatag cgttaaaggt cgttttacca tcagccgtga tgatgcacgt 420
aataccgttt atctgcaaat gaatagcctg aaaccggaag ataccgcagt gtattattgc 480
aacgttaacg tgggctttga atattggggt cagggcaccc aggttaccgt tagcagcaaa 540
ctcgagcggc cgcatcgtga cgcgtcgtct ggtcctgccg gctgccaagt cctttggggc 600
gtgaatcagt ggaacacagg tttcacggcg aatgttaccg tcaagaatac gtcctccgct 660
cctgttgacg gctggacctt gaccttcagt ttcccatcag gacaacaagt cactcaagcc 720
tggtcatcta ccgtgaccca gagtggatct gcggtcacag tacgtaacgc tccgtggaac 780
ggttcgattc ccgcgggcgg gactgctcag ttcgggttta acggaagcca cactggcact 840
aatgctgcac caactgcctt ctcacttaac ggcacgccgt gcaccgtagg cgaacagaaa 900

```
ctgattagcg aagaagatct ggaaaacctg tacttccagg gtgcgggcat tagcctgagc     960

gtggcgagcg gcgcggcgtg gcatggcgcg acccaggtgc tgcagagcgc gaccctgggc    1020

aaaggcggca cctgggtggt gaacgcggat agccgcgtgc aggatatgag catgcgcggc    1080

ggccgcgtgg aatttcaggc gccggcgccg gaagcgagct ataaaaccct gaccctgcag    1140

accctggatg gcaacggcgt gtttgtgctg aacaccaacg tggcggcggg ccagaacgat    1200

cagctgcgcg tgaccggccg cgcggatggc cagcatcgcg tgctggtgcg caacgcgggc    1260

ggcgaagcgg atagccgcgg cgcgcgcctg ggcctggtgc atacccaggg ccagggcaac    1320

gcgacctttc gcctggcgaa cgtgggcaaa gcggtggatc tgggcacctg gcgctatagc    1380

ctggcggaag atccgaaaac ccatgtgtgg agcctgcagc gcgcgggcca ggcgctgagc    1440

ggcgcggcga acgcggcggt gaacgcggcg gatctgagca gcattgcgct ggcggaaagc    1500

aacgcgctgg ataaacgcct gggcgaactg cgcctgcgcg cggatgcggg cggcccgtgg    1560

gcgcgcacct ttagcgaacg ccagcagatt agcaaccgcc atgcgcgcgc gtatgatcag    1620

accgtgagcg gcctggaaat tggcctggat cgcggctgga gcgcgagcgg cggccgctgg    1680

tatgcgggcg gcctgctggg ctatacctat gcggatcgca cctatccggg cgatggcggc    1740

ggcaaagtga aaggcctgca tgtgggcggc tatgcggcgt atgtgggcga tggcggctat    1800

tatctggata ccgtgctgcg cctgggccgc tatgatcagc agtataacat tgcgggcacc    1860

gatggcggcc gcgtgaccgc ggattatcgc accagcggcg cggcgtggag cctggaaggc    1920

ggccgccgct ttgaactgcc gaacgattgg tttgcggaac cgcaggcgga agtgatgctg    1980

tggcgcacca gcggcaaacg ctatcgcgcg agcaacggcc tgcgcgtgaa agtggatgcg    2040

aacaccgcga ccctgggccg cctgggcctg cgctttggcc gccgcattgc gctggcgggc    2100

ggcaacattg tgcagccgta tgcgcgcctg ggctggaccc aggaatttaa aagcaccggc    2160

gatgtgcgca ccaacggcat tggccatgcg ggcgcgggcc gccatggccg cgtggaactg    2220

ggcgcgggcg tggatgcggc gctgggcaaa ggccataacc tgtatgcgag ctatgaatat    2280

gcggcgggcg atcgcattaa cattccgtgg agctttcatg cgggctatcg ctatagcttt    2340

tga                                                                  2343
```

<210> SEQ ID NO 8
<211> LENGTH: 330
<212> TYPE: DNA
<213> ORGANISM: Artificial Sequence
<220> FEATURE:
<223> OTHER INFORMATION: CBM

<400> SEQUENCE: 8

```
gcgtcgtctg gtcctgccgg ctgccaagtc ctttggggcg tgaatcagtg gaacacaggt      60

ttcacggcga atgttaccgt caagaatacg tcctccgctc ctgttgacgg ctggaccttg     120

accttcagtt tcccatcagg acaacaagtc actcaagcct ggtcatctac cgtgacccag     180

agtggatctg cggtcacagt acgtaacgct ccgtggaacg gttcgattcc cgcgggcggg     240

actgctcagt tcgggtttaa cggaagccac actggcacta atgctgcacc aactgccttc     300

tcacttaacg gcacgccgtg caccgtaggc                                      330
```

<210> SEQ ID NO 9
<211> LENGTH: 696
<212> TYPE: DNA
<213> ORGANISM: Artificial Sequence
<220> FEATURE:

<223> OTHER INFORMATION: GFP-Nanobody CBM

<400> SEQUENCE: 9

```
gttcagctgg ttgaaagcgg tggtgcactg gttcagcctg gtggtagcct gcgtctgagc     60
tgtgcagcaa gcggttttcc ggttaatcgt tatagcatgc gttggtatcg tcaggcaccg    120
ggtaaagaac gtgaatgggt tgcaggtatg agcagtgccg gtgatcgtag cagctacgaa    180
gatagcgtta aaggtcgttt taccatcagc cgtgatgatg cacgtaatac cgtttatctg    240
caaatgaata gcctgaaacc ggaagatacc gcagtgtatt attgcaacgt taacgtgggc    300
tttgaatatt ggggtcaggg cacccaggtt accgttagca gcaaactcga gcggccgcat    360
cgtgacgcgt cgtctggtcc tgccggctgc caagtccttt ggggcgtgaa tcagtggaac    420
acaggtttca cggcgaatgt taccgtcaag aatacgtcct ccgctcctgt tgacggctgg    480
accttgacct tcagtttccc atcaggacaa caagtcactc aagcctggtc atctaccgtg    540
acccagagtg gatctgcggt cacagtacgt aacgctccgt ggaacggttc gattcccgcg    600
ggcgggactg ctcagttcgg gtttaacgga agccacactg gcactaatgc tgcaccaact    660
gccttctcac ttaacggcac gccgtgcacc gtaggc                              696
```

<210> SEQ ID NO 10
<211> LENGTH: 537
<212> TYPE: DNA
<213> ORGANISM: Artificial Sequence
<220> FEATURE:
<223> OTHER INFORMATION: InaK

<400> SEQUENCE: 10

```
atggtcttag acaaggcgct agttctacgt acctgcgcta ataatatggc cgatcactgc     60
ggcttgattt ggcctgcctc agggaccgtc gagtcaaggt attggcaatc tacacgtcgt    120
cacgagaacg gactggtagg tcttctttgg ggagcaggaa cttctgcttt cttgtcagtc    180
catgcagacg cccgctggat cgtgtgcgaa gtggctgttg ccgatattat ctccctagag    240
gagcccggaa tggttaaatt tcctcgggcc gaagtggtgc atgtgggcga tcgaatcagc    300
gcttctcatt ttatttcggc gcggcaggca gatcccgcga gtacgagtac ttcaacgtcg    360
acaagtactc ttactcccat gcccacggca atccccaccc ctatgccagc ggtggcgtca    420
gtgacgttac cggtggctga gcaagcgcgg catgaggtgt ttgatgtagc tagtgtgagc    480
gccgcggctg ctcccgtgaa cactttacct gtcacgacac cccaaaacct ccagacg       537
```

<210> SEQ ID NO 11
<211> LENGTH: 1305
<212> TYPE: DNA
<213> ORGANISM: Artificial Sequence
<220> FEATURE:
<223> OTHER INFORMATION: InaK-TEV-CBM-His-Myc-GFPNB

<400> SEQUENCE: 11

```
atggtcttag acaaggcgct agttctacgt acctgcgcta ataatatggc cgatcactgc     60
ggcttgattt ggcctgcctc agggaccgtc gagtcaaggt attggcaatc tacacgtcgt    120
cacgagaacg gactggtagg tcttctttgg ggagcaggaa cttctgcttt cttgtcagtc    180
catgcagacg cccgctggat cgtgtgcgaa gtggctgttg ccgatattat ctccctagag    240
gagcccggaa tggttaaatt tcctcgggcc gaagtggtgc atgtgggcga tcgaatcagc    300
gcttctcatt ttatttcggc gcggcaggca gatcccgcga gtacgagtac ttcaacgtcg    360
acaagtactc ttactcccat gcccacggca atccccaccc ctatgccagc ggtggcgtca    420
```

-continued

```
gtgacgttac cggtggctga gcaagcgcgg catgaggtgt ttgatgtagc tagtgtgagc    480
gccgcggctg ctcccgtgaa cactttacct gtcacgacac cccaaaacct ccagacggaa    540
aacctgtact tccagggtgc gtcgtctggt cctgccggct gccaagtcct ttggggcgtg    600
aatcagtgga acacaggttt cacggcgaat gttaccgtca agaatacgtc ctccgctcct    660
gttgacggct ggaccttgac cttcagtttc ccatcaggac aacaagtcac tcaagcctgg    720
tcatctaccg tgacccagag tggatctgcg gtcacagtac gtaacgctcc gtggaacggt    780
tcgattcccg cgggcgggac tgctcagttc gggtttaacg gaagccacac tggcactaat    840
gctgcaccaa ctgccttctc acttaacggc acgccgtgca ccgtaggcca ccatcaccat    900
caccatgttc agctggttga aagcggtggt gcactggttc agcctggtgg tagcctgcgt    960
ctgagctgtg cagcaagcgg ttttccggtt aatcgttata gcatgcgttg gtatcgtcag   1020
gcaccgggta aagaacgtga atgggttgca ggtatgagca gtgccggtga tcgtagcagc   1080
tacgaagata gcgttaaagg tcgttttacc atcagccgtg atgatgcacg taataccgtt   1140
tatctgcaaa tgaatagcct gaaaccggaa gataccgcag tgtattattg caacgttaac   1200
gtgggctttg aatattgggg tcagggcacc caggttaccg ttagcagcaa actcgagcgg   1260
ccgcatcgtg acgaacagaa actgattagc gaagaagatc tgtga                   1305
```

```
<210> SEQ ID NO 12
<211> LENGTH: 5561
<212> TYPE: DNA
<213> ORGANISM: Artificial Sequence
<220> FEATURE:
<223> OTHER INFORMATION: pAIDA-1

<400> SEQUENCE: 12
```

```
tttacacttt atgcttccgg ctcgtataat gtgtggaatt gtgagcggat aacaatttca     60
cacaggaaag cttcatatga ataaggccta cagtatcatt tggagccact ccagacaggc    120
ctggattgtg gcctcagagt tagccagagg acatggtttt gtccttgcaa aaaatacact    180
gctggtattg gcggttgttt ccacaatcgg aaatgcattt gcagtcgacc accatcacca    240
tcaccatctg gaagcgctgt tccagggtcc gggtacccag aaacagcgta ccgagctcga    300
aaacctgtac ttccagggtg aacagaaact gattagcgaa gaagatctgt ctagagtgaa    360
taacaatgga agcattgtca ttaataacag cattataaac gggaatatta cgaatgatgc    420
tgacttaagt tttggtacag caaagctgct ctctgctaca gtgaatggta gtcttgttaa    480
taacaaaaat atcattctta atcctacaaa agaaagtgcg gccgctatag gtaatactct    540
taccgtgtca aattatactg ggacaccggg aagtgttatt tctcttggtg gtgtgcttga    600
aggagataat tcacttacgg accgtctggt ggtgaaaggt aatacctctg gtcaaagtga    660
catcgtttat gtcaatgaag atggcagtgg tggtcagacg agagatggta ttaatattat    720
ttctgtagag ggaaattctg atgcagaatt ctctctgaag aaccgcgtag ttgccggagc    780
ttatgattac acactgcaga aaggaaacga gagtgggaca gataataagg gatggtattt    840
aaccagtcat cttcccacat ctgatacccg gcaatacaga ccggagaacg gaagttatgc    900
taccaatatg gcactggcta actcactgtt cctcatggat ttgaatgagc gtaagcaatt    960
cagggccatg agtgataata cacagcctga gtctgcatcc gtgtggatga agatcactgg   1020
aggaataagc tctggtaagc tgaatgacgg gcaaaataaa acaacaacca atcagtttat   1080
caatcagctc ggggggggata tttataaatt ccatgctgaa caactgggtg atttacctt   1140
```

-continued agggattatg ggaggatacg cgaatgcaaa aggtaaaacg ataaattaca cgagcaacaa 1200
agctgccaga aacacactgg atggttattc tgtcggggta tacggtacgt ggtatcagaa 1260
tggggaaaat gcaacagggc tctttgctga aacttggatg caatataact ggtttaatgc 1320
atcagtgaaa ggtgacggac tggaagaaga aaaatataat ctgaatggtt taaccgcttc 1380
tgcaggtggg ggatataacc tgaatgtgca cacatggaca tcacctgaag gaataacagg 1440
tgaattctgg ttacagcctc atttgcaggc tgtctggatg gggggttacac cggatacaca 1500
tcaggaggat aacggaacgg tggtgcaggg agcagggaaa aataatattc agacaaaagc 1560
aggtattcgt gcatcctgga aggtgaaaag caccctggat aaggataccg ggcggaggtt 1620
ccgtccgtat atagaggcaa actggatcca taacactcat gaatttggtg ttaaaatgag 1680
tgatgacagc cagttgttgt caggtagccg aaatcaggga gagataaaga caggtattga 1740
aggggtgatt actcaaaact tgtcagtgaa tggcggagtc gcatatcagg caggaggtca 1800
cgggagcaat gccatctccg gagcactggg gataaaatac agcttctgat aatgatcctg 1860
gcacgcggcg cgccccttgg tgcgcaaact attaactggc gaactactta ctctagcttc 1920
ccggcaacaa ttaatagact ggatggaggc ggataaagtt gcaggaccac ttctgcgctc 1980
ggcccttccg gctggctggt ttattgctga taaatctgga gccggtgagc gtgggtctcg 2040
cggtatcatt gcagcactgg ggccagatgg taagccctcc cgtatcgtag ttatctacac 2100
gacggggagt caggcaacta tggatgaacg aaatagacag atcgctgaga taggtgcctc 2160
actgattaag cattggtaac tgtcagacca agtttactca tatatacttt agattgattt 2220
aaaacttcat ttttaattta aaaggatcta ggtgaagatc ctttttgata atctcatgac 2280
caaaatccct taacgtgagt tttcgttcca ctgagcgtca gaccccttaa taagatgatc 2340
ttcttgagat cgttttggtc tgcgcgtaat ctcttgctct gaaaacgaaa aaaccgcctt 2400
gcagggcggt ttttcgaagg ttctctgagc taccaactct ttgaaccgag gtaactggct 2460
tggaggagcg cagtcaccaa aacttgtcct ttcagtttag ccttaaccgg cgcatgactt 2520
caagactaac tcctctaaat caattaccag tggctgctgc cagtggtgct tttgcatgtc 2580
tttccgggtt ggactcaaga cgatagttac cggataaggc gcagcggtcg gactgaacgg 2640
ggggttcgtg catacagtcc agcttggagc gaactgccta cccggaactg agtgtcaggc 2700
gtggaatgag acaaacgcgg ccataacagc ggaatgacac cggtaaaccg aaaggcagga 2760
acaggagagc gcacgaggga gccgccaggg ggaaacgcct ggtatcttta tagtcctgtc 2820
gggtttcgcc accactgatt tgagcgtcag atttcgtgat gcttgtcagg ggggcggagc 2880
ctatggaaaa acggctttgc cgcggccctc tcacttccct gttaagtatc ttcctggcat 2940
cttccaggaa atctccgccc cgttcgtaag ccatttccgc tcgccgcagt cgaacgaccg 3000
agcgtagcga gtcagtgagc gaggaagcgg aatatatcct gtatcacata ttctgctgac 3060
gcaccggtgc agcctttttt ctcctgccac atgaagcact tcactgacac cctcatcagt 3120
gccaacatag taagccagta tacactccgc tagcgctgag gtctgcctcg tgaagaaggt 3180
gttgctgact cataccaggc ctgaatcgcc ccatcatcca gccagaaagt gagggagcca 3240
cggttgatga gagctttgtt gtaggtggac cagttggtga ttttgaactt ttgctttgcc 3300
acggaacggt ctgcgttgtc gggaagatgc gtgatctgat ccttcaactc agcaaaagtt 3360
cgatttattc aacaaagcca cgttgtgtct caaaatctct gatgttacat tgcacaagat 3420
aaaaatatat catcatgaac aataaaactg tctgcttaca taaacagtaa tacaaggggt 3480
gttatgagcc atattcaacg ggaaacgtct tgctcgagta tccgctcatg agattatcaa 3540

```
aaaggatctt cacctagatc cttttgtaag aggttccaac tttcaccata atgaaataag   3600

atcactaccg ggcgtatttt ttgagttatc gagattttca ggagctaagg aagctaaaat   3660

ggagaaaaaa atcactggat ataccaccgt tgatatatcc caatggcatc gtaaagaaca   3720

ttttgaggca tttcagtcag ttgctcaatg tacctataac cagaccgttc agctggatat   3780

tacggccttt ttaaagaccg taaagaaaaa taagcacaag ttttatccgg cctttattca   3840

cattcttgcc cgcctgatga atgctcatcc ggagtttcgt atggcaatga aagacggtga   3900

gctggtgata tgggatagtg ttcacccttg ttacaccgtt ttccatgagc aaactgaaac   3960

gttttcatcg ctctggagtg aataccacga cgatttccgg cagtttctac acatatattc   4020

gcaagatgtg gcgtgttacg gtgaaaacct ggcctatttc cctaaagggt ttattgagaa   4080

tatgtttttc gtctcagcca atccctgggt gagtttcacc agttttgatt taaacgtggc   4140

caatatggac aacttcttcg cccccgtttt caccatgggc aaatattata cgcaaggcga   4200

caaggtgctg atgccgctgg cgattcaggt tcatcatgcc gtttgtgatg gcttccatgt   4260

cggcagaatg cttaatgaat tacaacagta ctgcgatgag tggcagggcg gggcgtaatt   4320

tttttaaggc gacaccatcg aatggcgcaa aacctttcgc ggtatggcat gatagcgccc   4380

ggaagagagt caattcaggg tggtgaatgt gaaaccagta acgttatacg atgtcgcaga   4440

gtatgccggt gtctcttatc agaccgtttc ccgcgtggtg aaccaggcca gccacgtttc   4500

tgcgaaaacg cgggaaaaag tggaagcggc gatggcggag ctgaattaca ttcccaaccg   4560

cgtggcacaa caactggcgg gcaaacagtc gttgctgatt ggcgttgcca cctccagtct   4620

ggccctgcac gcgccgtcgc aaattgtcgc ggcgattaaa tctcgcgccg atcaactggg   4680

tgccagcgtg gtggtgtcga tggtagaacg aagcggcgtc gaagcctgta aagcggcggt   4740

gcacaatctt ctcgcgcaac gcgtcagtgg gctgatcatt aactatccgc tggatgacca   4800

ggatgccatt gctgtggaag ctgcctgcac taatgttccg gcgttatttc ttgatgtctc   4860

tgaccagaca cccatcaaca gtattatttt ctcccatgaa gacggtacgc gactgggcgt   4920

ggagcatctg gtcgcattgg gtcaccagca aatcgcgctg ttagcgggcc cattaagttc   4980

tgtctcggcg cgtctgcgtc tggctggctg gcataaatat ctcactcgca atcaaattca   5040

gccgatagcg gaacgggaag gcgactggag tgccatgtcc ggttttcaac aaaccatgca   5100

aatgctgaat gagggcatcg ttcccactgc gatgctggtt gccaacgatc agatggcgct   5160

gggcgcaatg cgcgccatta ccgagtccgg gctgcgcgtt ggtgcggata tctcggtagt   5220

gggatacgac gataccgaag acagctcatg ttatatcccg ccgttaacca ccatcaaaca   5280

ggattttcgc ctgctggggc aaaccagcgt ggaccgcttg ctgcaactct ctcagggcca   5340

ggcggtgaag ggcaatcagc tgttgcccgt ctcactggtg aaaagaaaaa ccaccctggc   5400

gcccaatacg caaaccgcct ctccccgcgc gttggccgat tcattaatgc agctggcacg   5460

acaggtttcc cgactggaaa gcgggcaagt gagtggataa ccgtattacc gcctttgagt   5520

gagctgatac cgggaattct cactcattag gcaccccagg c                       5561
```

<210> SEQ ID NO 13
<211> LENGTH: 6242
<212> TYPE: DNA
<213> ORGANISM: Artificial Sequence
<220> FEATURE:
<223> OTHER INFORMATION: pAIDA-1_CBM-Nanobody

<400> SEQUENCE: 13

-continued

```
tttacacttt atgcttccgg ctcgtataat gtgtggaatt gtgagcggat aacaatttca     60
cacaggaaag cttcatatga ataaggccta cagtatcatt tggagccact ccagacaggc    120
ctggattgtg gcctcagagt tagccagagg acatggtttt gtccttgcaa aaaatacact    180
gctggtattg gcggttgttt ccacaatcgg aaatgcattt gcagtcgacc accatcacca    240
tcaccatctg gaagcgctgt tccagggtcc gggtaccgtt cagctggttg aaagcggtgg    300
tgcactggtt cagcctggtg gtagcctgcg tctgagctgt gcagcaagcg gttttccggt    360
taatcgttat agcatgcgtt ggtatcgtca ggcaccgggt aaagaacgtg aatgggttgc    420
aggtatgagc agtgccggtg atcgtagcag ctacgaagat agcgttaaag gtcgttttac    480
catcagccgt gatgatgcac gtaataccgt ttatctgcaa atgaatagcc tgaaaccgga    540
agataccgca gtgtattatt gcaacgttaa cgtgggcttt gaatattggg gtcagggcac    600
ccaggttacc gttagcagca aactcgagcg gccgcatcgt gacgcgtcgt ctggtcctgc    660
cggctgccaa gtcctttggg gcgtgaatca gtggaacaca ggtttcacgg cgaatgttac    720
cgtcaagaat acgtcctccg ctcctgttga cggctggacc ttgaccttca gtttcccatc    780
aggacaacaa gtcactcaag cctggtcatc taccgtgacc cagagtggat ctgcggtcac    840
agtacgtaac gctccgtgga acggttcgat tcccgcgggc gggactgctc agttcgggtt    900
taacggaagc cacactggca ctaatgctgc accaactgcc ttctcactta acggcacgcc    960
gtgcaccgta ggcgagctcg aaaacctgta cttccagggt gaacagaaac tgattagcga   1020
agaagatctg tctagagtga ataacaatgg aagcattgtc attaataaca gcattataaa   1080
cgggaatatt acgaatgatg ctgacttaag ttttggtaca gcaaagctgc tctctgctac   1140
agtgaatggt agtcttgtta ataacaaaaa tatcattctt aatcctacaa aagaaagtgc   1200
ggccgctata ggtaatactc ttaccgtgtc aaattatact gggacaccgg gaagtgttat   1260
ttctcttggt ggtgtgcttg aaggagataa ttcacttacg gaccgtctgg tggtgaaagg   1320
taatacctct ggtcaaagtg acatcgttta tgtcaatgaa gatggcagtg gtggtcagac   1380
gagagatggt attaatatta tttctgtaga gggaaattct gatgcagaat tctctctgaa   1440
gaaccgcgta gttgccggag cttatgatta cacactgcag aaaggaaacg agagtgggac   1500
agataataag ggatggtatt taaccagtca tcttcccaca tctgataccc ggcaatacag   1560
accggagaac ggaagttatg ctaccaatat ggcactggct aactcactgt tcctcatgga   1620
tttgaatgag cgtaagcaat tcagggccat gagtgataat acacagcctg agtctgcatc   1680
cgtgtggatg aagatcactg gaggaataag ctctggtaag ctgaatgacg ggcaaaataa   1740
aacaacaacc aatcagttta tcaatcagct cggggggat atttataaat tccatgctga    1800
acaactgggt gattttacct tagggattat gggaggatac gcgaatgcaa aaggtaaaac   1860
gataaattac acgagcaaca aagctgccag aaacacactg gatggttatt ctgtcggggt   1920
atacggtacg tggtatcaga atggggaaaa tgcaacaggg ctctttgctg aaacttggat   1980
gcaatataac tggtttaatg catcagtgaa aggtgacgga ctggaagaag aaaaatataa   2040
tctgaatggt ttaaccgctt ctgcaggtgg gggatataac ctgaatgtgc acacatggac   2100
atcacctgaa ggaataacag gtgaattctg gttacagcct catttgcagg ctgtctggat   2160
gggggttaca ccggatacac atcaggagga taacggaacg gtggtgcagg gagcagggaa   2220
aaataatatt cagacaaaag caggtattcg tgcatcctgg aaggtgaaaa gcaccctgga   2280
taaggatacc gggcggaggt tccgtccgta tatagaggca aactggatcc ataacactca   2340
tgaatttggt gttaaaatga gtgatgacag ccagttgttg tcaggtagcc gaaatcaggg   2400
```

agagataaag acaggtattg aaggggtgat tactcaaaac ttgtcagtga atggcggagt 2460
cgcatatcag gcaggaggtc acgggagcaa tgccatctcc ggagcactgg ggataaaata 2520
cagcttctga taatgatcct ggcacgcggc gcgccccttg gtgcgcaaac tattaactgg 2580
cgaactactt actctagctt cccggcaaca attaatagac tggatggagg cggataaagt 2640
tgcaggacca cttctgcgct cggcccttcc ggctggctgg tttattgctg ataaatctgg 2700
agccggtgag cgtgggtctc gcggtatcat tgcagcactg gggccagatg gtaagccctc 2760
ccgtatcgta gttatctaca cgacggggag tcaggcaact atggatgaac gaaatagaca 2820
gatcgctgag ataggtgcct cactgattaa gcattggtaa ctgtcagacc aagtttactc 2880
atatatactt tagattgatt taaaacttca tttttaattt aaaaggatct aggtgaagat 2940
cctttttgat aatctcatga ccaaaatccc ttaacgtgag ttttcgttcc actgagcgtc 3000
agaccccta ataagatgat cttcttgaga tcgttttggt ctgcgcgtaa tctcttgctc 3060
tgaaaacgaa aaaaccgcct tgcagggcgg tttttcgaag gttctctgag ctaccaactc 3120
tttgaaccga ggtaactggc ttggaggagc gcagtcacca aaacttgtcc tttcagttta 3180
gccttaaccg gcgcatgact tcaagactaa ctcctctaaa tcaattacca gtggctgctg 3240
ccagtggtgc ttttgcatgt ctttccgggt tggactcaag acgatagtta ccggataagg 3300
cgcagcggtc ggactgaacg gggggttcgt gcatacagtc cagcttggag cgaactgcct 3360
acccggaact gagtgtcagg cgtggaatga gacaaacgcg gccataacag cggaatgaca 3420
ccggtaaacc gaaaggcagg aacaggagag cgcacgaggg agccgccagg gggaaacgcc 3480
tggtatcttt atagtcctgt cgggtttcgc caccactgat ttgagcgtca gatttcgtga 3540
tgcttgtcag gggggcggag cctatggaaa aacggctttg ccgcggccct ctcacttccc 3600
tgttaagtat cttcctggca tcttccagga aatctccgcc ccgttcgtaa gccatttccg 3660
ctcgccgcag tcgaacgacc gagcgtagcg agtcagtgag cgaggaagcg gaatatatcc 3720
tgtatcacat attctgctga cgcaccggtg cagccttttt tctcctgcca catgaagcac 3780
ttcactgaca ccctcatcag tgccaacata gtaagccagt atacactccg ctagcgctga 3840
ggtctgcctc gtgaagaagg tgttgctgac tcataccagg cctgaatcgc cccatcatcc 3900
agccagaaag tgagggagcc acggttgatg agagctttgt tgtaggtgga ccagttggtg 3960
attttgaact tttgctttgc cacggaacgg tctgcgttgt cgggaagatg cgtgatctga 4020
tccttcaact cagcaaaagt tcgatttatt caacaaagcc acgttgtgtc tcaaaatctc 4080
tgatgttaca ttgcacaaga taaaaatata tcatcatgaa caataaaact gtctgcttac 4140
ataaacagta atacaagggg tgttatgagc catattcaac gggaaacgtc ttgctcgagt 4200
atccgctcat gagattatca aaaaggatct tcacctagat ccttttgtaa gaggttccaa 4260
ctttcaccat aatgaaataa gatcactacc gggcgtattt tttgagttat cgagattttc 4320
aggagctaag gaagctaaaa tggagaaaaa aatcactgga tataccaccg ttgatatatc 4380
ccaatggcat cgtaaagaac attttgaggc atttcagtca gttgctcaat gtacctataa 4440
ccagaccgtt cagctggata ttacggcctt tttaaagacc gtaaagaaaa ataagcacaa 4500
gttttatccg gcctttattc acattcttgc ccgcctgatg aatgctcatc cggagtttcg 4560
tatggcaatg aaagacggtg agctggtgat atgggatagt gttcaccctt gttacaccgt 4620
tttccatgag caaactgaaa cgttttcatc gctctggagt gaataccacg acgatttccg 4680
gcagtttcta cacatatatt cgcaagatgt ggcgtgttac ggtgaaaacc tggcctattt 4740

-continued

```
ccctaaaggg tttattgaga atatgttttt cgtctcagcc aatccctggg tgagtttcac   4800
cagttttgat ttaaacgtgg ccaatatgga caacttcttc gcccccgttt tcaccatggg   4860
caaatattat acgcaaggcg acaaggtgct gatgccgctg gcgattcagg ttcatcatgc   4920
cgtttgtgat ggcttccatg tcggcagaat gcttaatgaa ttacaacagt actgcgatga   4980
gtggcagggc ggggcgtaat ttttttaagg cgacaccatc gaatggcgca aaacctttcg   5040
cggtatggca tgatagcgcc cggaagagag tcaattcagg gtggtgaatg tgaaaccagt   5100
aacgttatac gatgtcgcag agtatgccgg tgtctcttat cagaccgttt cccgcgtggt   5160
gaaccaggcc agccacgttt ctgcgaaaac gcgggaaaaa gtggaagcgg cgatggcgga   5220
gctgaattac attcccaacc gcgtggcaca acaactggcg ggcaaacagt cgttgctgat   5280
tggcgttgcc acctccagtc tggccctgca cgcgccgtcg caaattgtcg cggcgattaa   5340
atctcgcgcc gatcaactgg gtgccagcgt ggtggtgtcg atggtagaac gaagcggcgt   5400
cgaagcctgt aaagcggcgg tgcacaatct tctcgcgcaa cgcgtcagtg ggctgatcat   5460
taactatccg ctggatgacc aggatgccat tgctgtggaa gctgcctgca ctaatgttcc   5520
ggcgttattt cttgatgtct ctgaccagac acccatcaac agtattattt tctcccatga   5580
agacggtacg cgactgggcg tggagcatct ggtcgcattg ggtcaccagc aaatcgcgct   5640
gttagcgggc ccattaagtt ctgtctcggc gcgtctgcgt ctggctggct ggcataaata   5700
tctcactcgc aatcaaattc agccgatagc ggaacgggaa ggcgactgga gtgccatgtc   5760
cggttttcaa caaaccatgc aaatgctgaa tgagggcatc gttcccactg cgatgctggt   5820
tgccaacgat cagatggcgc tgggcgcaat gcgcgccatt accgagtccg ggctgcgcgt   5880
tggtgcggat atctcggtag tgggatacga cgataccgaa gacagctcat gttatatccc   5940
gccgttaacc accatcaaac aggattttcg cctgctgggg caaaccagcg tggaccgctt   6000
gctgcaactc tctcagggcc aggcggtgaa gggcaatcag ctgttgcccg tctcactggt   6060
gaaaagaaaa accaccctgg cgcccaatac gcaaaccgcc tctccccgcg cgttggccga   6120
ttcattaatg cagctggcac gacaggtttc ccgactggaa agcgggcaag tgagtggata   6180
accgtattac cgcctttgag tgagctgata ccgggaattc tcactcatta ggcaccccag   6240
gc                                                                  6242
```

<210> SEQ ID NO 14
<211> LENGTH: 4341
<212> TYPE: DNA
<213> ORGANISM: Artificial Sequence
<220> FEATURE:
<223> OTHER INFORMATION: pET-9a

<400> SEQUENCE: 14

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatat ccggatatag ttcctccttt cagcaaaaaa cccctcaaga    420
cccgtttaga ggccccaagg ggttatgcta gttattgctc agcggtggca gcagccaact    480
cagcttcctt tcgggctttg ttagcagccg gatccgcgac ccatttgctg tccaccagtc    540
```

```
atgctagcca tatgtatatc tccttcttaa agttaaacaa aattatttct agagggaaac    600
cgttgtggtc tccctatagt gagtcgtatt aatttcgcgg gatcgagatc tcgatcctct    660
acgccggacg catcgtggcc ggcatcaccg gcgccacagg tgcggttgct ggcgcctata    720
tcgccgacat caccgatggg gaagatcggg ctcgccactt cgggctcatg agcgcttgtt    780
tcggcgtggg tatggtggca ggccccgtgg ccgggggact gttgggcgcc atctccttgc    840
atgcaccatt ccttgcggcg gcggtgctca acggcctcaa cctactactg ggctgcttcc    900
taatgcagga gtcgcataag ggagagcgtc gaccgatgcc cttgagagcc ttcaacccag    960
tcagctcctt ccggtgggcg cggggcatga ctatcgtcgc cgcacttatg actgtcttct   1020
ttatcatgca actcgtagga caggtgccgg cagcgctctg ggtcattttc ggcgaggacc   1080
gctttcgctg gagcgcgacg atgatcggcc tgtcgcttgc ggtattcgga atcttgcacg   1140
ccctcgctca agccttcgtc actggtcccg ccaccaaacg tttcggcgag aagcaggcca   1200
ttatcgccgg catggcggcc gacgcgctgg gctacgtctt gctggcgttc gcgacgcgag   1260
gctggatggc cttccccatt atgattcttc tcgcttccgg cggcatcggg atgcccgcgt   1320
tgcaggccat gctgtccagg caggtagatg acgaccatca gggacagctt caaggatcgc   1380
tcgcggctct taccagccta acttcgatca ctggaccgct gatcgtcacg gcgatttatg   1440
ccgcctcggc gagcacatgg aacgggttgg catggattgt aggcgccgcc ctataccttg   1500
tctgcctccc cgcgttgcgt cgcggtgcat ggagccgggc cacctcgacc tgaatggaag   1560
ccggcggcac ctcgctaacg gattcaccac tccaagaatt ggagccaatc aattcttgcg   1620
gagaactgtg aatgcgcaaa ccaacccttg gcagaacata tccatcgcgt ccgccatctc   1680
cagcagccgc acgcggcgca tctcgggcag cgttgggtcc tggccacggg tgcgcatgat   1740
cgtgctcctg tcgttgagga cccggctagg ctggcggggt tgccttactg gttagcagaa   1800
tgaatcaccg atacgcgagc gaacgtgaag cgactgctgc tgcaaaacgt ctgcgacctg   1860
agcaacaaca tgaatggtct tcggtttccg tgtttcgtaa agtctggaaa cgcggaagtc   1920
agcgccctgc accattatgt tccggatctg catcgcagga tgctgctggc taccctgtgg   1980
aacacctaca tctgtattaa cgaagcgctg gcattgaccc tgagtgattt ttctctggtc   2040
ccgccgcatc cataccgcca gttgtttacc ctcacaacgt tccagtaacc gggcatgttc   2100
atcatcagta acccgtatcg tgagcatcct ctctcgtttc atcggtatca ttacccccat   2160
gaacagaaat cccccttaca cggaggcatc agtgaccaaa caggaaaaaa ccgcccttaa   2220
catggcccgc tttatcagaa gccagacatt aacgcttctg gagaaactca acgagctgga   2280
cgcggatgaa caggcagaca tctgtgaatc gcttcacgac cacgctgatg agctttaccg   2340
cagctgcctc gcgcgtttcg gtgatgacgg tgaaaacctc tgacacatgc agctcccgga   2400
gacggtcaca gcttgtctgt aagcggatgc cgggagcaga caagcccgtc agggcgcgtc   2460
agcgggtgtt ggcgggtgtc ggggcgcagc catgacccag tcacgtagcg atagcggagt   2520
gtatactggc ttaactatgc ggcatcagag cagattgtac tgagagtgca ccatatatgc   2580
ggtgtgaaat accgcacaga tgcgtaagga gaaaataccg catcaggcgc tcttccgctt   2640
cctcgctcac tgactcgctg cgctcggtcg ttcggctgcg gcgagcggta tcagctcact   2700
caaaggcggt aatacggtta tccacagaat caggggataa cgcaggaaag aacatgtgag   2760
caaaaggcca gcaaaaggcc aggaaccgta aaaaggccgc gttgctggcg tttttccata   2820
ggctccgccc ccctgacgag catcacaaaa atcgacgctc aagtcagagg tggcgaaacc   2880
```

```
cgacaggact ataaagatac caggcgtttc cccctggaag ctccctcgtg cgctctcctg   2940

ttccgaccct gccgcttacc ggatacctgt ccgcctttct cccttcggga agcgtggcgc   3000

tttctcatag ctcacgctgt aggtatctca gttcggtgta ggtcgttcgc tccaagctgg   3060

gctgtgtgca cgaacccccc gttcagcccg accgctgcgc cttatccggt aactatcgtc   3120

ttgagtccaa cccggtaaga cacgacttat cgccactggc agcagccact ggtaacagga   3180

ttagcagagc gaggtatgta ggcggtgcta cagagttctt gaagtggtgg cctaactacg   3240

gctacactag aaggacagta tttggtatct gcgctctgct gaagccagtt accttcggaa   3300

aaagagttgg tagctcttga tccggcaaac aaaccaccgc tggtagcggt ggtttttttg   3360

tttgcaagca gcagattacg cgcagaaaaa aaggatctca agaagatcct ttgatctttt   3420

ctacggggtc tgacgctcag tggaacgaaa actcacgtta agggattttg gtcatgaaca   3480

ataaaactgt ctgcttacat aaacagtaat acaaggggtg ttatgagcca tattcaacgg   3540

gaaacgtctt gctcgaggcc gcgattaaat tccaacatgg atgctgattt atatgggtat   3600

aaatgggctc gcgataatgt cgggcaatca ggtgcgacaa tctatcgatt gtatgggaag   3660

cccgatgcgc cagagttgtt tctgaaacat ggcaaaggta gcgttgccaa tgatgttaca   3720

gatgagatgg tcagactaaa ctggctgacg gaatttatgc ctcttccgac catcaagcat   3780

tttatccgta ctcctgatga tgcatggtta ctcaccactg cgatccccgg gaaaacagca   3840

ttccaggtat tagaagaata tcctgattca ggtgaaaata ttgttgatgc gctggcagtg   3900

ttcctgcgcc ggttgcattc gattcctgtt tgtaattgtc cttttaacag cgatcgcgta   3960

tttcgtctcg ctcaggcgca atcacgaatg aataacggtt tggttgatgc gagtgatttt   4020

gatgacgagc gtaatggctg gcctgttgaa caagtctgga aagaaatgca taagcttttg   4080

ccattctcac cggattcagt cgtcactcat ggtgatttct cacttgataa ccttattttt   4140

gacgagggga aattaatagg ttgtattgat gttggacgag tcggaatcgc agaccgatac   4200

caggatcttg ccatcctatg gaactgcctc ggtgagtttt ctccttcatt acagaaacgg   4260

ctttttcaaa aatatggtat tgataatcct gatatgaata aattgcagtt tcatttgatg   4320

ctcgatgagt ttttctaaga a                                             4341
```

<210> SEQ ID NO 15
<211> LENGTH: 4981
<212> TYPE: DNA
<213> ORGANISM: Artificial Sequence
<220> FEATURE:
<223> OTHER INFORMATION: pGEX-6P-1_NoGST

<400> SEQUENCE: 15

```
acgttatcga ctgcacggtg caccaatgct tctggcgtca ggcagccatc ggaagctgtg     60

gtatggctgt gcaggtcgta aatcactgca taattcgtgt cgctcaaggc gcactcccgt    120

tctggataat gttttttgcg ccgacatcat aacggttctg gcaaatattc tgaaatgagc    180

tgttgacaat taatcatcgg ctcgtataat gtgtggaatt gtgagcggat aacaatttca    240

cacaggaaac agtattctcc cctatactag gttattggaa aattaagggc cttgtgcaac    300

ccactcgact tcttttggaa tatcttgaag aaaaatatga agagcatttg tatgagcgcg    360

atgaaggtga taaatggcga aacaaaaagt ttgaattggg tttggagttt cccaatcttc    420

cttattatat tgatggtgat gttaaattaa cacagtctat ggccatcata cgttatatag    480

ctgacaagca caacatgttg ggtggttgtc caaaagagcg tgcagagatt tcaatgcttg    540

aaggagcggt tttggatatt agatacggtg tttcgagaat tgcatatagt aaagactttg    600
```

-continued

```
aaactctcaa agttgatttt cttagcaagc tacctgaaat gctgaaaatg ttcgaagatc    660
gtttatgtca taaaacatat ttaaatggtg atcatgtaac ccatcctgac ttcatgttgt    720
atgacgctct tgatgttgtt ttatacatgg acccaatgtg cctggatgcg ttcccaaaat    780
tagtttgttt taaaaaacgt attgaagcta tcccacaaat tgataagtac ttgaaatcca    840
gcaagtatat agcatggcct ttgcagggct ggcaagccac gtttggtggt ggcgaccatc    900
ctccaaaatc ggatctggaa gttctgttcc aggggcccct gggatccccg gaattcccgg    960
gtcgactcga gcggccgcat cgtgactgac tgacgatctg cctcgcgcgt ttcggtgatg   1020
acggtgaaaa cctctgacac atgcagctcc cggagacggt cacagcttgt ctgtaagcgg   1080
atgccgggag cagacaagcc cgtcagggcg cgtcagcggg tgttggcggg tgtcggggcg   1140
cagccatgac ccagtcacgt agcgatagcg gagtgtataa ttcttgaaga cgaaagggcc   1200
tcgtgatacg cctattttta taggttaatg tcatgataat aatggtttct tagacgtcag   1260
gtggcacttt tcggggaaat gtgcgcggaa cccctatttg tttatttttc taaatacatt   1320
caaatatgta tccgctcatg agacaataac cctgataaat gcttcaataa tattgaaaaa   1380
ggaagagtat gagtattcaa catttccgtg tcgcccttat tccctttttt gcggcatttt   1440
gccttcctgt ttttgctcac ccagaaacgc tggtgaaagt aaaagatgct gaagatcagt   1500
tgggtgcacg agtgggttac atcgaactgg atctcaacag cggtaagatc cttgagagtt   1560
ttcgccccga agaacgtttt ccaatgatga gcacttttaa agttctgcta tgtggcgcgg   1620
tattatcccg tgttgacgcc gggcaagagc aactcggtcg ccgcatacac tattctcaga   1680
atgacttggt tgagtactca ccagtcacag aaaagcatct tacggatggc atgacagtaa   1740
gagaattatg cagtgctgcc ataaccatga gtgataacac tgcggccaac ttacttctga   1800
caacgatcgg aggaccgaag gagctaaccg cttttttgca caacatgggg gatcatgtaa   1860
ctcgccttga tcgttgggaa ccggagctga atgaagccat accaaacgac gagcgtgaca   1920
ccacgatgcc tgcagcaatg gcaacaacgt tgcgcaaact attaactggc gaactactta   1980
ctctagcttc ccggcaacaa ttaatagact ggatggaggc ggataaagtt gcaggaccac   2040
ttctgcgctc ggcccttccg gctggctggt ttattgctga taaatctgga gccggtgagc   2100
gtgggtctcg cggtatcatt gcagcactgg ggccagatgg taagccctcc cgtatcgtag   2160
ttatctacac gacggggagt caggcaacta tggatgaacg aaatagacag atcgctgaga   2220
taggtgcctc actgattaag cattggtaac tgtcagacca agtttactca tatatacttt   2280
agattgattt aaaacttcat ttttaattta aaaggatcta ggtgaagatc ctttttgata   2340
atctcatgac caaaatccct taacgtgagt tttcgttcca ctgagcgtca gaccccgtag   2400
aaaagatcaa aggatcttct tgagatcctt tttttctgcg cgtaatctgc tgcttgcaaa   2460
caaaaaaacc accgctacca gcggtggttt gtttgccgga tcaagagcta ccaactcttt   2520
ttccgaaggt aactggcttc agcagagcgc agataccaaa tactgtcctt ctagtgtagc   2580
cgtagttagg ccaccacttc aagaactctg tagcaccgcc tacatacctc gctctgctaa   2640
tcctgttacc agtggctgct gccagtggcg ataagtcgtg tcttaccggg ttggactcaa   2700
gacgatagtt accggataag gcgcagcggt cgggctgaac ggggggttcg tgcacacagc   2760
ccagcttgga gcgaacgacc tacaccgaac tgagatacct acagcgtgag ctatgagaaa   2820
gcgccacgct tcccgaaggg agaaaggcgg acaggtatcc ggtaagcggc agggtcggaa   2880
caggagagcg cacgagggag cttccagggg gaaacgcctg gtatctttat agtcctgtcg   2940
```

```
ggtttcgcca cctctgactt gagcgtcgat ttttgtgatg ctcgtcaggg gggcggagcc   3000

tatggaaaaa cgccagcaac gcggcctttt tacggttcct ggccttttgc tggccttttg   3060

ctcacatgtt ctttcctgcg ttatcccctg attctgtgga taaccgtatt accgcctttg   3120

agtgagctga taccgctcgc cgcagccgaa cgaccgagcg cagcgagtca gtgagcgagg   3180

aagcggaaga gcgcctgatg cggtattttc tccttacgca tctgtgcggt atttcacacc   3240

gcataaattc cgacaccatc gaatggtgca aaacctttcg cggtatggca tgatagcgcc   3300

cggaagagag tcaattcagg gtggtgaatg tgaaaccagt aacgttatac gatgtcgcag   3360

agtatgccgg tgtctcttat cagaccgttt cccgcgtggt gaaccaggcc agccacgttt   3420

ctgcgaaaac gcgggaaaaa gtggaagcgg cgatggcgga gctgaattac attcccaacc   3480

gcgtggcaca acaactggcg ggcaaacagt cgttgctgat tggcgttgcc acctccagtc   3540

tggccctgca cgcgccgtcg caaattgtcg cggcgattaa atctcgcgcc gatcaactgg   3600

gtgccagcgt ggtggtgtcg atggtagaac gaagcggcgt cgaagcctgt aaagcggcgg   3660

tgcacaatct tctcgcgcaa cgcgtcagtg ggctgatcat taactatccg ctggatgacc   3720

aggatgccat tgctgtggaa gctgcctgca ctaatgttcc ggcgttattt cttgatgtct   3780

ctgaccagac acccatcaac agtattattt tctcccatga agacggtacg cgactgggcg   3840

tggagcatct ggtcgcattg ggtcaccagc aaatcgcgct gttagcgggc ccattaagtt   3900

ctgtctcggc gcgtctgcgt ctggctggct ggcataaata tctcactcgc aatcaaattc   3960

agccgatagc ggaacgggaa ggcgactgga gtgccatgtc cggttttcaa caaaccatgc   4020

aaatgctgaa tgagggcatc gttcccactg cgatgctggt tgccaacgat cagatggcgc   4080

tgggcgcaat gcgcgccatt accgagtccg ggctgcgcgt tggtgcggat atctcggtag   4140

tgggatacga cgataccgaa gacagctcat gttatatccc gccgtcaacc accatcaaac   4200

aggattttcg cctgctgggg caaaccagcg tggaccgctt gctgcaactc tctcagggcc   4260

aggcggtgaa gggcaatcag ctgttgcccg tctcactggt gaaaagaaaa accaccctgg   4320

cgcccaatac gcaaaccgcc tctccccgcg cgttggccga ttcattaatg cagctggcac   4380

gacaggtttc ccgactggaa agcgggcagt gagcgcaacg caattaatgt gagttagctc   4440

actcattagg caccccaggc tttacacttt atgcttccgg ctcgtatgtt gtgtggaatt   4500

gtgagcggat aacaatttca cacaggaaac agctatgacc atgattacgg attcactggc   4560

cgtcgtttta caacgtcgtg actgggaaaa ccctggcgtt acccaactta atcgccttgc   4620

agcacatccc cctttcgcca gctggcgtaa tagcgaagag gcccgcaccg atcgcccttc   4680

ccaacagttg cgcagcctga atggcgaatg gcgctttgcc tggtttccgg caccagaagc   4740

ggtgccggaa agctggctgg agtgcgatct tcctgaggcc gatactgtcg tcgtcccctc   4800

aaactggcag atgcacggtt acgatgcgcc catctacacc aacgtaacct atcccattac   4860

ggtcaatccg ccgtttgttc ccacggagaa tccgacgggt tgttactcgc tcacatttaa   4920

tgttgatgaa agctggctac aggaaggcca gacgcgaatt atttttgatg gcgttggaat   4980

t                                                                   4981
```

```
<210> SEQ ID NO 16
<211> LENGTH: 7321
<212> TYPE: DNA
<213> ORGANISM: Artificial Sequence
<220> FEATURE:
<223> OTHER INFORMATION: pGEX-6P-1_NoGST_Brk-CBM

<400> SEQUENCE: 16
```

-continued

```
acgttatcga ctgcacggtg caccaatgct tctggcgtca ggcagccatc ggaagctgtg     60
gtatggctgt gcaggtcgta aatcactgca taattcgtgt cgctcaaggc gcactcccgt    120
tctggataat gttttttgcg ccgacatcat aacggttctg gcaaatattc tgaaatgagc    180
tgttgacaat taatcatcgg ctcgtataat gtgtggaatt gtgagcggat aacaatttca    240
cacaggaaac agtattctcc cctatactag gttattggaa aattaagggc cttgtgcaac    300
ccactcgact tcttttggaa tatcttgaag aaaaatatga agagcatttg tatgagcgcg    360
atgaaggtga taaatggcga aacaaaaagt ttgaattggg tttggagttt cccaatcttc    420
cttattatat tgatggtgat gttaaattaa cacagtctat ggccatcata cgttatatag    480
ctgacaagca caacatgttg ggtggttgtc caaaagagcg tgcagagatt tcaatgcttg    540
aaggagcggt tttggatatt agatacggtg tttcgagaat tgcatatagt aaagactttg    600
aaactctcaa agttgatttt cttagcaagc tacctgaaat gctgaaaatg ttcgaagatc    660
gtttatgtca taaaacatat ttaaatggtg atcatgtaac ccatcctgac ttcatgttgt    720
atgacgctct tgatgttgtt ttatacatgg acccaatgtg cctggatgcg ttcccaaaat    780
tagtttgttt taaaaaacgt attgaagcta tcccacaaat tgataagtac ttgaaatcca    840
gcaagtatat agcatggcct ttgcagggct ggcaagccac gtttggtggt ggcgaccatc    900
ctccaaaatc ggatctggaa gttctgttcc aggggcccct gggatccatg tatctggatc    960
gctttcgcca gtgcccgagc agcctgcaga ttccgcgcag cgcgtggcgc ctgcatgcgc   1020
tggcggcggc gctggcgctg gcgggcatgg cgcgcctggc gccggcggcg gcgcaggcgc   1080
cgcagccgcc ggtggcgggc gcgccgcatg cgcaggatgc gggccaccat caccatcacc   1140
atgttcagct ggttgaaagc ggtggtgcac tggttcagcc tggtggtagc ctgcgtctga   1200
gctgtgcagc aagcggtttt ccggttaatc gttatagcat gcgttggtat cgtcaggcac   1260
cgggtaaaga acgtgaatgg gttgcaggta tgagcagtgc cggtgatcgt agcagctacg   1320
aagatagcgt taaaggtcgt tttaccatca gccgtgatga tgcacgtaat accgtttatc   1380
tgcaaatgaa tagcctgaaa ccggaagata ccgcagtgta ttattgcaac gttaacgtgg   1440
gctttgaata ttggggtcag ggcacccagg ttaccgttag cagcaaactc gagcggccgc   1500
atcgtgacgc gtcgtctggt cctgccggct gccaagtcct ttggggcgtg aatcagtgga   1560
acacaggttt cacggcgaat gttaccgtca agaatacgtc ctccgctcct gttgacggct   1620
ggaccttgac cttcagtttc ccatcaggac aacaagtcac tcaagcctgg tcatctaccg   1680
tgacccagag tggatctgcg gtcacagtac gtaacgctcc gtggaacggt tcgattcccg   1740
cgggcgggac tgctcagttc gggtttaacg gaagccacac tggcactaat gctgcaccaa   1800
ctgccttctc acttaacggc acgccgtgca ccgtaggcga acagaaactg attagcgaag   1860
aagatctgga aaacctgtac ttccagggtg cgggcattag cctgagcgtg gcgagcggcg   1920
cggcgtggca tggcgcgacc caggtgctgc agagcgcgac cctgggcaaa ggcggcacct   1980
gggtggtgaa cgcggatagc cgcgtgcagg atatgagcat gcgcggcggc cgcgtggaat   2040
ttcaggcgcc ggcgccggaa gcgagctata aaccctgac cctgcagacc ctggatggca    2100
acggcgtgtt tgtgctgaac accaacgtgg cggcgggcca gaacgatcag ctgcgcgtga   2160
ccggccgcgc ggatggccag catcgcgtgc tggtgcgcaa cgcgggcggc gaagcggata   2220
gccgcggcgc gcgcctgggc ctggtgcata cccagggcca gggcaacgcg acctttcgcc   2280
tggcgaacgt gggcaaagcg gtggatctgg gcacctggcg ctatagcctg gcggaagatc   2340
```

-continued

```
cgaaaaccca tgtgtggagc ctgcagcgcg cgggccaggc gctgagcggc gcggcgaacg   2400
cggcggtgaa cgcggcggat ctgagcagca ttgcgctggc ggaaagcaac gcgctggata   2460
aacgcctggg cgaactgcgc ctgcgcgcgg atgcgggcgg cccgtgggcg cgcaccttta   2520
gcgaacgcca gcagattagc aaccgccatg cgcgcgcgta tgatcagacc gtgagcggcc   2580
tggaaattgg cctggatcgc ggctggagcg cgagcggcgg ccgctggtat gcgggcggcc   2640
tgctgggcta tacctatgcg gatcgcacct atccgggcga tggcggcggc aaagtgaaag   2700
gcctgcatgt gggcggctat gcggcgtatg tgggcgatgg cggctattat ctggataccg   2760
tgctgcgcct gggccgctat gatcagcagt ataacattgc gggcaccgat ggcggccgcg   2820
tgaccgcgga ttatcgcacc agcggcgcgg cgtggagcct ggaaggcggc cgccgctttg   2880
aactgccgaa cgattggttt gcggaaccgc aggcggaagt gatgctgtgg cgcaccagcg   2940
gcaaacgcta tcgcgcgagc aacggcctgc gcgtgaaagt ggatgcgaac accgcgaccc   3000
tgggccgcct gggcctgcgc tttggccgcc gcattgcgct ggcgggcggc aacattgtgc   3060
agccgtatgc gcgcctgggc tggacccagg aatttaaaag caccggcgat gtgcgcacca   3120
acggcattgg ccatgcgggc gcgggccgcc atggccgcgt ggaactgggc gcgggcgtgg   3180
atgcggcgct gggcaaaggc cataacctgt atgcgagcta tgaatatgcg gcgggcgatc   3240
gcattaacat tccgtggagc tttcatgcgg gctatcgcta tagcttttga gaattcccgg   3300
gtcgactcga gcggccgcat cgtgactgac tgacgatctg cctcgcgcgt ttcggtgatg   3360
acggtgaaaa cctctgacac atgcagctcc cggagacggt cacagcttgt ctgtaagcgg   3420
atgccgggag cagacaagcc cgtcagggcg cgtcagcggg tgttggcggg tgtcggggcg   3480
cagccatgac ccagtcacgt agcgatagcg gagtgtataa ttcttgaaga cgaaagggcc   3540
tcgtgatacg cctattttta taggttaatg tcatgataat aatggtttct tagacgtcag   3600
gtggcacttt tcggggaaat gtgcgcggaa cccctatttg tttatttttc taaatacatt   3660
caaatatgta tccgctcatg agacaataac cctgataaat gcttcaataa tattgaaaaa   3720
ggaagagtat gagtattcaa catttccgtg tcgcccttat tccctttttt gcggcatttt   3780
gccttcctgt ttttgctcac ccagaaacgc tggtgaaagt aaaagatgct gaagatcagt   3840
tgggtgcacg agtgggttac atcgaactgg atctcaacag cggtaagatc cttgagagtt   3900
ttcgccccga agaacgtttt ccaatgatga gcacttttaa agttctgcta tgtggcgcgg   3960
tattatcccg tgttgacgcc gggcaagagc aactcggtcg ccgcatacac tattctcaga   4020
atgacttggt tgagtactca ccagtcacag aaaagcatct tacggatggc atgacagtaa   4080
gagaattatg cagtgctgcc ataaccatga gtgataacac tgcggccaac ttacttctga   4140
caacgatcgg aggaccgaag gagctaaccg cttttttgca caacatgggg gatcatgtaa   4200
ctcgccttga tcgttgggaa ccggagctga atgaagccat accaaacgac gagcgtgaca   4260
ccacgatgcc tgcagcaatg gcaacaacgt tgcgcaaact attaactggc gaactactta   4320
ctctagcttc ccggcaacaa ttaatagact ggatggaggc ggataaagtt gcaggaccac   4380
ttctgcgctc ggcccttccg gctggctggt ttattgctga taaatctgga gccggtgagc   4440
gtgggtctcg cggtatcatt gcagcactgg ggccagatgg taagccctcc cgtatcgtag   4500
ttatctacac gacggggagt caggcaacta tggatgaacg aaatagacag atcgctgaga   4560
taggtgcctc actgattaag cattggtaac tgtcagacca agtttactca tatatacttt   4620
agattgattt aaaacttcat ttttaattta aaaggatcta ggtgaagatc ctttttgata   4680
atctcatgac caaaatccct taacgtgagt tttcgttcca ctgagcgtca gaccccgtag   4740
```

-continued

```
aaaagatcaa aggatcttct tgagatcctt tttttctgcg cgtaatctgc tgcttgcaaa   4800
caaaaaaacc accgctacca gcggtggttt gtttgccgga tcaagagcta ccaactcttt   4860
ttccgaaggt aactggcttc agcagagcgc agataccaaa tactgtcctt ctagtgtagc   4920
cgtagttagg ccaccacttc aagaactctg tagcaccgcc tacatacctc gctctgctaa   4980
tcctgttacc agtggctgct gccagtggcg ataagtcgtg tcttaccggg ttggactcaa   5040
gacgatagtt accggataag gcgcagcggt cgggctgaac ggggggttcg tgcacacagc   5100
ccagcttgga gcgaacgacc tacaccgaac tgagatacct acagcgtgag ctatgagaaa   5160
gcgccacgct tcccgaaggg agaaaggcgg acaggtatcc ggtaagcggc agggtcggaa   5220
caggagagcg cacgagggag cttccagggg gaaacgcctg gtatctttat agtcctgtcg   5280
ggtttcgcca cctctgactt gagcgtcgat ttttgtgatg ctcgtcaggg gggcggagcc   5340
tatggaaaaa cgccagcaac gcggcctttt tacggttcct ggccttttgc tggccttttg   5400
ctcacatgtt ctttcctgcg ttatcccctg attctgtgga taaccgtatt accgcctttg   5460
agtgagctga taccgctcgc cgcagccgaa cgaccgagcg cagcgagtca gtgagcgagg   5520
aagcggaaga gcgcctgatg cggtattttc tccttacgca tctgtgcggt atttcacacc   5580
gcataaattc cgacaccatc gaatggtgca aaacctttcg cggtatggca tgatagcgcc   5640
cggaagagag tcaattcagg gtggtgaatg tgaaaccagt aacgttatac gatgtcgcag   5700
agtatgccgg tgtctcttat cagaccgttt cccgcgtggt gaaccaggcc agccacgttt   5760
ctgcgaaaac gcgggaaaaa gtggaagcgg cgatggcgga gctgaattac attcccaacc   5820
gcgtggcaca acaactggcg ggcaaacagt cgttgctgat tggcgttgcc acctccagtc   5880
tggccctgca cgcgccgtcg caaattgtcg cggcgattaa atctcgcgcc gatcaactgg   5940
gtgccagcgt ggtggtgtcg atggtagaac gaagcggcgt cgaagcctgt aaagcggcgg   6000
tgcacaatct tctcgcgcaa cgcgtcagtg ggctgatcat taactatccg ctggatgacc   6060
aggatgccat tgctgtggaa gctgcctgca ctaatgttcc ggcgttattt cttgatgtct   6120
ctgaccagac acccatcaac agtattattt tctcccatga agacggtacg cgactgggcg   6180
tggagcatct ggtcgcattg ggtcaccagc aaatcgcgct gttagcgggc ccattaagtt   6240
ctgtctcggc gcgtctgcgt ctggctggct ggcataaata tctcactcgc aatcaaattc   6300
agccgatagc ggaacgggaa ggcgactgga gtgccatgtc cggttttcaa caaaccatgc   6360
aaatgctgaa tgagggcatc gttcccactg cgatgctggt tgccaacgat cagatggcgc   6420
tgggcgcaat gcgcgccatt accgagtccg ggctgcgcgt tggtgcggat atctcggtag   6480
tgggatacga cgataccgaa gacagctcat gttatatccc gccgtcaacc accatcaaac   6540
aggattttcg cctgctgggg caaaccagcg tggaccgctt gctgcaactc tctcagggcc   6600
aggcggtgaa gggcaatcag ctgttgcccg tctcactggt gaaaagaaaa accaccctgg   6660
cgcccaatac gcaaaccgcc tctccccgcg cgttggccga ttcattaatg cagctggcac   6720
gacaggtttc ccgactggaa agcgggcagt gagcgcaacg caattaatgt gagttagctc   6780
actcattagg caccccaggc tttacacttt atgcttccgg ctcgtatgtt gtgtggaatt   6840
gtgagcggat aacaatttca cacaggaaac agctatgacc atgattacgg attcactggc   6900
cgtcgtttta caacgtcgtg actgggaaaa ccctggcgtt acccaactta atcgccttgc   6960
agcacatccc cctttcgcca gctggcgtaa tagcgaagag gcccgcaccg atcgcccttc   7020
ccaacagttg cgcagcctga atggcgaatg gcgctttgcc tggtttccgg caccagaagc   7080
```

ggtgccggaa agctggctgg agtgcgatct tcctgaggcc gatactgtcg tcgtcccctc 7140
aaactggcag atgcacggtt acgatgcgcc catctacacc aacgtaacct atcccattac 7200
ggtcaatccg ccgtttgttc ccacggagaa tccgacgggt tgttactcgc tcacatttaa 7260
tgttgatgaa agctggctac aggaaggcca gacgcgaatt atttttgatg gcgttggaat 7320
t 7321

<210> SEQ ID NO 17
<211> LENGTH: 6283
<212> TYPE: DNA
<213> ORGANISM: Artificial Sequence
<220> FEATURE:
<223> OTHER INFORMATION: pGEX-6P-1_NoGST_InaK-CBM

<400> SEQUENCE: 17
acgttatcga ctgcacggtg caccaatgct tctggcgtca ggcagccatc ggaagctgtg 60
gtatggctgt gcaggtcgta aatcactgca taattcgtgt cgctcaaggc gcactcccgt 120
tctggataat gttttttgcg ccgacatcat aacggttctg gcaaatattc tgaaatgagc 180
tgttgacaat taatcatcgg ctcgtataat gtgtggaatt gtgagcggat aacaatttca 240
cacaggaaac agtattctcc cctatactag gttattggaa aattaagggc cttgtgcaac 300
ccactcgact tcttttggaa tatcttgaag aaaaatatga agagcatttg tatgagcgcg 360
atgaaggtga taaatggcga aacaaaaagt ttgaattggg tttggagttt cccaatcttc 420
cttattatat tgatggtgat gttaaattaa cacagtctat ggccatcata cgttatatag 480
ctgacaagca caacatgttg ggtggttgtc caaaagagcg tgcagagatt tcaatgcttg 540
aaggagcggt tttggatatt agatacggtg tttcgagaat tgcatatagt aaagactttg 600
aaactctcaa agttgatttt cttagcaagc tacctgaaat gctgaaaatg ttcgaagatc 660
gtttatgtca taaaacatat ttaaatggtg atcatgtaac ccatcctgac ttcatgttgt 720
atgacgctct tgatgttgtt ttatacatgg acccaatgtg cctggatgcg ttcccaaaat 780
tagtttgttt taaaaaacgt attgaagcta tcccacaaat tgataagtac ttgaaatcca 840
gcaagtatat agcatggcct ttgcagggct ggcaagccac gtttggtggt ggcgaccatc 900
ctccaaaatc ggatctggaa gttctgttcc aggggcccct gggatccatg gtcttagaca 960
aggcgctagt tctacgtacc tgcgctaata atatggccga tcactgcggc ttgatttggc 1020
ctgcctcagg gaccgtcgag tcaaggtatt ggcaatctac acgtcgtcac gagaacggac 1080
tggtaggtct tctttgggga gcaggaactt ctgctttctt gtcagtccat gcagacgccc 1140
gctggatcgt gtgcgaagtg gctgttgccg atattatctc cctagaggag cccggaatgg 1200
ttaaatttcc tcgggccgaa gtggtgcatg tgggcgatcg aatcagcgct tctcatttta 1260
tttcggcgcg gcaggcagat cccgcgagta cgagtacttc aacgtcgaca agtactctta 1320
ctcccatgcc cacggcaatc cccaccccta tgccagcggt ggcgtcagtg acgttaccgg 1380
tggctgagca agcgcggcat gaggtgtttg atgtagctag tgtgagcgcc gcggctgctc 1440
ccgtgaacac tttacctgtc acgacacccc aaaacctcca gacggaaaac ctgtacttcc 1500
agggtgcgtc gtctggtcct gccggctgcc aagtcctttg ggcgtgaat cagtggaaca 1560 caggtttcac ggcgaatgtt accgtcaaga atacgtcctc cgctcctgtt gacggctgga 1620
ccttgacctt cagtttccca tcaggacaac aagtcactca agcctggtca tctaccgtga 1680
cccagagtgg atctgcggtc acagtacgta acgctccgtg gaacggttcg attcccgcgg 1740
gcgggactgc tcagttcggg tttaacggaa gccacactgg cactaatgct gcaccaactg 1800
ccttctcact taacggcacg ccgtgcaccg taggccacca tcaccatcac catgttcagc 1860
tggttgaaag cggtggtgca ctggttcagc ctggtggtag cctgcgtctg agctgtgcag 1920
caagcggttt tccggttaat cgttatagca tgcgttggta tcgtcaggca ccgggtaaag 1980
aacgtgaatg ggttgcaggt atgagcagtg ccggtgatcg tagcagctac gaagatagcg 2040
ttaaaggtcg ttttaccatc agccgtgatg atgcacgtaa taccgtttat ctgcaaatga 2100
atagcctgaa accggaagat accgcagtgt attattgcaa cgttaacgtg ggctttgaat 2160
attggggtca gggcacccag gttaccgtta gcagcaaact cgagcggccg catcgtgacg 2220
aacagaaact gattagcgaa gaagatctgt gagaattccc gggtcgactc gagcggccgc 2280
atcgtgactg actgacgatc tgcctcgcgc gtttcggtga tgacggtgaa aacctctgac 2340
acatgcagct cccggagacg gtcacagctt gtctgtaagc ggatgccggg agcagacaag 2400
cccgtcaggg cgcgtcagcg ggtgttggcg ggtgtcgggg cgcagccatg acccagtcac 2460
gtagcgatag cggagtgtat aattcttgaa gacgaaaggg cctcgtgata cgcctatttt 2520
tataggttaa tgtcatgata ataatggttt cttagacgtc aggtggcact tttcggggaa 2580
atgtgcgcgg aacccctatt tgtttatttt tctaaataca ttcaaatatg tatccgctca 2640
tgagacaata accctgataa atgcttcaat aatattgaaa aaggaagagt atgagtattc 2700
aacatttccg tgtcgccctt attccctttt ttgcggcatt ttgccttcct gtttttgctc 2760
acccagaaac gctggtgaaa gtaaaagatg ctgaagatca gttgggtgca cgagtgggtt 2820
acatcgaact ggatctcaac agcggtaaga tccttgagag ttttcgcccc gaagaacgtt 2880
ttccaatgat gagcactttt aaagttctgc tatgtggcgc ggtattatcc cgtgttgacg 2940
ccgggcaaga gcaactcggt cgccgcatac actattctca gaatgacttg gttgagtact 3000
caccagtcac agaaaagcat cttacggatg gcatgacagt aagagaatta tgcagtgctg 3060
ccataaccat gagtgataac actgcggcca acttacttct gacaacgatc ggaggaccga 3120
aggagctaac cgcttttttg cacaacatgg gggatcatgt aactcgcctt gatcgttggg 3180
aaccggagct gaatgaagcc ataccaaacg acgagcgtga caccacgatg cctgcagcaa 3240
tggcaacaac gttgcgcaaa ctattaactg gcgaactact tactctagct tcccggcaac 3300
aattaataga ctggatggag gcggataaag ttgcaggacc acttctgcgc tcggcccttc 3360
cggctggctg gtttattgct gataaatctg gagccggtga gcgtgggtct cgcggtatca 3420
ttgcagcact ggggccagat ggtaagccct cccgtatcgt agttatctac acgacgggga 3480
gtcaggcaac tatggatgaa cgaaatagac agatcgctga gataggtgcc tcactgatta 3540
agcattggta actgtcagac caagtttact catatatact ttagattgat ttaaaacttc 3600
atttttaatt taaaaggatc taggtgaaga tcctttttga taatctcatg accaaaatcc 3660
cttaacgtga gttttcgttc cactgagcgt cagaccccgt agaaaagatc aaaggatctt 3720
cttgagatcc tttttttctg cgcgtaatct gctgcttgca aacaaaaaaa ccaccgctac 3780
cagcggtggt ttgtttgccg gatcaagagc taccaactct ttttccgaag gtaactggct 3840
tcagcagagc gcagatacca aatactgtcc ttctagtgta gccgtagtta ggccaccact 3900
tcaagaactc tgtagcaccg cctacatacc tcgctctgct aatcctgtta ccagtggctg 3960
ctgccagtgg cgataagtcg tgtcttaccg ggttggactc aagacgatag ttaccggata 4020
aggcgcagcg gtcgggctga acggggggtt cgtgcacaca gcccagcttg gagcgaacga 4080
cctacaccga actgagatac ctacagcgtg agctatgaga aagcgccacg cttcccgaag 4140

-continued

```
ggagaaaggc ggacaggtat ccggtaagcg gcagggtcgg aacaggagag cgcacgaggg   4200
agcttccagg gggaaacgcc tggtatcttt atagtcctgt cgggtttcgc cacctctgac   4260
ttgagcgtcg atttttgtga tgctcgtcag gggggcggag cctatggaaa aacgccagca   4320
acgcggcctt tttacggttc ctggcctttt gctggccttt tgctcacatg ttctttcctg   4380
cgttatcccc tgattctgtg gataaccgta ttaccgcctt tgagtgagct gataccgctc   4440
gccgcagccg aacgaccgag cgcagcgagt cagtgagcga ggaagcggaa gagcgcctga   4500
tgcggtattt tctccttacg catctgtgcg gtatttcaca ccgcataaat tccgacacca   4560
tcgaatggtg caaaaccttt cgcggtatgg catgatagcg cccggaagag agtcaattca   4620
gggtggtgaa tgtgaaacca gtaacgttat acgatgtcgc agagtatgcc ggtgtctctt   4680
atcagaccgt ttcccgcgtg gtgaaccagg ccagccacgt ttctgcgaaa acgcgggaaa   4740
aagtggaagc ggcgatggcg gagctgaatt acattcccaa ccgcgtggca caacaactgg   4800
cgggcaaaca gtcgttgctg attggcgttg ccacctccag tctggccctg cacgcgccgt   4860
cgcaaattgt cgcggcgatt aaatctcgcg ccgatcaact gggtgccagc gtggtggtgt   4920
cgatggtaga acgaagcggc gtcgaagcct gtaaagcggc ggtgcacaat cttctcgcgc   4980
aacgcgtcag tgggctgatc attaactatc cgctggatga ccaggatgcc attgctgtgg   5040
aagctgcctg cactaatgtt ccggcgttat ttcttgatgt ctctgaccag acacccatca   5100
acagtattat tttctcccat gaagacggta cgcgactggg cgtggagcat ctggtcgcat   5160
tgggtcacca gcaaatcgcg ctgttagcgg gcccattaag ttctgtctcg gcgcgtctgc   5220
gtctggctgg ctggcataaa tatctcactc gcaatcaaat tcagccgata gcggaacggg   5280
aaggcgactg gagtgccatg tccggttttc aacaaaccat gcaaatgctg aatgagggca   5340
tcgttcccac tgcgatgctg gttgccaacg atcagatggc gctgggcgca atgcgcgcca   5400
ttaccgagtc cgggctgcgc gttggtgcgg atatctcggt agtgggatac gacgataccg   5460
aagacagctc atgttatatc ccgccgtcaa ccaccatcaa acaggatttt cgcctgctgg   5520
ggcaaaccag cgtggaccgc ttgctgcaac tctctcaggg ccaggcggtg aagggcaatc   5580
agctgttgcc cgtctcactg gtgaaaagaa aaaccaccct ggcgcccaat acgcaaaccg   5640
cctctccccg cgcgttggcc gattcattaa tgcagctggc acgacaggtt tcccgactgg   5700
aaagcgggca gtgagcgcaa cgcaattaat gtgagttagc tcactcatta ggcaccccag   5760
gctttacact ttatgcttcc ggctcgtatg ttgtgtggaa ttgtgagcgg ataacaattt   5820
cacacaggaa acagctatga ccatgattac ggattcactg gccgtcgttt tacaacgtcg   5880
tgactgggaa aaccctggcg ttacccaact taatcgcctt gcagcacatc ccccttttcgc   5940
cagctggcgt aatagcgaag aggcccgcac cgatcgccct tcccaacagt tgcgcagcct   6000
gaatggcgaa tggcgctttg cctggtttcc ggcaccagaa gcggtgccgg aaagctggct   6060
ggagtgcgat cttcctgagg ccgatactgt cgtcgtcccc tcaaactggc agatgcacgg   6120
ttacgatgcg cccatctaca ccaacgtaac ctatcccatt acggtcaatc cgccgtttgt   6180
tcccacggag aatccgacgg gttgttactc gctcacattt aatgttgatg aaagctggct   6240
acaggaaggc cagacgcgaa ttatttttga tggcgttgga att                     6283
```

<210> SEQ ID NO 18
<211> LENGTH: 21
<212> TYPE: DNA
<213> ORGANISM: Artificial Sequence
<220> FEATURE:
<223> OTHER INFORMATION: synthetic primer F2 minCKO

<400> SEQUENCE: 18
aacaacaata atgcgtgcca t 21

<210> SEQ ID NO 19
<211> LENGTH: 20
<212> TYPE: DNA
<213> ORGANISM: Artificial Sequence
<220> FEATURE:
<223> OTHER INFORMATION: synthetic primer R2 minCKO

<400> SEQUENCE: 19
gcgctggcga tgattaatag 20

<210> SEQ ID NO 20
<211> LENGTH: 22
<212> TYPE: DNA
<213> ORGANISM: Artificial Sequence
<220> FEATURE:
<223> OTHER INFORMATION: synthetic primer F9 minCKO

<400> SEQUENCE: 20
agtaacaaca ataatgcgtg cc 22

<210> SEQ ID NO 21
<211> LENGTH: 16
<212> TYPE: DNA
<213> ORGANISM: Artificial Sequence
<220> FEATURE:
<223> OTHER INFORMATION: synthetic primer R9 minCKO

<400> SEQUENCE: 21
cgcgctggcg atgatt 16

<210> SEQ ID NO 22
<211> LENGTH: 21
<212> TYPE: DNA
<213> ORGANISM: Artificial Sequence
<220> FEATURE:
<223> OTHER INFORMATION: synthetic primer F7 minDKO

<400> SEQUENCE: 22
ttccgcgaga gaaagaaatc g 21

<210> SEQ ID NO 23
<211> LENGTH: 23
<212> TYPE: DNA
<213> ORGANISM: Artificial Sequence
<220> FEATURE:
<223> OTHER INFORMATION: synthetic primer R7 minDKO

<400> SEQUENCE: 23
gaccgttcaa ccgttaaatt gat 23

<210> SEQ ID NO 24
<211> LENGTH: 20
<212> TYPE: DNA
<213> ORGANISM: Artificial Sequence
<220> FEATURE:
<223> OTHER INFORMATION: synthetic primer F10 minDKO

<400> SEQUENCE: 24
ctgtgttttt cttccgcgag 20

<210> SEQ ID NO 25

-continued

<211> LENGTH: 25
<212> TYPE: DNA
<213> ORGANISM: Artificial Sequence
<220> FEATURE:
<223> OTHER INFORMATION: synthetic primer R10 minDKO

<400> SEQUENCE: 25
tcaaccgtta aattgatccc ttttt 25

<210> SEQ ID NO 26
<211> LENGTH: 20
<212> TYPE: DNA
<213> ORGANISM: Artificial Sequence
<220> FEATURE:
<223> OTHER INFORMATION: synthetic primer F6 minCDKO

<400> SEQUENCE: 26
tccgcgagag aaagaaatcg 20

<210> SEQ ID NO 27
<211> LENGTH: 17
<212> TYPE: DNA
<213> ORGANISM: Artificial Sequence
<220> FEATURE:
<223> OTHER INFORMATION: synthetic primer R6 minCDKO

<400> SEQUENCE: 27
cgcgctggcg atgatta 17

<210> SEQ ID NO 28
<211> LENGTH: 20
<212> TYPE: DNA
<213> ORGANISM: Artificial Sequence
<220> FEATURE:
<223> OTHER INFORMATION: synthetic primer F9 minCDKO

<400> SEQUENCE: 28
ctgtgttttt cttccgcgag 20

<210> SEQ ID NO 29
<211> LENGTH: 16
<212> TYPE: DNA
<213> ORGANISM: Artificial Sequence
<220> FEATURE:
<223> OTHER INFORMATION: synthetic primer R9 minCDKO

<400> SEQUENCE: 29
cgcgctggcg atgatt 16

<210> SEQ ID NO 30
<211> LENGTH: 20
<212> TYPE: DNA
<213> ORGANISM: Artificial Sequence
<220> FEATURE:
<223> OTHER INFORMATION: synthetic primer 3'minCKO_1

<400> SEQUENCE: 30
ggccggataa aacttgtgct 20

<210> SEQ ID NO 31
<211> LENGTH: 20
<212> TYPE: DNA
<213> ORGANISM: Artificial Sequence
<220> FEATURE:
<223> OTHER INFORMATION: synthetic primer 3'minCKO_2

<400> SEQUENCE: 31
agtcttcgga acatcatcgc 20

<210> SEQ ID NO 32
<211> LENGTH: 20
<212> TYPE: DNA
<213> ORGANISM: Artificial Sequence
<220> FEATURE:
<223> OTHER INFORMATION: synthetic primer 5'minCKO_1

<400> SEQUENCE: 32
ccctttgccc gaagtaacaa 20

<210> SEQ ID NO 33
<211> LENGTH: 20
<212> TYPE: DNA
<213> ORGANISM: Artificial Sequence
<220> FEATURE:
<223> OTHER INFORMATION: synthetic primer 5'minCKO_2

<400> SEQUENCE: 33
acggtgaaaa cctggcctat 20

<210> SEQ ID NO 34
<211> LENGTH: 23
<212> TYPE: DNA
<213> ORGANISM: Artificial Sequence
<220> FEATURE:
<223> OTHER INFORMATION: synthetic primer minC_check_4_1

<400> SEQUENCE: 34
tcaatttaac ggttgaacgg tca 23

<210> SEQ ID NO 35
<211> LENGTH: 20
<212> TYPE: DNA
<213> ORGANISM: Artificial Sequence
<220> FEATURE:
<223> OTHER INFORMATION: synthetic primer minC_check_4_2

<400> SEQUENCE: 35
atgtcaaaca cgccaatcga 20

<210> SEQ ID NO 36
<211> LENGTH: 23
<212> TYPE: DNA
<213> ORGANISM: Artificial Sequence
<220> FEATURE:
<223> OTHER INFORMATION: synthetic primer minD_check_2_1

<400> SEQUENCE: 36
ttatcctccg aacaagcgtt tga 23

<210> SEQ ID NO 37
<211> LENGTH: 23
<212> TYPE: DNA
<213> ORGANISM: Artificial Sequence
<220> FEATURE:
<223> OTHER INFORMATION: synthetic primer minD_check_2_2

<400> SEQUENCE: 37
atggcacgca ttattgttgt tac 23

COMPOSITIONS AND METHODS FOR THE ENCAPSULATION AND SCALABLE DELIVERY OF AGROCHEMICALS

CROSS-REFERENCE TO RELATED APPLICATIONS

This application is a National Stage Entry of International Application No. PCT/US2018/030329 filed on Apr. 30, 2018, which claims the benefit of priority to U.S. provisional application No. 62/570,368 filed on Oct. 10, 2017 and U.S. provisional application No. 62/491,608 filed on Apr. 28, 2017, each of which is hereby incorporated by reference in their entirety.

FIELD

The present disclosure is generally directed to platforms, compositions and methods for encapsulating agricultural compounds in achromosomal and/or anucleated cells. The present disclosure provides scalable delivery of agricultural compounds encapsulated in achromosomal and/or anucleated cells. Also, disclosed herein are methods for encapsulating and delivering agricultural compounds to a target in a scalable manner.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AGRO_002_00WO_SeqList_ST25.txt. The text file is ≈63.8 KB, was created on Apr. 27, 2018, and is being submitted electronically via EFS-Web.

BACKGROUND

With expected growth of world population to over 9 billion by 2050, human society will face the biggest challenges of being able to feed the people. The Food and Agriculture Organization of the United Nations (FAO) estimates that 80% of the necessary increases in food production keep pace with population growth are projected to come from increases in yields and the number of times per year crops can be grown on the same land. Only 20% of new food production is expected to come from expansion of farming land. Global efforts to increase future crop harvest and food production is required to meet future challenges. Pesticides play a significant role in agriculture and food production to prevent large crop losses. Pesticides can help producing food by controlling pest such as insects, rodents, weeds, bacteria, mold and fungus and by increasing yields and the number of times per year a crop can be grown on the same land.

However, there are a continuing concern about the negative effects of pesticides on human health and the surrounding environment. Pesticides are potentially toxic to humans and can have both acute and chronic health effects, depending on the quantity and ways in which a person is exposed. Some pesticides can remain for years in soil and water, which can make environment more contaminated and harmful. People who face the greatest health risks from exposure to pesticides are those who come into contact with them at work, in their home or garden.

Not only pesticides, but more generally, agrochemicals such as pesticides, herbicides, insecticides, fungicides, nematicides, have issues on reduced efficacy of the chemicals and losses of chemicals into the soil due to dripping off the plant while spraying or due to wash-out during rainfall, which may result in groundwater contamination, environmental damage, loss of biodiversity, and human and animal health consequences.

Thus, there is an unmet need to develop a new agrochemical delivery system to ensure the targeted delivery of agrochemicals. Also, there is a great need for an encapsulation and delivery platform for agrochemicals to sustain bioactivity of the agrochemicals and to hold on intended targets in a scalable, targeted, cost-effective manner.

SUMMARY OF THE DISCLOSURE

The present disclosure is directed to an anucleated cell-based platform for encapsulation and delivery of agricultural compounds and application of the platform to a desired locus such as a plant or a pest.

In some embodiments, an anucleated cell-based platform for the encapsulation and delivery of agricultural compounds is provided, which comprises: a) an intact anucleated cell, having within said cell at least one non-expressed agricultural compound. In embodiments, the anucleated cell-based platform further comprises: b) at least one agriculturally acceptable carrier. In embodiments, said intact anucleated cell is derived from a prokaryotic cell. In embodiments, said intact anucleated cell is a bacterially derived minicell. In embodiments, said intact anucleated cell is produced from a gram negative bacterial genus. In embodiments, said intact anucleated cell is produced from a bacterial genus selected from the group consisting of: *Escherichia, Salmonella, Shigella, Pseudomonas*, and *Agrobacterium*. In embodiments, said intact anucleated cell is produced from a bacterial species selected from the group consisting of: *Escherichia coli, Salmonella typhimurium, Shigella flexneri*, and *Pseudomonas aeruginosa*. In embodiments, said intact anucleated cell is produced from a P678-54 *E. coli* parental bacterial cell. In embodiments, said intact anucleated cell is produced from a gram positive bacterial genus. In embodiments, said intact anucleated cell is produced from a bacterial genus selected from the group consisting of: *Bacillus, Corynebacterium*, and *Lactobacillus*. In embodiments, said intact anucleated cell is produced from a bacterial species selected from the group consisting of: *Bacillus subtilis, Corynebacterium glutamicum*, and *Lactobacillus acidophilus*. In embodiments, said intact anucleated cell is a bacterially derived minicell that is produced from a parental bacterial cell deficient in WprA protease. In embodiments, said intact anucleated cell is a bacterially derived minicell that is produced from a protease deficient *B. subtilis* parental bacterial cell. In embodiments, said intact anucleated cell is a bacterially derived minicell that is produced from a protease deficient KO7 *B. subtilis* parental bacterial cell. In embodiments, said intact anucleated cell is a bacterially derived minicell that is produced from a protease deficient *B. subtilis* parental bacterial cell selected from the group consisting of: (1) CU403,DIVIVA; (2) CU403,DIVIVB,SPO-; (3) CU403,DIVIVB; and (4) CU403,DIVIVB1, wherein at least one protease encoding gene has been repressed, deleted, or silenced. In embodiments, said intact anucleated cell is a bacterially derived minicell that is produced from a protease deficient parental bacterial cell. In embodiments, said intact anucleated cell is a bacterially derived minicell that is produced from a parental bacterial cell deficient in Lon and OmpT proteases. In embodiments, said intact anucleated cell is a bacterially derived minicell that is produced from a protease deficient *E. coli* parental bacterial cell. In embodiments, said intact anucleated cell is a bacterially derived minicell that is produced from a protease deficient *E. coli* parental bacterial cell selected from the group consisting of: BL21, BL21 (DE3), BL21-AI, LPS-modified BL21 (DE3) and B8. In embodiments, said intact anucleated cell is derived from a eukaryotic cell.

In some embodiments, an anucleated cell-based platform for the encapsulation and delivery of agricultural compounds is provided, which comprises an intact anucleated cell, having within said cell at least one non-expressed agricultural compound. In embodiments, the at least one non-expressed agricultural compound is selected from the group consisting of: a pesticide, an herbicide, an insecticide, a fungicide, a nematicide, a fertilizer and a hormone or a chemical growth agent. In embodiments, the at least one non-expressed agricultural compound is a pesticide. In embodiments, the at least one non-expressed agricultural compound is an herbicide. In embodiments, the at least one non-expressed agricultural compound is a sulfonylurea herbicide. In embodiments, the at least one non-expressed agricultural compound is foramsulfuron. In embodiments, the at least one non-expressed agricultural compound is an insecticide. In embodiments, the at least one non-expressed agricultural compound is a neonicotinoid insecticide. In embodiments, the at least one non-expressed agricultural compound is clothianidin. In embodiments, the at least one non-expressed agricultural compound is a keto-enol insecticide. In embodiments, the at least one non-expressed agricultural compound is spirotetramat. In embodiments, the at least one non-expressed agricultural compound is a fungicide. In embodiments, the at least one non-expressed agricultural compound is a strobilurin fungicide. In embodiments, the at least one non-expressed agricultural compound is pyraclostrobin. In embodiments, the at least one non-expressed agricultural compound is a nematicide. In embodiments, wherein the at least one non-expressed agricultural compound is a fertilizer. In embodiments, the at least one non-expressed agricultural compound is a fertilizer selected from the group consisting of: nitrogen, phosphorous, and potassium. In embodiments, the at least one non-expressed agricultural compound is a hormone or a chemical growth agent. In embodiments, the at least one non-expressed agricultural compound is a hormone or a chemical growth agent selected from the group consisting of: abscisic acid, auxins, cytokinins, ethylene, gibberellins, brassinosteroids, salicylic acid, jasmonates, polyamines, nitric oxide, strigolactones, karrikins, and triacontanol.

In some embodiments, an anucleated cell-based platform for the encapsulation and delivery of agricultural compounds is provided, which comprises an intact anucleated cell, having within said cell at least one non-expressed agricultural compound. In embodiments, the anucleated cell expresses a polypeptide on its surface. In embodiments, the anucleated cell expresses a heterologous polypeptide on its surface. In embodiments, the anucleated cell expresses a fusion protein. In embodiments, the anucleated cell expresses a fusion protein, which comprises at least one surface expressing moiety and at least one plant cell adhesion moiety. In embodiments, the anucleated cell expresses a fusion protein, which comprises at least one surface expressing moiety and at least one plant cell adhesion moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence). In embodiments, the anucleated cell expresses a fusion protein, which comprises at least one surface expressing moiety and at least one plant cell adhesion moiety, wherein said surface expressing moiety comprises an exported bacterial protein and is selected from the group consisting of: selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), B1a (TEM-1 B-lactamase), F1 or M13 major coat (derived from Gene VIII), and F1 or M13 minor coat (Gene III). In embodiments, the anucleated cell expresses a fusion protein, which comprises at least one surface expressing moiety and at least one plant cell adhesion moiety, wherein said plant cell adhesion moiety comprises a carbohydrate binding module. In embodiments, the anucleated cell expresses a fusion protein, which comprises at least one surface expressing moiety and at least one plant cell adhesion moiety, wherein said plant cell adhesion moiety comprises a carbohydrate binding module selected from the group consisting of: a cellulose binding domain, a xylan binding domain, a chitin binding domain, and a lignin binding domain. In embodiments, the anucleated cell expresses a polypeptide on its surface that increases adhesion to a plant surface. In embodiments, the anucleated cell expresses a plant adhesion polypeptide on its surface. In embodiments, the anucleated cell expresses a carbohydrate binding module that is displayed on its surface. In embodiments, the anucleated cell expresses a heterologous carbohydrate binding module that is displayed on its surface. In embodiments, the anucleated cell expresses a cellulose binding domain that is displayed on its surface. In embodiments, the anucleated cell expresses a heterologous cellulose binding domain that is displayed on its surface.

In some embodiments, an anucleated cell-based platform for the encapsulation and delivery of agricultural compounds is provided, which comprises an intact anucleated cell, having within said cell at least one non-expressed agricultural compound. In embodiments, the anucleated cell-based platform is formulated as a liquid, dry composition, powder, granule, seed coating, drench, in-furrow composition, or foliar spray.

In some embodiments, the present disclosure provides a method of delivering an agricultural compound to a locus, comprising: applying the anucleated cell-based platform to a desired locus. In embodiments, the anucleated cell-based platform is applied to a plant, wherein the plant comprises the seed, stalk, flower, fruit, leaves, roots, or rhizome. In embodiments, a method of delivering an agricultural compound to a crop comprises applying the anucleated cell-based platform to a crop, or locus in proximity to said crop.

In some embodiments, the anucleated cell-based platform comprises an anucleated cell that is treated with a solvent. In embodiments, the anucleated cell-based platform according to claim 58, wherein said solvent is ethanol, DMSO, polyethylene glycol, or glycerol. In embodiments, the anucleated cell is treated with an agent, in addition to said solvent. In embodiments, said agent is a fixative, a preservative or a cross-linking agent. In embodiments, said cross-linking agent is glutaraldehyde, formaldehyde, genipin, or epigallocatechin gallat. In embodiments, said solvent increases solubility of the agricultural compounds into the anucleated cell. In embodiments, said solvent increases solubility of the agricultural compounds into the anucleated cell, and wherein said solvent increases diffusion of the agricultural compounds into the anucleated cell. In embodiments, said agent captures the agricultural compounds within a membrane of the anucleated cell. In embodiments, said agent captures the agricultural compounds within a membrane of the anucleated cell, and wherein said agent cross-links the agricultural compounds to the anucleated cell, which improves stability of the anucleated cell. In embodiments, said agent enhances loading capacity of the agricultural compounds into the anucleated cell. In embodiments, said agent enhances loading capacity of the agricultural compounds into the anucleated cell, and wherein said agent controls a release rate of the agricultural compounds from the anucleated cell.

In some embodiments, the anucleated cell exhibits a controlled release rate of the at least one non-expressed agricultural compound. In embodiments, the anucleated cell exhibits a controlled release rate of the at least one non-expressed agricultural compound, and wherein said at least one non-expressed agricultural compound is released at a steady rate. In embodiments, the anucleated cell exhibits an initial burst release of the at least one non-expressed agricultural compound. In embodiments, the anucleated cell exhibits an initial burst release of the at least one non-expressed agricultural compound, said burst release comprising a release of at least about 40% of the at least one non-expressed agricultural compound. In embodiments, the anucleated cell exhibits a controlled release rate of the at least one non-expressed agricultural compound, and wherein the controlled release rate is less than 40%, less than 30%, less than 20%, less than 15%, less than 10%, or less than 5% of the at least one non-expressed agricultural compound being released from the anucleated cell per day. In embodiments, the controlled release rate is less than 15% of the non-expressed agricultural compound released from the anucleated cell per day. In embodiments, the controlled release rate is less than 10% of the non-expressed agricultural compound released from the anucleated cell per day. In embodiments, the controlled release rate is about 10% of the non-expressed agricultural compound released from the anucleated cell per day.

BRIEF DESCRIPTION OF THE FIGURES

FIG. 8A shows His-Tag staining of CBM expressed from non-permeabilized protease-deficient minicells. FIG. 8B shows His-Tag staining of CBM expressed from permeabilized protease-deficient minicells. FIG. 8C shows no or little CBM expression from non-permeabilized control minicells. FIG. 8D also shows no or little CBM expression from permeabilized control minicells. Arrow points out the expressed CBMs.

FIG. 9A illustrates that minicells are treated with 1% (v/v) Glutaraldehyde and untreated (0% (v/v) Glutaraldehyde) at 25° C. for 15 days. FIG. 9B illustrates that minicells are treated with three different concentrations of Glutaraldehyde (5%, 1%, and 0.25% (v/v), compared to an untreated control at 37° C. for 15 days.

In FIGS. 10A and 10B, top left is a bright field image of the protease free wild type cells taken at a 40× objective. Top right is an image of cells excited with a blue LED in order to visualize the presence of FDA (fluorescein diacetate) within the cells on the cellulose. Bottom left is an image of the cells excited with a green LED in order to visualize presence of cellulose with PI (propidium iodide) adsorbed to the surface of the cells and penetrated into cell membranes of any present cells. Bottom right is an overlaid image of all three imaging conditions. Arrow points out the stained celluloses on the minicell.

DETAILED DESCRIPTION

Figure 1:
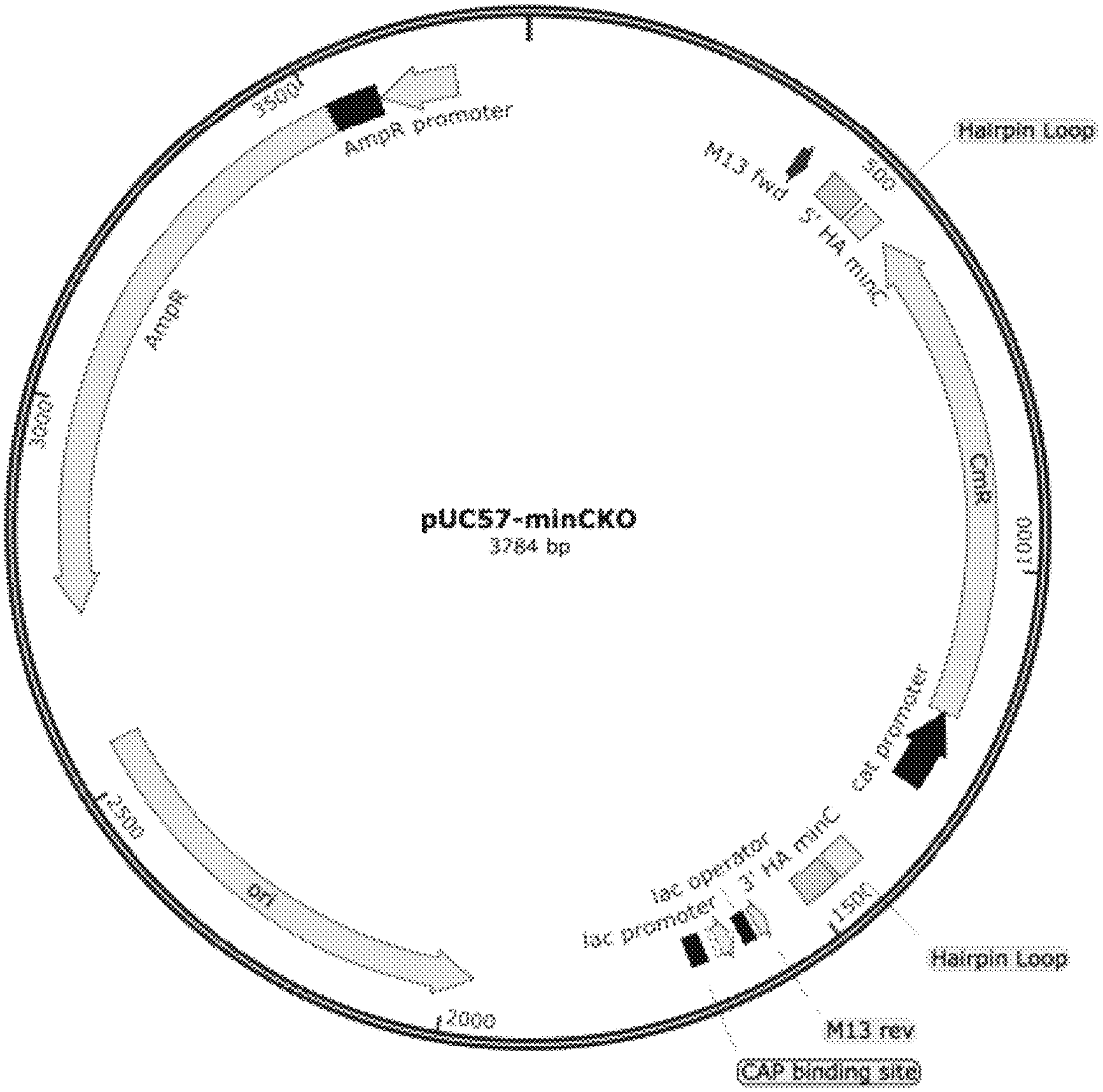
FIG. 1 illustrates an exemplary bacterial minicell-inducing vector for a minC knockout to produce protease-deficient minicells. The pUC57 vector was inserted with a recombinant DNA insert comprising 5' end nucleotide sequence of minC gene, a chloramphenicol resistant gene (CmR) with cat promoter, and 3' end nucleotide sequence of minC gene. The hairpin loops flanked by 5' and 3' ends of minC gene are inserted into the insert to stop transcriptional regulation of other neighboring genes in the genome where the insert is integrated.

There are many causes of the off-target drift of agricultural compounds applied to a subject. For example, the hydrophobic, waxy surface of plants is a primary obstacle in the targeted delivery of agricultural compounds such as agrochemicals. Up to 90% of applied pesticides are lost in the environment or unable to reach their target. These losses are mainly caused by emissions as well as leaching, evaporation, deposition, being washed away, photolysis, hydrolysis, and microbial activity. (Nuruzzaman, M., Rahman, M. M., Liu, Y., & Naidu, R. (2016). *Journal of Agricultural and Food Chemistry,* 64(7), 1447-1483). Especially, the volatilization of agricultural compounds is a pervasive problem that has recently been exacerbated due to the widespread use of agricultural compounds that are especially prone to volatilization.

The present disclosure provides a new platform for the encapsulation and delivery of agricultural compounds. The most common forms of agricultural compounds are pesticides, herbicides, insecticides, fungicides, nematicides, fertilizers, which are used to provide nutrients to plants. While agricultural compounds are traditionally synthetic compounds, there is currently great interest in the agricultural industry to begin replacing some of these synthetic compounds with their biologically derived counterparts. These new biologically derived agricultural compounds can be broadly categorized as biocontrols and biostimulants. Some examples of these biological agricultural compounds include hormones and biochemical growth agents. These actives include abscisic acid (involved in dormancy mechanisms under stress), auxins (positively influence plant growth), cytokinins (influence cell division and shoot formation), ACC Deaminase (lowers inhibitory growth effects of ethylene), gibberellins (positively influence plant growth by elongating stems and stimulating pollen tube growth), and many others (brassinosteroids, salicylic acid, jasmonates, plant peptide hormones, polyamines, nitric oxide, strigolactones, karrikins, and triacontanol), which are used to both positively and negatively regulate the growth of plants. In some embodiments, an anucleated cell-based platform disclosed herein can encapsulate agricultural compounds and deliver them in a scalable, targeted, cost-effective manner.

Definitions

The present disclosure relates generally to compositions and methods for immobilizing enzymes of interest on the surface of achromosomal and/or anucleate cells. In particular, the present disclosure provides compositions and methods for production of minicells having immobilized enzymatically active polypeptides on their surface and uses thereof.

In some embodiments, the present disclosure provides compositions and methods for immobilizing enzymatically active polypeptides including, but are not limited to, lipases, phospholipases, transacylases, transaminases, pectinase, proteases, amylases, cellulases, cutinases, esterases, acylases, invertases, isomerases, lyases, glucosidases, oxidoreductases, transferases, ligases, and amidases, displayed on the surface of achromosomal and/or anucleate cells. In other embodiments, enzymatically active polypeptides comprise lipase, glucose isomerase, alpha amylase, cellulase (endoglucanases, exoglucanases, beta-glucosidases), beta amylase, pectin lyase, isomerase, protease, transglutaminase, desaturase, peroxidase, lipoxygenase, catalase, alkaline phosphatase, tyrosinase, urease, dehydrogenases (e.g. alcohol dehydrogenases, lactate dehydrogenases, acetaldehyde dehydrogenases, aldehyde dehydrogenases, pyruvate dehydrogenases, and succinate dehydrogenases), xylanase, phytase, mannanase, and laccase. Also, enzymatically active polypeptides further comprise amyloglucosidase, pullulanase, cyclodextrin-glycosyltransferase, pectin methyl esterase, glucose oxidase, lactase, beta-glucanase, acetolactate decarboxylase, pectate lyase, nitrilase, and amyloglucosidase. In some embodiments, the enzymatically active polypeptide is lipase. In some embodiments, the enzymatically active polypeptide is glucose isomerase.

In some embodiments, the achromosomal and/or anucleate cells are derived from eubacterial, archaebacterial, and/or eukaryotic cell. In other embodiments, minicells having immobilized enzymes on their surface can have applications for agriculture, animal feed, food, beverages, industrial enzymes, textiles, pulp and paper, biofuels, fermentation, bioremediation, bioenergy, electronics, defense, bioenergy, household care, pharmaceuticals, and others uses.

Definitions

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists.

The term "prokaryotes" is art recognized and refers to cells that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified. In the disclosure, "wild type strain" or "wild strain" or "wild type cell line" refers to a cell strain/line that can produce minicells. In some embodiments, wild type bacterial strains and/or cell lines such as *E. coli* strain p678-54 and *B. subtilis* strain CU403 can make miniature cells deficient in DNA. Methods for producing such minicells are known in the art. See, for example, Adler et al., 1967, *Proc. Natl. Acad. Sci. USA* 57:321-326; Inselburg J, 1970 *J. Bacteriol.* 102(3):642-647; Frazer 1975,

*Curr. Topics Microbiol. Immunol.* 69:1-84, Reeve et al 1973, *J. Bacteriol.* 114(2):860-873; and Mendelson et al 1974 *J Bacteriol.* 117(3):1312-1319.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that rearranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, a "synthetic amino acid sequence" or "synthetic peptide" or "synthetic protein" is an amino acid sequence that is not known to occur in nature or that is not naturally occurring. Generally, such a synthetic protein sequence will comprise at least one amino acid difference when compared to any other naturally occurring protein sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a nonnative source or location, and that have been artificially supplied to a biological system.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode an enzymatically active portion of a genetic regulatory element. An enzymatically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. Also, "construct", "vector", and "plasmid" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218: 78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

As used herein, the term "display" refers to the exposure of the polypeptide of interest on the outer surface of the minicell. By way of non-limiting example, the displayed polypeptide may be a protein or a protein domain which is either expressed on the minicell membrane or is associated with the minicell membrane such that the extracellular domain or domain of interest is exposed on the outer surface of the minicell (expressed and displayed on the surface of the minicell or expressed in the parental cell to be displayed on the surface of the segregated/budded minicell). In all instances, the "displayed" protein or protein domain is available for interaction with extracellular components. A membrane-associated protein may have more than one extracellular domain, and a minicell of the disclosure may display more than one membrane-associated protein.

As used herein, the terms "polypeptide", "protein" and "protein domain" refer to a macromolecule made up of a single chain of amino acids joined by peptide bonds. Polypeptides of the invention may comprise naturally occurring amino acids, synthetic amino acids, genetically encoded amino acids, non-genetically encoded amino acids, and combinations thereof. Polypeptides may include both L-form and D-form amino acids.

As used herein, the term "enzymatically active polypeptide" refers to a polypeptide which encodes an enzymatically functional protein. The term "enzymatically active polypeptide" includes but not limited to fusion proteins which perform a biological function. Exemplary enzymatically active polypeptides, include but not limited to enzymes/enzyme moiety (e.g. wild type, variants, or engineered variants) that specifically bind to certain receptors or biological/chemical substrates to effect a biological function such as biological signal transduction or chemical inactivation.

As used herein, the term "protease-deficient strain" refers to a strain that is deficient in one or more endogenous proteases. For example, protease deficiency can be created by deleting, removing, knock-out, silencing, suppressing, or otherwise downregulating at lease on endogenous protease. Said proteases can include catastrophic proteases. For example, BL21 (DE3) *E. coli* strain is deficient in proteases Lon and OmpT. *E. coli* strain has cytoplasmic proteases and membrane proteases that can significantly decrease protein production and localization to the membrane. In some embodiments, a protease-deficient strain can maximize production and localization of a protein of interest to the membrane of the cell. "Protease-deficient" can be interchangeably used as "protease-free" in the present disclosure.

As used herein, the term "anucleated cell" refers to a cell that lacks a nucleus and also lacks chromosomal DNA and which can also be termed as an "anucleate cell". Because eubacterial and archaebacterial cells, unlike eukaryotic cells, naturally do not have a nucleus (a distinct organelle that contains chromosomes), these non-eukaryotic cells are of course more accurately described as being "without chromosomes" or "achromosomal." Nonetheless, those skilled in the art often use the term "anucleated" when referring to bacterial minicells in addition to other eukaryotic minicells. Accordingly, in the present disclosure, the term "minicells" encompasses derivatives of eubacterial cells that lack a chromosome; derivatives of archaebacterial cells that lack their chromosome(s), and anucleate derivatives of eukaryotic cells that lack a nucleus and consequently a chromosome. Thus, in the present disclosure, "anucleated cell" or "anucleate cell" can be interchangeably used with the term "achromosomal cell."

As used herein, the term "non-expressed" agricultural compound refers to an agricultural compound that is not endogenously, innately or naturally produced from a host cell. For example, *Bacillus thurigenesis* produces a toxin that can kill plant chewing insect larvae as well as mosquito larvae. This toxin that can be used as an agricultural compound is a Cry protein endogenously expressed from *B. thurigenesis*. In the present disclosure, this naturally expressed Cry protein is not considered as a non-expressed agricultural compound.

As used herein, the term "binding site," means a molecular structure or compound, such as a protein, a polypeptide, a polysaccharide, a glycoprotein, a lipoprotein, a fatty acid, a lipid or a nucleic acid or a particular region in such molecular structure or compound or a particular conformation of such molecular structure or compound, or a combination or complex of such molecular structures or compounds. In certain embodiments, at least one binding site is on an intact living plant. An "intact living plant," as used herein, means a plant as it grows, whether it grows in soil, in water or in artificial substrate, and whether it grows in the field, in a greenhouse, in a yard, in a garden, in a pot or in hydroponic culture systems. An intact living plant preferably comprises all plant parts (roots, stem, branches, leaves, needles, thorns, flowers, seeds etc.) that are normally present on such plant in nature, although some plant parts, such as, e.g., flowers, may be absent during certain periods in the plant's life cycle.

A "binding domain," as used herein, means the whole or part of a proteinaceous (protein, protein-like or protein containing) molecule that is capable of binding using specific intermolecular interactions to a target molecule. A binding domain can be a naturally occurring molecule, it can be derived from a naturally occurring molecule, or it can be entirely artificially designed. A binding domain can be based on domains present in proteins, including but not limited to microbial proteins, protease inhibitors, toxins, fibronectin, lipocalins, single-chain antiparallel coiled coil proteins or repeat motif proteins. Non-limiting examples of such binding domains are carbohydrate binding modules (CBM) such as cellulose binding domain to be targeted to plants. In some embodiments, a cell adhesion moiety comprises a binding domain.

As used herein, "carrier," "acceptable carrier," or "agriculturally acceptable carrier" refers to a diluent, adjuvant, excipient, or vehicle with which a composition can be administered to its target, which does not detrimentally effect the composition.

Minicells

Minicells are the result of aberrant, asymmetric cell division, and contain membranes, peptidoglycan, ribosomes, RNA, protein, and often plasmids but no chromosome. (Frazer A C and Curtiss III, Production, Properties and Utility of Bacterial Minicells, *Curr. Top. Microbial. Immunol.* 69:1-84 (1975)). Because minicells lack chromosomal DNA, minicells cannot divide or grow, but they can continue other cellular processes, such as ATP synthesis, replication and transcription of plasmid DNA, and translation of mRNA. Although chromosomes do not segregate into minicells, extrachromosomal and/or episomal genetic expression elements may segregate, or may be introduced into minicells after segregation from parent cells.

In embodiments, the minicells described herein are non-naturally occurring.

In some embodiments, the disclosure provides a composition comprising a plurality of minicells, wherein each minicell of said plurality comprises an enzymatically active polypeptide displayed on the surface of the minicell, wherein said enzymatically active polypeptide has enzymatic activity. The enzymatic activity is derived from enzymatically active polypeptides disclosed in the present disclosure. In some embodiments, the invention provides a composition comprising a plurality of intact, bacterially-derived minicells, wherein each minicell of said plurality comprises an enzymatically active polypeptide displayed on the surface of the bacterial minicell, wherein said enzymatically active polypeptide has enzymatic activity. In some embodiments, the composition comprises minicells which further comprise a second polypeptide displayed on the surface of the bacterial minicell, to increase adhesion to a subject and/or subjects including, but are not limited to substrates of enzymes, receptors, metal, plastic, soil, bacteria, fungi, pathogens, germs, plants, animals, human, and the like. In some embodiments, the composition comprises a mixture of minicells, wherein certain minicells within the mixed minicell population display the enzymatically active polypeptide or display the second polypeptide including subject adhesion increasing polypeptide or display both.

Eubacterial Minicells

One type of minicell is a eubacterial minicell. For reviews of eubacterial cell cycle and division processes, see Rothfield et al., *Annu. Rev. Genet.,* 33:423-48, 1999; Jacobs et al., *Proc. Natl. Acad. Sci. USA,* 96:5891-5893, May, 1999; *Koch, Appl. and Envir. Microb*., Vol. 66, No. 9, pp. 3657-3663; Bouche and Pichoff, *Mol Microbiol,* 1998. 29: 19-26; Khachatourians et al., *J Bacteriol,* 1973. 116: 226-229; Cooper, *Res Microbiol,* 1990. 141: 17-29; and Danachie and Robinson, "Cell Division: Parameter Values and the Process," in: *Escherichia Coli* and *Salmonella Typhimurium: Cellular and Molecular Biology*, Neidhardt, Frederick C., Editor in Chief, American Society for Microbiology, Washington, D.C., 1987, Volume 2, pages 1578-1592, and references cited therein; and Lutkenhaus et al., "*Cell Division,*" Chapter 101 in: *Escherichia coli* and *Salmonella typhimurium: Cellular and Molecular Biology,* $2^{nd}$ Ed., Neidhardt, Frederick C., Editor in Chief, American Society for Microbiology, Washington, D.C., 1996, Volume 2, pages 1615-1626, and references cited therein. When DNA replication and/or chromosomal partitioning is altered, membrane-bounded vesicles "pinch off" from parent cells before transfer of chromosomal DNA is completed. As a result of this type of dysfunctional division, minicells are produced which contain an intact outer membrane, inner membrane, cell wall, and all of the cytoplasm components but do not contain chromosomal DNA.

In some embodiments, the bacterially-derived minicells are produced from a strain, including, but are not limited to a strain of *Escherichia coli, Bacillus* spp., *Salmonella* spp., *Listeria* spp., *Mycobacterium* spp., *Shigella* spp., or *Yersinia* spp. In some embodiments, the bacterially-derived minicells are produced from a strain that naturally produces minicells. Such natural minicell producing strains produce minicells, for example, at a 2:1 ratio (2 bacterial cells for every one minicell). In certain embodiments, exemplary bacterial strains that naturally produce minicells include, but are not limited to *E. coli* strain number P678-54, *Coli* Genetic Stock Center (CGSC) number: 4928 and *B. subtilis* strain CU403.

As one example, mutations in *B. subtilis* smc genes result in the production of minicells (Britton et al., 1998, *Genes and Dev.* 12:1254-1259; Moriya et al., 1998, *Mol Microbiol* 29:179-87). Disruption of smc genes in various cells is predicted to result in minicell production therefrom.

As another example, mutations in the divIVA gene of *Bacillus subtilis* results in minicell production. When expressed in *E. coli, B. subtilis* or yeast *Schizosaccharo mycespombe*, a DivIVA-GFP protein is targeted to cell division sites therein, even though clear homologs of DivIVA do not seem to exist in *E. coli, B. subtilis* or *S. pombe* (David et al., 2000, EMBO J. 19:2719-2727. Over- or under-expression of *B. subtilis* DivIVA or a homolog thereof may be used to reduce minicell production in a variety of cells.

In some embodiments, the minicell-producing bacteria is a Gram-negative bacteria. The Gram-negative bacteria includes, but is not limited to, *Escherichia coli, Salmonella* spp. including *Salmonella typhimurium, Shigella* spp. including *Shigella flexneri, Pseudomonas aeruginosa, Agrobacterium, Campylobacter jejuni, Lactobacillus* spp., *Neisseria gonorrhoeae*, and *Legionella pneumophila*. In some embodiments, the minicell-producing gram-negative bacteria can produce minicells naturally caused by endogenous or exogenous mutation(s) associated with cell division and/or chromosomal partitioning. In some embodiments, the minicell-producing bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing gram-negative bacteria is deficient in protease and/or its activity naturally and/or by genetic engineering techniques disclosed herein. In some embodiments, the protease-deficient minicell-producing gram-negative bacteria comprises a recombinant expression vector comprising a gene or genes that is involved in a protein of interest disclosed in the present disclosure.

In some embodiments, the minicell-producing bacteria can be a Gram-positive bacteria. The Gram-positive bacteria includes, but is not limited to, *Bacillus subtilis, Bacillus cereus, Corynebacterium Glutamicum, Lactobacillus acidophilus, Staphylococcus* spp., or *Streptococcus* spp. In some embodiments, the minicell-producing gram-positive bacteria can produce minicells naturally caused by endogenous or exogenous mutation(s) associated with cell division and/or chromosomal partitioning. In some embodiments, the minicell-producing gram-positive bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing gram-positive bacteria is deficient in protease and/or its activity naturally and/or by genetic engineering techniques disclosed herein. In some embodiments, the protease-deficient minicell-producing gram-positive bacteria comprises a recombinant expression vector comprising a gene or genes that is involved in a protein of interest disclosed in the present disclosure.

The minicell-producing bacteria can be a Extremophilic bacteria. The Extremophilic bacteria includes, but is not limited to, Thermophiles including *Thermus aquaticus*, Psychrophiles, Piezophiles, Halophilic bacteria, Acidophile, Alkaliphile, Anaerobe, Lithoautotroph, Oligotroph, Metallotolerant, Oligotroph, Xerophil or Polyextremophile. In some embodiments, the minicell-producing Extremophilic bacteria can produce minicells naturally caused by endogenous or exogenous mutation(s) associated with cell division and/or chromosomal partitioning. In some embodiments, the minicell-producing Extremophilic bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing Extremophilic bacteria is deficient in protease and/or its activity naturally and/or by genetic engineering techniques disclosed herein. In some embodiments, the protease-deficient minicell-producing Extremophilic bacteria comprises a recombinant expression vector comprising a gene or genes that is involved in a protein of interest disclosed in the present disclosure.

Eukaryotic Minicells

Achromosomal eukaryotic minicells (i.e., anucleate cells) are within the scope of the disclosure. Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleate yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997).

In some embodiments, the eukaryotic minicells can be produced from yeast cells, such as *Saccharomyces cerevisiae, Pichia pastoris* and/or *Schizosaccharomyces pombe.*

As one example, mutations in the yeast genes encoding TRF topoisomerases result in the production of minicells, and a human homolog of yeast TRF genes has been stated to exist (Castano et al., 1996, *Nucleic Acids Res* 24:2404-10). Mutations in a yeast chromodomain ATPase, Hrp1, result in abnormal chromosomal segregation; (Yoo et al., 2000 *Nuc. Acids Res.* 28:2004-2011). Disruption of TRF and/or Hrp1 function is predicted to cause minicell production in various cells. Genes involved in septum formation in fission yeast (see, e.g., Gould et al., 1997 *Genes and Dev.* 11:2939-2951) can be used in like fashion.

Platelets are a non-limiting example of eukaryotic minicells. Platelets are anucleate cells with little or no capacity for de novo protein synthesis. The tight regulation of protein synthesis in platelets (Smith et al., 1999, Vasc Med 4:165-72) may allow for the over-production of exogenous proteins and, at the same time, under-production of endogenous proteins. Thrombin-activated expression elements such as those that are associated with Bcl-3 (Weyrich et al., Signal-dependent translation of a regulatory protein, Bcl-3, in activated human platelets, Cel Biology 95:5556-5561, 1998) may be used to modulate the expresion of exogneous genes in platelets.

As another non-limiting example, eukaryotic minicells are generated from tumor cell lines (Gyongyossy-Issa and Khachatourians, Tumour minicells: single, large vesicles released from cultured mastocytoma cells (1985) Tissue Cell 17:801-809; Melton, Cell fusion-induced mouse neuroblastomas HPRT revertants with variant enzyme and elevated HPRT protein levels (1981) *Somatic Cell Genet.* 7: 331-344).

Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleate yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997). In some embodiments, the present disclosure teaches production of yeast minicells.

Archaebacterial Minicells

The term "archaebacterium" is defined as is used in the art and includes extreme thermophiles and other Archaea (Woese, C. R., L. Magrum. G. Fox. 1978. Archaebacteria. *Journal of Molecular Evolution.* 11:245-252). Three types of Archaebacteria are halophiles, thermophiles and methanogens. By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage. Non-limiting examples of halophiles include *Halobacterium cutirubrum* and *Halogerax mediterranei*. Non-limiting examples of methanogens include *Methanococcus voltae; Methanococcus vanniela; Methanobacterium thermoautotrophicum; Methanococcus voltae; Methanothermus fervidus*; and *Methanosarcina barkeri*. Non-limiting examples of thermophiles include *Azotobacter vinelandii; Thermoplasma acidophilum; Pyrococcus horikoshii; Pyrococcus furiosus*; and Crenarchaeota (extremely thermophilic archaebacteria) species such as *Sulfolobus solfataricus* and *Sulfolobus acidocaldarius.*

Archaebacterial minicells are within the scope of the invention. Archaebacteria have homologs of eubacterial minicell genes and proteins, such as the MinD polypeptide from *Pyrococcus furiosus* (Hayashi et al., *EMBO J* 20:1819-28, 2001). It is thus possible to create Archaebacterial minicells by methods such as, by way of non-limiting example, overexpressing the product of a min gene isolated from a prokaryote or an archaebacterium; or by disrupting expression of a min gene in an archaebacterium of interest by, e.g., the introduction of mutations thereof or antisense molecules thereto. See, e.g., Laurence et al., *Genetics* 152: 1315-1323, 1999.

By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage. In some embodiments, the present disclosure teaches production of archaeal minicells.

Bacterial Minicell Production

Minicells are produced by parent cells having a mutation in, and/or overexpressing, or under expressing a gene involved in cell division and/or chromosomal partitioning, or from parent cells that have been exposed to certain conditions, that result in aberrant fission of bacterial cells and/or partitioning in abnormal chromosomal segregation during cellular fission (division). The term "parent cells" or "parental cells" refers to the cells from which minicells are produced. Minicells, most of which lack chromosomal DNA (Mulder et al., *Mol Gen Genet,* 221: 87-93, 1990), are generally, but need not be, smaller than their parent cells. Typically, minicells produced from *E. coli* cells are generally spherical in shape and are about 0.1 to about 0.3 um in diameter, whereas whole *E. coli* cells are about from about 1 to about 3 um in diameter and from about 2 to about 10 um in length. Micrographs of *E. coli* cells and minicells that have been stained with DAPI (4:6-diamidino-z-phenylindole), a compound that binds to DNA, show that the minicells do not stain while the parent *E. coli* are brightly stained. Such micrographs demonstrate the lack of chromosomal DNA in minicells. (Mulder et al., *Mol. Gen. Genet.* 221:87-93, 1990).

Minicells are achromosomal, membrane-encapsulated biological nanoparticles (≤400 nm) that are formed by bacteria following a disruption in the normal division apparatus of bacterial cells. Minicells can also be 400 nm to 650 nm in size. In essence, minicells are small, metabolically active replicas of normal bacterial cells with the exception that they contain no chromosomal DNA and as such, are non-dividing and non-viable. Although minicells do not contain chromosomal DNA, the ability of plasmids, RNA, native and/or recombinantly expressed proteins, and other metabolites have all been shown to segregate into minicells. Some methods of construction of minicell-producing bacterial strains are discussed in detail in U.S. patent application Ser. No. 10/154,951 (US Publication No. US/2003/0194798 A1), which is hereby incorporated by reference in its entirety.

Disruptions in the coordination between chromosome replication and cell division lead to minicell formation from the polar region of most rod-shaped prokaryotes. Disruption of the coordination between chromosome replication and cell division can be facilitated through the overexpression of some of the genes involved in septum formation and binary fission. Alternatively, minicells can be produced in strains that harbor mutations in genes that modulate septum formation and binary fission. Impaired chromosome segregation mechanisms can also lead to minicell formation as has been shown in many different prokaryotes.

Plasmid Based Methods of Minicell Production

In some embodiments, minicell production can be achieved by the overexpression or mutation of genes involved in the segregation of nascent chromosomes into daughter cells. For example, mutations in the parC or mukB loci of *E. coli* have been demonstrated to produce minicells. Both affect separate requisite steps in the chromosome segregation process in bacteria. Manipulation of wild type levels of any given gene involved in the chromosome segregation process that result in minicell production will have similar effects in other family members.

Because the cell division and chromosome replication processes are so critical to survival, there exists a high level of genetic and functional conservancy amongst prokaryotic family members with respect to genes responsible for these processes. The overexpression or mutation of a cell division gene capable of driving minicell production in one family member, can be used to produce minicells in another. For example, it has been shown that the overexpression *E. coli* ftsZ gene in other Enterobacteriacea family members such as *Salmonella* spp. and *Shigella* spp as well as other class members such as *Pseudomonas* spp. will result in similar levels of minicell production.

In some embodiments, minicells can be produced in *E. coli* by the overproduction of the protein FtsZ which is an essential component of the Min division system by which *E. coli* operates. This protein polymerizes during cell division to form a ring-like structure at the potential site of division. This ring recruits other proteins which complete the division. Overproduction of this protein in *E. coli* results in the inability for this ring to be spatially restricted to the midsection of the cell, thus resulting in production of minicells upon cell division.

Because the overproduction of FtsZ can create minicells, it can be overexpressed using a plasmid based system.

The same can be demonstrated in the mutation-based minicell producing bacterial strains. For example, deletion of the Min locus in any of bacterial strains results in minicell production. Cell division genes in which mutation can lead to minicell formation include but are not limited to the min genes (such as minC, minD, and minE).

In some embodiments, *E. coli* rely on the min system in order to ensure proper replication of parent cells into daughter cells. This min system (known as the minB operon) consists of 3 parts, minD, minC, and minE. These genes work together in order to control the placement of the Z-ring which is comprised of polymerized FtsZ protein. MinC consists of two distinct domains, both of which interact directly with the FtsZ protein in order to inhibit polymerization (Z-ring formation). MinD is a protein that is associated with the membrane that forms at one of the cell's poles and polymerizes toward the cell's mid-point. It binds MinC which is distributed throughout the cytoplasm. MinE is a protein that binds to MinD as well and releases MinC. It polymerizes into a ring like shape and oscillates from pole to pole in the cell.

This system results in the sequestering of MinC bound to FtsZ (inactivating it) to the polar ends of the cell. By doing this, and due to the oscillating effect of MinE, the system creates a high chance that FtsZ polymerizes in the middle of cell and forms a Z-ring. This sets the division septum of the cell at the midpoint in the cell, which results in two cells with equal genetic information upon completion of division.

In some embodiments, this system can be manipulated in order to shift the Z-ring to a polar end of the cell which excludes the nucleoid DNA upon completion of replication. The Z-ring can be shifted by not allowing the cell to sequester MinC to the polar ends of the cell. In the absence of MinC or MinD, or overexpression of MinE, *E. coli* cells will form achromosomal and/or anucleate cells. The FtsZ and the Min systems for causing asymmetrical cell division are exemplified by Piet et al, 1990, *Proc. Natl. Acad. Sci. USA* 87:1129-1133 and Xuan-Chuan et al, 2000, *J. Bacteriol.* 182(21):6203-62138, each of which is incorporated herein by reference.

In some embodiments, the present disclosure is compatible with all genetic design and cloning methods. That is, in some embodiments, the present disclosure teaches the use of traditional cloning techniques such as polymerase chain reaction, restriction enzyme digestions, ligation, homologous recombination, RT PCR, and others generally known in the art and are disclosed in for example: Sambrook et al. (2001) Molecular Cloning: A Laboratory Manual ($3^{rd}$ ed., Cold Spring Harbor Laboratory Press, Plainview, N.Y.), incorporated herein by reference.

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

In some embodiments, minicells are produced by deleting, mutating, knocking out, or disrupting minC, minD, and/or minC and minD gene(s) in bacteria by traditional gene engineering techniques including homologous recombination. In other embodiments, minicells are produced by overexpressing certain genes such as ftsZ and/or minE in bacteria.

Controlled Production of Minicells

In some embodiments, the present disclosure teaches mutating cell populations by introducing, deleting, or replacing selected portions of genomic DNA. Thus, in some embodiments, the present disclosure teaches methods for targeting mutations to a specific locus such as ftsZ, minC, minD, minC/D, and minE. In other embodiments, the present disclosure teaches the use of gene editing technologies such as ZFNs, TALENS, CRISPR or homing endonucleases, to selectively edit target DNA regions. In aspects, the targeted DNA regions is ftsZ, minC, minD, minC/D, and minE.

Engineered nucleases such as zinc finger nucleases (ZFNs), Transcription Activator Like Effector Nucleases (TALENs), engineered homing endonucleases, and RNA or DNA guided endonucleases, such as CRISPR/Cas such as Cas9 or CPF 1, are particularly appropriate to carry out some of the methods of the present disclosure. Additionally or alternatively, RNA targeting systems can use used, such as CRISPR/Cas systems have RNA targeting nucleases.

In some embodiments, the present disclosure teaches uses of gene editing using a Type II CRISPR system such as Cas9 Type II CRISPR systems, or "Cas9-like" systems. Type II systems rely on a i) single endonuclease protein, ii) a transactiving crRNA (tracrRNA), and iii) a crRNA where a ~20-nucleotide (nt) portion of the 5' end of crRNA (i.e. "guide sequence" or "spacer") is complementary to a target nucleic acid.

In some embodiments, the tracrRNA and crRNA components of a Type II system can be replaced by a single-guide RNA (sgRNA). The sgRNA can include, for example, a nucleotide sequence that comprises an at least 12-20 nucleotide sequence complementary to the target DNA sequence (guide sequence) and can include a common scaffold RNA sequence at its 3' end. As used herein, "a common scaffold RNA" refers to any RNA sequence that mimics the tracrRNA sequence or any RNA sequences that function as a tracrRNA.

Cas9 endonucleases produce blunt end DNA breaks, and are recruited to target DNA by a combination of a crRNA and a tracrRNA oligos, which tether the endonuclease via complementary hybridization of the RNA CRISPR complex. DNA recognition by the crRNA/endonuclease complex requires additional complementary base-pairing with a protospacer adjacent motif (PAM) (e.g., 5'-NGG-3') located in a 3' portion of the target DNA, downstream from the target protospacer. (Jinek, M., et. al., Science. 2012:337; 816-821). In some embodiments, the PAM motif recognized by a Cas9 varies for different Cas9 proteins.

In some embodiments, one skilled in the art can appreciate that the Cas9 disclosed herein can be any variant described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M. et al. Science. 2012 337:816-21; and Jinek M. et al. Science. 2014 Mar. 14; 343(6176); see also U.S. patent application Ser. No. 13/842,859 filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, deactivated Cas9 (dCas9) that has no nuclease activity, or other mutants with modified nuclease activity.

In some examples, a Type II nuclease may be catalytically dead (e.g. dCas9, "dead Cas9," "deactivated Cas9") such that it binds to a target sequence, but does not cleave.

In some embodiments, minicell production results from the disruption of the Min division system. This can be done with overexpression of FtsZ in a plasmid based system like described above, or by stopping expression of a gene within the Min system. Stopping expression of gene can be done by removing the gene (non-inducible minicell formation) or it can be done by knocking down the gene. Knocking down the gene allows for controllable repression or expression of the gene of interest. In some embodiments, the present disclosure teaches to integrate a dCAS9 gene within a non-essential operon within the *E. coli* genome. dCAS9 is a variant of the CAS9 protein (CRISPR) that has had its active site altered to no longer be able to edit genomes, but can still bind to highly specific segments of the genome using a guide RNA. This protein can stop transcription of the gene if bound.

In some embodiments, the dCAS9 gene can be placed under inducible control so that its expression would be controlled. The guide RNA corresponding to the knockout within the Min system could be included on a plasmid or cut into the genome and placed under inducible control. Upon induction with this system, the guide RNA would direct the dCAS9 protein to the gene within the Min system in order to stop its expression. The stopping of expression of this gene such as minC, minD, and minC/D would result in the formation of minicells.

Antibiotic Resistance Knock in-Knock Out

In some embodiments, the present disclosure teaches uses of the genetic manipulation technique using Lambda-Red recombination system in order to edit genome integrated with exogenous expression cassette such as an selectable marker such as antibiotic resistant gene. In some embodiments, an selectable marker such as antibiotic resistant gene is integrated into the host genome (e.g. bacteria) in order to knockout minC/D/CD gene for inducing minicell production. If the marker with antibiotic resistance is no longer desired after successfully selecting the minicells in which the target gene (such as minC/D/CD) is knocked out, the flippase can be used to remove the integrated antibiotic resistant gene cassette from the host genome. A fragment of linear DNA is inserted into the genome directed by that fragment homology to the genome. This can be used to knock in genes of interest or to knockout genes of interest by replacing them with an antibiotic resistance cassette such as Chloramphenicol-resistant gene, kanamycin-resistant gene, spectinomycin-resistant gene, streptomycin-resistant gene, ampicillin-resistant gene, tetracycline-resistant gene, erythromycin-resistant gene, bleomycin-resistant gene, and bleomycin-resistant gene. A successful genetic manipulation is then selected for using this antibiotic resistance cassette. If a flippase recombination target (FRT) site is included within the resistance cassette for further genetic manipulations, it can be used for removing the antibiotic resistant gene integrated into the genome in vivo after selection of target minicells. The enzyme used for this is recombinase flippase and is often expressed from a plasmid that can be removed from the cell line using a temperature sensitive origin of replication. Recombinase flippase recognizes two identical FRT sites on both the 5' and 3' ends of the antibiotic resistance cassette and removes the DNA between the two sites. In some embodiments, the FRT site can be included within an antibiotic resistance cassette to remove the antibiotic resistance cassette after its use.

Strains for Minicell Production

A *E. coli* P678-54 strain is obtained from *Coli* Genetic Stock Center (CGSC), and is used to produce minicells (Adler et al., 1967, *Proc. Natl. Acad. Sci. USA* 57:321-326; Inselburg J, 1970 *J. Bacteriol.* 102(3):642-647; Frazer 1975, *Curr. Topics Microbiol. Immunol.* 69:1-84).

In some embodiments, an anucleated cell is produced from a P678-54 *E. coli* parental strain. The anucleated cell produced from P678-54 parental bacterial strain is used as an anucleated cell-based platform for the encapsulation and delivery of agricultural compounds.

Protease-Deficient Bacterial Strains

The present disclosure provides the production of minicells from B strains using genetically-engineering techniques including B strains including BL21, BL21 (DE3), and BL21-AI are deficient in Lon protease (cytoplasm) and OmpT protease (outer membrane). Accordingly, B strains as protease-deficient strains can be utilized to create protease-deficient and/or protease-deficient minicells. The DE3 designation means that respective strains contain the λDE3 lysogen that carries the gene for T7 RNA polymerase under control of the lacUV5 promoter. IPTG is required to maximally induce expression of the T7 RNA polymerase in order to express recombinant genes cloned downstream of a T7 promoter. BL21(DE3) is suitable for expression from a T7 or T7-lac promoter or promoters recognized by the *E. coli* RNA polymerase: e.g. lac, tac, trc, ParaBAD, PrhaBAD and also the T5 promoter. The genotype of BL21 (DE3) is: fhuA2 [lon] ompT gal (λ DE3) [dcm] ΔhsdS λ DE3=λ sBamHIo ΔEcoRI-B int:: (lacI::PlacUV5::T7 gene1) i21 Δnin5.

BL21-AI *E. coli* contains a chromosomal insertion of the gene encoding T7 RNA polymerase (RNAP) into the araB locus of the araBAD operon, placing regulation of T7 RNAP under the control of the arabinose-inducible araBAD promoter. Therefore, this strain is especially useful for the expression of genes that may be toxic to other BL21 strains where basal expression of T7 RNAP is leaky. The BL21-AI strain does not contain the Ion protease and is deficient in the outer membrane protease, OmpT. The genotype of BL21-AI is $F^-$ompT $hsdS_B$ ($r_B^-$ $m_B^-$) gal dcm araB::T7RNAP-tetA. The BL21-AI has an arabinose promoter that controls the production T7 RNA Polymerase, while the BL21 (DE3) has a lac promoter that controls the production of the T7 RNA Polymerase. This is significant because the lac promotion system is leaky. Therefore, the BL21-AI protein production is more tightly regulated due to the arabinose promotion system.

The present disclosure teaches that LPS (Lipopolysaccharide) modified BL21 (DE3) cells can be used. The LPS of the *E. Coli* is modified to be significantly less toxic. This LPS modified BL21 (DE3) cells if necessary. This could also be branched out to other gram-negative bacterial cells. Safe usage of gram-negative cells can be beneficial for anucleated cell-based platform.

ClearColi® BL21(DE3) cells are the commercially available competent cells with a modified LPS (Lipid IVA) that does not trigger the endotoxic response in diverse cells. For example, ClearColi cells lack outer membrane agonists for hTLR4/MD-2 activation; therefore, activation of hTLR4/MD-2 signaling by ClearColi® is several orders of magnitude lower as compared with *E. coli* wild-type cells. Heterologous proteins prepared from ClearColi® are virtually free of endotoxic activity. After minimal purification from ClearColi cells, proteins or plasmids (which may contain Lipid IVA) can be used in most applications without eliciting an endotoxic response in human cells. In ClearColi cells, two of the secondary acyl chains of the normally hexa-acylated LPS have been deleted, eliminating a key determinant of endotoxicity in eukaryotic cells. The six acyl chains of the LPS are the trigger which is recognized by the Toll-like receptor 4 (TLR4) in complex with myeloid differentiation factor 2 (MD-2), causing activation of NF-κB and production of proinflammatory cytokines. The deletion of the two secondary acyl chains results in lipid IVA, which does not induce the formation of the activated heterotetrameric TLR4/MD-2 complex and thus does not trigger the endotoxic response. In ClearColi® BL21(DE3) Electrocompetent Cells 4 MA145 Rev. 310CT2016 addition, the oligosaccharide chain is deleted, making it easier to remove the resulting lipid IVA from any downstream product.

In some embodiments, protease-deficient minicells disclosed herein are produced from protease-deficient parental strains including, but are not limited to, BL21 (DE3), BL21-AI and LPS-modified BL21 (DE3). In other embodiments, BL21 (DE3), BL21-AI and LPS-modified BL21 (DE3) strains are genetically engineered by deleting, mutating, knocking out, or disrupting minC, minD, and/or minC and minD gene(s) to induce minicell production. In other embodiments, BL21 (DE3), BL21-AI and LPS-modified BL21 (DE3) strains are genetically engineered by overexpressing ftsZ and/or minE genes to induce minicell production.

In further embodiments, the present disclosure provides a new minicell-producing strain named as B8. This strain is the protease-deficient minicell-producing strain without the T7 RNA Polymerase. This minicell strain is produced from the BL21 (DE3) strain. While knocking out minC/D/CD, the T7 RNA Polymerase was silenced due to the homology of the introduced knockout via Lambda Red Transformation. This strain can be used for a need of a protease-deficient minicell, but not having the T7 RNA Polymerase. In some embodiments, minicells displayed an enzymatically active polypeptide such as complicated or toxic proteins on their surface, need to be more controlled and slower expression of the desired but complicated or toxic proteins.

The present disclosure teaches genotypes of newly-generated protease-deficient minicell strains comprising i) minC-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC, ii) minD-deleted BL21(DE3); fhuA2 [lon] ompT gal (λ DE3) [dcm] ΔhsdS λ

DE3=λ sBamHIo ΔEcoRI-B int::(lacI::PlacUV5::T7 gene1) i21 Δnin5 ΔminD, iii) minC/D-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD; iv) minC-deleted BL21-AI; $F^-$ompT $hsdS_B$ ($r_B^-$ $m_B^-$) gal dcm araB::T7RNAP-tetA ΔminC, v) minD-deleted BL21-AI; $F^-$ompT $hsdS_B$ ($r_B^-$ $m_B^-$) gal dcm araB:: T7RNAP-tetA ΔminD, vi) minC/D-deleted BL21-AI; $F^-$ompT $hsdS_B$ ($r_B^-$ $m_B^-$) gal dcm araB::T7RNAP-tetA ΔminC ΔminD; vii) minC-deleted LPS-modified BL21 (DE3); msbA148 ΔgutQ ΔkdsD ΔlpxL ΔlpxM ΔpagP ΔlpxP ΔeptA ΔminC, viii) minD-deleted LPS-modified BL21 (DE3); msbA148 ΔgutQ ΔkdsD ΔlpxL ΔlpxM ΔpagP ΔlpxP ΔeptA ΔminD, ix) minC/D-deleted LPS-modified BL21 (DE3); msbA148 ΔgutQ ΔkdsD ΔlpxL ΔlpxM ΔpagP ΔlpxP ΔeptA ΔminC, ΔminD, x) minC-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC; xi) minD-deleted B8 with suppression on T7 RNA polymerase activity; fhuA2 [lon] ompT gal (λ DE3) [dcm]ΔhsdS λ DE3=λ sBamHIo ΔEcoRI-B int::(lacI::PlacUV5::T7 gene1) i21 Δnin5 ΔminD; and xii) minC/D-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD.

Minicells that have segregated from parent cells lack chromosomal and/or nuclear components, but retain the cytoplasm and its contents, including the cellular machinery required for protein expression. In some embodiments, minicells are protease-deficient because the parent cells are protease-deficient strains. Although chromosomes do not segregate into minicells, extrachromosomal and/or episomal genetic expression elements may segregate, or may be introduced into minicells after segregation from parent cells. In some embodiments, the disclosure is drawn to protease-deficient minicells comprising an expression element, which may be an inducible expression element. The inducible expression element such as an inducible promoter can be introduced to a recombinant plasmid used for homologous recombination to knock out and/or delete gene(s) involved to cell division and/or chromosomal partitioning such as minC, minD, and minC/D, a recombinant expression vector to overexpress gene(s) involved to cell division and/or chromosomal partitioning such as ftsZ and minE, and a recombinant expression vector for expressing an enzymatically active polypeptide including a protein of interest disclosed herein. In further embodiments, the inducible expression element comprises expression sequences operably linked to an open reading frame (ORF) that encodes proteins of interest disclosed herein. Optionally, at any point in the method, an inducing agent is provided in order to induce expression of an ORF that encodes proteins of interest disclosed herein.

In some embodiments, the disclosure teaches methods of making a protease-deficient bacterial minicell comprising a recombinant fusion protein that is not naturally found in parental cells. In some embodiment, the disclosure teaches method of preparing protease-deficient minicells from the host cells.

Figure 16:
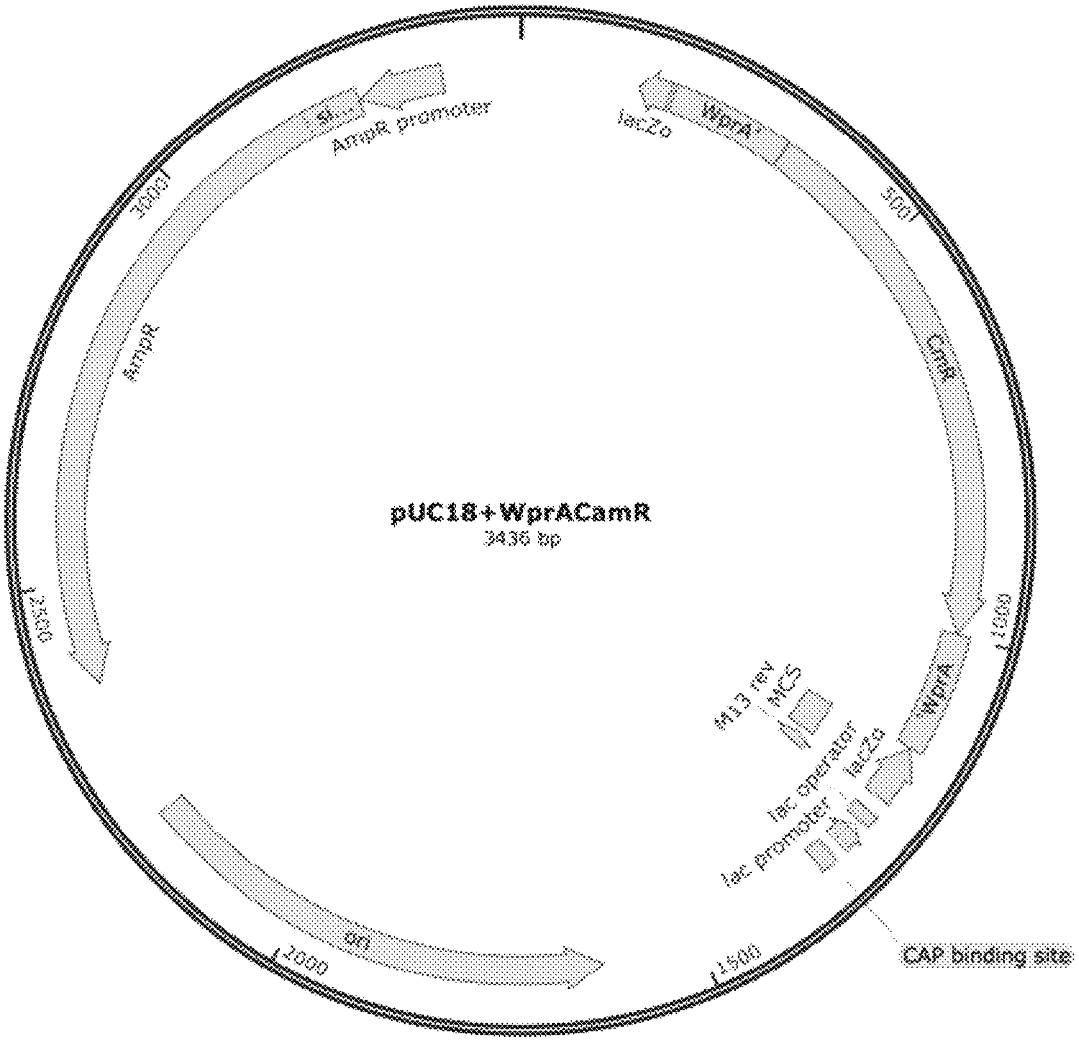
FIG. 16 illustrates an exemplary pUC18 vector for a protease WprA knockout to produce protease-deficient minicells from bacterial strains with WprA protease. The pUC18 vector was inserted with a recombinant DNA insert comprising 5' end nucleotide sequence of WprA nucleotide sequence gene, a chloramphenicol resistant gene (CmR) with cat promoter, and 3' end of WprA gene. The hairpin loops flanked by 5' and 3' ends of wprA gene are inserted into the insert to stop transcriptional regulation of other neighboring genes in the genome where the insert is integrated.

In other embodiments, the present disclosure teaches production of protease-deficient minicells from *B. subtilis* strains such as CU403 DIVIVA, CU403,DIVIVB,SPO-, CU403,DIVIVB and CU403,DIVIVB1 using by deleting, mutating, knocking out, or disrupting gene encoding WprA protease. FIG. 16 illustrate an exemplary recombinant vector for this purpose of suppressing and/or removing WprA protease activity to make protease-deficient condition in *B. subtilis.*

*B. subtilis* genetic manipulations work slightly differently than genetic manipulations in *E. coli. B. subtilis* is known to readily undergo homologous recombination if DNA containing homology to the existing genome is inserted. This is unlike *E. coli; E. coli* has mechanisms in place to degrade any non-natural linear DNA present. This difference can be utilized in order to knockout genes by designing an antibiotic resistance cassette flanked by homologous arms which correspond to the start and end of the gene that is desired to be knockout out.

The present disclosure provides the production of minicells from *B. subtilis* using genetically-engineering techniques. In some embodiments, *B. subtilis* strains including, but are not limited to CU403 DIVIVA (BGSC No. 1A196), CU403,DIVIVB,SPO-(BGSC No. 1A197), CU403,DIVIVB (BGSC No. 1A292), CU403,DIVIVB1 (BGSC No. 1A513), KO7 can be used as parental bacterial cells to produce minicells. *B. subtilis* strains are the commercially available and can be obtained from *Bacillus* Genetic Stock Center (BGSC). The catalog of strains is available on the document provided by publicly accessible BGSC webpage (www.bgsc.org/_catalogs/Catpart1.pdf).

In some embodiments, *Bacillus Subtilis* stains including, but are not limited to CU403 DIVIVA, CU403,DIVIVB, SPO-, CU403,DIVIVB and CU403,DIVIVB1 can be genetically modified by knocking out gene encoding WprA Protease in these strains. WprA protease is known as one of the harshest proteases.

In order to knock out, delete, and or remove WprA-encoding gene from *B. subtilis* strains, the pUC18 WprA-CamR vector is used as illustrated in FIG. 16. This vector has the homologous arms corresponding to the gene coding for WprA cell wall protease that naturally occurs in *B. subtilis* which is undesirable for protein surface expression. These homologous arms flank a chloramphenicol resistance cassette in order to allow for selection. After the homologous recombination via the homologous arms within the host cells, the WprA-encoding nucleotide except the homologous arm is replaced with the chloramphenicol selection marker gene. This plasmid can replicate within *E. coli* due to its origin of replication, thus when transformed into *B. subtilis* it cannot replicate. After transformation, colonies are selected for using chloramphenicol in order to isolate the colonies in which the knockout of WprA successfully occurs. Because the plasmid cannot replicate in *B. subtilis*, only the cells can survive against the presence of chloramphenicol if the recombinant cassette having the chloramphenicol resistant marker gene is integrated to the genome of the *B. subtilis* cell by homologous recombination.

*B. subtilis* secretes no fewer than seven proteases during vegetative growth and stationary phase. Strains in which multiple protease genes have been inactivated have proved to be superior to wild type strains in production of foreign proteins. The KO7 is prototrophic, free of secreted proteases, and have marker-free deletions in PY79 genetic background. This KO7 is available from the BGSC as accession number 1A1133. KO7 Genotype: ΔnprE ΔaprE Δepr Δmpr ΔnprB Δvpr Δbpr In some embodiments, a seven-protease deletion strain, *B. subtilis* KO7, can be used for *B. subtilis* minicell production by knocking out DIV-IVA and DIV-IVB using genetic engineering techniques described in the present disclosure.

In some embodiments, an anucleated cell is produced from a P678-54 *E. coli* wild strain. In other embodiments, an anucleated cell is produced from a protease-deficient *E. coli* strain including BL21, BL21(DE3), BL21-AI, LPS-modified BL21 (DE3) and B8. In some embodiments, an anucleated cell is produced from a parental bacterial cell deficient in WprA protease. In some embodiments, an anucleated cell is produced from a protease deficient *B. subtilis* parental bacterial cell. In some embodiments, an anucleated cell is produced from produced from a protease deficient KO7 *B. subtilis* parental bacterial cell. In other embodiments, an anucleated cell is produced from a protease deficient *B. subtilis* parental bacterial cell selected from the group consisting of: (1) CU403,DIVIVA; (2) CU403,DIVIVB,SPO-; (3) CU403,DIVIVB; and (4) CU403,DIVIVB1, wherein at least one protease encoding gene has been repressed, deleted, or silenced. In further embodiments, an anucleated cell is produced from an eukaryotic cell. In further embodiments, the anucleated cell produced as described above is used as an anucleated cell-based platform for the encapsulation and delivery of agricultural compounds.

Minicell Separation and Purification

A variety of methods are used to separate minicells from parent cells (i.e., the cells from which the minicells are produced) in a mixture of parent cells and minicells. In general, such methods are physical, biochemical and genetic, and can be used in combination.

Physical Separation of Minicells from Parent Cells

By way of non-limiting example, minicells are separated from parent cells glass-fiber filtration (Christen et al., Gene 23:195-198, 1983), and differential and zonal centrifugation (Barker et al., J. Gen. Microbiol. 111:387-396, 1979), size-exclusion chromatography, e.g. gel-filtration, differential sonication (Reeve, J. N., and N. H. Mendelson. 1973. Biochem. Biophys. Res. Commun. 53:1325-1330), and UV-irradiation (Tankersley, W. G., and J. M. Woodward. 1973. Proc Soc Exp Biol Med. 1974 March; 145(3):802-805).

Some techniques involve different centrifugation techniques, e.g., differential and zonal centrifugation. By way of non-limiting example, minicells may be purified by the double sucrose gradient purification technique described by Frazer and Curtiss, Curr. Topics Microbiol. Immunol. 69:1-84, 1975. The first centrifugation involves differential centrifugation, which separates parent cells from minicells based on differences in size and/or density. The percent of sucrose in the gradient (graduated from about 5 to about 20%), Ficol or glycerol is designed to allow only parent cells to pass through the gradient.

The supernatant, which is enriched for minicells, is then separated from the pellet and is spun at a much higher rate (e.g., ≥11,000 g). This pellets the minicells and any parent cells that did not pellet out in the first spin. The pellet is then resuspended and layered on a sucrose gradient.

The band containing minicells is collected, pelleted by centrifugation, and loaded on another gradient. This procedure is repeated until the minicell preparation is essentially depleted of parent cells, or has a concentration of parent cells that is low enough so as to not interfere with a chosen minicell application or activity. By way of non-limiting example, buffers and media used in these gradient and resuspension steps may be LB, defined minimal media, e.g. M63 salts with defined carbon, nitrogen, phosphate, magnesium, and sulfate levels, complex minimal media, e.g. defined minimal media with casamino acid supplement, and/or other buffer or media that serves as an osmo-protectant, stabilizing agent, and/or energy source, or may contain agents that limit the growth of contaminating parental cells, e.g azide, antibiotic, or lack an auxotrophic supplemental requirement, e.g. thiamine.

Other physical methods may also be used to remove parent cells from minicell preparations. By way of non-limiting example, mixtures of parent cells and minicells are frozen to −20° C. and then thawed slowly (Frazer and Curtiss, Curr. Topics Microbiol. Immunol. 69:1-84, 1975).

Biochemical Separation of Minicells from Parent Cells

Contaminating parental cells may be eliminated from minicell preparations by incubation in the presence of an agent, or under a set of conditions, that selectively kills dividing cells. Because minicells can neither grow nor divide, they are resistant to such treatments.

Examples of biochemical conditions that prevent or kill dividing parental cells is treatment with an antibacterial agent, such as penicillin or derivatives of penicillin. Penicillin has two potential affects. First, penicillin prevent cell wall formation and leads to lysis of dividing cells. Second, prior to lysis dividing cells form filaments that may assist in the physical separation steps described above. In addition to penicillin and its derivatives, other agents may be used to prevent division of parental cells. Such agents may include azide. Azide is a reversible inhibitor of electron transport, and thus prevents cell division. As another example, D-cycloserine or phage MS2 lysis protein may also serve as a biochemical approach to eliminate or inhibit dividing parental cells. (Markiewicz et al., FEMS Microbiol. Lett. 70:119-123, 1992). Khachatourians (U.S. Pat. No. 4,311,797) states that it may be desirable to incubate minicell/parent cell mixtures in brain heart infusion broth at 36° C. to 38° C. prior to the addition of penicillin G and further incubations.

Genetic Separation of Minicells from Parent Cells

Alternatively or additionally, various techniques may be used to selectively kill, preferably lyse, parent cells. For example, although minicells can internally retain M13 phage in the plasmid stage of the M13 life cycle, they are refractory to infection and lysis by M13 phage (Staudenbauer et al., Mol. Gen. Genet. 138:203-212, 1975). In contrast, parent cells are infected and lysed by M13 and are thus are selectively removed from a mixture comprising parent cells and minicells. A mixture comprising parent cells and minicells is treated with M13 phage at an M.O.I.=5 (phage cells). The infection is allowed to continue to a point where ≥50% of the parent cells are lysed, preferably 75%, more preferably ≥95% most preferably ≥99%; and ≥25% of the minicells are lysed or killed, preferably ≤15%, most preferably ≤1%.

As another non-limiting example of a method by which parent cells can be selectively killed, and preferably lysed, a chromosome of a parent cell may include a conditionally lethal gene. The induction of the chromosomal lethal gene will result in the destruction of parent cells, but will not affect minicells as they lack the chromosome harboring the conditionally lethal gene. As one example, a parent cell may contain a chromosomal integrated bacteriophage comprising a conditionally lethal gene. One example of such a bacteriophage is an integrated lambda phage that has a temperature sensitive repressor gene (e.g., lambda ci857). Induction of this phage, which results in the destruction of the parent cells but not of the achromosomal minicells, is achieved by simply raising the temperature of the growth media. A preferred bacteriophage to be used in this method is one that kills and/or lyses the parent cells but does not produce infective particles. One non-limiting example of this type of phage is one that lyses a cell but which has been engineered to as to not produce capsid proteins that are surround and protect phage DNA in infective particles. That is, capsid proteins are required for the production of infective particles.

As another non-limiting example of a method by which parent cells can be selectively killed or lysed, toxic proteins may be expressed that lead to parental cell lysis. By way of non-limiting example, these inducible constructs may employ a system to control the expression of a phage holing gene. Holin genes fall with in at least 35 different families with no detectable orthologous relationships (Grundling, A., et al. 2001. Proc. Natl. Acad. Sci. 98:9348-9352) of which each and any may be used to lyse parental cells to improve the purity of minicell preparations.

In some embodiments, minicells are substantially separated from the minicell-producing parent cells in a composition comprising minicells. After separation, the compositions comprising the minicells is at least about 99.9%, about 99.8%, about 99.7%, about 99.6%, about 99.5%, about 99.4%, about 99.3%, about 99.2%, about 99.1%, about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 65%, about 60%, about 55%, about 50%, about 45%, about 40%, about 35%, about 30%, about 25% or about 20% free of minicell-producing parent cells. Thus, the compositions of the disclosure can comprise minicells that are substantially free of the parental cell.

In some aspects, the present invention provides a method for making minicells, the method comprising (a) culturing a minicell-producing parent cell, wherein the parent cell comprises an recombinant construct, wherein the recombinant construct comprises a nucleotide sequence homologous to a target gene associated with regulating cell division, and (b) separating the minicells from the parent cell, thereby generating a composition comprising minicells. In some embodiments, the method further comprises (c) purifying the minicells from the composition by centrifugation and/or filtration. In some embodiments, one or more additional expression constructs can be introduced into the minicell-producing parent cell which comprise genes associated with cell division. In such instances, the expression constructs may be simultaneously or sequentially introduced into the parent cell prior to induction for minicell formation, and can comprise one or more selection markers (e.g., antibiotic resistance genes) and/or reporter genes to allow for selection and/or visualization of minicells expressing the protein(s) of interest. In other embodiments, the expression construct can express one or more additional proteins, which are driven by the same or different promoters, including inducible promoters. In further embodiments, genes associated with cell division are minC, minD, and/or both minC and minD.

Eubacterial cells and minicells are bounded by an inner membrane, which is surrounded by a cell wall, wherein the cell wall is itself enclosed within an outer membrane. That is, proceeding from the external environment to the cytoplasm of a minicell, a molecule first encounters the outer membrane (OM), then the cell wall and finally, the inner membrane (IM).

In some embodiments, the present disclosure teaches disruption or degradation of the OM, cell wall or IM of a eubacterial minicell. Such treatments are used, by way of non-limiting example, in order to increase or decrease the immunogenicity, and/or to alter the permeability characteristics, of a minicell.

In some embodiments, minicells are (i) fully intact, (ii) protoplasts (outer membrane and cell wall removed) or, (iii) poroplasts (outer membrane removed or permeabilized) in which surface-expressing moieties such as membrane-associated protein, transmembrane protein/domain, and linker protein/domain are found. In some embodiments, the surface-expressing moieties can be fused to enzymatically active polypeptides including, but are not limited to lipases, phospholipases, transacylases, transaminases, pectinase, proteases, amylases, cellulases, cutinases, esterases, acylases, invertases, isomerases, lyases, glucosidases, oxidoreductases, transferases, ligases, and amidases, displayed on the surface of achromosomal and/or anucleate cells. In other embodiments, enzymatically active polypeptides comprise lipase, glucose isomerase, alpha amylase, cellulase (endoglucanases, exoglucanases, beta-glucosidases), beta amylase, pectin lyase, isomerase, protease, transglutaminase, desaturase, peroxidase, lipoxygenase, catalase, alkaline phosphatase, tyrosinase, urease, dehydrogenases (e.g. alcohol dehydrogenases, lactate dehydrogenases, acetaldehyde dehydrogenases, aldehyde dehydrogenases, pyruvate dehydrogenases, and succinate dehydrogenases), xylanase, phytase, mannanase, and laccase. Also, enzymatically active polypeptides further comprise amyloglucosidase, pullulanase, cyclodextrin-glycosyltransferase, pectin methyl esterase, glucose oxidase, lactase, beta-glucanase, acetolactate decarboxylase, pectate lyase, nitrilase, and amyloglucosidase. In some embodiments, the enzymatically active polypeptide is lipase. In some embodiments, the enzymatically active polypeptide is glucose isomerase.

Eubacterial cells and minicells with altered membranes and/or cell walls are called “poroplasts” “spheroplasts,” and “protoplasts.” Herein, the terms “spheroplast” and “protoplast” refer to spheroplasts and protoplasts prepared from minicells. In contrast, “cellular spheroplasts” and “cellular protoplasts” refer to spheroplasts and protoplasts prepared from cells. Also, as used herein, the term “minicell” encompasses not only minicells per se but also encompasses poroplast, spheroplasts and protoplasts.

In a poroplast, the eubacterial outer membrane (OM) and LPS have been removed. In a spheroplast, portions of a disrupted eubacterial OM and/or disrupted cell wall either may remain associated with the inner membrane of the minicell, but the membrane and cell wall is nonetheless porous because the permeability of the disrupted OM and cell wall has been increased. A membrane is said to be “disrupted” when the membrane’s structure has been treated with an agent, or incubated under conditions, that leads to the partial degradation of the membrane, thereby increasing the permeability thereof. In contrast, a membrane that has been “degraded” is essentially, for the applicable intents and purposes, removed. In preferred embodiments, irrespective of the condition of the OM and cell wall, the eubacterial inner membrane is not disrupted, and membrane proteins displayed on the inner membrane are accessible to compounds that are brought into contact with the minicell, poroplast, spheroplast, protoplast or cellular poroplast, as the case may be.

Encapsulation

Encapsulation is a process of enclosing the substances within an inert material which protects from environment as well as control release of active compounds. Two type of encapsulation has been well studies; 1) Nanoencapsulation that is the coating of various substances within another material at sizes on the nano scale, and 2) Microencapsulation that is similar to nanoencapsulation aside from it involving larger particles and having been done for a greater period of time than nanoencapsulation. Encapsulation is a new technology that has wide applications in pharmaceutical industries, agrochemical, food industries and cosmetics.

In some embodiments, an anucleated cell-based platform comprising eubacterial, archaebacterial, and eukaryotic cells is utilized to produce to encapsulate agricultural compounds. The bacterial cells including gram-negative bacteria, gram-negative bacteria, and Extremophilic bacteria, can produce the platform which can encapsulate the desired agricultural compounds. The anucleated cells comprises minicells that are produced from parental bacterial cells disclosed herein naturally and/or by genetic engineering techniques taught herein.

The present disclosure teaches the benefit of using bacterial minicells which simplify purification of anucleated cell-based platform and reduce costs of encapsulation thereof. By employing encapsulation to agricultural compounds, the compounds are protected from external factors that causes degradation of the compounds and reduces life cycle of the compounds.

Current agrochemical encapsulation techniques include oils, invert suspensions, polymer-based nanomaterials, lipid-based nanomaterials, porous inorganic nanomaterials, and clay-based nanomaterials.

COC (Crop Oil Concentrate) and MSO (Methylated Seed Oil) technologies are used for oil encapsulation. They act as humectants to move the active ingredient droplets through the spray nozzle and reconfigure the droplets on the outside to keep the active ingredients from evaporating.

Invert suspension is an oil sub-category providing either a suspension of water encapsulated within an oil shell or water surrounded by an oil coating used to minimize the creation of driftable fines (sub 105 microns) after being sprayed through a nozzle tip. This technology works on reducing driftable fines for the active ingredients.

Polymer-based nanomaterials consist of a polymer that has nanoparticles or nanofillers dispersed within the polymer matrix. Typically, the polymers are contrasting (one hydrophobic, one hydrophilic) to sustain amphiphilic properties. Either synthetic or natural polymers (guar gum) act to increase the viscosity of the spray solution and affect the rheological profile by producing larger spray particles. Polymer-based adjuvants increase the possibility of spray particles shattering, increasing drift. However, use of polymer-based drift reduction technology adjuvants for aerial applications of active ingredients is not recommend. Although they have an efficient loading capacity, the necessary polymers are expensive, limiting scalability.

Lipid-based nanomaterials have great potential to encapsulate hydrophilic, hydrophobic, and lipophilic active ingredients, and are commonly used in the pharmaceutical field. However, scalable production is significantly limited by cost.

Porous inorganic nanomaterials, such as silica nanoparticles, are effective at encapsulating bioactive molecules, but face limitations in biodegradability and scalability. These polymer-coated nanoparticles suffer from various limitations such as poor thermal and chemical stability, rapid elimination by the plant enzyme system, and degradation of some polymers, resulting in the formation of acidic monomers and decreased pH value within the polymer matrix. Clay nanoparticles are economically viable and provide great opportunities for developing multifunctional nanocarrier materials, but are energy intensive, requiring high heat for production. These alternatives cannot be modified as easily to provide targeted delivery to plants.

In some embodiments, an anucleated cell-based minicell platform has advantages in cost and biodegradability. The minicell platforms are easily scaled through common, industrial fermentation practices. Once scaled, they can be purified through a series of centrifugation and/or filtration steps. The self-assembly of the carbohydrate-binding modules to the surface of minicells significantly cuts the cost of making a targeting bioparticle. Additionally, an anucleated cell-based minicell platform is advantageous compared to other encapsulation technologies in terms of biocompatibility for plant and environmental use; this is because the anucleated cell-based minicell platform is derived by safe, commonly found microbes that are native to the applied areas and can safely biodegrade to be reused by the ecosystem. This platform suitable for scalable, non-toxic delivery can play an significant role in the field of agriculture.

In order to solve problems of conventional agrochemicals that are easily degraded or evaporated before they reach their intended target, the present disclosure provides an anucleated cell-based platform for the encapsulation and delivery of agricultural compounds aims to protect the bioactivity from external factors until the compounds are applied to a target and to be slowly released to the intended target. The various mechanisms by which agrochemicals are typically lost to the environment are averted using the disclosed minicell-based encapsulation and delivery platform. This is because the lipid-bilayer of the minicell acts as an effective layer of protection against harsh environmental conditions. Specifically, the internalization of the active inside of the minicell protects the compounds against sharp changes in temperature, pH, or strong exposure to light. In other words, the minicell protects the compounds against volatilization, photolytic degradation, and hydrolysis. Therefore, the agricultural compounds can remain protected from adverse external factors and is allowed for gradual and/or controlled release to intended targets via minicell-based platform that encapsulates the agricultural compound of interest.

Furthermore, the other benefit of the present disclosure provides an anucleated cell-based platform for the encapsulation and delivery of agricultural compounds is that this platform offers the improved and enhanced targeting capability to the plant and its microenvironment. Due to degradation and evaporation, agrochemicals are heavily lost. On the other hand, agrochemicals are also lost and even contaminate the environment by drifting off plants and leaching into the soil and groundwater systems, and then goes through aerosolization. The inherent surface chemistry of the outer membrane of the minicell-based bioparticle naturally mimics that of bacteria. This is significant because there are many types of bacteria that live symbiotically in a microbiome on the surface of plant leaves, stems, and in their root system. By using the minicell-based platform, biological membrane of the minicell has natural adherence to the various surfaces of plants. This feature allows for delivering encapsulated agrochemical in the minicell chassis that is targeted to adhere to plant surfaces and the soil microenvironment around the plant's root system. In addition to relying on the natural adherence of the minicell-based bioparticle to plants, the present disclosure teaches uses of genetic engineering to give rise to surface-expressing moiety fused with specific binding domain on the membrane of the minicell. In this way its ability to target the plant or the pest is significantly enhanced.

In some embodiments, the present disclosure provides the genetic engineering techniques to make minicell-based platform with binding domains/motifs that functionalize the surface of the minicell. Proteins including specific binding domains and/or motifs are expressed on the surface of the minicells and specifically target binding sites that are present on the surface of plants or pests.

In some embodiments, minicell-based platform can be functionalized by proteins with carbohydrate binding modules (CBMs) that can target and bind to carbohydrates such as cellulose, xylan, chitin, and lignin, which are important and ubiquitous structural components of plant cell walls. Because CBMs can recognize their binding site present on a subject such as a plant or a pest, the minicell-based platform comprising the functionalized binding domain allows for targeting with high specificity.

In some embodiments, the use of CBMs is not limited to agriculture uses. CBMs can be used for the purification of active ingredients or biomolecules through the means of cellulose columns. Supplementary to the surface chemistry of the minicell-based platform, the relative mass of the bioparticle can also significantly mitigate the off-target exposure of active compounds due to aerosolization and leaching. By concentrating and encapsulating actives in the relatively large chassis of the minicell before being sprayed, the compound is less susceptible to aerosolization or drift caused by wind when compared to spraying free-floating compounds. Furthermore, the larger size of the minicell encapsulation and delivery platform can mitigate the leaching of actives through the soil and into groundwater supplies.

Agricultural Compounds

The present disclosure provides an anucleated cell-based platform for the encapsulation and delivery of agricultural compounds. In some embodiments, agricultural compounds comprise agrochemicals.

The term "agrochemical" as used herein means a chemical substance, whether naturally or synthetically obtained, which is applied to a plant, to a pest or to a locus thereof to result in expressing a desired biological activity. The term "biological activity" as used herein means elicitation of a stimulatory, inhibitory, regulatory, therapeutic, toxic or lethal response in a plant or in a pest such as a pathogen, parasite or feeding organism present in or on a plant or the elicitation of such a response in a locus of a plant, a pest or a structure. The term "plant" includes but shall not be limited to all food, fiber, feed and forage crops (pre and post harvest, seed and seed treatment), trees, turf and ornamentals. Examples of agrochemical substances include, but are not limited to, chemical pesticides (such as herbicides, algicides, fungicides, bactericides, viricides, insecticides, acaricides, miticides, nematicides and molluscicides), herbicide safeners, plant growth regulators (such as hormones and cell grown agents), fertilizers and nutrients, gametocides, defoliants, desiccants, mixtures thereof and the like.

In some embodiments, an agricultural compound includes, but is not limited to a pesticide, an herbicide, an insecticide, a fungicide, a nematicide, a fertilizer, a nutrient, a plant growth regulator such as a hormone or a chemical growth agent, and any combination thereof.

Pesticides/Insecticides

In some embodiments, a composition for a stable and targeted delivery of agricultural compounds comprises an anucleated cell produced according to methods described herein and/or having at least one non-expressed agricultural compound as described herein. The composition may include one or more insecticides/pesticides. The pesticides/insecticides include, but are not limited to ammonium carbonate, aqueous potassium silicate, boric acid, copper sulfate, elemental sulfur, lime sulfur, sucrose octanoate esters, 4-[[(6-Chlorpyridin-3-yl)methyl](2, 2-difluorethyl)amino]furan-2(5H)-on, abamectin, notenone, fenazaquin, fenpyroximate, pyridaben, pyrimedifen, tebufenpyrad, tolfenpyrad, acephate, emamectin benzoate, lepimectin, milbemectin, hdroprene, kinoprene, methoprene, fenoxycarb, pyriproxyfen, methryl bromide and other alkyl halides, fulfuryl fluoride, chloropicrin, borax, disodium octaborate, sodium borate, sodium metaborate, tartar emetic, dazomet, metam, pyrifluquinazon, flofentezine, diflovidazin, hexythiazox, bifenazate, thiamethoxam, fenpyroximate, azadirachtin, permethrin, esfenvalerate, acetamiprid, azadirachtin, pyrethrin, imidicloprid, beta-cyfluthrin, sulfotep, tebupirimfos, temephos, terbufos, tetrachlorvinphos, thiometon, triazophos, alanycarb, aldicarb, bendiocarb, benfluracarb, butocarboxim, butoxycarboxim, carbaryl, carbofuran, carbosulfan, ethiofencarb, fenobucarb, formetanate, furathiocarb, isoprocarb, methiocarb, methymyl, metolcarb, oxamyl, primicarb, propoxur, thiodicarb, thiofanox, triazamate, trimethacarb, XMC, xylylcarb, acephate, azamethiphos, azinphos-ethyl, azinphos-methyl, cadusafos, chlorethoxyfox, trichlorfon, vamidothion, chlordane, endosulfan, ethiprole, fipronil, acrinathrin, allethrin, bioallethrin, bioalletherin X-cyclopentenyl, bioresmethrin, cyclorothrin, cyfluthrin, cyhalothrin, cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, halfenprox, kadathrin, phenothrin [(1R)-trans-isomer] prallethrin, pyrethrins (pyrethrum), resmethrin, silafluofen, tefluthrin, tetramethrin, tetramethrin [(1R)-isomers], tralomethrin, transfluthrin, alpha-cypermethrin, beta-cyfluthrin, beta-cypermethrin, d-cis-trans allethrin, d-trans allethrin, gamma-cyhalothrin, lamda-cyhalothrin, tau-fluvalinate, theta-cypermethrin, zeta-cypermethrin, methoxychlor, nicotine, sulfoxaflor, acetamiprid, clothianidin, dinotefuran, nitenpyram, thiacloprid, thiamethoxan, tebuprimphos, beta-cyfluthrin, clothianidin, flonicamid, hydramethylnon, amitraz, flubendiamide, blorantraniliprole, lambda cyhalothrin, spinosad, gamma cyhalothrin, *Beauveria bassiana, capsicum* oleoresin extract, garlic oil, carbaryl, chlorpyrifos, sulfoxaflor, lambda cyhalothrin, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphosflu-acrypyrim, tebufenozide, chlorantraniliprole, *Bacillus thuringiensis* subs. Kurstaki, terbufos, mineral oil, fenpropathrin, metaldehyde, deltamethrin, diazinon, dimethoate, diflubenzuron, pyriproxyfen, reosemary oil, peppermint oil, geraniol, azadirachtin, piperonyl butoxide, cyantraniliprole, alpha cypermethrin, tefluthrin, malathion, *Bacillus thuringiensis* subsp. *israelensis*, dicofol, bromopropylate, benzoximate, azadirachtin, flonicamid, soybean oil, Chromobacterium subtsugae strain PRAA4-1, zeta cypermethrin, phosmet, methoxyfenozide, paraffinic oil, spirotetramat, methomyl, Metarhizium anisopliae strain F52, ethoprop, tetradifon, propargite, fenbutatin oxide, azocyclotin, cyhexatin, diafenthiuron, *Bacillus sphaericus*, etoxazole, flupyradifurone, azadirachtin, *Beauveria bassiana*, cyflumetofen, azadirachtin, chinomethionat, acephate, Isariafumosorosea Apopka strain 97, sodium tetraborohydrate decahydrate, emamectin benzoate, cryolite, spinetoram, *Chenopodium ambrosioides* extract, dinotefuran, carbaryl, acequinocyl, flupyradifurone, iron phosphate, kaolin, buprofezin, cyromazine, chromafenozide, halofenozide, methoxyfenozide, tebufenozide, bistrifluron, chlorfluazuron, diflubenzuron, flucycloxuron, flufenoxuron, hexaflumuron, lufenuron, nocaluron, noviflumuron, teflubenzuron, triflumuron, bensultap, cartap hydrochloride, thiocyclam, thiosultap-sodium, DNOC, chlorfenapyr, sulfuramid, phorate, tolfenpyrad, sulfoxaflor, neem oil, *Bacillus thuringiensis* subsp. tenebrionis strain SA-10, cyromazine, heat-killed *Burkholderia* spp., cyantraniliprole, cyenopyrafen, cyflumetofen, sodium cyanide, potassium cyanide, calcium cyanide, aluminum phosphide, calcium phosphide, phosphine, zinc phosphide, spriodiclofen, spiromesifen, spirotetramat, metaflumizone, flubendiamide, pyflubumide, oxamyl, *Bacillus thuringiensis* subsp. *aizawai*, etoxazole, and esfenvalerate.

Herbicides

In some embodiments, a composition for a stable and targeted delivery of agricultural compounds comprises an anucleated cell produced according to methods described herein and/or having at least one non-expressed agricultural compound as described herein. The composition may include one or more herbicides. The herbicides include, but are not limited to 2,4-D, 2,4-DB, acetochlor, acifluorfen, alachlor, ametryn, atrazine, aminopyralid, benefin, bensulfuron, bensulide, bentazon, bromacil, bromoxynil, butylate, carfentrazone, chlorimuron, chlorsulfuron, clethodim, clomazone, clopyralid, cloransulam, cycloate, DCPA, desmedipham, dicambia, dichlobenil, diclofop, diclosulam, diflufenzopyr, dimethenamid, diquat, diuron, DSMA, endothall, EPTC, ethalfluralin, ethofumesate, fenoxaprop, fluazifop-P, flucarbzone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaflutole, lactofen, linuron, MCPA, MCPB, mesotrione, metolachlor-s, metribuzin, indaziflam, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithio ac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, and triflusulfuron.

Fungicides

In some embodiments, a composition for a stable and targeted delivery of agricultural compounds comprises an anucleated cell produced according to methods described herein and/or having at least one non-expressed agricultural compound as described herein. The composition may include one or more fungicides. The fungicides include, but are not limited to captan, carboxin, ethaboxam, fludioxonil, mefenoxam, fludioxonil, thiabendazole, thiabendaz, ipconazole, cyazofamid, zoxamide, metalaxyl, PCNB, metaconazole, pyraclostrobin, *Bacillus subtilis* strain QST 713, sedaxane, thiamethoxam, fludioxonil, thiram, tolclofos-methyl, trifloxystrobin, *Bacillus subtilis* strain MBI 600, pyraclostrobin, fluoxastrobin, *Bacillus pumilus* strain QST 2808, chlorothalonil, copper, flutriafol, fluxapyroxad, gludioxonil, penthiopyrad, triazole, propiconaozole, tebuconazole, fluoxastrobin, pyraclostrobin, picoxystrobin, qols, tetraconazole, trifloxystrobin, cyproconazole, flutriafol, SDHI, EBDCs, sedaxane, MAXIM QUATTRO (gludioxonil, mefenoxam, and thiabendaz), RAXIL (tebuconazole, metalaxyl, and ethoxylated tallow alkyl amines), and benzovindiflupyr.

In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil.

In some examples, fungicide can be a systemic fungicide, including, but are not limited to the following: carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances which can kill or otherwise prevent the growth of fungi.

Nematicides

In some embodiments, a composition for a stable and targeted delivery of agricultural compounds comprises an anucleated cell produced according to methods described herein and/or having at least one non-expressed agricultural compound as described herein. The composition may include one or more nematicides. The nematicides include, but are not limited to D-D, 1,3-dichloropropene, ethylene dibromide, 1,2-dibromo-3-chloropropane, methyl bromide, chloropicrin, metam sodium, dazomet, methylisothiocyanate, sodium tetrathiocarbonate, aldicarb, aldoxycarb, carbofuran, oxamyl, ethoprop, fenamiphos, cadusafos, fosthiazate, terbufos, fensulfothion, phorate, DiTera, clandosan, sincocin, methyl iodide, propargyl bromide, 2,5-dihydroxymethyl-3,4-dihydroxypyrrolidine (DMDP), any one or more of the avermectins, sodium azide, furfural, *Bacillus firmus*, abamectrin, thiamethoxam, fludioxonil, clothiandin, salicylic acid, and benzo-(1,2,3)-thiadiazole-7-carbothioic acid S-methyl ester.

Fertilizers

In some embodiments, a composition for a stable and targeted delivery of agricultural compounds comprises an anucleated cell produced according to methods described herein and/or having at least one non-expressed agricultural compound as described herein. The composition may include one or more fertilizers. For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. Further examples of fertilizers which may be useful in embodiments include Ammonium nitrate, Ammonium sulfate, anhydrous ammonia, calcium nitrate/urea, oxamide, potassium nitrate, urea, urea sulfate, ammoniated superphosphate, diammonium phosphate, nitric phosphate, potassium carbonate, potassium metaphosphate, calcium chloride, magnesium ammonium phosphate, magnesium sulfate, ammonium sulfate, potassium sulfate, and others disclosed herein.

Growth Regulators

In some embodiments, a composition for a stable and targeted delivery of agricultural compounds comprises an anucleated cell produced according to methods described herein and/or having at least one non-expressed agricultural compound as described herein. The composition may include one or more growth regulators. The growth regulators include, but are not limited to Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-triiodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Other Agricultural Compounds

In some embodiments, some examples of rodenticides may include selected from the group of substances consisting of 2-isovalerylindan-1,3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In some embodiments, control agents have antibacterial properties. The control agents with antibacterial properties include, but are not limited to Streptomycin, oxytetracycline, oxolinic acid, or gentamicin. Other examples of antibacterial compounds include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

Exemplary agricultural compounds include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Veqetables Insecticides: Aldicarb, *Bacillus thuringiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin benzoate, Forthiazate, Fenamiphos, Cadusaphos, Pyriproxifen, Fenbutatin oxide, Hexthiazox, Methomyl, 4-[[(6-Chlorpyridin-3-yl)methyl](2,2-difluorethyl)amino]furan-2(5H)-on; Fruits Vegetables Fungicides: Carbendazim, Chlorothalonil, EBDCs, Sulphur, Thiophanate-methyl, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, loxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, lodosulfuron, Propoxycarbazone, Picolin-afen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Fluoxastrobin; Cereals Insecticides: Dimethoate, Lambda-cyhalothrin, Deltamethrin, alpha-Cypermethrin, β-cyfluthrin, Clothianidin, Thiamethoxam, Thiacloprid, Acetamiprid, Dinetofuran, Clorphyriphos, Metamidophos, Oxidemethon methyl, Pirimicarb, Methiocarb; Maize Herbicides: Atrazine, Alachlor, Bromoxynil, Acetochlor, Dicamba, Clopyralid, S-Dimethenamid, Glufosinate, Glyphosate, Isoxaflutole, S-Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Fipronil, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Lufenuron, Triflumoron, Tefluthrin, Tebupirim-phos, Ethiprole, Cyazypyr, Thiacloprid, Acetamiprid, Dinetofuran, Avermectin, Methiocarb, Spirodiclofen, Spiro-tetramat; Maize Fungicides: Fenitropan, Thiram, Tebuconazole, Trifloxystrobin; Rice Herbicides: Butachlor, Propanil, Azimsulfuron, Bensulfuron, Cyhalo-fop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pre-tilachlor, Mesotrione, Tefuryltrione, Oxadiazone, Fenox-aprop, Pyrimisulfan; Rice Insecticides: Diazinon, Fenitro-thion, Fenobucarb, Monocrotophos, Benfuracarb, Buprofezin, Dinotefuran, Fipronil, Isopro-carb, Thiacloprid, Chromafenozide, Thiacloprid, Dinote-furan, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cyper-methrin, Chlorpyriphos, Cartap, Methamidophos, Etofen-prox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl) methyl] (2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, 3-Cyfluthrin, gamma and lambda Cyhalothrin, 4-[[(6-Chlorpyridin-3-yl)methyl] (2,2-difluorethyl)amino]furan-2(5H)-on, Spirotetramat, Spinodiclofen, Triflumuron, Flonicamid, Thiodicarb, beta-Cyfluthrin; Soybean Fungi-cides: Cyproconazole, Epoxiconazole, Flutriafol, Pyraclostrobin, Tebuconazole, Trifloxystrobin, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepral-oxydim, Quizalofop; Sugarbeet Insecticides: Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluor-ethyl) amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Trifluralin Ethametsulfuron, Quinmerac, Quizalofop, Clethodim, Tepraloxydim; Canola Fungicides: Azox-ystrobin, Carbendazim, Fludioxonil, Iprodione, Vinclozolin; Canola Insecticides: Carbofuran organophos-phates, Pyrethroids, Thiacloprid, Deltamethrin, Clothianidin, Thiamethoxam, Acetamiprid, Dineto-furan, 3-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl] (2,2-difluorethyl)amino]furan-2 (5H)-on.

TABLE 1

Exemplary agricultural compounds - insecticides - associated with various modes of action

| Mode of Action | Compound class | Exemplary insecticides | Physiological function(s) affected |
|---|---|---|---|
| acetylcholinesterase (AChE) inhibitors | carbamates | Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, Xylylcarb | Nerve and muscle |
| acetylcholinesterase (AChE) inhibitors | organo-phosphates | Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/ DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, | Nerve and muscle |

TABLE 1-continued

Exemplary agricultural compounds - insecticides - associated with various modes of action

| Mode of Action | Compound class | Exemplary insecticides | Physiological function(s) affected |
|---|---|---|---|
| | | Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, Vamidothion | |
| GABA-gated chloride channel blockers | cyclodiene organochlorines | Chlordane, Endosulfan | Nerve and muscle |
| GABA-gated chloride channel blockers | phenylpyrazoles (Fiproles) | Ethiprole, Fipronil | Nerve and muscle |
| sodium channel modulators | pyrethroids, pyrethrins | Acrinathrin, Allethrin, Bioallethrin, Bioallethrin S-cyclopentenyl, Bioresmethrin, Cycloprothrin, Cyfluthrin, Cyhalothrin, Cypermethrin, Cyphenothrin [(1R)-trans- isomers], Deltamethrin, Empenthrin [(EZ)-(1R)- isomers], Esfenvalerate, Etofenprox, Fenpropathrin, Fenvalerate, Flucythrinate, Flumethrin, Halfenprox, Kadathrin, Phenothrin [(1R)-trans- isomer], Prallethrin, Pyrethrins (pyrethrum), Resmethrin, Silafluofen, Tefluthrin, Tetramethrin, Tetramethrin [(1R)-isomers], Tralomethrin, Transfluthrin, alpha-Cypermethrin, beta-Cyfluthrin, beta-Cypermethrin, d-cis-trans Allethrin, d-trans Allethrin, gamma-Cyhalothrin, lambda-Cyhalothrin, tau-Fluvalinate, theta-Cypermethrin, zeta-Cypermethrin | Nerve and muscle |
| sodium channel modulators | DDT, methoxychlor | DDT, methoxychlor | Nerve and muscle |
| nicotinic acetylcholine receptor (nAChR) competitive modulators | neonicotinoids | Acetamiprid, Clothianidin, Dinotefuran, Nitenpyram, Thiacloprid, Thiamethoxam | Nerve and muscle |

TABLE 1-continued

Exemplary agricultural compounds - insecticides - associated with various modes of action

| Mode of Action | Compound class | Exemplary insecticides | Physiological function(s) affected |
|---|---|---|---|
| nicotinic acetylcholine receptor (nAChR) competitive modulators | nicotine | nicotine | Nerve and muscle |
| nicotinic acetylcholine receptor (nAChR) competitive modulators | sulfoximines | sulfoxaflor | Nerve and muscle |
| nicotinic acetylcholine receptor (nAChR) competitive modulators | butenolides | Flupyradifurone | Nerve and muscle |
| nicotinic acetylcholine receptor (nAChR) allosteric modulators | spinosyns | Spinetoram, Spinosad | Nerve and muscle |
| Glutamate-gated chloride channel (GluCl) allosteric modulators | avermectins, milbemycins | Abamectin, Emamectin benzoate, Lepimectin, Milbemectin | Nerve and muscle |
| juvenile hormone mimics | juvenile hormone analogues | Hydroprene, Kinoprene, Methoprene | Growth |
| juvenile hormone mimics | Fenoxycarb | Fenoxycarb | Growth |
| juvenile hormone mimics | Pyriproxyfen | Pyriproxyfen | Growth |
| miscellaneous non-specific (multi-site) inhibitors | alkyl halides | Methyl bromide and other alkyl halides | Unknown or non-specific |
| miscellaneous non-specific (multi-site) inhibitors | Chloropicrin | Chloropicrin | Unknown or non-specific |
| miscellaneous non-specific (multi-site) inhibitors | fluorides | Cryolite, sulfuryl fluoride | Unknown or non-specific |
| miscellaneous non-specific (multi-site) inhibitors | borates | Borax, Boric acid, Disodium octaborate, Sodium borate, Sodium metaborate | Unknown or non-specific |
| miscellaneous non-specific (multi-site) inhibitors | tartar emetic | tartar emetic | Unknown or non-specific |
| miscellaneous non-specific (multi-site) inhibitors | methyl isothiocyanate generators | Dazomet, Metam | Unknown or non-specific |
| modulators of chordotonal organs | Pyridine azomethine derivatives | Pyrifluquinazon | Nerve and muscle |
| mite growth inhibitors | Clofentezine, Diflovidazin, Hexythiazox | Clofentezine, Diflovidazin, Hexythiazox | Growth |
| mite growth inhibitors | Etoxazole | Etoxazole | Growth |
| microbial disruptors of insect midgut membranes | *Bacillus thuringiensis* and the insecticidal proteins they produce | Bt var. *aizawai*, Bt var. *israelensis*, Bt var. *kurstaki*, Bt var. *tenebrionensis* | Midgut |

TABLE 1-continued

Exemplary agricultural compounds - insecticides - associated with various modes of action

| Mode of Action | Compound class | Exemplary insecticides | Physio-logical function(s) affected |
|---|---|---|---|
| microbial disruptors of insect midgut membranes | *Bacillus sphaericus* | *Bacillus sphaericus* | Midgut |
| inhibitors of mitochondrial ATP synthase | Diafenthiuron | Diafenthiuron | Respira-tion |
| inhibitors of mitochondrial ATP synthase | organotin miticides | Azocyclotin, Cyhexatin, Fenbutatin oxide | Respira-tion |
| inhibitors of mitochondrial ATP synthase | Propargite | Propargite | Respira-tion |
| inhibitors of mitochondrial ATP synthase | Tetradifon | Tetradifon | Respira-tion |
| uncouplers of oxidative phosphorylation via disruption of the proton gradient | Chlorfenapyr, DNOC, Sulfuramid | Chlorfenapyr, DNOC, Sulfuramid | Respira-tion |
| Nicotinic acetylcholine receptor (nAChR) channel blockers | nereistoxin analogues | Bensultap, Cartap hydrochloride, Thiocyclam, Thiosultap-sodium | Nerve and muscle |
| inhibitors of chitin biosynthesis, type 0 | benzoylureas | Bistrifluron, Chlorfluazuron, Diflubenzuron, Flucycloxuron, Flufenoxuron, Hexaflumuron, Lufenuron, Noviflumuron, Teflubenzuron, Triflumuron | Growth |
| inhibitors of chitin biosynthesis, type 1 | Buprofezin | Buprofezin | Growth |
| moulting disruptor, Dipteran | Cyromazine | Cyromazine | Growth |
| ecdysone receptor agonists | diacylhydra-zines | Chromafenozide, Halofenozide, Methoxyfenozide, Tebufenozide | Growth |
| octopamine receptor agonists | Amitraz | Amitraz | Nerve and muscle |
| mitochondrial complex III electron transport inhibitors | Hydra-methylnon | Hydramethylnon | Respira-tion |
| mitochondrial complex III electron transport inhibitors | Acequinocyl | Acequinocyl | Respira-tion |
| mitochondrial complex III electron transport inhibitors | Fluacrypyrim | Fluacrypyrim | Respira-tion |
| mitochondrial complex III electron transport inhibitors | Bifenazate | Bifenazate | Respira-tion |
| mitochondrial complex I electron transport inhibitors | Meti acaricides and insecticides | Fenazaquin, Fenpyroximate, Pyridaben, Pyrimidifen, Tebufenpyrad, Tolfenpyrad | Respira-tion |
| mitochondrial complex I electron transport inhibitors | Rotenone | Rotenone | Respira-tion |
| voltage-dependent sodium channel blockers | semicarbazones | Metaflumizone | Nerve and muscle |
| inhibitors of acetyl CoA carboxylase | tetronic and tetramic acid derivatives | Spirodiclofen, Spiromesifen, Spirotetramat | Growth |

TABLE 1-continued

Exemplary agricultural compounds - insecticides - associated with various modes of action

| Mode of Action | Compound class | Exemplary insecticides | Physio-logical function(s) affected |
|---|---|---|---|
| mitochondrial complex IV electron transport inhibitors | phosphides | Aluminium phosphide, Calcium phosphide, Phosphine, Zinc phosphide | Respira-tion |
| mitochondrial complex IV electron transport inhibitors | cyanides | Calcium cyanide, Potassium cyanide, Sodium cyanide | Respira-tion |
| mitochondrial complex II electron transport inhibitors | beta-ketonitrile derivatives | Cyenopyrafen, Cyflumetofen | Respira-tion |
| mitochondrial complex II electron transport inhibitors | carboxanilides | Pyflubumide | Respira-tion |
| ryanodine receptor modulators | diamides | Chlorantraniliprole, Cyantraniliprole, Flubendiamide | Nerve and muscle |
| Chordotonal organ modulators - undefined target site | Flonicamid | Flonicamid | Nerve and muscle |
| compounds of unknown or uncertain mode of action | Azadirachtin | Azadirachtin | Unknown |
| compounds of unknown or uncertain mode of action | Benzoximate | Benzoximate | Unknown |
| compounds of unknown or uncertain mode of action | Bromopropylate | Bromopropylate | Unknown |
| compounds of unknown or uncertain mode of action | Chinomethionat | Chinomethionat | Unknown |
| compounds of unknown or uncertain mode of action | Dicofol | Dicofol | Unknown |
| compounds of unknown or uncertain mode of action | lime sulfur | lime sulfur | Unknown |
| compounds of unknown or uncertain mode of action | Pyridalyl | Pyridalyl | Unknown |
| compounds of unknown or uncertain mode of action | sulfur | sulfur | Unknown |

Agriculturally Acceptable Carrier

Compositions described herein can comprise an agriculturally acceptable carrier. The composition useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a dessicant, a bactericide, a nutrient, or any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide).

In some embodiments, an anucleated cell-based platform described herein can be mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

Additional examples of agriculturally acceptable carriers include dispersants (e.g., polyvinylpyrrolidone/vinyl acetate PVPIVA S-630), surfactants, binders, and filler agents.

Binding Domain for Cell Adhesion

In some embodiments, the anucleated cell-based platform described herewith express binding domains. These domains allow for better retention of the minicells on plant surfaces, which prevents runoff or drift of agrochemicals encapsulated within the minicells. They can also improve adhesion to the targeted pests to ensure the administration of an effective dose of the agrochemicals. Once the minicells are on the plant, the chemical will slowly release into the environment.

In some embodiments, the anucleated cell described herewith expresses a fusion protein, which comprises at least one surface expressing moiety and at least one plant cell adhesion moiety. The plant cell adhesion moiety comprises a carbohydrate binding module comprising a carbohydrate binding module selected from the group consisting of: a cellulose binding domain, a xylan binding domain, a chitin binding domain, and a lignin binding domain.

In some embodiments, the anucleated cell expresses a polypeptide on its surface that increases adhesion to a plant surface. The polypeptide is a plant adhesion polypeptide on its surface. In some embodiments, the polypeptide is a carbohydrate binding module that is displayed on its surface. In other embodiments, the polypeptide is a carbohydrate binding module that is displayed on its surface.

A carbohydrate-binding module (CBM) is a protein domain found in carbohydrate-active enzymes (for example glycoside hydrolases). The majority of these domains have carbohydrate-binding activity. Some of these domains are found on cellulosomal scaffoldin proteins. CBMs are also known as cellulose-binding domains. CBMs are classified into numerous families, based on amino acid sequence similarity. CBMs of microbial glycoside hydrolases play a central role in the recycling of photosynthetically fixed carbon through their binding to specific plant structural polysaccharides. CBMs can recognize both crystalline and amorphous cellulose forms. CBMs are the most common non-catalytic modules associated with enzymes active in plant cell-wall hydrolysis. Many putative CBMs have been identified by amino acid sequence alignments but only a few representatives have been shown experimentally to have a carbohydrate-binding function. By binding to polysaccharides, CBMs bring appended catalytic domains into intimate contact with target substrates and thus potentiate catalysis. CBMs with the capacity to bind cellulose are associated with enzymes that hydrolyze both cellulose and other cell wall polymers such as xylan, mannan, pectin, and noncellulosic (3-glucans.

Cellulose binding domains (CBDs) have been described as useful agents for attachment of molecular species to cellulose (U.S. Pat. Nos. 5,738,984 and 6,124,117). Indeed, as cotton is made up of 90% cellulose, CBDs have proved useful for delivery of so called "benefit agents" onto cotton fabrics, as is disclosed in WO9800500 where direct fusions between a CBD and an enzyme were used utilizing the affinity of the CBD to bind to cotton fabric. The use of similar multifunctional fusion proteins for delivery of encapsulated benefit agents was claimed in WO03031477, wherein the multifunctional fusion proteins consist of a first binding domain which is a celllulose binding domain and a second binding domain, wherein either the first binding domain or the second binding domain can bind to a microparticle. WO03031477 is exemplified using a bifunctional fusion protein consisting of a CBD and an anti-RR6 antibody fragment binding to a microparticle, which complex is deposited onto cotton treads or cut grass.

In some embodiments, the enzymatically active polypeptide displayed by the minicells of the invention comprises a CBM. Exemplary CBM from Cellulomonasfimi that is within the scope of the disclosure is used. In some embodiments, the cell adhesion moiety is fused to surface-expressing moiety. In other embodiments, the CBM is fused to surface-expressing moiety and is displayed on the surface of the minicells.

Surface Expression System

In some embodiments, the present disclosure teaches surface-expressing moiety that is fused to cell adhesion moiety. The surface-expressing moiety can be transmembrane protein and/or transmembrane domains that function as a linker protein to display the enzymatically active polypeptides having cell adhesion moiety on the surface of cells.

In some embodiments, surface-expressing moiety can be membrane-associated proteins including, but not limited to, transmembrane protein, membrane-anchoring protein, linker protein and/or domain thereof.

In some embodiments, the invention is drawn to display produced membrane-associated protein(s) fused to proteins of interest disclosed herein on the surface of the minicell. By way of non-limiting example, this structure may be an internally expressed membrane protein or chimeric construct to be inserted in or associated with the minicell membrane such that the extracellular domain or domain of interest is exposed on the outer surface of the minicell (expressed and displayed on the surface of the minicell or expressed in the parental cell to be displayed on the surface of the segregated minicell).

The displayed domain fused to a membrane-associated linker protein may be an cell adhesion domain including carbohydrate binding modules. In other embodiments.

Contacting such minicells with the appropriate substrate of the enzyme allows the substrate to be converted to reactant. When either the substrate or reactant is detectable, the reaction catalyzed by the membrane-bound enzyme may be quantified. In the latter instance, the minicells may be used to identify and isolate, from a pool of compounds, one or more compounds that inhibit or stimulate the activity of the enzyme represented by the displayed enzymatic moiety.

In some embodiments, the membrane-associated protein can be a fusion protein, i.e., a protein that comprises a first polypeptide having a first amino acid sequence and a second polypeptide having a second amino acid sequence, wherein the first and second amino acid sequences are not naturally present in the same polypeptide. At least one polypeptide in a membrane fusion protein is a "transmembrane protein/domain" "membrane-anchoring protein/domain" or "linker protein/domain". The transmembrane and membrane-anchoring domains of a fusion protein may be selected from membrane proteins that naturally occur in a prokaryote such as bacteria, a eukaryote, such as a fungus, a unicellular eukaryote, a plant and an animal, such as a mammal including a human. Such domains may be from a viral membrane protein naturally found in a virus such as a bacteriophage or a eukaryotic virus, e.g., an adenovirus or a retrovirus. Such domains may be from a membrane protein naturally found in an archaebacterium such as a thermophile.

Exemplary surface-expressing moieties include but are not limited to ice nucleation protein (INP) *Bordetella* serum-resistance killing protein (BRK), Adhesin Involved in Diffuse Adherence protein (AIDA) and/or an exported bacterial protein. "Exported bacterial proteins," generally refers to bacterial proteins that are transported across the plasma membrane and function as an anchor for membrane proteins. Exemplary exported bacterial proteins encompassed by the present invention, include, but are not limited to LamB (GenBank Accession No. AMC96895), OprF (GenBank Accession No. NP_792118), OmpA (GenBank Accession No. AIZ93785), Lpp (GenBank Accession No. P69776), MalE (GenBank Accession No. POAEX9), PhoA (GenBank Accession No. AIZ92470.1), B1a (GenBank Accession No. P62593), F1 or M13 major coat (J7I0P6—Uniprot No.), and F1 or M13 minor coat (P69168—Uniprot No.).

In some embodiments, for gram negative bacterial expression systems, enzymes of interest disclosed herein are immobilized to the surface of the minicells via wild type or mutant versions of the exported bacterial proteins such as LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), B1a (TEM-1 B-lactamase), F1 or M13 major coat (derived from Gene VIII), F1 or M13 minor coat (Gene III).

In other embodiments, a wild type and/or truncated version of the Ice Nucleation Protein (INP) can be used to immobilize enzymes on the surface of bacteria.

Surface Display System

Bacterial surface display technique enables the exogenous proteins or polypeptides displayed on the bacterial surface, while maintaining their relatively independent spatial structures and biological activities. The technique makes recombinant bacteria possess the expectant functions, subsequently, directly used for many applications. Many proteins could be used to achieve bacterial surface display, among them, autotransporter, a member of the type V secretion system of gram-negative bacteria, has been extensively studied because of its modular structure and apparent simplicity. However, autotransporter has not been widely used at present due to lack of a convenient genetic vector system.

The present disclosure teaches that autodisplay of an protein/polypeptide of interest requires an autotransporter protein in order to surface display a protein or peptide in a gram negative bacteria. The autotransporter proteins are broken down into 3 different subgroups, classical autotransporters (type Va), trimeric autotransporters adhesins (type Vb), and two partner secretion systems (type Vc).

Classic autotransporters (type Va) are thought to all share a common general structure which consists of a N-terminus signal peptide fused to the passenger protein that takes place of autotransport precursor protein, which provides transport across the cytoplasmic membrane. The N-terminus signal peptide normally utilizes the Secretion machinery in order to provide transport. This signal peptide is cleaved once the protein crosses the inner membrane. Outer membrane translocation is facilitated by the C-terminal domain of the autotransporter. This domain, known as the translocator domain, forms a β-barrel within the outer membrane. This autotransporter requires an additional linker domain due to the β-strand that closes barrel is directed towards the periplasm. Over 30 different proteins have been expressed as the passenger protein using this mechanism.

The trimeric autotransporters (type Vb) are similar to the classical autotransporters except that they cannot transport just one protein to the surface, they transport 3 (trimeric) proteins to the surface.

Type Vc autotransporters consist of a passenger and translocation domain, however both domains are expressed in separate genes. Both domains are transported across the inner membrane by the Secretion machinery, but interact with the periplasm via the polypeptide transport associated domain (POTRA). Due to the similarities between this mechanism of transport and the systems of transport that exist in chloroplasts and mitochondria, this system is expected to be able to transport extremely complex protein structures, but Vb or Vc systems of autotransport have been rarely used.

Enzymes are immobilized to the surface of the minicell by means of protein mediated membrane localization mechanisms including, but are not limited to the following linking proteins and mechanisms. In some embodiments, these systems include the BrkA protein, and AIDA-1 protein. The comparison of autotransporter and Ice Nucleation Protein as carrier proteins for protein display on the cell surface of *E. coli* is reported by Yang et al. 2013, *Progress in Biochemistry and Biophysics* 40(12): 1209-1219, which is herein incorporated by reference in its entirety.

AIDA-I Autotransporter System

One of the most widely studied autotransporter is AIDA-1 which naturally occurs in *E. coli*. It was originally discovered in a pathogenic strain of *E. coli* but was subsequently transferred to laboratory *E. coli* strains using both the pAIDA-1 plasmid and the pDT1 plasmids.

Figure 4A:
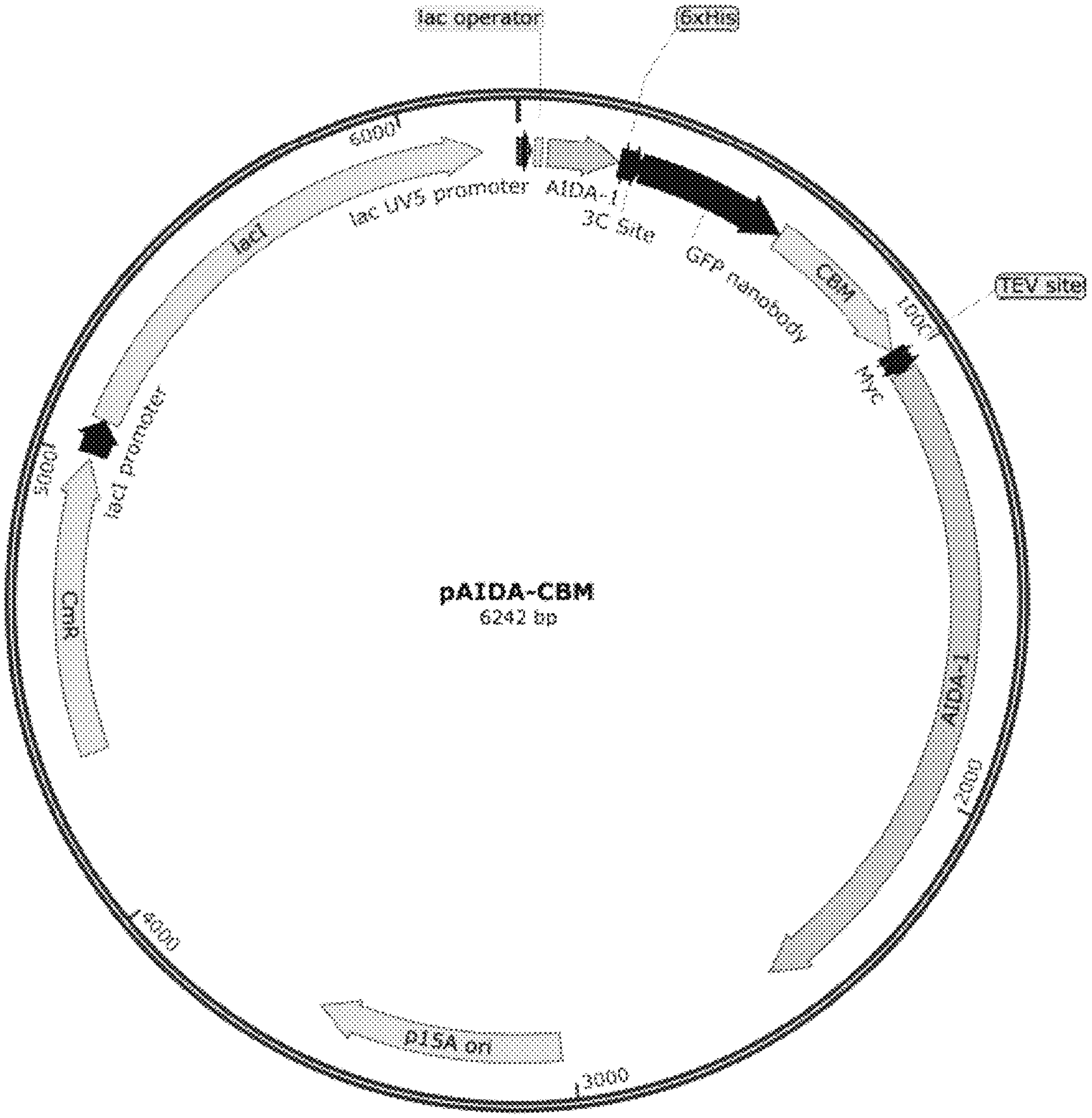
FIG. 4A illustrates an exemplary pAIDA-1-CBM vector with an AIDA-1 surface expression system for display of a CBM (Carbohydrate binding module) protein flanked by 6×His, GFP nanobody and Myc tags on the surface of minicells.
Figure 4B:
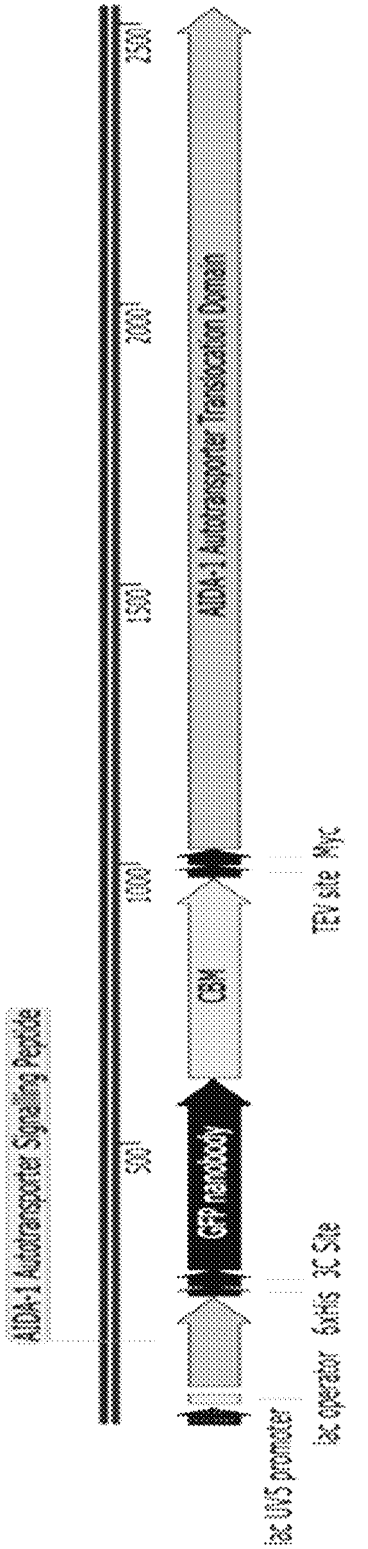
FIG. 4B illustrates an exemplary pAIDA-1 lipase surface expression cassette, comprising nucleotide sequences encoding AIDA-1 Autotransporter signal peptide, GFP nanopbody, CBM, and AIDA-1 autotransporter translocation domain with tags including 6×His Tag and Myc Tag as well as two protease cleavage sites including HRV3C and TEV.

In some embodiments, the present disclosure provides the pAIDA-1 expression vector in which a polynucleotide sequence encoding a protein of interest including CBM. For example, the recombinant pAIDA-1 expression vector with CBM-encoding gene is illustrated in FIGS. 4A and 4B. The AIDA-I autotransport system consists of an N-terminus 5 kDa signaling peptide, a 5 kDa linker region, and a 47 kDA C-terminus translocation unit. The passenger domain is located between the signaling peptide and the linker domain. This autotransporter with no protein in its passenger domain is a total of 63 kDa. The protein of interest is inserted into the passenger domain in order to enable surface expression. This corresponds genetically to the signaling peptide region of the protein being located between the NdeI and SalI, the passenger domain between KpnI and SacI, the linker region of the peptide between the XbaI and NotI restriction sites, and the rest of the protein corresponding to the C-terminus translocation unit.

The pAIDA-1-CBM expression vector contains the AIDA-I gene under inducible control with a lacUV5 promoter and includes 2 protein tags (6×His Tag and Myc Tag) and 2 protease cleavage sites (HRV3C and TEV) in order to enable surface expression analysis. FIGS. 4A and 4B illustrates the pAIDA-1 CBM expression vector. The TEV site is an amino acid sequence recognized by the tobacco etch virus. It is a well-known, highly specific protease. The HRV3C site is another highly specific protease cleavage site located C-terminus to the 6×His tag. Both of these protease cleavage sites are used for protein tag removal for analytical purposes if desired. The 6×His tag is located between the SalI and the KpnI site. This 6×his tag was used for immunofluorescent staining with THE™ His Tag antibody [FITC] from Genscript® as well as used for Cobalt Immobilized Metal Affinity Chromatography for purification of the protein for assay confirmation of presence. The TEV site is N-terminus of the Myc tag and located between SacI and XbaI restriction site within the AIDA-I gene located in the pAIDA-I plasmid. The Myc tag present on the plasmid can be used for immunofluorescent staining, however this capability was not utilized.

Further components of the plasmid include a lac operator and a lacI repressor gene placed under control of the lacI promoter. These three components work in conjunction with the lacUV promoter in order to regulate expression of the AIDA-I gene. The pAIDA-1 plasmid maintained in vivo by the pi 5a origin of replication which is a medium copy origin of replication. This differs from a low copy or high copy origin of replication simply by the relative number of copies of the plasmid maintained within the cell. The antibiotic resistance gene for this plasmid is chloramphenicol (CmR) under control of its own promoter.

Brk Auto Display

The Brk has been recently discovered as autotransporter (autodisplay) protein.

An autotransporter domain is a structural domain found in some bacterial outer membrane proteins. The domain is located at the C-terminal end of the protein and forms a beta-barrel structure. The barrel is oriented in the membrane such that the N-terminal portion of the protein, termed the passenger domain, is presented on the cell surface. With recently characterized autotransporter BrkA (*Bordetella* serum-resistance killing protein A) from *Bordetell apertussis*, BrkAutoDisplay system works better for surface display compared to other systems such as using the Ice Nucleation Protein (INP). The BrkAutoDisplay system for functional display of multiple exogenous proteins on the *E. coli* surface using BrkA autotransporter is exemplified by Sun et al. 2015, Microb. Cell Fact. 14:129, which is herein incorporated by reference in its entirety.

The BrkA protein (GenBank WP≥010931506.1) is found as a 1010 amino acid chain length protein in its native form. The first 59 amino acids represent the signal peptide and the Beta barrel is formed between amino acids 693-1010. The Translocation domain corresponds to amino acids 545-1010. The passenger domain corresponds to amino acids 60-544, which is replaced with the proteins of interest such as lipase and/or glucose isomerase. The first 59 amino acids and the Beta barrel region, 693-1010, represent the minimal translocation domain.

Figure 6A:
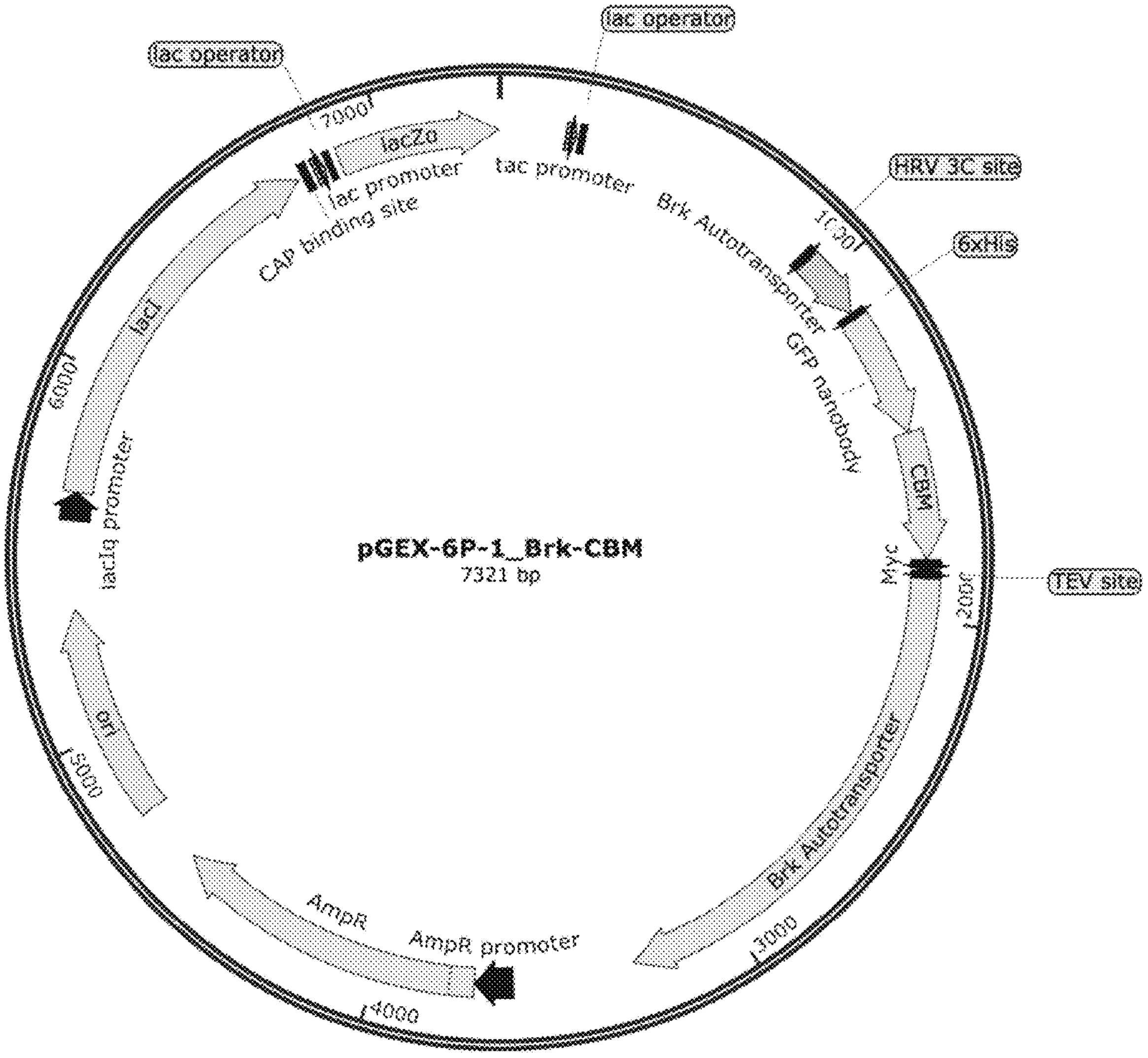
FIG. 6A illustrates an exemplary pGEX-6P-1 Brk-CBM vector with a serum resistance autotransporter BrkA surface expression system for display of a CBM protein flanked by 6×His, GFP nanobody and Myc tags on the surface of minicells.
Figure 6B:
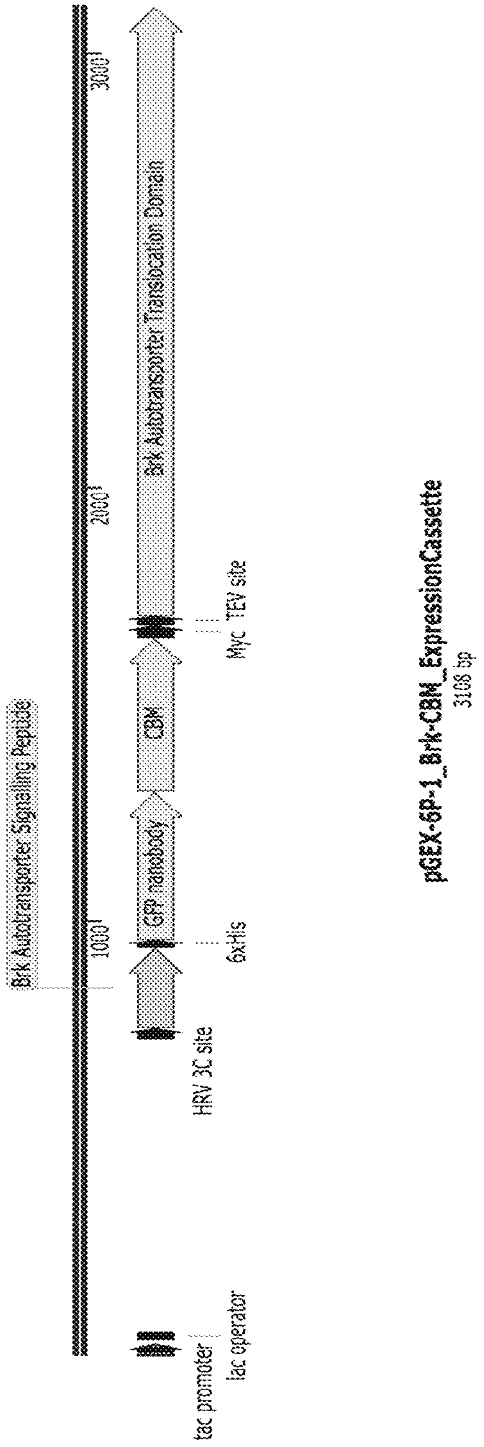
FIG. 6B illustrates an exemplary Brk-CBM surface expression cassette, comprising nucleotide sequences encoding Brk Autotransporter signal peptide, GFP nanopbody, CBM, and Brk autotransporter translocation domain with tags including 6× His Tag and Myc Tag as well as two protease cleavage sites including HRV3C and TEV.

The present disclosure teaches that a recombinant expression vector/construct for expression a fusion protein possesses two polynucleotide sequences encoding i) the first 228 amino acids (signal peptide and 5' partial passenger domain) and ii) the 694-1010 amino acid (Beta barrel domain) sequence of the BrkA protein. In this recombinant expression vector, polynucleotide sequences encoding protein of interest such as lipase are inserted between these two segments (i) one for the signal peptide and 5' partial passenger domain, and ii) the other for the Beta barrel domain) of the BrkA protein. Once the fusion protein is trafficked to the membrane, it is cleaved between the Asn731 and Ala732 residues corresponding to location of the wild-type BrkA protein, upon which the protein of interest including lipase located between the signal peptide and the B-barrel translocation domain, adopts its mature conformation and is displayed externally on the surface of the cells. The recombinant expression vector used herein is illustrated in FIGS. 6A and 6B. The pGEX-6P-1 Brk-lipase expression vector contains the AIDA-I gene under control with a tac promoter and includes protein tags (6×His Tag and Myc Tag) and two protease cleavage sites (HRV3C and TEV) in order to enable surface expression analysis. The uses of 6×His tag and Myc tag are well described above.

In further embodiments, the BrkAutodisplay system in the *E. coli* B strains including, but are not limited to BL21, BL21(DE3), LPS-modified BL21(DE3), B8 and BL21-AI shows a greater aggregation towards the polar ends of the cell membrane, resulting in a greater retention in the minicells because minicells bud off the polar ends from the parent cells. However, this phenomenon is not observed in the other minicell-producing cell lines such as the wild type P678-54 strain. The present disclosure teaches that the application of this autotransporter with *E. coli* B strain derivatives provides an advantage of greater retention of the surface displayed protein/enzyme of interest in the final minicell product.

Vectors

In some embodiments, pUC-57 vector is used for knocking out a gene of target including minC, minD, and minC/D for including the production of minicells from the protease-deficient strain. From the 5' and 3' ends of the gene of target, about 50 base pairs of nucleotide sequence (homologous arms) corresponding to the gene of target within the genome are used for homologous recombination to knock out the gene of target. This directs the gene of interest to the place in the genome to replace the gene of target that are aimed to be knocked out. Just inside of the homologous arms, hairpin loops were inserted. These hairpin loops, when transcribed to mRNA, do not allow for any translation of what is contained between the loops in which the translation starts outside of the hairpin loops. These hairpin loops are formed upon translation of DNA to RNA and are also known as stem loops. This allows for the insert to not interfere with the native promotion of the other genes in the min system. Due to the hairpin loops, the chloramphenicol cassette (CmR) that was contained within the insert was placed under control of its own promoter, the cat promoter. By including the hairpin loops, this promoter would also not affect the regulation of any genes.

Figure 18A:
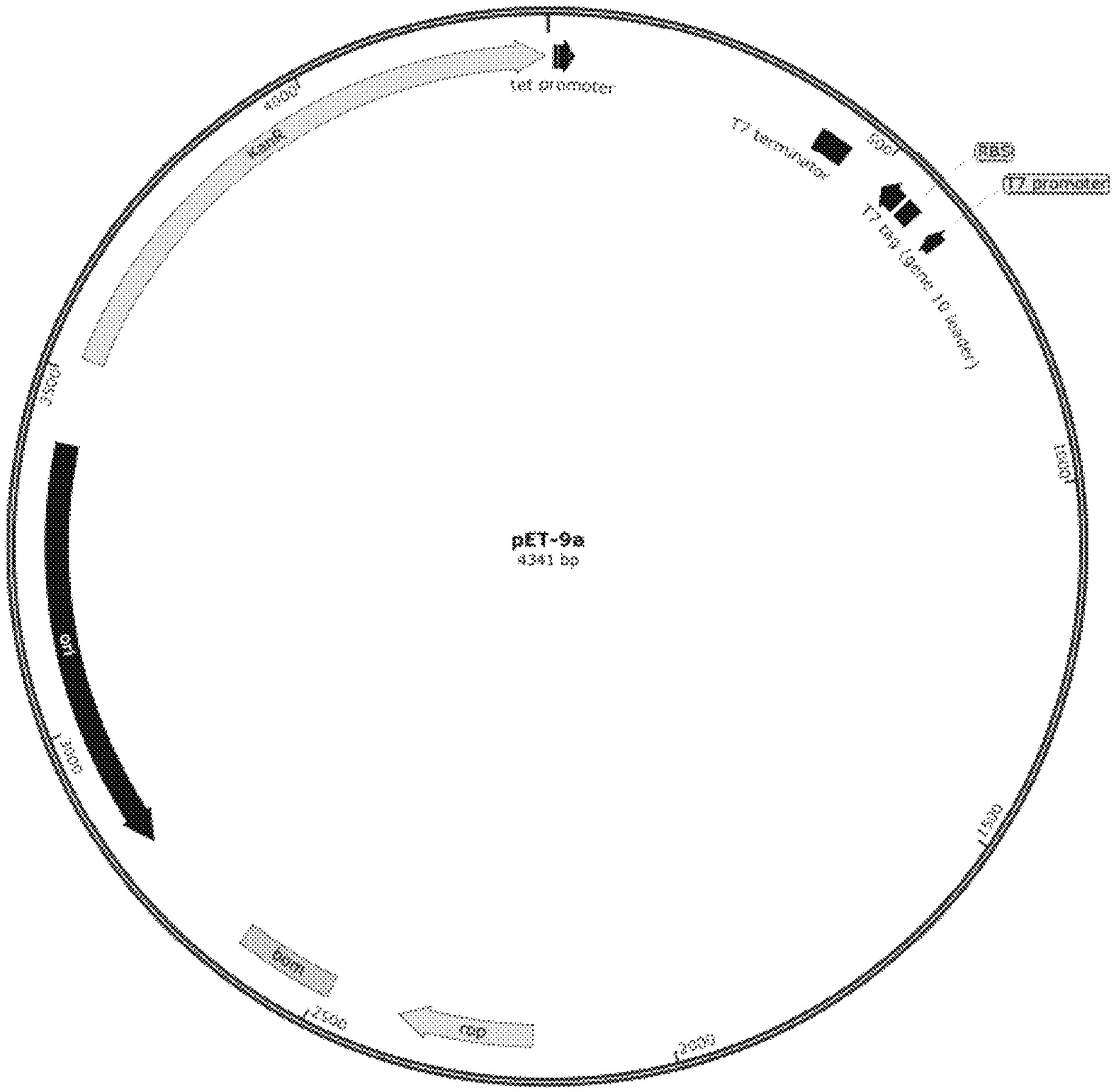
FIG. 18A illustrates an exemplary pET-9a vector for expression of a protein of interest in the protease-deficient strain with T7 RNA polymerase.

In some embodiments, the pET-9a plasmid can be used for expressing a protein of interest when the protease-deficient strain in which the protein of interest can be expressed has its own T7 RNA polymerase activity. The pEF-9a expression vector is illustrated in FIG. 18A. This plasmid is operated under the T7 promotion system which includes a promoter region upstream of the gene of interest. This promoter sequence is essentially a recognition site of the T7 RNA polymerase located under inducible control within the genome of the cell line in which the vector is transformed. Thus, production of the protein of interest is controlled by the promoter that controls the T7 rather than a promoter present on the plasmid. Because the plasmid is under control of the T7 promoter, directly after the gene is a T7 terminator region. This is to ensure that only the gene of interest is overexpressed. C-terminus to the protein of interest is the T7 epitope tag which can be used for immunofluorescent staining purposes. This plasmid is maintained in vivo by the pBR322 origin of replication which is normally a high copy origin of replication. However, T7 promotion with a high copy origin of replication is undesirable (toxic levels of protein) so the rop gene was also included in order to keep the copy number low. This plasmid contains a kanamycin resistance cassette (KanR) under control of its own promoter and thus is selected for with kanamycin.

Figure 18B:
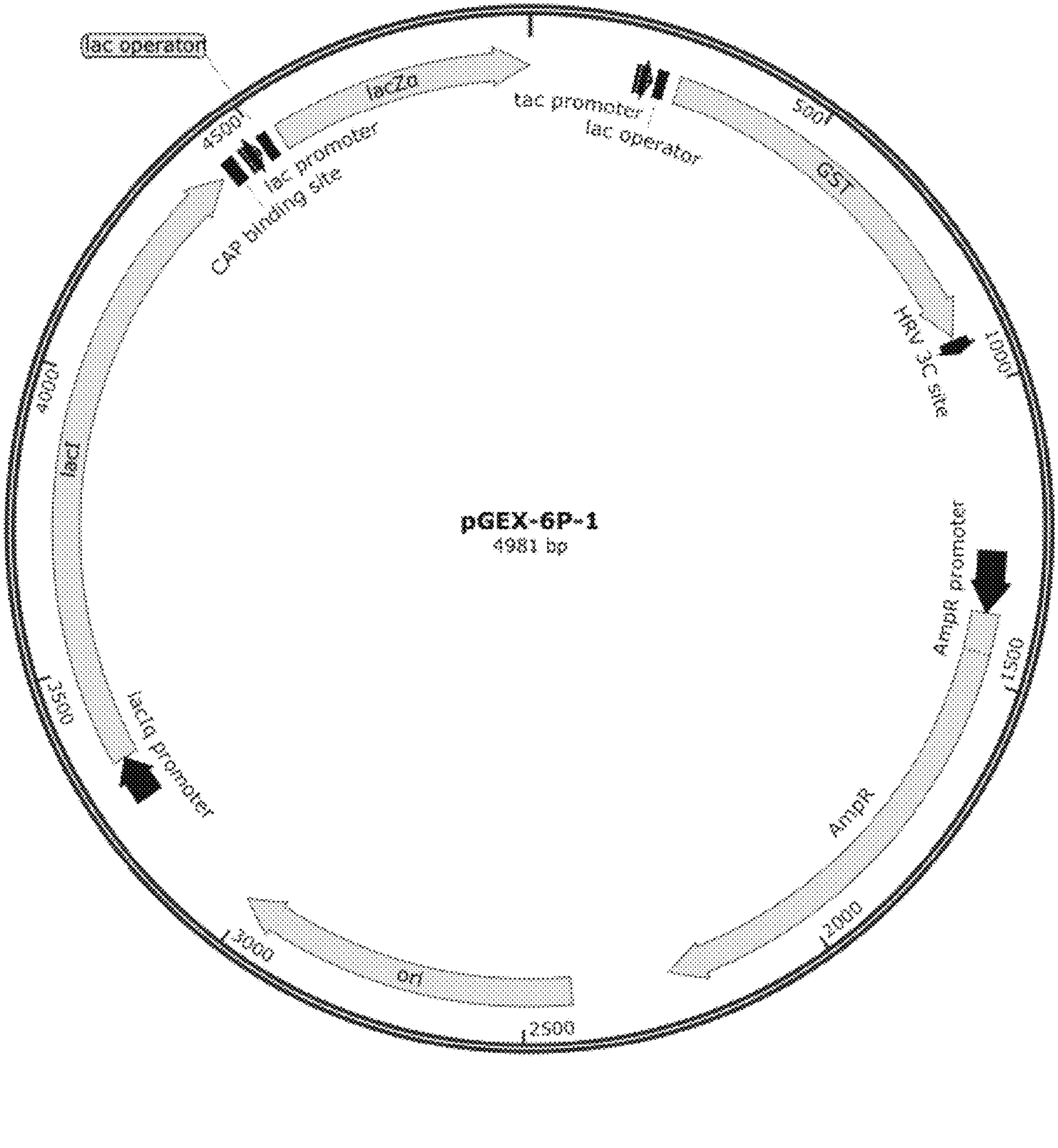
FIG. 18B illustrates an exemplary pGEX-6P-1 vector for expression of a protein of interest in the protease-deficient strain without T7 RNA polymerase.

In some embodiments, the pGEX-6P-1 plasmid can be used for expressing a protein of interest when the protease-deficient strain in which the protein of interest can be expressed does not have a T7 RNA polymerase activity. The pGEX-6P-1 expression vector is illustrated in FIG. 18B. The pGEX-6P-1 is operated under the tac promotion system. The tac promotion system is a hybrid promotion system between the trp promoter and the lac promoter. By hybridizing the promotion system, the binding/release lacI protein (inhibitor) is the mechanism of modulation of the promotion system, but it allows for tunable expression levels by varying the concentration of the induction agent (normally IPTG). This lacI gene and its promoter are included on the plasmid in order to mitigate any basal level of gene expression thus enhancing the degree of expression control resulting from the tac promoter.

This pGEX plasmid normally contains a glutathione S-transferase tag (GST) which enables for protein purification or immunochemical applications. However, given the purpose of the present disclosure, the start codon (ATG) for the GST tag was removed from the pGEX-6P-1 plasmid in order to decrease the size of the overall protein of interest to ensure adequate overexpression. This plasmid also contains an HRV3C cleavage site C-terminus of the GST tag for removal of the tag post purification.

This plasmid is maintained in vivo by the pBR322 origin of replication which is a high copy origin of replication. Unlike the T7 promotion system, the level of protein accumulated using the tac promotion system with a high copy plasmid is not toxic due to the use of the native RNA polymerase for mRNA production. This pGEX plasmid contains an ampicillin resistance cassette (AmpR) under the control of its own promoter.

Enzyme Immobilization on Surface of Gram Positive Bacterial Derivatives

Enzymes are immobilized to the surface of the minicell by means of protein mediated membrane localization mechanisms including but not limited to the following linking proteins and mechanisms: Sortase linking mechanism. Sortase is one of autotransporters for enzyme immobilization that specifically works in gram positive bacteria cells like *Bacillus Subtilis*. This sortase is induced with D (+) xylose. Sortase is a transpeptidase that attaches surface proteins to the cell wall; it cleaves between the Gly and Thr of the LPXTG motif and catalyzes the formation of an amide bond between the carboxyl-group of threonine and the amino-group of the cell-wall peptidoglycan. In some embodiments, the LPXTG motif can be inserted into the end of the C-terminus of the enzymatically active polypeptide of interest to express on the surface of gram positive bacterial cell. The Sortase can recognize this motif and covalently bind the enzymatically active polypeptide to the surface of the gram positive bacterial cell.

Likewise, minicells can be engineered from Extremophiles such that they retain the resilient physical and chemical properties of the parent species. For instance minicells from thermophiles would retain the resistance to high temperatures. Fluorescent protein fusions, ATP synthase mediated protein localization, Succinate dehydrogenase mediated protein localization. The focalization of membrane proteins and linking mechanisms in Gram-Positive Bacteria is reported by Mitra S D et al 2016, Trends in Microbiology, 24 (8):611-621, which is herein incorporated by reference in its entirety.

Enzyme Immobilization on the Surface of Yeast Derivatives

Enzymes can be immobilized to the surface of the yeast minicell via surface display proteins. Minicells can be produced from yeast strains, including but not limited to *Saccharomyes cervisiae, Pichia pastoris* and *Schizosaccharomyces pombe*.

The crystal structures of mammalian membrane proteins derived from recombinant sources were solved from protein expressed in yeast cells: the $Ca^{2}$+-ATPase (SERCAla) from rabbit. This protein was overexpressed in *Saccharomyces cerevisiae*. Also, the rat voltage-dependent potassium ion channel, Kv1.2 was produced in *Pichia pastoris* to understand its structure. Since then, several other host cells have been used for eukaryotic membrane protein production including *Escherichia coli*, baculovirus-infected insect cells and mammalian cell-lines. Whilst all host systems have advantages and disadvantages, yeasts have remained a consistently-popular choice in the eukaryotic membrane protein field. As microbes, they are quick, easy and cheap to culture; as eukaryotes they are able to post-translationally process eukaryotic membrane proteins. Very recent crystal structures of recombinant transmembrane proteins produced in yeast include those of human aquaporin 2, chicken bestrophin-1, the human TRAAK channel, human leukotriene C4 synthase, an algal P-glycoprotein homologue and mouse P-glycoprotein using *P. pastoris*-derived samples; the structures of the *Arabidopsis thaliana* NRT1.1 nitrate transporter, a fungal plant pathogen TMEM16 lipid scramblase and the yeast mitochondrial ADP/ATP carrier were solved using recombinant protein produced in *S. cerevisiae*. Due to its features as an eukaryotic cells, yeast cells can be used for the purpose of enzyme-immobilized minicell production.

The yeast membrane differs in composition from that of mammalian membranes. This is relevant to subsequent structural and functional studies of recombinant membrane proteins produced in yeast because lipids have a particularly important role in the normal function of membrane proteins by contributing to membrane fluidity and may directly interact with membrane proteins.

In an attempt to "humanize" the yeast membrane, yeast strains have been developed that synthesize cholesterol rather than the native yeast sterol, ergosterol. This was achieved by replacing the ERG5 and ERG6 genes of the ergosterol biosynthetic pathway with the mammalian genes DHRC24 and DHRC7 and, respectively. The gene products of DHRC7 and DHRC24 were identified as key enzymes that saturate sterol intermediates at positions C7 and C24 in cholesterol (but not ergosterol) synthesis. Erg5p introduces a double bond at position C22 and Erg6p adds a methyl group at position C24 in the ergosterol biosynthetic pathway and therefore competes with the gene product of DHRC24 for its substrate.

In addition to the open reading frame (ORF) of the gene of interest, a typical expression plasmid usually incorporate a number of other sequences in its expression cassette. The *S. cerevisiae* α-mating factor signal sequence is a common addition to commercial expression plasmids because it is believed to correctly-target recombinant membrane proteins to the yeast membrane. For example, its presence had a positive impact on the yield of the mouse 5-$HT_{5A}$ serotonin receptor but dramatically reduced expression of the histamine $H_1$ receptor. Alternative signal sequences have been used (albeit much less frequently) such as the STE2 leader sequence of the fungal GPCR, Ste2p. The known signal sequences in yeast can be another advantage for trafficking a protein of interest fused to membrane-associated protein/domain and immobilizing the protein of interest on the surface of yeast cell.

Release of Agricultural Compounds Encapsulated by Minicell

The present disclosure teaches that agricultural compounds is retained within the minicell and be released over time. The disclosure teaches a high value, low volume product of an anucleated minicell encapsulating at least one agricultural compounds and/or expressing a fusion protein that has at least one surface expressing moiety and at least cell adhesion moiety. In some embodiments, the anucleated cell-based product can be sprayed much less than other commercially available agrochemical products and also retain the desired effects of the active compounds over a longer period of time.

The term "controlled release" as used herein means that one or more agrochemicals encapsulated by an anucleated cell described in the present disclosed is released over time in a controlled manner. The controlled release is meant for purposes of the present disclosure that, once the agricultural compound is released from the formulation, it is released at a controlled rate such that levels and/or concentrations of the compounds are sustained and/or delayed over an extended period of time from the start of compound release, e.g., providing a release over a time period with a prolonged interval.

Current controlled release mechanism of agrochemical is based mainly on fully encapsulation of fertilizer (e.g. Agrium, ICL, Kingenta and Ekompany) or pesticides (e.g. Adama, Syngenta, Bayer). Fully encapsulation of fertilizer is usually based on resins (e.g. polyurethanes) or sulfur base mixture. Pesticides are loaded into micro polymeric capsules. Products of encapsulated fertilizer are limited to milligrams scale of dry fertilizer, due to the need of thick wall opposing the high inner pressure. This pressure is build up due to water entering the capsule driven by the negative osmotic potential of the dissolve fertilizer. As more fertilizer is encapsulated, more pressure will build up and a thicker wall is required. The feasible ratio between fertilizer amounts to wall thickness is in the tens of milligrams scale. Nevertheless encapsulated fertilizer is still very expensive and costs up to four times over the fertilizer price.

Moreover, the release mechanism is based on transport through faults and cracks distributed in the casing. Meaning, coating must be uniform throughout the all surface area, which is in turn a manufacturing challenge. On top of that, the materials being used for coating are temperature sensitive and change their structural properties extremely in small temperature range (17° C.-25° C.), leading to radical changes in release rates (up to double the rate). Thus, conventional encapsulation of agrochemicals has challenges of uniform coating and temperature dependent.

If it is desired to permit fast release of the encapsulated composition during drying of the formulation on a leaf, or similar, surface it is necessary to have thin walled microcapsules. Typically microcapsules with a mean diameter of about 2 microns require a polymer wall concentration in the formulation of about 3% by weight. Greater quantities of polymer will slow the release rate. The diameter of the capsules and the quantity of wall forming polymer can be used to tune the performance of the capsules, depending on the required pesticide and the conditions of use.

The increasing use of agrochemicals such as pesticides, herbicides, fungicides, insecticides, nematicides, fertilizer and the like, poses serious health and environmental problems which must be controlled in order to minimize the harmful effects of those products. One problem frequently encountered with herbicides, such as alachlor, metolachlor, norflurazon and sulfometuron is leaching and migration, which results in loss of herbicidal efficiency and can cause damage to other crops and contaminate water.

The present disclosure teaches that agricultural compounds encapsulated by minicells disclosed herein can be released in a controlled manner. In some embodiments, the controlled release of the compounds are determined by a treatment of an agent such as glutaraldehyde, formaldehyde, as well as natural compounds, such as genipin, and epigallocatechin gallat, derivatives of ethylene glycol di(meth)acrylate, derivatives of methylenebisacrylamide, and formaldehyde-free crosslinking agent DVB (Divinyl Benzene). In some embodiments, a varying concentration of the agent (e.g. glutaraldehyde) can prevent the degradation of minicells encapsulating the agricultural compounds in different degrees.

In other embodiments, the agent includes, but is not limited to glutaraldehyde, formaldehyde, as well as natural compounds, such as genipin, and epigallocatechin gallat, derivatives of ethylene glycol di(meth)acrylate, derivatives of methylenebisacrylamide, and formaldehyde-free crosslinking agent DVB (Divinyl Benzene).

In some embodiments, agricultural compounds encapsulated by minicells disclosed herein can be released at a rate of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% of a desired minicell unit/input per day. In other embodiments, an amount of the desired minicell unit/input accounts for encapsulated agricultural compounds. Encapsulation amount of agricultural compounds can calculate encapsulation fraction and mass fraction, which determines the desired minicell unit and/or input per day.

The desired end product for encapsulated agrochemicals is one that has a high total mass fraction. The improved encapsulation is related to high encapsulation efficiency. Therefore, it is desired to maximize loading efficiency of agrochemicals using higher concentrations of agrochemicals. Mass fraction is useful to measure encapsulation efficiency of agrochemicals. The mass fraction is calculated by dividing the total mass of the encapsulated agrochemical by the total mass of the encapsulated agrochemical plus the total mass of the bioparticle used for encapsulation. For example, if 20 micrograms are encapsulated within 80 micrograms of bioparticles, the mass fraction is 20% because (20/(20+80)*100)=20%. In other industries where the active ingredient is expensive, especially the pharmaceutical industry, encapsulation efficiency is also an important metric. This value is the total mass encapsulated divided by the starting total mass. Therefore, if 20 micrograms were encapsulated and the starting mass was 200 micrograms, an encapsulation efficiency of 10% would be achieved (20/200*100(%)). FIG. 11C-14C are an exemplary results of mass fraction of four pesticides disclosed in the present disclosure.

In some embodiments, minicells without treatment of an agent (e.g. glutaraldehyde) may have an initial fast release of 10%, 20%, 30%, 40%, 50%, 60%, 70%, or 80% of their desired unit/input per day and are followed by a controlled release of minicells treated with a varying concentration of the agent (e.g. glutaraldehyde), which give rise to a controlled release of 1%, 2%, 3%, 4%, 5%, 6%, 7%, 8%, 9%, 10%, 11%, 12%, 13%, 14%, 15%, 16%, 17%, 18%, 19%, or 20% of the desired input per day. In some embodiments, a varying concentration of the agent (e.g. glutaraldehyde) can prevent the degradation of minicells encapsulating the agricultural compounds in different degrees. In some embodiments, the agent includes, but is not limited to glutaraldehyde, formaldehyde, as well as natural compounds, such as genipin, and epigallocatechin gallat, derivatives of ethylene glycol di(meth)acrylate, derivatives of methylenebisacrylamide, and formaldehyde-free crosslinking agent DVB (Divinyl Benzene).

Improved Encapsulation and Retention

In order to improve encapsulation and retention, the present disclosure teaches that solvents can be used in the agrochemical cell encapsulation solution to increase the solubility of the agrochemicals that are less hydrophilic. These solvents include, but are not limited to, ethanol, DMSO, polyethylene glycol, and glycerol. Not only can these solvents be used to increase the solubility of certain agrochemicals, but they may be used to increase the diffusion of the active ingredient into the cell through certain protein channels or through the lipid bilayer of the outer membrane. In addition to the use of solvents to enhance the encapsulation process of the anucleated cell-based platform, certain fixatives, preservatives, and cross-linking agents can be used to trap the active ingredient within the membrane of the minicell, cross-link certain active compounds to the minicell itself, and improve the stability of the minicell. The relative concentration of these stabilizing/cross-linking agents can be tuned to achieve the required loading capacity for the active ingredient as well as the release kinetics of the active ingredient from the cell. These agents include, but are not limited to synthetic compounds, such as glutaraldehyde, formaldehyde, as well as natural compounds, such as genipin, and epigallocatechin gallat.

Agricultural Compound Delivery Amounts

In some embodiments, agricultural compounds are encapsulated within the anucleated cells described herein and delivered to a desired locus. Amounts of an agricultural compound of interest are provided herein with percent weight proportions of the various components used in the preparation of the anucleated cell for the encapsulation and deliver of agricultural compounds.

The percent weight proportions of the various components used in the preparation of the anucleated cell for the encapsulation and deliver of agricultural compounds can be varied as required to achieve optimal results. In some embodiments, the agrochemical compounds including, but are not limited to a pesticide, an herbicide, an insecticide, a fungicide, a nematicide, a fertilizer and a hormone or a chemical growth agent, is present in an amount of about 0.1 to about 90% by weight, is present in an amount of about 0.5 to about 80% by weight, 1 to about 70% by weight, 2 to about 60% by weight, 3 to about 55% by weight, 5 to about 50% by weight, 10 to about 45% by weight, and 15 to about 40% by weight, based on the total weight of the anucleated cell within which an agrochemical compound of interest is encapsulated. When a polymer is used in the preparation of the anucleated cell disclosed herein, according to one embodiment it is present in an amount of about 0.01 to about 10% by weight based on the total weight of the anucleated cell disclosed herein. When a co-solvent is used in the preparation of the anucleated cell disclosed herein, according to one embodiment it is present in an amount of about 0.1 to about 30% by weight based on the total weight of the anucleated cell disclosed herein. Alternate percent weight proportions are also envisioned. For example, the agricultural compound of interest can be present in an amount of up to about 50% by weight; the solvent can be present in an amount of up to about 70% by weight; the surfactant can be present in an amount of up to about 40% by weight and the water can be present in an amount of from about 1 to about 90% by weight, based on the total weight of the anucleated cell disclosed herein.

Among the various aspects of the present disclosure is an anucleated cell in the form of encapsulation of an agricultural compound of interest at least about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, by weight of the agricultural compound within the anucleated cell.

In other embodiments, the agricultural compound within the anucleated cell is present in an amount of at least about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 30, about 40, about 50, about 60, about 70, about 80, about 90, or about 100 g/L.

In another embodiment, the agricultural compound of interest and the anucleated cell are present in compositions of the disclosure in a weight ratio of at least 1:200, 1:195, 1:190, 1:185, 1:180, 1:175, 1:170, 1:165, 1:160, 1:155, 1:150, 1:145, 1:140, 1:135, 1:130, 1:125, 1:120, 1:115, 1:110, 1:105, 1:100, 1:95, 1:90, 1:85, 1:80, 1:75, 1:70, 1:65, 1:60, 1:55, 1:50, 1:45, 1:40, 1:35, 1:30, 1:25, 1:20, 1:15, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1 or 200:1. In another embodiment, the agricultural compound of interest and the anucleated cell are present in a weight ratio of from about 1:50 to about 50:1, from about 1:40 to about 40:1, from about 1:30 to about 30:1, from about 1:20 to about 20:1, from about 1:10 to about 10:1, or from about 1:5 to about 5:1.

In further embodiments, the density of the formulation of the anucleated cell encapsulating the agricultural compound is at least 0.1, at least about 0.2, at least about 0.3, at least about 0.4, at least about 0.5, at least about 0.6, at least about 0.7, at least about 0.8, at least about 0.9, at least about 1.0, at least 1.1, at least about 1.2, at least about 1.3, at least about 1.4, at least about 1.5, at least about 1.6, at least about 1.7, at least about 1.8, at least about 1.9, at least about 2.0, at least 2.1, at least about 2.2, at least about 2.3, at least about 2.4, at least about 2.5, at least about 2.6, at least about 2.7, at least about 2.8, at least about 2.9, at least about 3.0, at least 3.1, at least about 3.2, at least about 3.3, at least about 3.4, at least about 3.5, at least about 3.6, at least about 3.7, at least about 3.8, at least about 3.9, at least about 4.0, at least 4.1, at least about 4.2, at least about 4.3, at least about 4.4, at least about 4.5, at least about 4.6, at least about 4.7, at least about 4.8, at least about 4.9, at least about 5.0, at least about 5.5, at least about 6.0, at least about 6.5, at least about 7.0, at least about 7.5, at least about 8.0, at least about 8.5, at least about 9.0, at least about 9.5, or at least about 10.0 grams/liter.

In some embodiments, an agricultural compound of interest, for example, is present in at least about 20% of the total mass of the formulated product. In further embodiments, about 20 to 40% of the total mass of the formulated product is provided for the agricultural compound disclosed herein and the remaining about 60 to 80% of the mass is from the anucleated cell.

In some embodiments, more than one non-expressed agricultural compounds can be encapsulated within the anucleated cell. In another embodiment, the formulated product comprises two agricultural compounds that are present in compositions of the disclosure in a weight ratio of at least 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1.

In terms of amounts of the agricultural compound, about a concentration of about 0.01-20, about 0.1-15, about 0.2-10, about 0.3-9, about 0.3-8, about 0.5-5, about 1-3 g/L is provided for the formulated product.

In some embodiments, the targeted delivery and controlled release disclosed herein can improve efficacy of the agricultural compounds so that the amounts of the agricultural compound can be used less. The formulation of the anucleated cell-based platform can be in a liquid or solid form. In some embodiments, the formulated product is a liquid form such as a solution. In some embodiments, the formulated product is a solid form such as a powder.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will occur to those skilled in the art.

Example 1. Production of Protease-Deficient Minicells

Figure 17A:
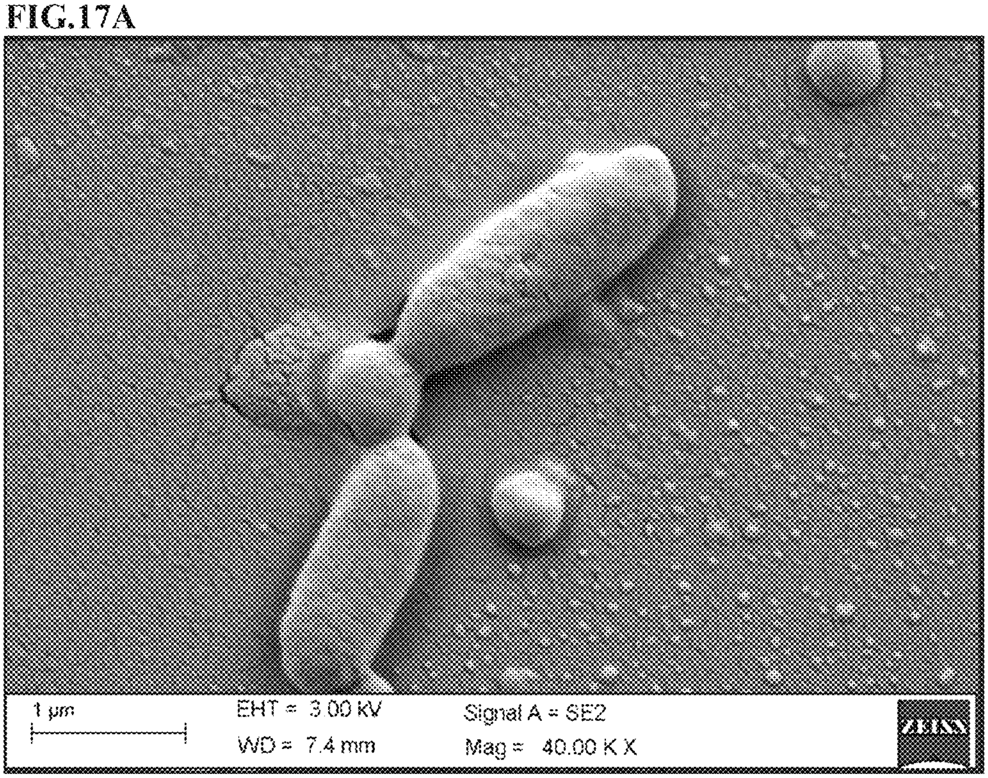
FIG. 17A-B shows scanning electron micrograph images of minicell formation in *E. coli* (FIG. 17A) and of protease-deficient anucleate minicells in which minC, minD, and/or minC/D gene is knocked out and/or removed (FIG. 17B). The size of exemplary minicells is less than one micrometer as shown in FIG. 17B.
Figure 17B:
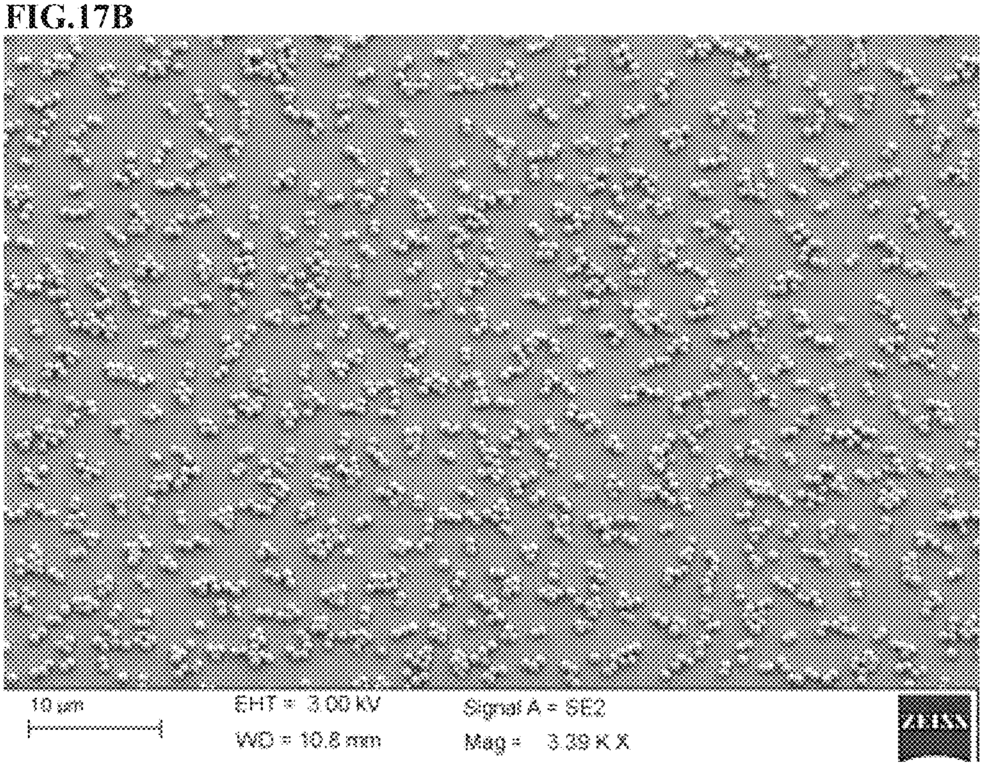

The success of these knockouts was determined by PCR amplification (Eppendorf Mastercycler 5333) and morphological characterization using the Laxco LMC4000 microscope (40× Objective, brightfield and fluorescent LED light sources) in conjunction with the Zeiss Sigma VP HD field SEM (UVA Advanced Microscopy Core). Based on the results shown in FIGS. 17A and 17B, it was determined that the minC, minD, and/or minC/D knockouts produced the minicells closest in morphological characteristics to the original wild type P678-54 strain producing minicells (Adler et al., 1967, *Proc. Natl. Acad. Sci. USA* 57:321-326; Inselburg J, 1970 *J. Bacteriol.* 102(3):642-647; Frazer 1975, *Curr. Topics Microbiol. Immunol.* 69:1-10). As an example, FIG. 17B shows the minicells in which minC gene is deleted.

To further investigate which gene knockout was responsible for producing minicells closest to the minicell-producing wild type p678-54 strains, the Lambda Red homologous recombination system was used. This lambda red recombinant-engineering system relies on three different proteins (Beta, Gam, and Exo) required for facilitating insertion of double stranded linear DNA into the genome guided by homology to the already existing genome, as exemplified by Murphy K C, 2011 Methods Mol. Biol. 765:27-42. All of these proteins are expressed via a plasmid with the pSC101 origin of replication containing the RepA protein which only allows for plasmid replication at 30° C. Thus, once the genetic manipulation is complete, the plasmid is removed from the cell line by growth at 37° C.

The genes that were inserted into the genome were designed to have 50 base pairs of homology to both the 5' and 3' ends of a targeted gene to be knocked out. The homology corresponded to 50 base pairs at the 5' (SEQ ID NO:1) and 3' end (SEQ ID NO:2) of minC in order to knockout minC, at the 5' (SEQ ID NO:3) and 3' end (SEQ ID NO:4) of minD in order to knockout minD, or 5' end (SEQ ID NO:3) of minD and 3' end (SEQ ID NO:2) of minC in order to knockout minCD, respectively. A chloramphenicol cassette with its promoter flanked by two hairpin loops was inserted in place of either minC, minD, or minC/D. The hairpin loops were included in the insert in order to not interfere with the regulation of other genes in the same area of the genome, due to their ability to stop transcription.

Figure 2:
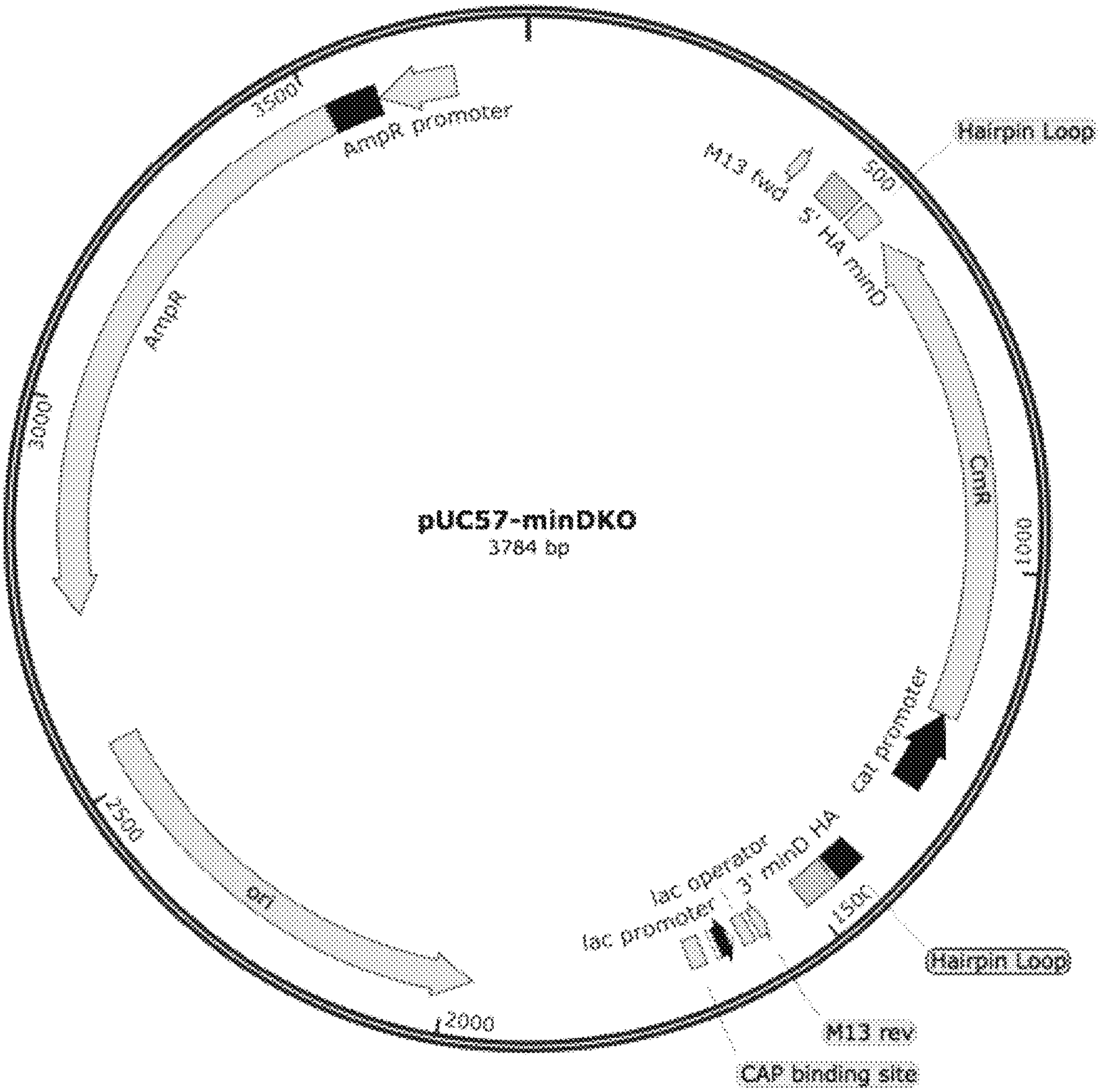
FIG. 2 illustrates an exemplary bacterial minicell-inducing vector for a minD knockout to produce protease-deficient minicells. The pUC57 vector was inserted with a recombinant DNA insert comprising 5' end nucleotide sequence of minD gene, a chloramphenicol resistant gene (CmR) with cat promoter, and 3' end nucleotide sequence of minD gene. The hairpin loops flanked by 5' and 3' ends of minD gene are inserted into the insert to stop transcriptional regulation of other neighboring genes in the genome where the insert is integrated.
Figure 3:
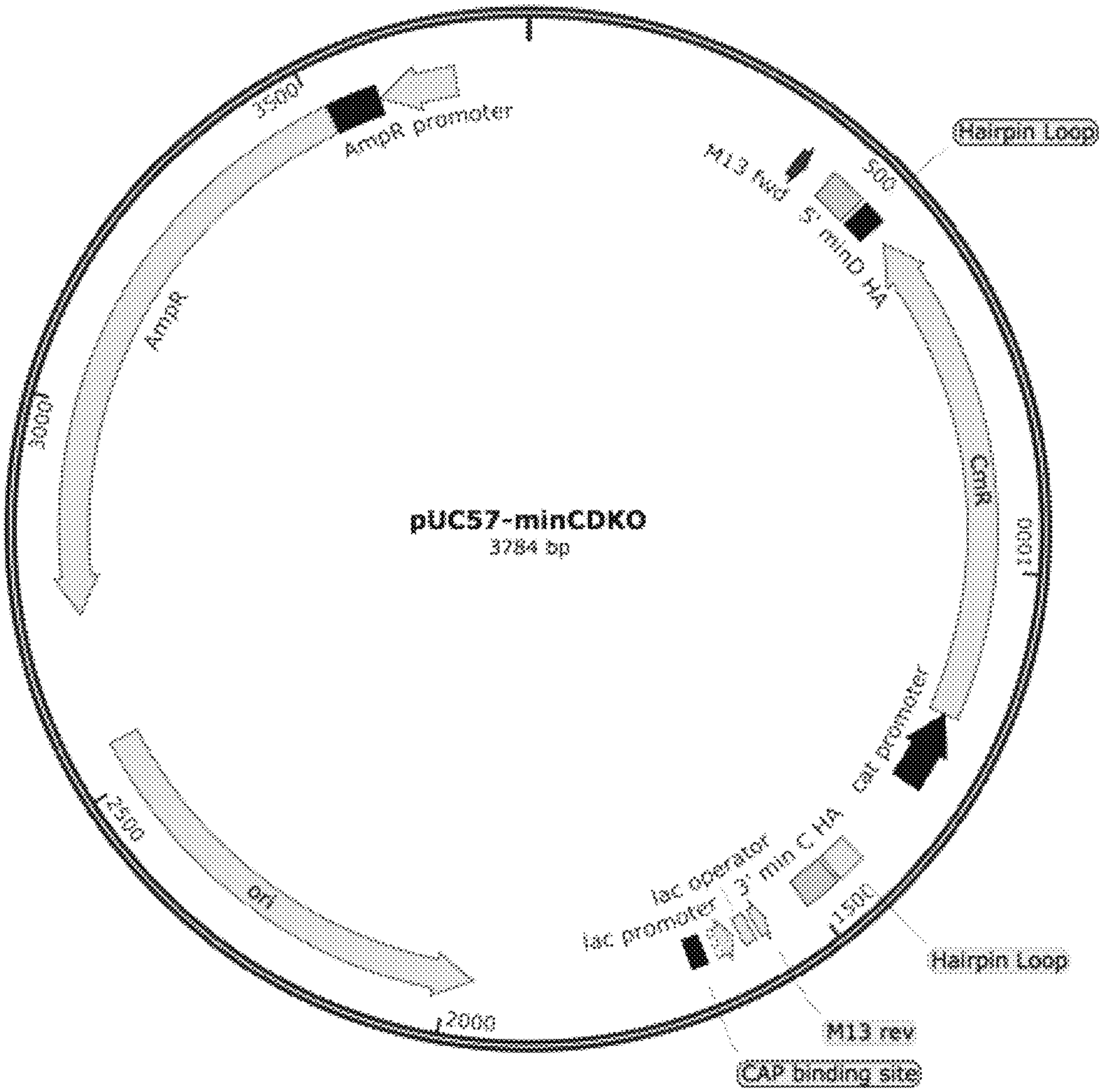
FIG. 3 illustrates an exemplary bacterial minicell-inducing vector for a minC/minD knockout to produce protease-deficient minicells. The pUC57 vector was inserted with recombinant DNA insert comprising 5' end of minD gene, a chloramphenicol resistant gene (CmR) with cat promoter, and 3' end of minC gene. The hairpin loops, flanked by 5' end of minD gene and 3' ends of minC gene, are inserted into the insert to stop transcriptional regulation of other neighboring genes in the genome where the insert is integrated.

These genes were inserted into a pUC57 backbone as shown in FIGS. 1-3. This plasmid was used as a template to then amplify out the gene of interest to verify that the sequence information is accurate before integrate them into the host genome. All amplifications were run across 6 different annealing temperatures with the following components and conditions as shown in Tables 3 and 4. Table 2 displays that two different sets of primers were designed per each gene knockout amplification. All primers were synthesized by the service provider, Integrated DNA Technologies (IDT).

TABLE 2

| Information on primer sets for testing min gene knockout | | |
|---|---|---|
| Name | Amplification Sequence | Designation |
| F2 minCKO | AACAACAATAATGCGTGCCAT | A |
| R2 minCKO | GCGCTGGCGATGATTAATAG | A |
| F9 minCKO | AGTAACAACAATAATGCGTGCC | B |
| R9 minCKO | CGCGCTGGCGATGATT | B |
| F7 minDKO | TTCCGCGAGAGAAAGAAATCG | C |
| R7 minDKO | GACCGTTCAACCGTTAAATTGAT | C |
| F10 minDKO | CTGTGTTTTTCTTCCGCGAG | D |
| R10 minDKO | TCAACCGTTAAATTGATCCCTTTTT | D |
| F6 minCDKO | TCCGCGAGAGAAAGAAATCG | E |
| R6 minCDKO | CGCGCTGGCGATGATTA | E |
| F9 minCDKO | CTGTGTTTTTCTTCCGCGAG | F |
| R9 minCDKO | CGCGCTGGCGATGATT | F |

TABLE 3

| Components for PCR reaction | | |
|---|---|---|
| Contents Component | Volume (uL) | Final Concentration |
| Nuclease Free Water | 17.5 | N/A |
| Template DNA (5 ng/uL) | 1 | 5 ng |
| 10 uM Forward Primer | 2.5 | 500 nM |
| 10 uM Reverse Primer | 2.5 | 500 nM |
| DMSO | 1.5 | 3% |
| Phusion HF Master Mix | 25 | 1X |

TABLE 4

| Conditions for PCR reaction | | |
|---|---|---|
| Conditions Steps | 55 Cycles Temperature (° C.) | Time (seconds) |
| Initial Denaturation | 98 | 30 |
| Cycle Denaturation | 98 | 10 |
| Cycle Annealing | 64, 4° Gradient | 30 |
| Cycle Extension | 72 | 30 |
| Final Extension | 72 | 600 |
| Hold | 4 | N/A |

Six series amplifications from A to F (Table 2) were run with each of the following annealing temperatures shown in Table 5. The number following the letter correspond to the position on the PCR plate with a gap between each well because of the slight increase in temperature from well to well. (example: well number A2 was the A series amplification run with Tm 1; A4—A series amplification run with Tm 2; A6—A series amplification run with Tm 3; A8—A series amplification run with Tm 4; A10—A series amplification run with Tm 5; A12—A series amplification run with Tm 6; and A1, A3, A5, A7, A9, and A11 are empty wells)

TABLE 5

| Information on annealing temperatures for PCR reaction | |
|---|---|
| Annealing Temperatures Tm Number | Tm ° C. |
| 1 | 59.8 |
| 2 | 60.8 |
| 3 | 62.8 |
| 4 | 65.1 |
| 5 | 66.9 |
| 6 | 67.6 |

All amplifications were cleaned up using the Monarch® PCR and DNA Cleanup kit according to their standard protocol. All DNA was eluted with enough elution buffer in order to provide for adequate DNA quantification and quality determination. After cleanup, all amplifications were run on a gel against the 1 kB plus ladder from Invitrogen® to determine success of the PCR reaction. All amplifications run at all annealing temperatures were successful by visualization of a single band at about 1080 base pairs. All DNA visualization was accomplished using a 1% Agarose (w/v) gel prepared with 1×TAE and SYBR safe stain in conjunction with the Invitrogen Safe Imager 2.0.

These bands were extracted from the gel using the disposable scalpels and the Monarch® DNA gel extraction kit according to their standard protocol. After extraction the DNA was quantified, its quality was determined before sending off for sequencing from Eton Biosciences. Primers used for amplification (Table 2) were used for sequencing determination. All sequences came back with ~99% identity, thus they were deemed suitable for insertion into the genome.

The lambda red plasmid was transformed into a chemically competent protease-deficient *E. coli* strain via the heat shock method (see examples; Rahimzadeh et al. 2016, Mol. Boil. Res. Commun. 5(4):257-261). It was plated on a selective LB Agar plate, and re-streaked the following day in order to be sure that a single colony was isolated for lambda red recombination.

In order to introduce the PCR generated DNA into the genome, the TransformAid Bacterial Transformation Kit from Thermon Scientific™ was used with a modified protocol.

A single colony was grown in C-medium at 30° C. overnight. Next day, a 1:100 dilution of the cultured cells were inoculated into fresh C-medium. This was grown at 30° C. until it reached an optical density of about 0.2 (measured at 600 nm). This culture was induced with 1 mM IPTG for 20 minutes to allow for sufficient production and accumulation of the three proteins vital for this procedure (Beta, Gam, and Exo). After induction for every 1.5 mL of inoculated culture volume, the cells were pelleted for 1 minute at 10,000 rcf and resuspended in 300 uL of cold T-solution and incubated for 5 minutes. The cells were then pelleted again and resuspended in 120 uL of cold T-solution for 5 minutes. After the final incubation step, 50 uL of cells and 50 ng of PCR amplification were combined for each transformation and incubated on ice for 5 minutes. From here, 250 uL of SOC medium was added to each transformation and let grow for 90 minutes at 37° C. After the 90 minute outgrowth, all 300 uL of transformation was plated on Chloramphenicol LB Agar plates (10 ug/mL) and let the transformed cells grow overnight.

This protocol resulted in the successful transformation of almost all of the genes attempted (3 from each series). The morphology of the transformed cells was examined from each successful transformant on the Laxco LMC4000 (40× objective, brightfield) and it was determined that the minC knockouts (A and B) produced the most morphologically similar minicells to the control p678-54 strain from which minicells were discovered. These BL21 and BL21-AI strains were two strains that were used for protease-deficient minicells and analyzed genetically.

In order to confirm presence of the knockouts in the genome, primers were designed to amplify out specific parts of the knockouts of minC and/or minD. The 5' and 3' end of the insert was confirmed by having the primers span regions both inside and outside of the insert. The primers in Table 6 were used according to the following conditions in Tables 7-9.

TABLE 6

Information on primer sets for testing min gene knockout

| Name | Annealing Sequence | Designation |
|---|---|---|
| 3'minCKO_1 | GGCCGGATAAAACTTGTGCT | 1 |
| 3'minCKO_2 | AGTCTTCGGAACATCATCGC | 2 |
| 5'minCKO_1 | CCCTTTGCCCGAAGTAACAA | 3 |
| 5'minCKO_2 | ACGGTGAAAACCTGGCCTAT | 4 |
| minC_check_4_1 | TCAATTTAACGGTTGAACGGTCA | 5 |
| minC_check_4_2 | ATGTCAAACACGCCAATCGA | 6 |
| minD_check_2_1 | TTATCCTCCGAACAAGCGTTTGA | 7 |
| minD_check_2_2 | ATGGCACGCATTATTGTTGTTAC | 8 |

TABLE 7

Components for PCR reaction

| Component | 50 uL Reaction | Final Concentration |
|---|---|---|
| 10 uM Forward Primer | 2.5 uL | 0.5 uM |
| 10 uM Reverse Primer | 2.5 uL | 0.5 uM |
| DMSO | 1.5 uL | 3% |
| 2X Phusion Master Mix | 25 uL | 1x |
| Genomic DNA | 1 uL | 2 ng/uL |
| Nuclease Free Water | 17.5 uL | N/A |

TABLE 8

Conditions for PCR reaction

| Conditions Steps | 55 Cycles Temperature (° C.) | Time (seconds) |
|---|---|---|
| Initial Denaturation | 98 | 30 |
| Cycle Denaturation | 98 | 10 |
| Cycle Annealing | 65, 5° Gradient | 30 |
| Cycle Extension | 72 | 30 |
| Final Extension | 72 | 600 |
| Hold | 4 | N/A |

TABLE 9

Information on annealing temperatures for PCR reaction

| Annealing Temperatures Tm Number | Tm ° C. |
|---|---|
| 1 | 59.9 |
| 2 | 61.3 |
| 3 | 63.8 |
| 4 | 66.6 |
| 5 | 69.7 |
| 6 | 67.6 |

After PCR amplification, all products were cleaned up using either the Monarch® PCR and DNA Clean up Kit or the DNA Clean & Concentrator Kit™-5 with Zymo-Spin IC Columns. The purified PCR amplicants were then run in a DNA Agarose gel with the above conditions and visualized the same way. For both the A and B series, reactions using a pair of primers 1-2 and another pair of primers 3-4 produced primarily a single band at the appropriate size, respectively. Reaction with a set of primers 7-8 produced only a single band corresponding to the minD gene. Reaction using a set of primers 5-6 was run to check for presence of minC, and this reaction produced a stratification of bands indicating a nonspecific PCR product which is to be expected after knocking out minC. All of these reactions were also run on the wild type genome for comparison. Reactions using sets of primers 1-2 and 3-4 produced a stratification of bands which is to be expected from BL21 and/or BL21-AI strains with the insert of min C and/or D knock-out system, but not in the wild type because the recombinant insert was not present in the wild type genome. Reactions using sets of primers 5-6 and 7-8 produced a single band indicating a specific PCR product, respectively.

All bands indicating a specific PCR product were extracted from the gel using the Monarch® gel extraction kit and the DNA sequences were analyzed by Eton Biosciences. All DNA sequencing results showed almost identical (99%) sequence homology to the expected sequence with min C and/or D knocked out.

To isolation minicells from parental cells, the entire culture including parent cells and minicells is spun down at 2,000 rcf for 10 minutes to pellet the parental cells. The supernatant is then collected and spun down again at 10,000 rcf for 10 minutes to pellet the minicells. The supernatant is discarded and the pelleted minicells are resuspended in PBS or any other buffer based on their intended use.

TABLE 10

Listing of Sequences in Sequence File

| SEQ ID NO | Type | Description |
|---|---|---|
| 1 | DNA | minC 5' recombination site (5' Homologous Arm of minC) |
| 2 | DNA | minC 3' recombination site (3' Homologous Arm of minC) |
| 3 | DNA | minD 5' recombination site (5' Homologous Arm of minD) |
| 4 | DNA | minD 5' recombination site (3' Homologous Arm of minD) |
| 5 | DNA | AIDA-1 surface expression cassette |
| 6 | DNA | BrkAutoTransporter surface expression cassette |
| 7 | DNA | BrkAutoTransporter surface expression cassette fused with CBM-encoding nucleic acid |
| 8 | DNA | CBM (Carbohydrate Binding Module) -encoding nucleic acid |
| 9 | DNA | GFP-Nanobody sequence with CBM-encoding nucleic acid |
| 10 | DNA | InaK surface expression cassette |
| 11 | DNA | InaK surface expression cassette with CBM-encoding nucleic acid |

TABLE 10-continued

| Listing of Sequences in Sequence File | | |
|---|---|---|
| SEQ ID NO | Type | Description |
| 12 | DNA | pAIDA-1 vector |
| 13 | DNA | pAIDA-1 vecotr with CBM-encoding nucleic acid |
| 14 | DNA | pET-9a vector |
| 15 | DNA | pGEX-6P-1 vector without ATG for GST tag |
| 16 | DNA | pGEX-6P-1 vector without ATG for GST tag, containing BrkAutoTransporter surface expression cassette fused with CBM-encoding nucleic acid |
| 17 | DNA | pGEX-6P-1 vector without ATG for GST tag, containing InaK surface expression cassette fused with CBM-encoding nucleic acid |
| 18 | DNA | F2 minCKO primer |
| 19 | DNA | R2 minCKO primer |
| 20 | DNA | F9 minCKO primer |
| 21 | DNA | R9 minCKO primer |
| 22 | DNA | F7 minDKO primer |
| 23 | DNA | R7 minDKO primer |
| 24 | DNA | F10 minDKO primer |
| 25 | DNA | R10 minDKO primer |
| 26 | DNA | F6 minCDKO primer |
| 27 | DNA | R6 minCDKO primer |
| 28 | DNA | F9 minCDKO primer |
| 29 | DNA | R9 minCDKO primer |
| 30 | DNA | 3'minCKO_1 primer |
| 31 | DNA | 3'minCKO_2 primer |
| 32 | DNA | 5'minCKO_1 primer |
| 33 | DNA | 5'minCKO_2 primer |
| 34 | DNA | minC_check_4_1 primer |
| 35 | DNA | minC_check_4_2 primer |
| 36 | DNA | minD_check_2_1 primer |
| 37 | DNA | 3'minCKO_1_primer |

Example 2. Transformation of CBM Expression Cassette into Minicells

The genetically modified minicell-producing bacterial strain was transformed with a linker protein fused CBM expression plasmid.

The CBM-encoding gene was inserted into the AIDA-1 surface expression cassette of the pAIDA-1 vector using KpnI and SacI restriction sites, which allows the CBM protein to be expressed and displayed by the fusion with the transmembrane autotransporter protein AIDA-1 (Adhesin Involved in Diffuse Adherence) as shown in FIG. 4B. This construction was conducted with primarily designed pAIDA-1 plasmid (from Addgene, Cambirdge, Mass.) in which the CBM-encoding gene was ligated into the passenger domain within the AIDA-I autotransporter using KpnI and SacI sites as illustrated in FIG. 4A. The tags existed on the pAIDA-1 plasmid prior were used for further analysis on CBM expression. After the ligation is completed, the 6×His tag and HRV3C site are located at N-terminus of the CBM-encoding gene and the Myc tag and TEV site are placed at C-terminus of the CBM-encoding gene. The 6×His tag, which is the 5' end of the surface-expressed fusion CBM protein was used for Cobalt immobilized metal affinity chromatography (IMAC) and for immunofluorescent staining with THE His Tag antibody [FITC] from Genscript. The pAIDA-1 vector has a chloramphenicol resistant gene so that the recombinant pAIDA-CBM expression vector can be transformed into p567-48 wild type strain, BL21 (DE3) strain, and BL21-AI strain. In order to induce minicell production from BL21 (DE3) strain and BL21-AI strain, the present disclosure uses a minC, minD, and/or minC/D knockout system by replacing the min locus with a chloramphenicol resistant gene. In this case, the new protease-deficient minicell-producing strains (e.g. minC, D, or C/D-depleted BL21 (DE3) strain and/or minC, D, or C/D-depleted BL21-AI strain) cannot be transformed with the recombinant pAIDA-1 CBM expression vector due to the presence of the same chloramphenicol resistant gene in both vector and the minicell-producing strains.

Figure 5A:
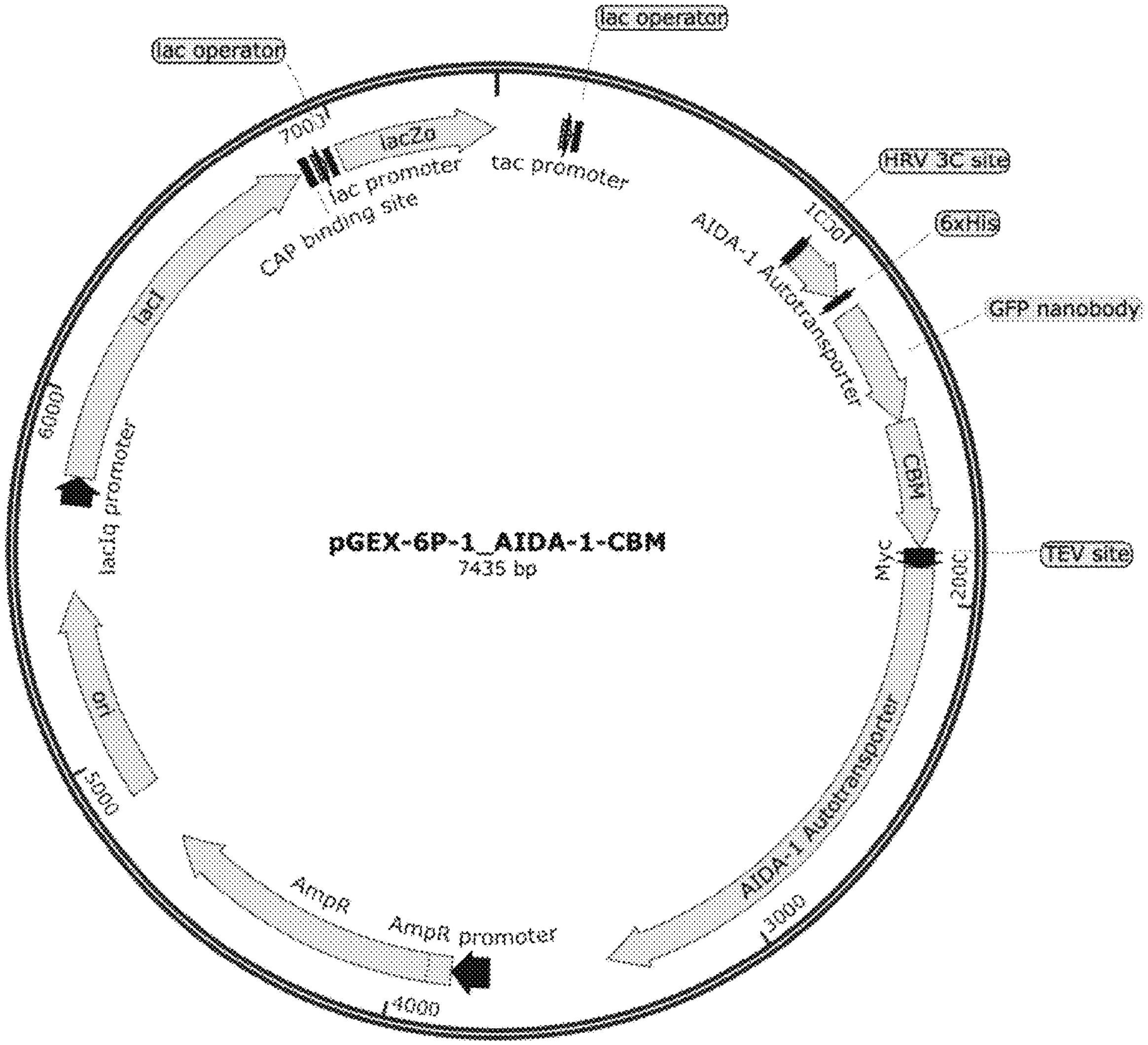
FIG. 5A illustrates an exemplary pGEX-6P-1 AIDA-1-CBM vector with AIDA-1 surface expression system for display of a lipase protein flanked by 6×His, GFP nanobody and Myc tags on the surface of minicells.
Figure 5B:
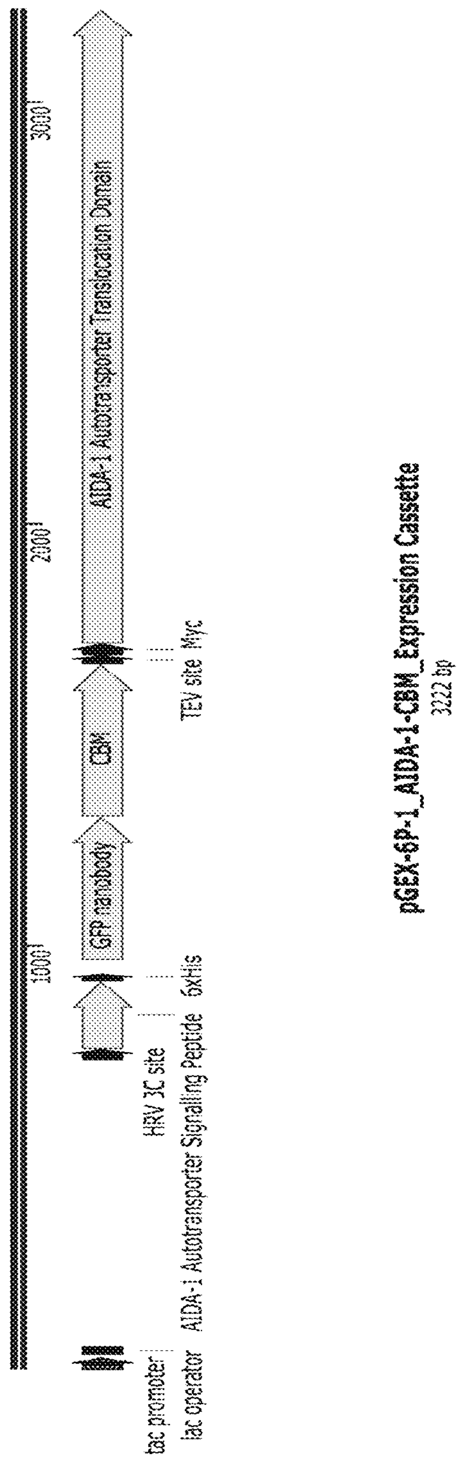
FIG. 5B illustrates an exemplary AIDA-1 CBM surface expression cassette, comprising nucleotide sequences encoding AIDA-1 Autotransporter signal peptide, GFP nanopbody, CBM, and AIDA-1 autotransporter translocation domain with tags including 6×His Tag and Myc Tag as well as two protease cleavage sites including HRV3C and TEV.

In order to express the AIDA-1 CBM fusion protein, another recombinant AIDA-CBM expression plasmid was constructed in the backbone of pGEX-6P-1 vector. The AIDA-1 CBM surface expression cassette was cut from the pAIDA-1 CBM expression vector and cloned into the pGEX-6P-1 vector as illustrated in FIG. 5A. In this way, the new protease-deficient minicells, which has chloramphenicol resistant gene, can be selected with chloramphenicol because the pGEX-6P-1 AIDA-1-CBM vector possess Amphicilin-resistant gene.

For a bacterial surface display system named as BrkAutoDisplay based on the structure of autotransporter BrkA (*Bordetella* serum-resistance killing protein A) was used to host an exogenous gene encoding CBM. To construct a recombinant Brk-CBM expression vector, Brk autotransporter gene was first cloned into the pGEX-6P-1 plasmid. Using BamHI and EcoRI restriction sites, the CBM-encoding gene was ligated with the Brk autotransporter gene, as illustrated in FIG. 6A. As illustrated in FIG. 6B, the CBM-encoding gene was inserted into the passenger domain of BrkA autotransporter gene. The first 177 nucleotides of the expression cassette correspond to the signaling peptide portion of the Brk autotransporter. This is the most N-terminus region of the fusion protein. This portion is cleaved during the translocation process. Immediately at the end of C-terminus of the signaling peptide is located the 6×His tag used for purification and staining. This 6×His tag is the surface expressed N-terminus end of the fusion protein after the signal peptide is cut off. C-terminus to the His tag is fused to the CBM-encoding gene, which is followed by the Myc tag and the TEV site sequentially. Then, the translocation domain of the BrkA autotransporter is located right after the TEV site. This translocation domain of the fusion protein is the most C-terminus region of the protein that is embedded in the membrane.

Figure 7A:
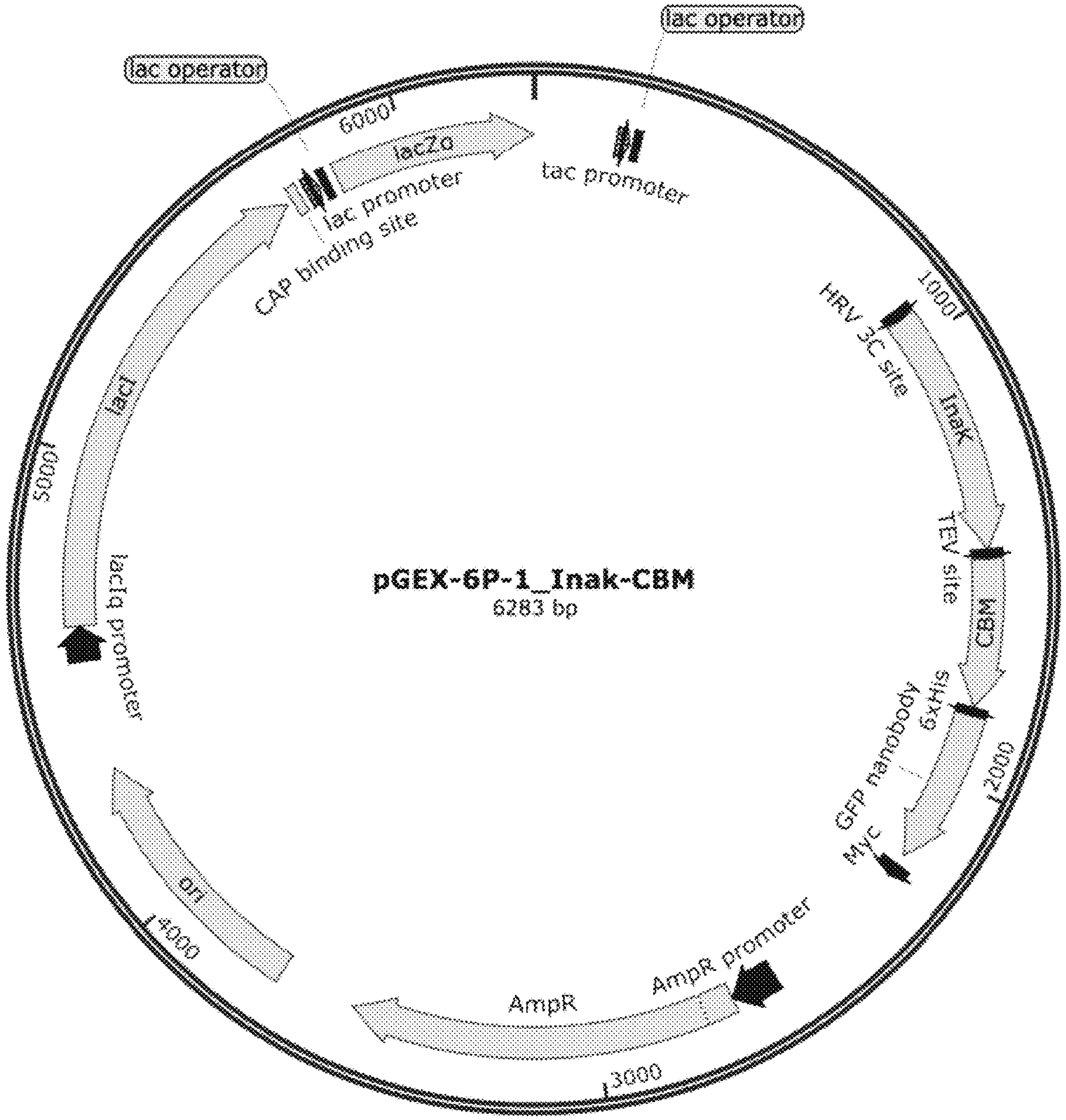
FIG. 7A illustrates an exemplary pGEX-6P-1 Inak-CBM vector with an Ice Nucleation Protein InaK surface expression system for display of a CBM protein on the surface of minicells. The CBM-encoding nucleotide sequence is ligated at its 5' end to Inak and at its 3' end to 6×His, GFP nanobody and Myc tags.

Another bacterial surface display protein, Ice Nucleation Protein K (InaK) was used for expressing recombinant CBM proteins fused to anchoring linker protein (motif) that direct the incorporated fusion protein on the surface of minicells. Like BrkAutoDisplay, polynucleotide encoding InaK transmembrane protein and the CBM-encoding gene were inserted into the pGEX-6P-1 vector for producing the bacterial surface display CBM protein as illustrated in FIG. 7A. For all InaK-CBM fusions, the CBM-encoding gene has a 6×His tag and an Myc tag at the C-terminus, while the TEV site is fused to N-terminus of the CBM-encoding gene. In this construct, the polynucleotide sequence encoding InaK is located before N-terminus of the TEV site. Since C-terminus of InaK protein is surface expressed and the N-terminus end becomes embedded in the membrane, the CBM-encoding gene is inserted after InaK-encoding polynucleotide sequence, which allows the CBM to be displayed on the surface while the InaK can function as a membrane anchor. The 6×His tag was used for the Cobalt immobilized metal affinity chromatography (IMAC) and for immunofluorescent staining with THE His Tag antibody [FITC] from Genscript®. The Myc tag can be used for immunofluorescent staining. The TEV site can be used for digesting off the protein of interest such as CBM for surface expression confirmation.

After construction of bacterial expression vectors for bacterial surface display fusion proteins using AIDA-1, BrkA, and InaK system was completed, transformation of each expression vector was conducted using the TransformAid Bacterial Transformation Kit (Thermo Scientific™) according to their standard protocol into the protease-deficient cell lines, BL21 and/or BL21-AI strains. The CBM was fused to each linker protein of AIDA-1, BrkA, and InaK to ensure surface-expression of the CBM. These expression plasmid can be transformed into the wild-type p678-54 strain and protease-deficient minicell-producing bacterial strains generated by the method taught in the present disclosure (e.g. minC, D, or C/D-depleted BL21 (DE3) strain and/or minC, D, or C/D-depleted BL21-AI strain).

In order to confirm presence of plasmid in the transformed bacterial strains, a miniprep was done on a culture from the strains using GeneJet Plasmid MiniPrep Kit, and the purified plasmid was submitted for DNA sequencing analysis. All sequencing confirmed the presence of the surface expression CBM plasmids in the transformed bacterial strains.

Example 3. CBM Production

The transformed strain was grown overnight in a 5 mL culture with the appropriate antibiotic. The next day, 1:100 inoculation (4.5 mL of overnight culture in 550 mL of 2×YT media) was performed in 2×YT media plus appropriate antibiotic. The 2×YT media provided the surplus of nutrients necessary for efficient protein production. Once the culture reached the exponential growth stage (OD~0.4), it was induced with 1 mM IPTG and is incubated at 30° C. overnight. The culture was analyzed the next day for CBM production.

After overnight IPTG induction, the sample was removed from the incubator shaker and poured into three 250 mL centrifuge bottles, 150 mL of sample in each. The bottles were spun down at 2,000 rcf to pellet the bacterial cells. The supernatant was transferred to three clean 250 mL centrifuge bottles. The supernatant was spun down at 10,000 rcf to pellet the minicells. The minicells were resuspended in PBS. The volume depends on the number of encapsulation variables, 3 mL of minicells per variable and another 3 mL of minicells for the control. the OD of the minicells was measured around 1.0 for each Microcentrifuge tube. 3 mL of minicells was used in 3 microcentrifuge tubes (1 mL per tube at OD of 1.0) for one variable.

Example 4. CBM Staining

The cultured cells are subjected to staining in order to determine the presence surface-expressed CBM. Slides were developed for both the CBM-expressing minicell-producing bacterial BL21 and/or BL21-AI strain and the minicell-producing bacterial p678-54 strain that has not been transformed with the recombinant linker protein-fused CBM expression plasmid. 250 uL of poly-L-lysine was pipetted on slides for 15 minutes. After washing three times with 500 uL PBS, 500 uL of the correct cell type was pipetted on slides for 15 minutes. After washing three times with 500 uL PBS, 750 uL of 4% paraformaldehyde was pipetted on slides for 15 minutes in order to fix the cell samples to the slides. After washing three times with PBS, 500 uL of 0.1% triton x-100 PBS was added to slides allocated as permeabilized samples for 10 minutes. For non-permeabilized samples, 500 uL of PBS was added to slides during this step. After washing three times with PBS, 100 uL of 2% bovine serum albumin was pipetted on all slides as a blocking agent. After washing three times with PBS, on the slides it was pipetted 100 uL of 1 mg/mL GenScript® THE™ His Tag Antibody [FITC], mAb, Mouse antibody, which binds to the 6×-HIS tag component of the CBM fusion protein. Then, the slides were incubated with the antibody at room temperature for 1 hour while protected from light. After washing 5-10 times with PBS, 3-4 drops of Fluoroshield Mounting Medium with DAPI were added before mounting coverslips to the slides. Fluorescent microscopy can then be implemented to analyze localization between brightfield cells and fluorescent probes that are indicative of cell presence and surface-expressed protein presence.

Figure 8A:
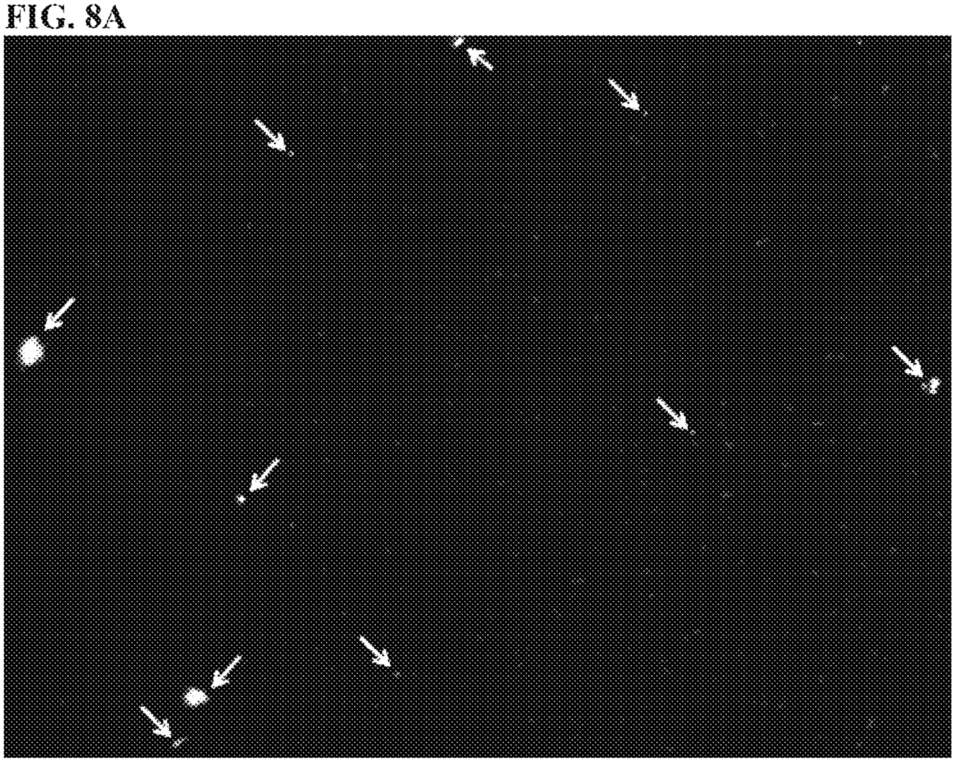
FIG. 8A-D shows His-Tag staining results of CBM protein fused with AIDA-1 linker protein on the surface of minicells. The minicells were either non-permeabilized (FIGS. 8A and 8C) or permeabilized (FIGS. 8B and 8D). The fusion CBMs were expressed from the recombinant fusion CBM expression vector on the surface of the transformed minicells (FIGS. 8A and 8B), compared to control minicells that did not have the recombinant AIDA-1 CBM expression vector (FIGS. 8C and 8D).
Figure 8B:
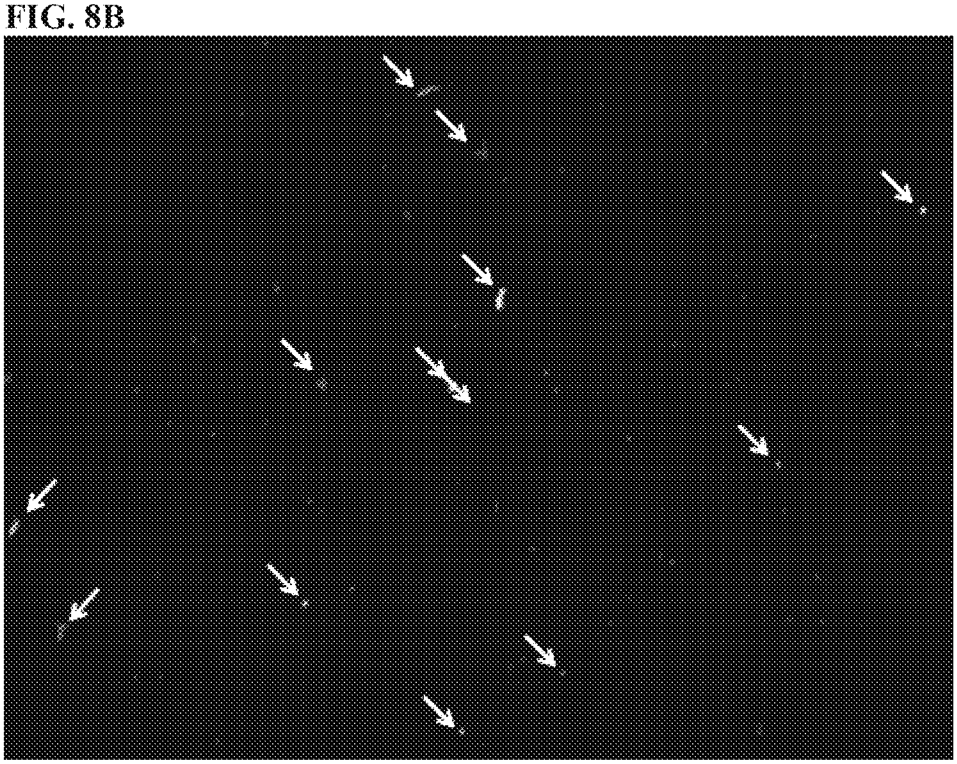
Figure 8C:
Figure 8D:
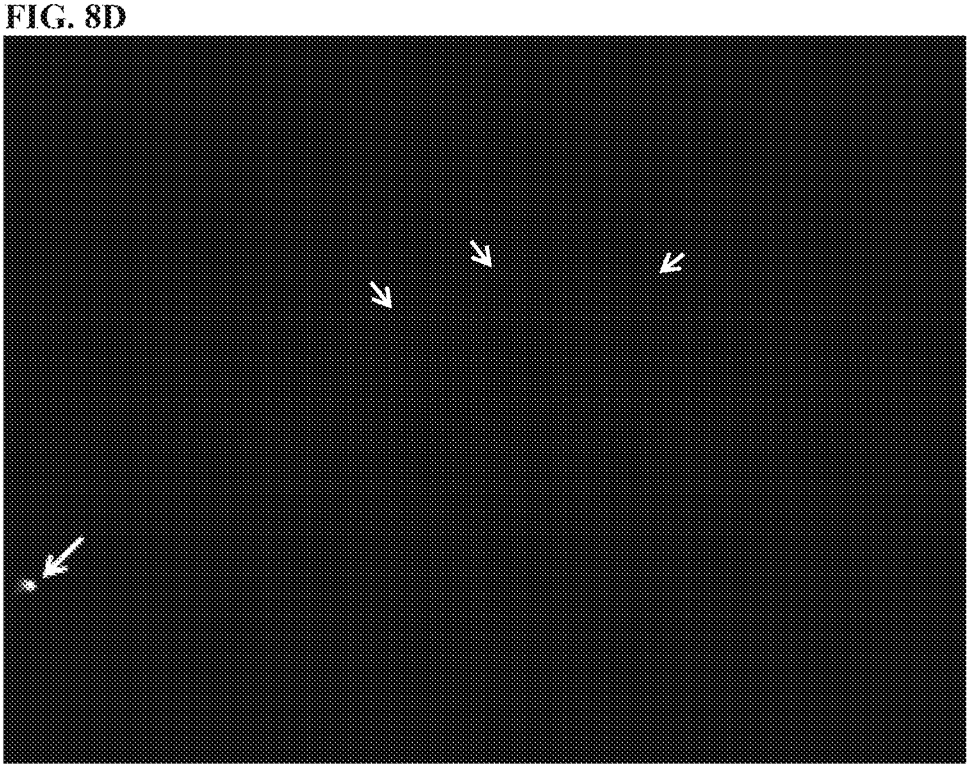

In both permeabilized and nonpermeabilized minicells, the staining with His-tag antibody showed a strong signal in a majority of the population of the cells that expressing AIDA-1-CBM fusion proteins (FIGS. 8A and 8B). However, the His-tag antibody detected little to no signal in the control samples (FIGS. 8C and 8D). The control samples are wild type p678-54 minicells that do not contain the recombinant CBM expressing plasmid so that the fusion protein cannot be detectable. Therefore, the His tag staining results indicate the expression of the fusion CBM from the minicells transformed with the recombinant CBM expression plasmid, but not the control cells. Non-permeabilized minicells (FIG. 8A) show the surface expressed CBM proteins, indicating that CBM is immobilized via the AIDA-1 linker protein on the surface of the minicells. However, the recombinant CBM is not all surface expressed from the comparison of non-permeabilized cells with permeabilized cells (FIG. 8B), indicating that endogenous CBMs and/or recombinant fusion CBM minicells can be also expressed within the minicells. On the other hand, a false positive by staining any endogenously produced CBMs within the transformed minicells can be detected as illustrated in in the control minicells (FIGS. 8C and 8D).

Example 5. Cell Retention Test

Figure 9A:
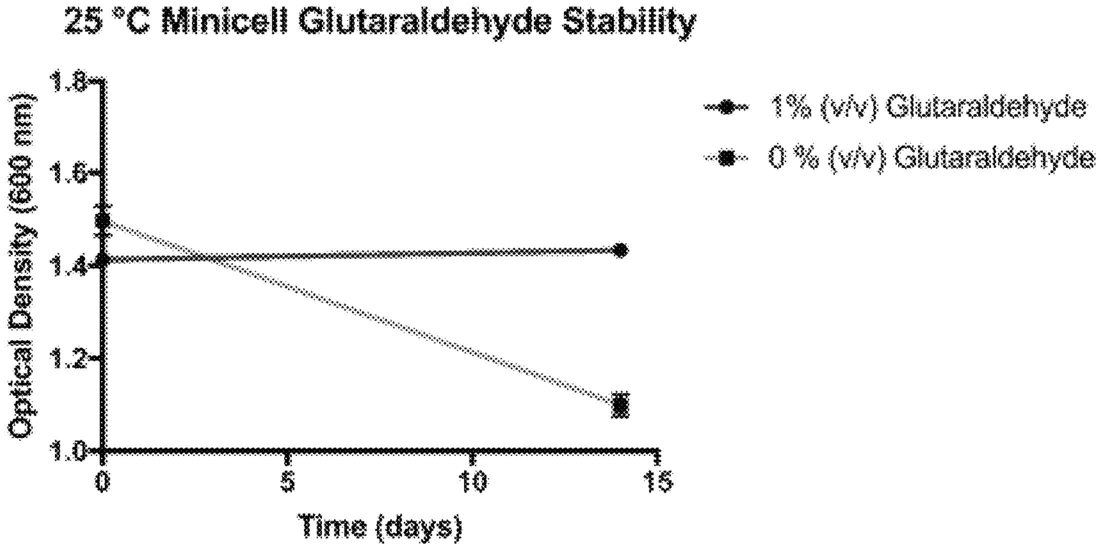
FIG. 9A-B shows optical density of minicells treated with glutaraldehyde at two different temperature to show cell retention for three weeks.
Figure 9B:
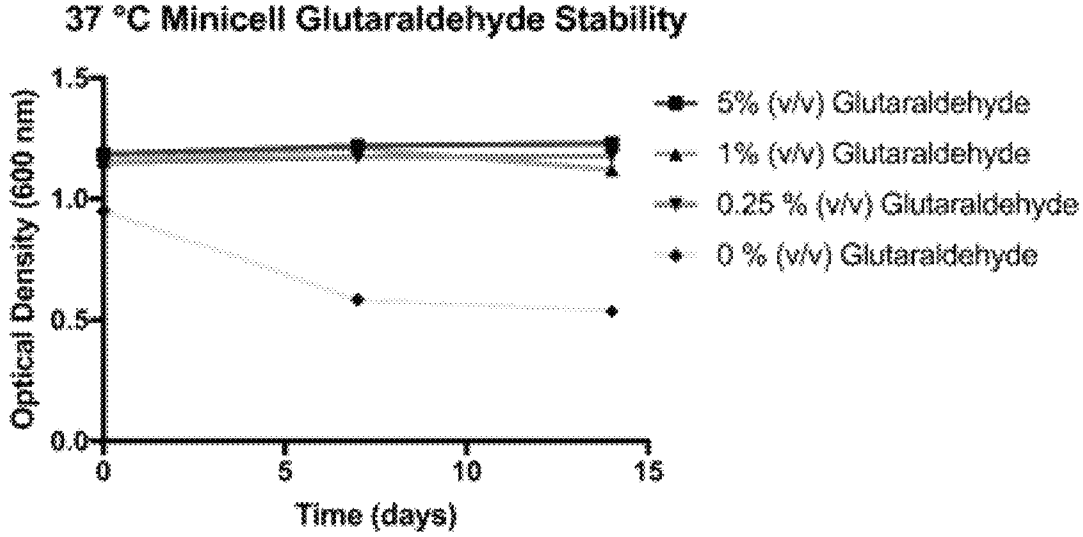

In order to test cell retention over two weeks with two variables; 1) temperature-dependent an 2) glutaraldehyde treatment. In one condition, minicells are treated with 1% (v/v) glutaraldehyde and untreated at room temperature for 15 days. In the other condition, minicells are treated with three varying concentrations of glutaraldehyde (5%, 1%, and 0.25% (v/v), compared to an untreated control at 37° C. for 15 days. As shown in FIG. 9A, the optical density of the untreated minicells drops more significantly than the optical density of the treated minicells. However, minicells treated with 1% (v/v) glutaraldehyde were not degraded and/or died. This indicates that glutaraldehyde helps prevent the early degradation of minicells at room temperature for 15 days, which ensures extended retention of active ingredients within the minicells. Also, optical density of the untreated minicells as illustrated in FIG. 9B, shows that at high temperate the glutaraldehyde-treated minicells maintained their viability without degradation.

The results indicate that release of agrochemical from the minicell can be controlled by creating a formulation in which a certain portion of minicells are treated with glutaraldehyde and another portion of minicells are not. This would allow for the untreated minicells to break down much more quickly and initially release more of the active, while the treated cells will break down slower and release the active over time.

Example 6. Crystalline Cellulose Study

Figure 7B:
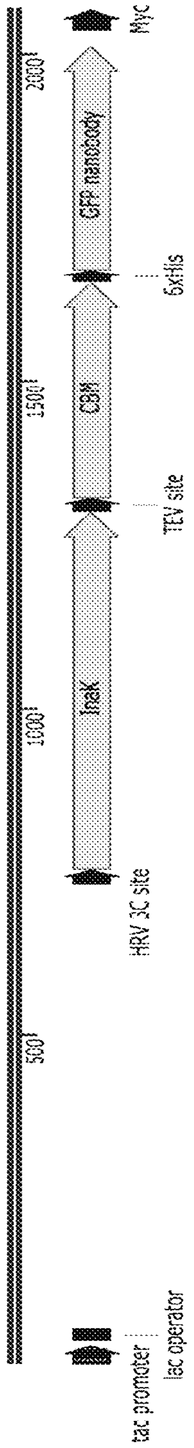
FIG. 7B illustrates an exemplary Inak-CBM surface expression cassette, comprising nucleotide sequences encoding Inak autotransporter translocation domain, CBM, and GFP nanopbody, with tags including 6×His Tag and Myc Tag as well as two protease cleavage sites including HRV3C and TEV.

In order to elucidate efficacy of trapping minicells using microcrystalline cellulose and the surface expressed cellulose binding module, an assay was developed with both qualitative and quantitative measures incorporated. The two cell lines that used for testing the efficacy were the protease-free cell line wild type and the protease-free cell line containing the pGEX-Inak-CBM as illustrated in FIG. 7. The protease-free cell line wild type was chosen as the control for this experiment to account for any non-enzymatic binding of the minicells to the cellulose. All minicells were isolated from their parent cells using our standard minicell purification protocol after our standard protein expression protocol. These cells were then incubated with Fluorescein Diacetate (FDA, 0.08 mg/mL) for 1 hour for fluorescent microscopy staining. 5 mL of those cells from each of the cell lines were incubated with the 100 mg microcrystalline cellulose (Avicel PH-101) for 20 minutes shaking at 37° C. at 180 rpm. After incubation, propidium iodide (was added to solution in order to assist with the marking of the cells due its binding affinity for DNA. Propidium iodide was useful due to its observed adsorptive properties to cellulose; essentially it helps mark the cellulose red for fluorescent imagery. After incubation, the microcrystalline cellulose was spun down away from the cells (100 rcf) based on larger size (~50 uM). The cellulose was taken here for imaging from both the control and experimental cell lines and imaged for binding of cells to the cellulose. The cellulose and cell solution from each condition were added to an empty chromatography column (Bio-rad Econopac, 20 mL). The cell solution was allowed to pass through the column leaving the majority of the cellulose behind. After passing through the column, the cells were syringe filtered through a 1 uM filter in order to remove any residual cellulose.

The difference between the starting optical density (600 nM) and the filtered column pass-through optical density (600 nM) was taken in order to determine if the experimental cells which had the surface expressed CBM were more retained by the cellulose than the control cells which did not have the surface expressed CBM. Because there was a filtration step, cells from both starting populations were filtered through the filter and the starting and final OD600's were measured. From this experiment, it was determined that upon filtration, ~35.6% of cells are lost through the filter. To account for this in the CBM assay, the final cell counts (after passing through the column) were multiplied by 1.356 prior to taking the difference between the starting and final OD600's. This resulted in an OD600 loss of 0.11 through the cellulose containing column for the protease-free wild type and an OD600 loss of 0.169 through the cellulose containing column for the protease-free strain with a surface expressed CBM. This indicates that a 15% greater increase in retention of cells expressing the CBM versus cells that do not express the CBM.

Figure 10A:
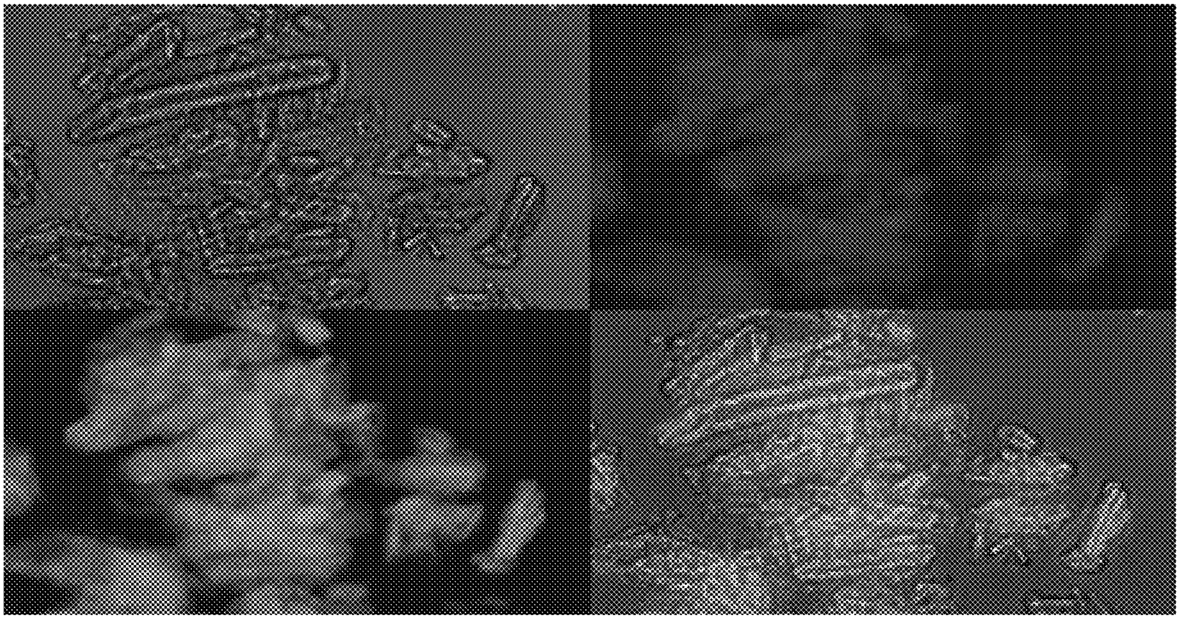
FIG. 10A-B shows CBM microcrystalline cellulose assay results of protease-deficient minicells, obtained from the protease free wild type strain as a control (FIG. 10A), and the protease free strain containing the pGEX-InaK-CBM (FIG. 10B).
Figure 10B:
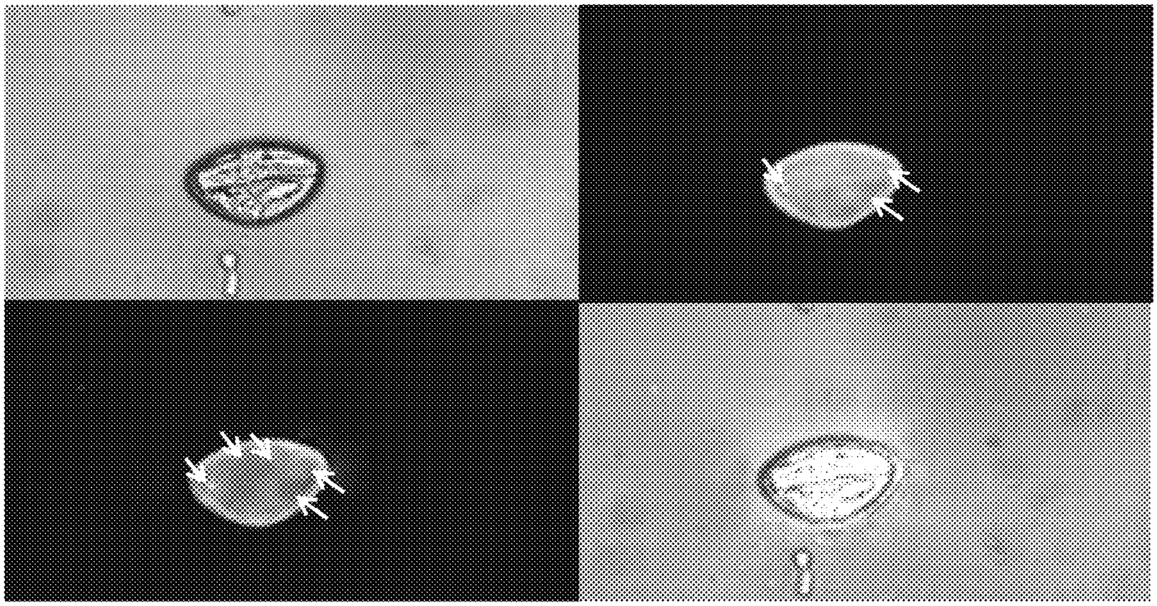

FIG. 10 shows CBM microcrystalline cellulose assay results of protease-deficient minicells, obtained from the protease free wild type strain as a control (FIG. 10A), and the protease free strain containing the pGEX-InaK-CBM (FIG. 10B). When overlaying the bottom left image (PI image) with the top right image (FDA image) in FIG. 10A, it demonstrates that no stained cells are present on the cellulose. Bottom right is an overlaid image of all three imaging conditions which demonstrates that cells are not bound to the cellulose. However, in FIG. 10B, the top right image clearly shows the FDA signal coming from the surface of the bound cell as well as the bottom left image shows the same although the PI signal is washed out due to the FDA signal coming from the bound cells. However, these images demonstrates that cells can clearly be seen bound to the cellulose.

Example 7. Encapsulation Via Minicell Technology i) Setting Up Standard Curve A predetermined mass of agrochemical (~100 mg) such as pesticide, herbicide, insecticide, fungicide is weighed out on a scale and then dissolved in PBS or Ethanol, based on its solubility. Once a liquid solution of the pesticide is made (lmg/mL), dilutions are made in PBS or Milli Q Water, to create a standard curve. The detection limit for each pesticide varies, therefore a range of concentrations (0 ug/mL, 1 ug/mL, 5 ug/mL, 10 ug/mL, 20 ug/mL, 25 ug/mL, 50 ug/mL, 75 ug/mL, 100 ug/mL, 150 ug/mL, 200 ug/mL, 250 ug/mL, 300 ug/mL, 500 ug/mL, 750 ug/mL, and 1000 ug/mL) are made to build a strong standard curve. Attempt the standard curve until an R squared value of greater than 0.95 is obtained.

ii) Preparing For Encapsulation

One minicell-producing bacterial colony is picked from an agar plate and inoculated in a culture of Luria Broth (~450 mL). This sample is to be placed in an incubator shaker for overnight growth. During the overnight growth process, the bacterial cells produce minicells. The next day, the sample is removed from the incubator shaker and poured into three 250 mL centrifuge bottles, 150 mL of sample in each. The bottles are spun down at 2,000 rcf to pellet the bacterial cells. The supernatant is transferred to three clean 250 mL centrifuge bottles. The supernatant is spun down at 10,000 rcf to pellet the minicells. The minicells are resuspended in PBS. The volume depends on the number of encapsulation variables, 3 mLs of minicells per variable and another 3 mLs of minicells for the control. Make sure the OD of the minicells is around 1.0 for each Microcentrifuge tube. 3 mLs of minicells will be used in 3 microcentrifuge tubes (1 mL per tube at OD of 1.0) for one variable.

iii) Encapsulation Process

Various methods can be used to encapsulate agrochemicals in minicells. These methods can be either passive or active. Passive methods rely on diffusion of the agrochemical down the concentration gradient through channels/pores of the minicell via incubation alone. The concentration of the agrochemical can be modified based on the desired loading amount. Increasing the concentration of the agrochemical, allows for more available agrochemical molecules, leading to higher encapsulation amounts. On average, an incubation time of two hours would suffice for these experiments. Once the minicells are obtained (1 mL per tube at OD of 1.0), they are pelleted down via centrifugation at max speed (~15,000 rcf) and the supernatant is discarded. For passive encapsulation, the minicells are resuspended in the agrochemical for incubation. The agrochemical is dissolved in Phosphate Buffered Saline at a pH of 7. The minicells will incubate and shake at 37° C. in the agrochemical solution for two hours prior to analysis. For controls, minicells resuspended in Phosphate Buffered Saline at a pH of 7 and the agrochemical solution without minicells are also incubated and shaked for two hours at 37° C.

For active encapsulation, techniques are used to improve the solubility of the agrochemical, increase the permeability of the minicell membrane, or both. These methods include modifying the pH of the agrochemical solution, heat shocking or electroporating cells, using Tris/EDTA/Sucrose buffers, using calcium chloride or magnesium chloride, using different weights of PolyEthylene Glycol, expressing protein channels to improve agrochemical influx, and growing cells in the desired agrochemical. Once one of these methods are employed, two hour incubation at 37° C. is then employed to achieve higher encapsulation.

Example 8. Total Encapsulation Analysis

Total encapsulation can be analyzed via a spectrophotometer and more accurately by a mass spectrometer. Both analytical methods require a standard curve. Once the two hour incubation period has concluded, the samples being incubated are centrifuged at max speed for front end analysis. The supernatant is analyzed in these solutions. The relative drop in pesticide concentration in experimental samples that contain minicells when compared to pesticide samples that do not contain minicells is a direct measure of pesticide encapsulated within the mincell. Then, the minicells pellets are lysed for back end analysis. Theoretically, the supernatant and lysed pellets should be total 100% of the available agrochemical. When working at concentrations higher than the range of quantification of the spectrophotometer, dilutions are necessary prior to analysis.

A protocol for encapsulation of pesticides into minicell is presented as follows:

(1) Pick a colony of minicell producing bacterial strain in 500 ml of LB media. Let grow overnight.

(2) Purify minicells from parent cells using a 2 step centrifugation purification process. The first centrifugation step at 2000 g removes most of the parent cells in the pellet; the supernatant from this first step is then spun down again at 10000 g. This second pellet of purified minicells is then resuspended in PBS (pH 7.4) to reach an OD600 of ~2.0.

(3) 3-5 ml of the cell solution is aliquoted out into 50 ml tubes. Equal volume of the pesticide solution is introduced to the cell solution for the experimental sample. The pesticide solution is an aqueous solution that contains 25% Ethanol and 25% PEG600 (v/v %). After mixing the cell solution and the pesticide solution, the effective concentration of cells in solution becomes 8x10^8 cells/ml (OD600: ~1) and the effective concentration of PEG600 and Ethanol both become 12.5% (v/v %). For the control sample, the cell solution is mixed with equal volume of PBS with 25% PEG600 and 25% Ethanol (v/v %) to reach the same effective concentration for the solvents as the experimental samples.

(4) The cell and pesticide solution is then allowed to incubate for 2 hours (rpm 180, 37° C.). Then, 1 ml samples of the solution are removed from incubation and spun down (15000 g, 10 minutes) to prepare them for analysis. If cells are to be treated with a fixative (e.g. glutaraldehyde), 1 ml samples of the solution are removed from incubation and treated with glutaraldehyde at an effective concentration of 2.5%. Glutarldehyde treatment is allowed to proceed overnight at room temperature; then the cell and pesticide solution is spun down to prepare them for analysis.

(5) Cells are analyzed by removing the pesticide solution supernatant and resuspending the pellets in PBS to wash away any residual free pesticide that was not encapsulated. Then, cells are spun down again (15000 g, 10 minutes) and the pellet is resuspended in 850 ul of lysis solution from the GeneJET plasmid miniprep kit.

(6) The lysed solution is then spun down (15000 g, 10 minutes) and the supernatant is analyzed for absorbance at a wavelength that is specific to the pesticide compound using a spectrophotometer. The signal from the control sample (cells incubated with no pesticide but washed and lysed) is subtracted as background from the signal of the experimental sample. This ensures that the analysis accurately represents the concentration of pesticide in solution.

Agrochemical Example 1. Foramsulfuron Encapsulation Via Minicell Technology

Figure 11A:
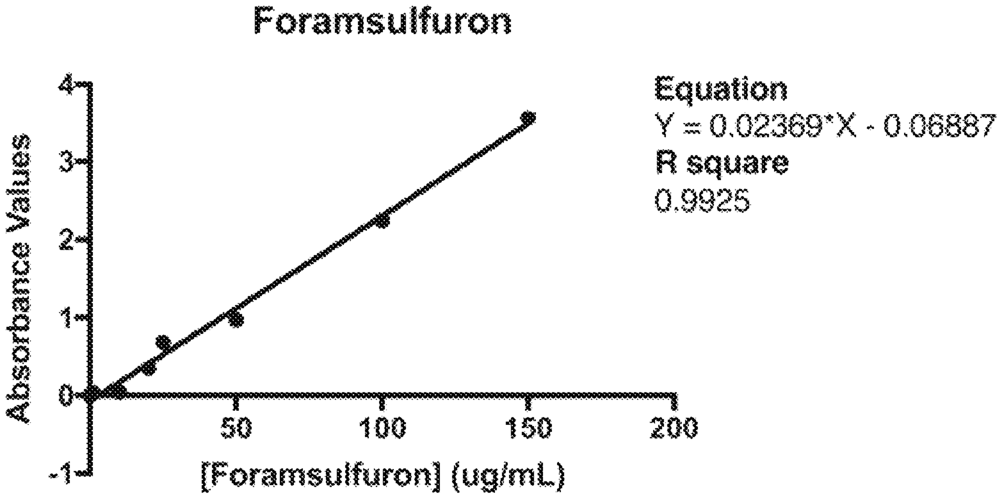
FIG. 11A shows a standard curve used for foramsulfuron for total encapsulation analysis. The standard curve was generated from 0 to 150 microgram of foramsulfuron. Three separate foramsulfuron experiments were performed with three different starting concentrations in triplicate.
Figure 11B:
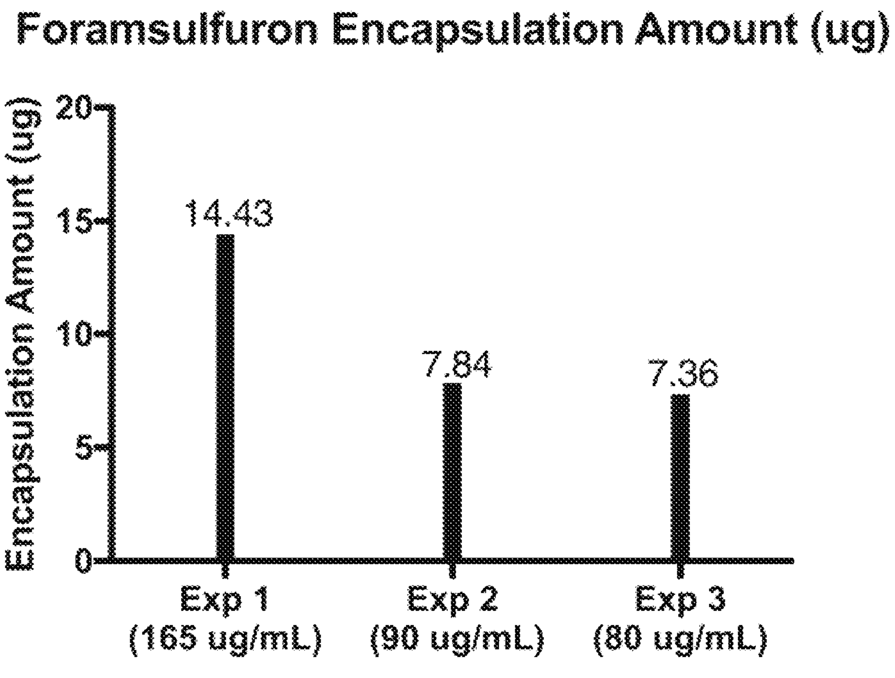
FIG. 11B shows the amount of foramsulfuron encapsulation in three different starting concentration.
Figure 11C:
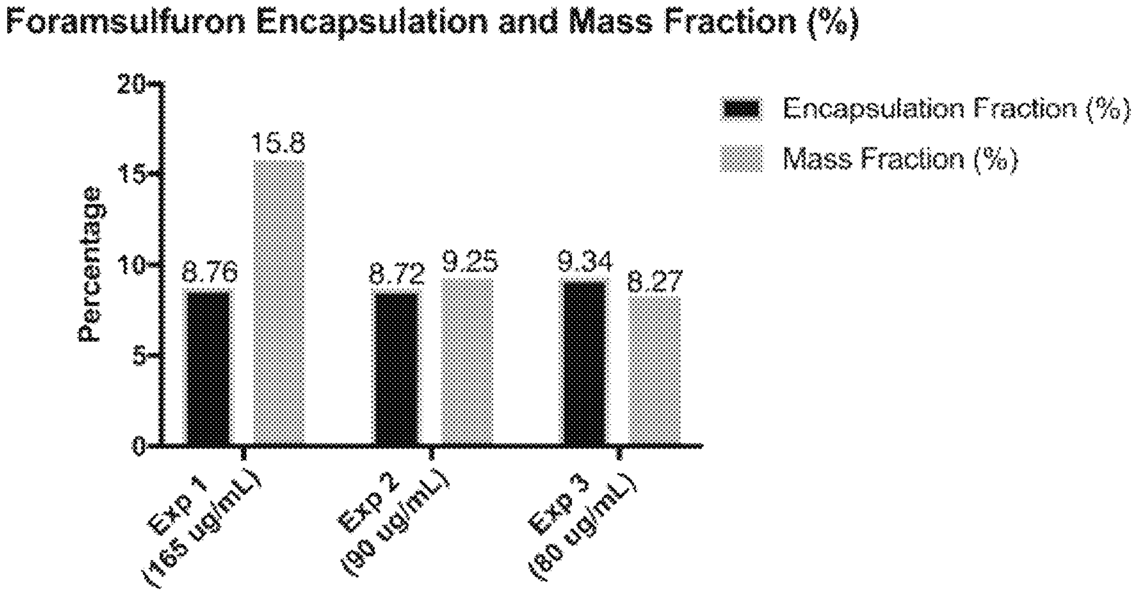
FIG. 11C shows ratios of foramsulfuron encapsulation fraction and mass fraction.

Describes herein is the anucleated minicell platform that encapsulates Foramsulfuron. Foramsulfuron, or 2-[(4,6-dimethoxypyrimidin-2-yl) carbamoyl sulfamoyl]-4-formamido-N,N-dimethylbenzamide, is an herbicide of the sulfonylurea class. Foramsulfuron absorbs at 233 nanometers; therefore, Corning UV-Transparent Plates are used in conjunction with a spectrophotometer to collect encapsulation data. Absorbance metrics are converted to foramsulfuron concentrations by using the standard curve as shown in FIG. 11A.

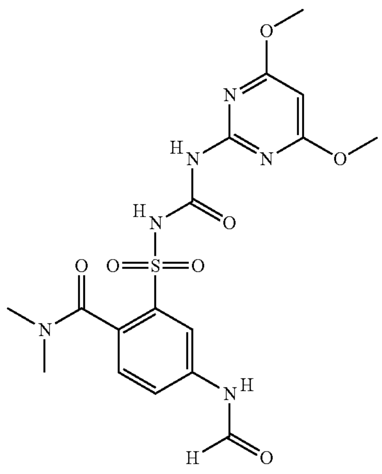

Foramsulfuron Molecule

The standard curve was created from 0 to 150 micrograms. Dilutions were necessary for experiment one since a concentration greater than the sensitivity of the spectrophotometer was assessed. Dilutions were not required for experiments two and three. The three experiments were ran as described in the methods section above. Concentration was the only modified variable. For all three experiments, 1 mL of minicells OD ~1.0 was used for each sample. Minicells were incubated with Foramsulfuron for two hours prior to analysis. Standard Curve with $R^2$ value >0.99. Three separate Foramsulfuron experiments with three different starting concentrations were conducted in triplicate. Results on mass encapsulated, encapsulation fraction, and mass fraction are presented in FIGS. 11B and 11C.

Agrochemical Example 2. Spirotetramat Encapsulation Via Minicell Technology

Figure 12A:
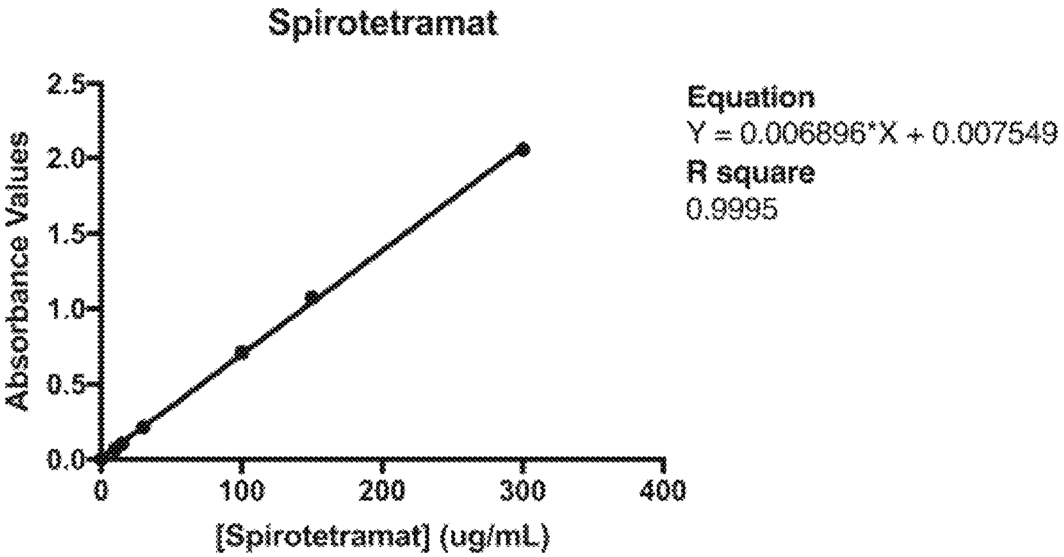
FIG. 12A shows a standard curve used for spirotetramat for total encapsulation analysis. The standard curve was generated from 0 to 300 microgram of spirotetramat. Three separate spirotetramat experiments were performed with three different starting concentrations in triplicate.
Figure 12B:
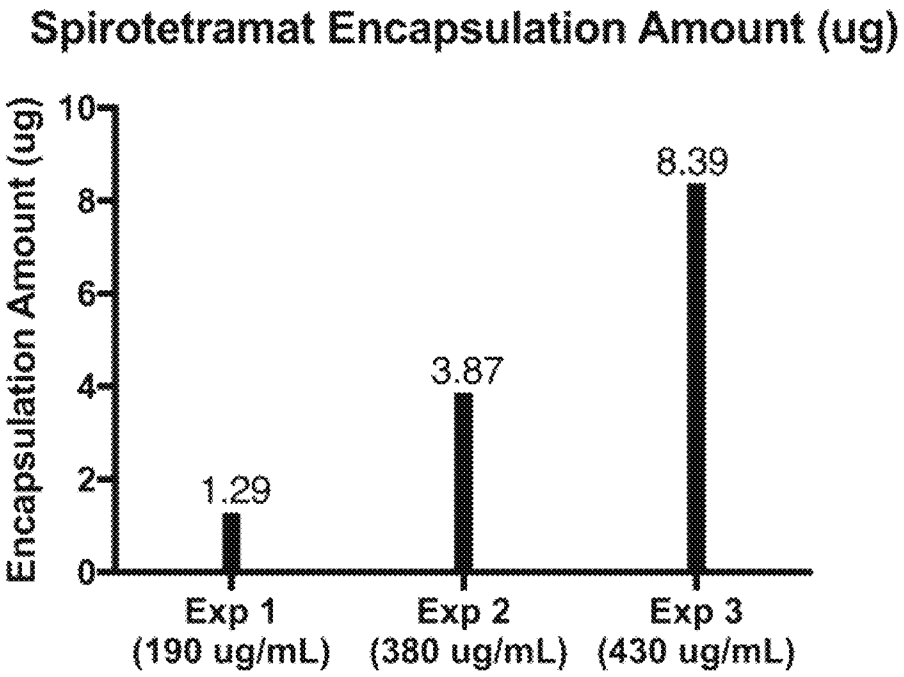
FIG. 12B shows the amount of spirotetramat encapsulation in three different starting concentration.
Figure 12C:
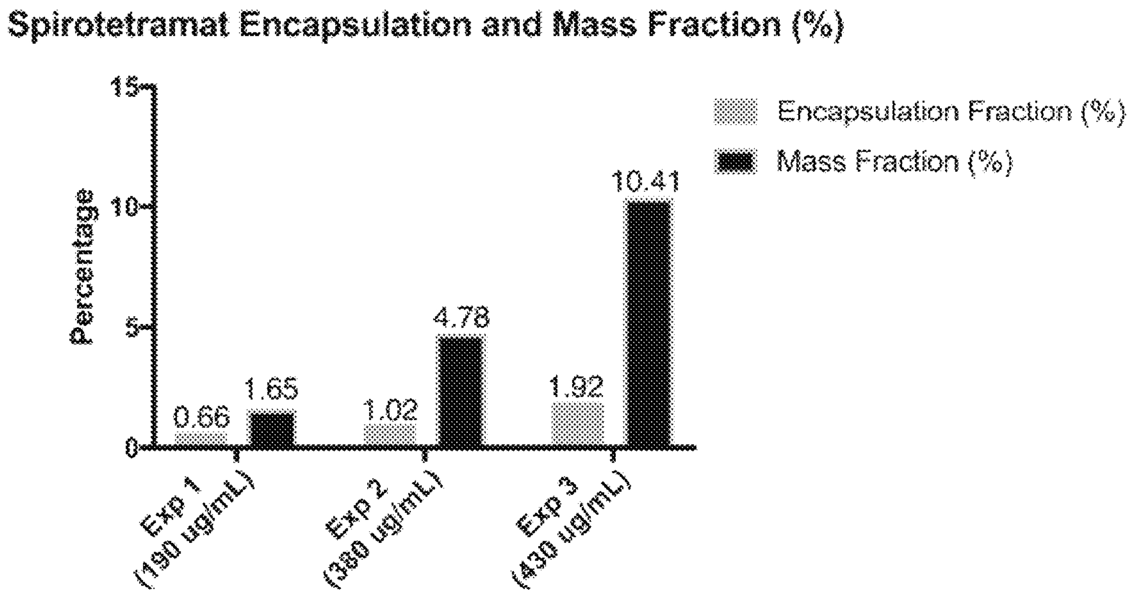
FIG. 12C shows ratios of spirotetramat encapsulation fraction and mass fraction.

Describes herein is the minicell technology to encapsulate Spirotetramat. Spirotetramat, or [3-(2,5-dimethylphenyl)-8-methoxy-2-oxo-1-azaspiro[4.5]dec-3-en-4-yl] ethyl carbonate, is an insecticide of the keto-enol class. Spirotetramat absorbs at 250 nanometers; therefore, Corning UV-Transparent Plates are used in conjunction with a spectrophotometer to collect encapsulation data. Absorbance metrics are converted to spirotetramat concentrations by using the standard curve as shown in FIG. 12A.

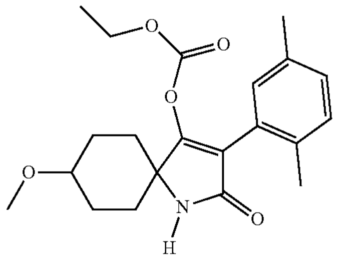 [SMILES: CCOC(=O)OC1=C(c2cc(C)ccc2C)C(=O)NC12CCC(OC)CC2]

Spirotetramat Molecule

The standard curve was created from 0 to 300 micrograms. Dilutions were necessary for experiments two and three since a concentration greater than the sensitivity of the spectrophotometer was assessed. Dilutions were not required for experiment one. The three experiments were ran as described in the methods section above. Concentration and time incubated were the only modified variables. For all three experiments, 1 mL of minicells OD ~1.0 was used for each sample. Minicells were incubated with Spirotetramat for two hours, except for experiment three which was incubated at two and a half hours, prior to analysis. Standard Curve with $R^2$>0.99. Three separate Spirotetramat experiments with three different starting concentrations were performed in triplicate. Experiment 1 and 2 show increased encapsulation by increasing the concentration of starting material. Since the goal is to boost mass fraction, in experiment three, spirotetramat concentration was increased and incubation time was increased from two hours to two and a half hours. The results on mass encapsulated, encapsulation fraction, and mass fraction are presented in FIGS. 12B and 12C.

Agrochemical Example 3. Pyraclostrobin Encapsulation Via Minicell Technology

Figure 13A:
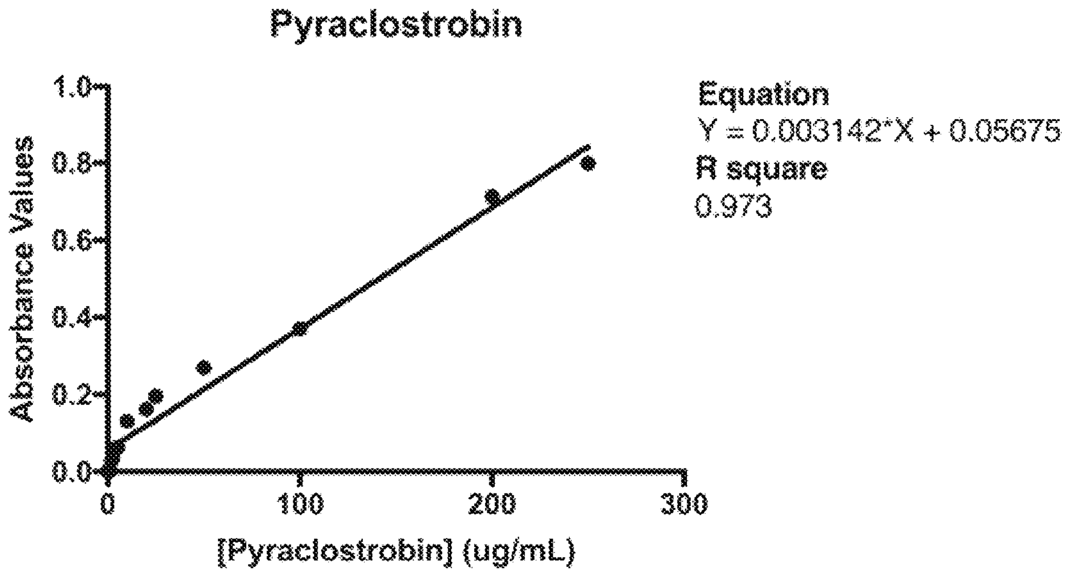
FIG. 13A shows a standard curve used for pyraclostrobin for total encapsulation analysis. The standard curve was generated from 0 to 250 microgram of pyraclostrobin. Three separate pyraclostrobin experiments were performed with three different starting concentrations in triplicate.
Figure 13B:
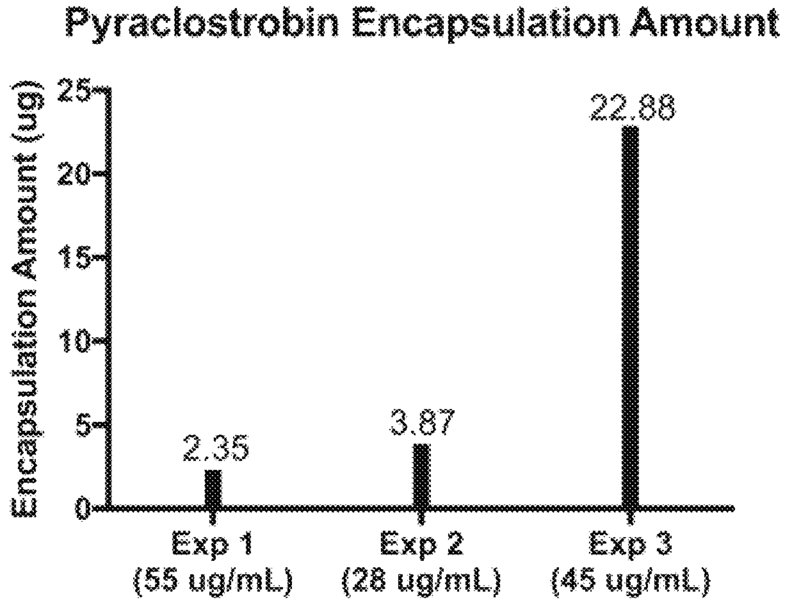
FIG. 13B shows the amount of pyraclostrobin encapsulation in three different starting concentration.
Figure 13C:
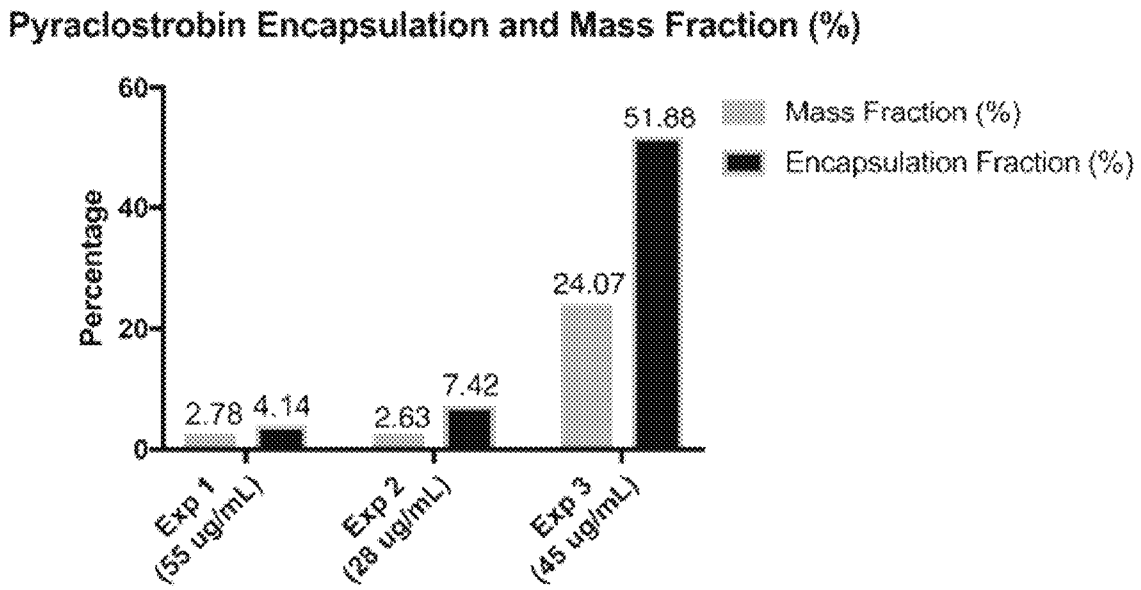
FIG. 13C shows ratios of pyraclostrobin encapsulation fraction and mass fraction.
Figure 14A:
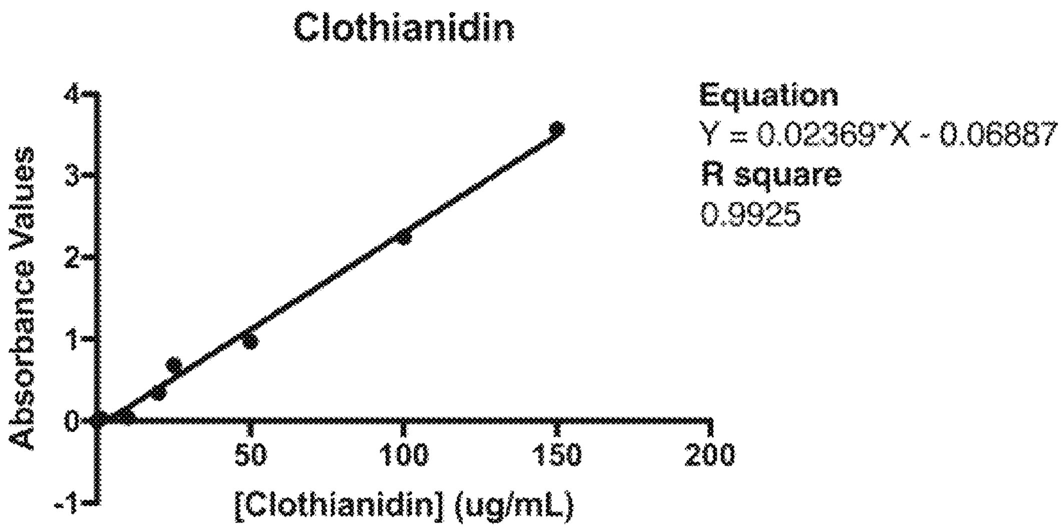
FIG. 14A shows a standard curve used for clothianidin for total encapsulation analysis. The standard curve was generated from 0 to 150 microgram of clothianidin. Three separate clothianidin experiments were performed with three different starting concentrations in triplicate.
Figure 14B:
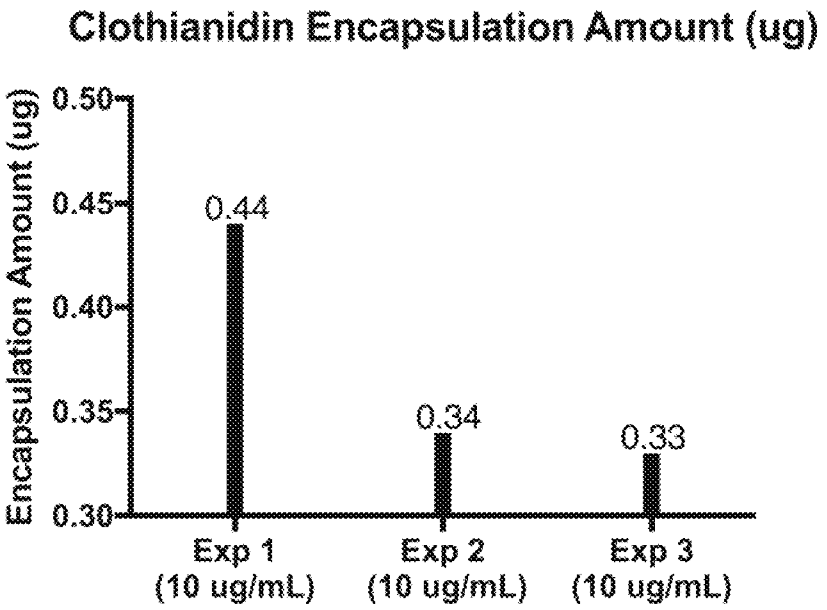
FIG. 14B shows the amount of clothianidin encapsulation in three different starting concentration.
Figure 14C:
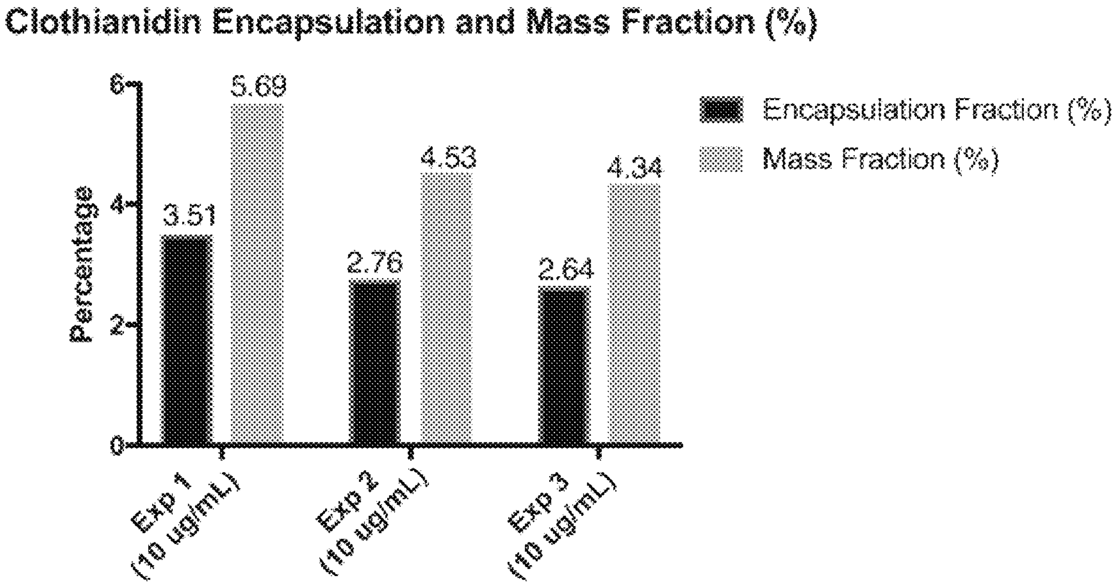
FIG. 14C shows ratios of clothianidin encapsulation fraction and mass fraction.
Figure 15A:
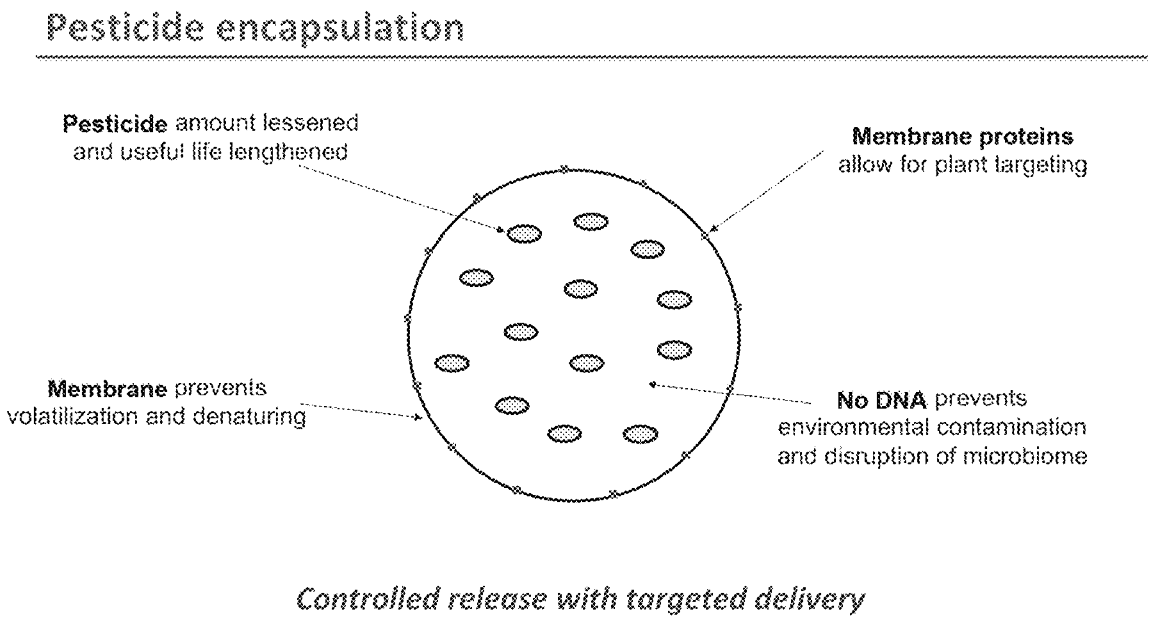
FIG. 15A illustrates an anucleated cell-based platform for encapsulation and delivery of agricultural compounds such as pesticide. This platform can be used for controlled release of agricultural compounds with targeted delivery using a fusion protein of membrane protein and a protein of interest for targeting a subject such as plant.
Figure 15B:
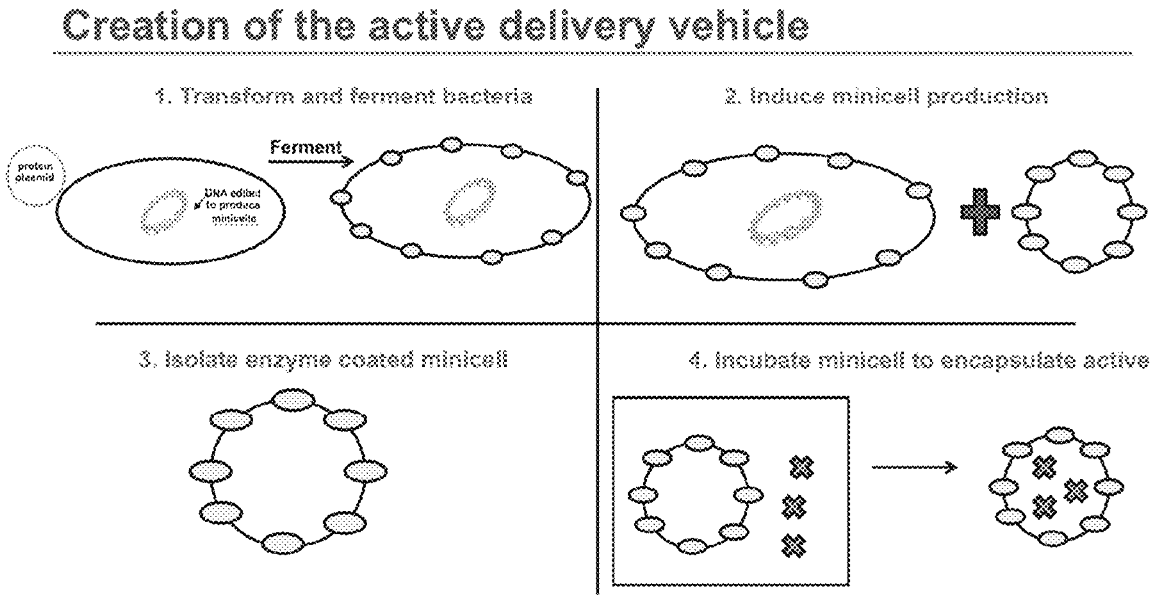
FIG. 15B illustrates a process of creation of the active delivery vehicle. The active delivery vehicle is generated by 1) transforming and ferment bacteria with DNA edited to produce minicells, 2) inducing minicell production, 3) isolating enzyme coated minicell, and 4) incubating minicell to encapsulate active agricultural compounds.

Describes herein is the minicell technology to encapsulate Pyraclostrobin. Pyraclostrobin, or methyl N-[2-[[1-(4-chlorophenyl) pyrazol-3-yl]oxy methyl]phenyl]-N-methoxycarbamate, is a fungicide in the strobilurin class. Pyraclostrobin absorbs at 275 nanometers; therefore, Corning UV-Transparent Plates are used in conjunction with a spectrophotometer to collect encapsulation data. Absorbance metrics are converted to pyraclostrobin concentrations by using the standard curve as shown in FIG. 13A.

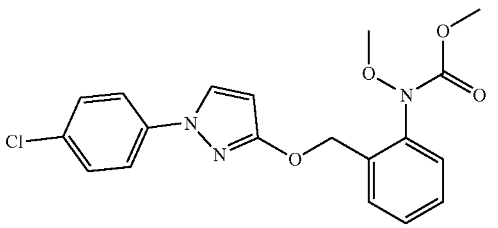 [SMILES: COC(=O)N(OC)c1ccccc1COc1ccn(-c2ccc(Cl)cc2)n1]

Pyraclostrobin Molecule

The standard curve was created from 0 to 250 micrograms. Dilutions were not required for these experiments. The three experiments were ran as described in the methods section above. Concentration and time incubated were the only modified variables. For all three experiments, 1 mL of minicells OD ~1.0 was used for each sample. Minicells were incubated with Pyraclostrobin for two hours, except for experiment three which was incubated at two and a half hours, prior to analysis. Standard Curve with $R^2$>0.97. Three separate Pyraclostrobin experiments with three different starting concentrations were performed in triplicate. Experiment 1 and 2 shows encapsulation at different concentrations of starting material. Since the goal is to boost mass fraction, in experiment three, pyraclostrobin incubation time was increased from two hours to two and a half hours. The results on mass encapsulated, encapsulation fraction, and mass fraction are presented in FIGS. 13B and 13C.

Agrochemical Example 4. Clothianidin Encapsulation Via Minicell Technology

Describes herein is the minicell technology to encapsulate Clothianidin. Clothianidin, or 1-[(2-chloro-1,3-thiazol-5-yl) methyl]-2-methyl-3-nitroguanidine, is an insecticide in the neonicotinoid class. Clothianidin absorbs at 270 nanometers; therefore, Corning UV-Transparent Plates are used in conjunction with a spectrophotometer to collect encapsulation data. Absorbance metrics are converted to clothianidin concentrations by using the standard curve in FIG. 14A.

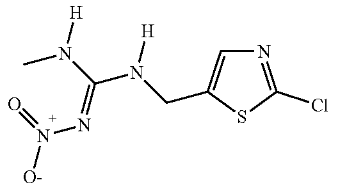

Clothianidin Molecule

The standard curve was created from 0 to 20 micrograms. Dilutions were not required for these experiments. The three experiments were ran as described in the methods section above. For all three experiments, 1 mL of minicells OD ~1.0 was used for each sample. Minicells were incubated with Clothianidin for two hours prior to analysis. Standard Curve with $R^2$ value >0.99. Three separate Clothianidin experiments with three different starting concentrations were performed in triplicate. Three identical experiments show similar results in the encapsulation of Clothianidin. The results on mass encapsulated, encapsulation fraction, and mass fraction are presented in FIGS. 14B and 14C.

Example 9. Application of Minicell Platform Encapsulating Agricultural Compound

As described in Example 7 and 8, minicells can encapsulate agricultural compounds and/or agrochemicals. The agrochemical encapsulated minicells can be formulated as a liquid, dry composition, powder, granule, seed coating, drench, in-furrow composition, or foliar spray. The formulated minicells encapsulating agrochemicals can be applied to a plant. Experiments will be conducted that directly and/or indirectly applies the formulated minicells encapsulating agricultural compounds unto a plant of interest, a part of which includes seed, stalk, flower, fruit, leaves, roots, or rhizome.

First, one of herbicides (e.g. foramsulfuron) encapsulated in minicells can be applied to an agricultural crop, including, but are not limited to sorghum, canola, tomato, strawberry, barley, rice, maize, and wheat. Second, one of insecticides (e.g. spirotetramat) encapsulated in minicells can be applied to an agricultural crop, including, but are not limited to sorghum, canola, tomato, strawberry, barley, rice, maize, and wheat. Third, another type of insecticides (e.g. Clothianidin) encapsulated in minicells can be applied to an agricultural crop, including, but are not limited to sorghum, canola, tomato, strawberry, barley, rice, maize, and wheat. Fourth, one of fungicide (e.g. Pyraclostrobin) encapsulated in minicells can be applied to an agricultural crop, including, but are not limited to sorghum, canola, tomato, strawberry, barley, rice, maize, and wheat.

NUMBERED EMBODIMENTS OF THE DISCLOSURE

Notwithstanding the appended claims, the disclosure sets forth the following numbered embodiments:

Platform

1. An anucleated cell-based platform for the encapsulation and delivery of agricultural compounds, comprising:
   a. an intact anucleated cell, having within said cell at least one non-expressed agricultural compound.
2. The anucleated cell-based platform as in any one of the preceding clauses, further comprising:
   b. at least one agriculturally acceptable carrier.
3. The anucleated cell-based platform as in any one of the preceding clauses, wherein said intact anucleated cell is derived from a prokaryotic cell.
4. The anucleated cell-based platform as in any one of the preceding clauses, wherein said intact anucleated cell is a bacterially derived minicell.
5. The anucleated cell-based platform as in any one of the preceding clauses, wherein said intact anucleated cell is produced from a gram negative bacterial genus.
6. The anucleated cell-based platform as in any one of the preceding clauses, wherein said intact anucleated cell is produced from a bacterial genus selected from the group consisting of: *Escherichia, Salmonella, Shigella, Pseudomonas*, and *Agrobacterium.*
7. The anucleated cell-based platform as in any one of the preceding clauses, wherein said intact anucleated cell is produced from a bacterial species selected from the group consisting of: *Escherichia coli, Salmonella typhimurium, Shigella flexneri*, and *Pseudomonas aeruginosa.*
8. The anucleated cell-based platform as in any one of the preceding clauses, wherein said intact anucleated cell is produced from a P678-54 *E. coli* parental bacterial cell.
9. The anucleated cell-based platform as in any one of the preceding clauses, wherein said intact anucleated cell is produced from a gram positive bacterial genus.
10. The anucleated cell-based platform as in any one of the preceding clauses, wherein said intact anucleated cell is produced from a bacterial genus selected from the group consisting of: *Bacillus, Corynebacterium*, and *Lactobacillus.*
11. The anucleated cell-based platform as in any one of the preceding clauses, wherein said intact anucleated cell is produced from a bacterial species selected from the group consisting of: *Bacillus subtilis, Corynebacterium glutamicum*, and *Lactobacillus acidophilus.*
12. The anucleated cell-based platform as in any one of the preceding clauses, wherein said intact anucleated cell is a bacterially derived minicell that is produced from a parental bacterial cell deficient in WprA protease.
13. The anucleated cell-based platform as in any one of the preceding clauses, wherein said intact anucleated cell is a bacterially derived minicell that is produced from a protease deficient *B. subtilis* parental bacterial cell.
14. The anucleated cell-based platform as in any one of the preceding clauses, wherein said intact anucleated cell is a bacterially derived minicell that is produced from a protease deficient KO7 *B. subtilis* parental bacterial cell.
15. The anucleated cell-based platform as in any one of the preceding clauses, wherein said intact anucleated cell is a bacterially derived minicell that is produced from a protease deficient *B. subtilis* parental bacterial cell selected from the group consisting of: (1) CU403, DIVIVA; (2) CU403,DIVIVB,SPO-; (3) CU403,DIVIVB; and (4) CU403,DIVIVB1, wherein at least one protease encoding gene has been repressed, deleted, or silenced.
16. The anucleated cell-based platform as in any one of the preceding clauses, wherein said intact anucleated cell is a bacterially derived minicell that is produced from a protease deficient parental bacterial cell.
17. The anucleated cell-based platform as in any one of the preceding clauses, wherein said intact anucleated cell is a bacterially derived minicell that is produced from a parental bacterial cell deficient in Lon and OmpT proteases.
18. The anucleated cell-based platform as in any one of the preceding clauses, wherein said intact anucleated cell is a bacterially derived minicell that is produced from a protease deficient *E. coli* parental bacterial cell.
19. The anucleated cell-based platform as in any one of the preceding clauses, wherein said intact anucleated cell is a bacterially derived minicell that is produced from a protease deficient *E. coli* parental bacterial cell selected from the group consisting of: BL21, BL21 (DE3), BL21-AI, LPS-modified BL21 (DE3) and B8.
20. The anucleated cell-based platform as in any one of the preceding clauses, wherein said intact anucleated cell is derived from a eukaryotic cell.
21. The anucleated cell-based platform as in any one of the preceding clauses, wherein the at least one non-expressed agricultural compound is selected from the group consisting of: a pesticide, an herbicide, an insecticide, a fungicide, a nematicide, a fertilizer and a hormone or a chemical growth agent.
22. The anucleated cell-based platform as in any one of the preceding clauses, wherein the at least one non-expressed agricultural compound is a pesticide.
23. The anucleated cell-based platform as in any one of the preceding clauses, wherein the at least one non-expressed agricultural compound is an herbicide.
24. The anucleated cell-based platform as in any one of the preceding clauses, wherein the at least one non-expressed agricultural compound is a sulfonylurea herbicide.
25. The anucleated cell-based platform as in any one of the preceding clauses, wherein the at least one non-expressed agricultural compound is foramsulfuron.
26. The anucleated cell-based platform as in any one of the preceding clauses, wherein the at least one non-expressed agricultural compound is an insecticide.
27. The anucleated cell-based platform as in any one of the preceding clauses, wherein the at least one non-expressed agricultural compound is a neonicotinoid insecticide.

28. The anucleated cell-based platform as in any one of the preceding clauses, wherein the at least one non-expressed agricultural compound is clothianidin.
29. The anucleated cell-based platform as in any one of the preceding clauses, wherein the at least one non-expressed agricultural compound is a keto-enol insecticide.
30. The anucleated cell-based platform as in any one of the preceding clauses, wherein the at least one non-expressed agricultural compound is spirotetramat.
31. The anucleated cell-based platform as in any one of the preceding clauses, wherein the at least one non-expressed agricultural compound is a fungicide.
32. The anucleated cell-based platform as in any one of the preceding clauses, wherein the at least one non-expressed agricultural compound is a strobilurin fungicide.
33. The anucleated cell-based platform as in any one of the preceding clauses, wherein the at least one non-expressed agricultural compound is pyraclostrobin.
34. The anucleated cell-based platform as in any one of the preceding clauses, wherein the at least one non-expressed agricultural compound is a nematicide.
35. The anucleated cell-based platform as in any one of the preceding clauses, wherein the at least one non-expressed agricultural compound is a fertilizer.
36. The anucleated cell-based platform as in any one of the preceding clauses, wherein the at least one non-expressed agricultural compound is a fertilizer selected from the group consisting of: nitrogen, phosphorous, and potassium.
37. The anucleated cell-based platform as in any one of the preceding clauses, wherein the at least one non-expressed agricultural compound is a hormone or a chemical growth agent.
38. The anucleated cell-based platform as in any one of the preceding clauses, wherein the at least one non-expressed agricultural compound is a hormone or a chemical growth agent selected from the group consisting of: abscisic acid, auxins, cytokinins, ethylene, gibberellins, brassinosteroids, salicylic acid, jasmonates, polyamines, nitric oxide, strigolactones, karrikins, and triacontanol.
39. The anucleated cell-based platform as in any one of the preceding clauses, wherein the anucleated cell expresses a polypeptide on its surface.
40. The anucleated cell-based platform as in any one of the preceding clauses, wherein the anucleated cell expresses a heterologous polypeptide on its surface.
41. The anucleated cell-based platform as in any one of the preceding clauses, wherein the anucleated cell expresses a fusion protein.
42. The anucleated cell-based platform as in any one of the preceding clauses, wherein the anucleated cell expresses a fusion protein, which comprises at least one surface expressing moiety and at least one plant cell adhesion moiety.
43. The anucleated cell-based platform as in any one of the preceding clauses, wherein the anucleated cell expresses a fusion protein, which comprises at least one surface expressing moiety and at least one plant cell adhesion moiety,
    wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).
44. The anucleated cell-based platform as in any one of the preceding clauses,
    wherein the anucleated cell expresses a fusion protein, which comprises at least one surface expressing moiety and at least one plant cell adhesion moiety, wherein said surface expressing moiety comprises an exported bacterial protein and is selected from the group consisting of: selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), B1a (TEM-1 B-lactamase), F1 or M13 major coat (derived from Gene VIII), and F1 or M13 minor coat (Gene III).
45. The anucleated cell-based platform as in any one of the preceding clauses, wherein the anucleated cell expresses a fusion protein, which comprises at least one surface expressing moiety and at least one plant cell adhesion moiety, wherein said plant cell adhesion moiety comprises a carbohydrate binding module.
46. The anucleated cell-based platform as in any one of the preceding clauses, wherein the anucleated cell expresses a fusion protein, which comprises at least one surface expressing moiety and at least one plant cell adhesion moiety,
    wherein said plant cell adhesion moiety comprises a carbohydrate binding module selected from the group consisting of: a cellulose binding domain, a xylan binding domain, a chitin binding domain, and a lignin binding domain.
47. The anucleated cell-based platform as in any one of the preceding clauses, wherein the anucleated cell expresses a polypeptide on its surface that increases adhesion to a plant surface.
48. The anucleated cell-based platform as in any one of the preceding clauses, wherein the anucleated cell expresses a plant adhesion polypeptide on its surface.
49. The anucleated cell-based platform as in any one of the preceding clauses, wherein the anucleated cell expresses a carbohydrate binding module that is displayed on its surface.
50. The anucleated cell-based platform as in any one of the preceding clauses, wherein the anucleated cell expresses a heterologous carbohydrate binding module that is displayed on its surface.
51. The anucleated cell-based platform as in any one of the preceding clauses, wherein the anucleated cell expresses a cellulose binding domain that is displayed on its surface.
52. The anucleated cell-based platform as in any one of the preceding clauses, wherein the anucleated cell expresses a heterologous cellulose binding domain that is displayed on its surface.
53. The anucleated cell-based platform as in any one of the preceding clauses, formulated as a liquid, dry composition, powder, granule, seed coating, drench, in-furrow composition, or foliar spray.
54. A method of delivering an agricultural compound to a locus, comprising: applying the anucleated cell-based platform as in any one of the preceding clauses to a desired locus.
55. A method of delivering an agricultural compound to a plant, comprising: applying the anucleated cell-based platform as in any one of the preceding clauses to a plant.

56. A method of delivering an agricultural compound to a plant, comprising: applying the anucleated cell-based platform as in any one of the preceding clauses to a plant, wherein the plant comprises the seed, stalk, flower, fruit, leaves, roots, or rhizome.
57. A method of delivering an agricultural compound to a crop, comprising: applying the anucleated cell-based platform as in any one of the preceding clauses to a crop, or locus in proximity to said crop.
58. The anucleated cell-based platform as in any one of the preceding clauses, wherein the anucleated cell is treated with a solvent.
59. The anucleated cell-based platform as in any one of the preceding clauses, wherein said solvent is ethanol, DMSO, polyethylene glycol, or glycerol.
60. The anucleated cell-based platform as in any one of the preceding clauses, wherein the anucleated cell is treated with an agent, in addition to said solvent.
61. The anucleated cell-based platform as in any one of the preceding clauses, wherein said agent is a fixative, a preservative or a cross-linking agent.
62. The anucleated cell-based platform as in any one of the preceding clauses, wherein said cross-linking agent is glutaraldehyde, formaldehyde, genipin, or epigallocatechin gallat.
63. The anucleated cell-based platform as in any one of the preceding clauses, wherein said solvent increases solubility of the agricultural compounds into the anucleated cell.
64. The anucleated cell-based platform as in any one of the preceding clauses, wherein said solvent increases solubility of the agricultural compounds into the anucleated cell, and wherein said solvent increases diffusion of the agricultural compounds into the anucleated cell.
65. The anucleated cell-based platform as in any one of the preceding clauses, wherein said agent captures the agricultural compounds within a membrane of the anucleated cell.
66. The anucleated cell-based platform as in any one of the preceding clauses, wherein said agent captures the agricultural compounds within a membrane of the anucleated cell, and wherein said agent cross-links the agricultural compounds to the anucleated cell, which improves stability of the anucleated cell.
67. The anucleated cell-based platform as in any one of the preceding clauses, wherein said agent enhances loading capacity of the agricultural compounds into the anucleated cell.
68. The anucleated cell-based platform as in any one of the preceding clauses, wherein said agent enhances loading capacity of the agricultural compounds into the anucleated cell, and wherein said agent controls a release rate of the agricultural compounds from the anucleated cell.
69. The anucleated cell-based platform as in any one of the preceding clauses, wherein the anucleated cell exhibits a controlled release rate of the at least one non-expressed agricultural compound.
70. The anucleated cell-based platform as in any one of the preceding clauses, wherein the anucleated cell exhibits a controlled release rate of the at least one non-expressed agricultural compound, and wherein said at least one non-expressed agricultural compound is released at a steady rate.
71. The anucleated cell-based platform as in any one of the preceding clauses, wherein the anucleated cell exhibits an initial burst release of the at least one non-expressed agricultural compound.
72. The anucleated cell-based platform as in any one of the preceding clauses, wherein the anucleated cell exhibits an initial burst release of the at least one non-expressed agricultural compound, said burst release comprising a release of at least about 40% of the at least one non-expressed agricultural compound.
73. The anucleated cell-based platform as in any one of the preceding clauses, wherein the anucleated cell exhibits a controlled release rate of the at least one non-expressed agricultural compound, and wherein the controlled release rate is less than 40%, less than 30%, less than 20%, less than 15%, less than 10%, or less than 5% of the at least one non-expressed agricultural compound being released from the anucleated cell per day.
74. The anucleated cell-based platform as in any one of the preceding clauses, wherein the controlled release rate is less than 15% of the non-expressed agricultural compound released from the anucleated cell per day.
75. The anucleated cell-based platform as in any one of the preceding clauses, wherein the controlled release rate is less than 10% of the non-expressed agricultural compound released from the anucleated cell per day.
76. The anucleated cell-based platform as in any one of the preceding clauses, wherein the controlled release rate is about 10% of the non-expressed agricultural compound released from the anucleated cell per day.

Agricultural Compositions

1. A composition for the stable and targeted delivery of agricultural compounds, comprising:
    a. an intact anucleated cell, having within said cell at least one non-expressed agricultural compound; and
    b. at least one agriculturally acceptable carrier.
2. The composition as in any one of the preceding clauses, wherein said intact anucleated cell is derived from a prokaryotic cell.
3. The composition as in any one of the preceding clauses, wherein said intact anucleated cell is a bacterially derived minicell.
4. The composition as in any one of the preceding clauses, wherein said intact anucleated cell is produced from a gram negative bacterial genus.
5. The composition as in any one of the preceding clauses, wherein said intact anucleated cell is produced from a bacterial genus selected from the group consisting of: *Escherichia, Salmonella, Shigella, Pseudomonas*, and *Agrobacterium*.
6. The composition as in any one of the preceding clauses, wherein said intact anucleated cell is produced from a bacterial species selected from the group consisting of: *Escherichia coli, Salmonella typhimurium, Shigella flexneri*, and *Pseudomonas aeruginosa*.
7. The composition as in any one of the preceding clauses, wherein said intact anucleated cell is produced from a P678-54 *E. coli* parental bacterial cell.
8. The composition as in any one of the preceding clauses, wherein said intact anucleated cell is produced from a gram positive bacterial genus.
9. The composition as in any one of the preceding clauses, wherein said intact anucleated cell is produced from a bacterial genus selected from the group consisting of: *Bacillus, Corynebacterium*, and *Lactobacillus*.
10. The composition as in any one of the preceding clauses, wherein said intact anucleated cell is produced from a bacterial species selected from the group consisting of: *Bacillus subtilis, Corynebacterium glutamicum*, and *Lactobacillus acidophilus.*

11. The composition as in any one of the preceding clauses, wherein said intact anucleated cell is a bacterially derived minicell that is produced from a parental bacterial cell deficient in WprA protease.
12. The composition as in any one of the preceding clauses, wherein said intact anucleated cell is a bacterially derived minicell that is produced from a protease deficient *B. subtilis* parental bacterial cell.
13. The composition as in any one of the preceding clauses, wherein said intact anucleated cell is a bacterially derived minicell that is produced from a protease deficient KO7 *B. subtilis* parental bacterial cell.
14. The composition as in any one of the preceding clauses, wherein said intact anucleated cell is a bacterially derived minicell that is produced from a protease deficient *B. subtilis* parental bacterial cell selected from the group consisting of: (1) CU403,DIVIVA; (2) CU403,DIVIVB,SPO-; (3) CU403,DIVIVB; and (4) CU403,DIVIVB1, wherein at least one protease encoding gene has been repressed, deleted, or silenced.
15. The composition as in any one of the preceding clauses, wherein said intact anucleated cell is a bacterially derived minicell that is produced from a protease deficient parental bacterial cell.
16. The composition as in any one of the preceding clauses, wherein said intact anucleated cell is a bacterially derived minicell that is produced from a parental bacterial cell deficient in Lon and OmpT proteases.
17. The composition as in any one of the preceding clauses, wherein said intact anucleated cell is a bacterially derived minicell that is produced from a protease deficient *E. coli* parental bacterial cell.
18. The composition as in any one of the preceding clauses, wherein said intact anucleated cell is a bacterially derived minicell that is produced from a protease deficient *E. coli* parental bacterial cell selected from the group consisting of: BL21, BL21(DE3), BL21-AI, LPS-modified BL21 (DE3) and B8.
19. The composition as in any one of the preceding clauses, wherein said intact anucleated cell is derived from a eukaryotic cell.
20. The composition as in any one of the preceding clauses, wherein the at least one non-expressed agricultural compound is selected from the group consisting of: a pesticide, an herbicide, an insecticide, a fungicide, a nematicide, a fertilizer and a hormone or a chemical growth agent.
21. The composition as in any one of the preceding clauses, wherein the at least one non-expressed agricultural compound is a pesticide.
22. The composition as in any one of the preceding clauses, wherein the at least one non-expressed agricultural compound is an herbicide.
23. The composition as in any one of the preceding clauses, wherein the at least one non-expressed agricultural compound is a sulfonylurea herbicide.
24. The composition as in any one of the preceding clauses, wherein the at least one non-expressed agricultural compound is foramsulfuron.
25. The composition as in any one of the preceding clauses, wherein the at least one non-expressed agricultural compound is an insecticide.
26. The composition as in any one of the preceding clauses, wherein the at least one non-expressed agricultural compound is a neonicotinoid insecticide.
27. The composition as in any one of the preceding clauses, wherein the at least one non-expressed agricultural compound is clothianidin.
28. The composition as in any one of the preceding clauses, wherein the at least one non-expressed agricultural compound is a keto-enol insecticide.
29. The composition as in any one of the preceding clauses, wherein the at least one non-expressed agricultural compound is spirotetramat.
30. The composition as in any one of the preceding clauses, wherein the at least one non-expressed agricultural compound is a fungicide.
31. The composition as in any one of the preceding clauses, wherein the at least one non-expressed agricultural compound is a strobilurin fungicide.
32. The composition as in any one of the preceding clauses, wherein the at least one non-expressed agricultural compound is pyraclostrobin.
33. The composition as in any one of the preceding clauses, wherein the at least one non-expressed agricultural compound is a nematicide.
34. The composition as in any one of the preceding clauses, wherein the at least one non-expressed agricultural compound is a fertilizer.
35. The composition as in any one of the preceding clauses, wherein the at least one non-expressed agricultural compound is a fertilizer selected from the group consisting of: nitrogen, phosphorous, and potassium.
36. The composition as in any one of the preceding clauses, wherein the at least one non-expressed agricultural compound is a hormone or a chemical growth agent.
37. The composition as in any one of the preceding clauses, wherein the at least one non-expressed agricultural compound is a hormone or a chemical growth agent selected from the group consisting of: abscisic acid, auxins, cytokinins, ethylene, gibberellins, brassinosteroids, salicylic acid, jasmonates, polyamines, nitric oxide, strigolactones, karrikins, and triacontanol.
38. The composition as in any one of the preceding clauses, wherein the anucleated cell expresses a polypeptide on its surface.
39. The composition as in any one of the preceding clauses, wherein the anucleated cell expresses a heterologous polypeptide on its surface.
40. The composition as in any one of the preceding clauses, wherein the anucleated cell expresses a fusion protein.
41. The composition as in any one of the preceding clauses, wherein the anucleated cell expresses a fusion protein, which comprises at least one surface expressing moiety and at least one plant cell adhesion moiety.
42. The composition as in any one of the preceding clauses, wherein the anucleated cell expresses a fusion protein, which comprises at least one surface expressing moiety and at least one plant cell adhesion moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).
43. The composition as in any one of the preceding clauses, wherein the anucleated cell expresses a fusion protein, which comprises at least one surface expressing moiety and at least one plant cell adhesion moiety, wherein said surface expressing moiety comprises an exported bacterial protein and is selected from the group consisting of: selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), B1a (TEM-1 B-lactamase), F1 or M13 major coat (derived from Gene VIII), and F1 or M13 minor coat (Gene III).

44. The composition as in any one of the preceding clauses, wherein the anucleated cell expresses a fusion protein, which comprises at least one surface expressing moiety and at least one plant cell adhesion moiety, wherein said plant cell adhesion moiety comprises a carbohydrate binding module.

45. The composition as in any one of the preceding clauses, wherein the anucleated cell expresses a fusion protein, which comprises at least one surface expressing moiety and at least one plant cell adhesion moiety, wherein said plant cell adhesion moiety comprises a carbohydrate binding module selected from the group consisting of: a cellulose binding domain, a xylan binding domain, a chitin binding domain, and a lignin binding domain.

46. The composition as in any one of the preceding clauses, wherein the anucleated cell expresses a polypeptide on its surface that increases adhesion to a plant surface.

47. The composition as in any one of the preceding clauses, wherein the anucleated cell expresses a plant adhesion polypeptide on its surface.

48. The composition as in any one of the preceding clauses, wherein the anucleated cell expresses a carbohydrate binding module that is displayed on its surface.

49. The composition as in any one of the preceding clauses, wherein the anucleated cell expresses a heterologous carbohydrate binding module that is displayed on its surface.

50. The composition as in any one of the preceding clauses, wherein the anucleated cell expresses a cellulose binding domain that is displayed on its surface.

51. The composition as in any one of the preceding clauses, wherein the anucleated cell expresses a heterologous cellulose binding domain that is displayed on its surface.

52. The composition as in any one of the preceding clauses, formulated as a liquid, dry composition, powder, granule, seed coating, drench, in-furrow composition, or foliar spray.

53. A method of delivering an agricultural compound to a locus, comprising: applying the composition as in any one of the preceding clauses to a desired locus.

54. A method of delivering an agricultural compound to a plant, comprising: applying the composition as in any one of the preceding clauses to a plant.

55. A method of delivering an agricultural compound to a plant, comprising: applying the composition as in any one of the preceding clauses to a plant, wherein the plant comprises the seed, stalk, flower, fruit, leaves, roots, or rhizome.

56. A method of delivering an agricultural compound to a crop, comprising: applying the composition according to claim 1 to a crop, or locus in proximity to said crop.

57. The composition as in any one of the preceding clauses, wherein the anucleated cell is treated with a solvent.

58. The composition as in any one of the preceding clauses, wherein said solvent is ethanol, DMSO, polyethylene glycol, or glycerol.

59. The composition as in any one of the preceding clauses, wherein the anucleated cell is treated with an agent, in addition to said solvent.

60. The composition as in any one of the preceding clauses, wherein said agent is a fixative, a preservative or a cross-linking agent.

61. The composition as in any one of the preceding clauses, wherein said cross-linking agent is glutaraldehyde, formaldehyde, genipin, or epigallocatechin gallat.

62. The composition as in any one of the preceding clauses, wherein said solvent increases solubility of the agricultural compounds into the anucleated cell.

63. The composition as in any one of the preceding clauses, wherein said solvent increases solubility of the agricultural compounds into the anucleated cell, and wherein said solvent increases diffusion of the agricultural compounds into the anucleated cell.

64. The composition as in any one of the preceding clauses, wherein said agent captures the agricultural compounds within a membrane of the anucleated cell.

65. The composition as in any one of the preceding clauses, wherein said agent captures the agricultural compounds within a membrane of the anucleated cell, and wherein said agent cross-links the agricultural compounds to the anucleated cell, which improves stability of the anucleated cell.

66. The composition as in any one of the preceding clauses, wherein said agent enhances loading capacity of the agricultural compounds into the anucleated cell.

67. The composition as in any one of the preceding clauses, wherein said agent enhances loading capacity of the agricultural compounds into the anucleated cell, and wherein said agent controls a release rate of the agricultural compounds from the anucleated cell.

68. The composition as in any one of the preceding clauses, wherein the anucleated cell exhibits a controlled release rate of the at least one non-expressed agricultural compound.

69. The composition as in any one of the preceding clauses, wherein the anucleated cell exhibits a controlled release rate of the at least one non-expressed agricultural compound, and wherein said at least one non-expressed agricultural compound is released at a steady rate.

70. The composition as in any one of the preceding clauses, wherein the anucleated cell exhibits an initial burst release of the at least one non-expressed agricultural compound.

71. The composition as in any one of the preceding clauses, wherein the anucleated cell exhibits an initial burst release of the at least one non-expressed agricultural compound, said burst release comprising a release of at least about 40% of the at least one non-expressed agricultural compound.

72. The composition as in any one of the preceding clauses, wherein the anucleated cell exhibits a controlled release rate of the at least one non-expressed agricultural compound, and wherein the controlled release rate is less than 40%, less than 30%, less than 20%, less than 15%, less than 10%, or less than 5% of the at least one non-expressed agricultural compound being released from the anucleated cell per day.

73. The composition as in any one of the preceding clauses, wherein the controlled release rate is less than 15% of the non-expressed agricultural compound released from the anucleated cell per day.
74. The composition as in any one of the preceding clauses, wherein the controlled release rate is less than 10% of the non-expressed agricultural compound released from the anucleated cell per day.
75. The composition as in any one of the preceding clauses, wherein the controlled release rate is about 10% of the non-expressed agricultural compound released from the anucleated cell per day.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

REFERENCES

POURTAHERI P., ZOMORODI S., DAVIS Z. G., SHAKEEL A. M., Frank J., MOSHASHA S. R., KHOKHLACHEV A., Kester M., Compositions and methods for pesticide degradation, WO2017/180650 A1

Sabbadini R., Berkley N., Surber M., Klepper R., Minicell based delivery of biologically active compounds U.S. Pat. No. 9,017,986 B2

Giacalone M. J., Maloy S., Tsuji S., Regulated genetic suicide mechanism compositions and methods, U.S. Pat. No. 9,045,761 B2

Giacalone M. J, Newman M. J., Therapeutic compositions and methods for antibody and fc-containing targeting molecule-based targeted delivery of bioactive molecules by bacterial minicells, US2/012/0207754 A1

*Enzyme Immobilization—Advances in Industry, Agriculture,* |Alka Dwevedi|Springer. (n.d.). Retrieved from http://www.springer.com/us/book/9783319414164

Gai, S. A., & Wittrup, K. D. (2007). Yeast surface display for protein engineering and characterization. *Current Opinion in Structural Biology,* 17(4), 467-473. https://doi.org/10.1016/j.sbi.2007.08.012

Karlsson, S., Holmbom, B., Spetz, P., Mustranta, A., & Buchert, J. (2001). Reactivity of *Trametes laccases* with fatty and resin acids. *Applied Microbiology and Biotechnology,* 55(3), 317-320.

Mitra, S. D., Afonina, I., & Kline, K. A. (2016). Right Place, Right Time: Focalization of Membrane Proteins in Gram-Positive Bacteria. *Trends in Microbiology,* 24(8), 611-621.

Lee, S. H., Lee, S. Y., & Park, B. C. (2005). Cell Surface Display of Lipase in *Pseudomonas putida* KT2442 Using OprF as an Anchoring Motif and Its Biocatalytic Applications. *Applied and Environmental Microbiology,* 71(12), 8581-8586.

Routledge, S. J., Mikaliunaite, L., Patel, A., Clare, M., Cartwright, S. P., Bawa, Z., . . . Bill, R. M. (2016). The synthesis of recombinant membrane proteins in yeast for structural studies. *Methods,* 95, 26-37.

Vinh, D. Khue, N. Study on Minicell Generation of *Lactobacillus acidophilus* VTCC-B-871 for Drug Delivery. Journal of Applied Pharmaceutical Science. Vol. 3 (05), 33-36.

Wieczorek, A. S., Biot-Pelletier, D., & Martin, V. J. J. (2013). Recombinant Cellulase and Cellulosome Systems.

Patent US20130337545 Minicell Based Delivery of Biologically Active Compounds

Fersht A. Structure and mechanism in protein science: a guide to enzyme catalysis and protein folding. New York: W. H. Freeman & Company; 1998. p. 615.

Powers R. Comparison of protein active site structures for functional annotation of Proteins and drug design. Proteins Struct Funct Bioinf. 2006; 65:124-35.

Nelson J M, Hitchcock D I. The activity of adsorbed invertase. J Am Chem Soc. 1921; 43:1956-61.

Mclaren A D. Concerning the pH dependence of enzyme reactions on cells, particulates and in solution. Science. 1957; 125:697.

Mosbach K, Mosbach R. Entrapment of enzymes and microorganisms in synthetic cross-linked polymers and their application in column techniques. Acta Chem Scand. 1966; 20:2807-10.

Chen L F, Richardson R. Enzyme derivatives containing reactive groups. Immobilization of alpha-amylase on human erythrocytes. Pharmacol Res Commun. 1974; 6:273-80.

Kennedy J F, Zamir A. The use of cellulose xanthate for the immobilisation of biological molecules. Carbohydr Res. 1975; 41:227-33.

Cordonnier M, Lawny F, Chapot D, Thomas D. Magnetic enzyme membranes as active elements of electrochemical sensors. Lactose, saccharose, maltose bienzyme electrodes. FEBS Lett. 1975; 59:263-7.

Sin M L, Mach K E, Wong P K, Liao J C. Advances and challenges in biosensor-based diagnosis of infectious diseases. Expert Rev Mol Diagn. 2014; 14:225-44.

Horton H R, Swaisgood H E. Immobilization as a means of investigating the acquisition of tertiary structure in chymotrypsinogen. Methods Enzymol. 1976; 44:516-26.

Das N, Kayastha AM, Malhotra O P. Immobilization of urease from pigeonpea (Cajanus cajan L.) on polyacrylamide gels and calcium alginate beads. Biotechnol Appl Biochem. 1998; 27:25-9.

Nakarani M, Kayastha AM. Kinetics and diffusion studies in urease-alginate biocatalyst beads. Orient Pharm Exp Med. 2007; 7:79-84.

Alloue W A, Destain J, El Medjoub T, Ghalfi H, Kabran P, Thonart P. Comparison of *Yarrowia lipolytica* lipase immobilization yield of entrapment, adsorption, and covalent bond techniques. Appl Biochem Biotechnol. 2008; 150:51-63.

Hage D S, Walters R R, Hethcote H W. Split-peak affinity chromatographic studies of the immobilization-dependent adsorption kinetics of protein A. Anal Chem. 1986; 58:274-9.

Marquez L D S, Cabral B V, Freitas F F, Cardoso V L, Ribeiro E J. Optimization of invertase immobilization by adsorption in ionic exchange resin for sucrose hydrolysis. J Mol Catal B: Enzym. 2008; 51:86-92.

Das N, Prabhakar P, Kayastha A M, Srivastava R C. Enzyme entrapped inside the reverse micelle in the fabrication of a new urea sensor. Biotechnol Bioeng. 1997; 54:329-32.

Iso M, Shirahase T, Hanamura S, Urushiyama S, Omi S. Immobilization of enzyme by microencapsulation and application of the encapsulated enzyme in the catalysis. J Microencapsul. 1989; 6:165-76.

Iso M, Kando T, Omi S. A fundamental study of the microencapsulation procedure utilizing coacervation in a polystyrene-cyclohexane solution. J Microencapsul. 1985; 2:275-87.

Mauguet M C, Legrand J, Brujes L, Carnelle G, Larre C, Popineau Y. Gliadin matrices for microencapsulation processes by simple coacervation method. J Microencapsul. 2002; 19:377-84.

Kayastha A M, Srivastava P K, Miksa B, Slomkowski S. Unique activity of ureases immobilized on poly (styrene-co-acrolein) microspheres. J Bioact Compat Polym. 2003; 18:113-24.

Reddy K R C, Kayastha A M. Improved stability of urease upon coupling to alkylamine and arylamine glass and its analytical use. J Mol Catal B: Enzym. 2006; 38:104-12.

Trevan M D. Enzyme immobilization by covalent bonding. Methods Mol Biol. 1988; 3:495-510.

Williams R A, Blanch H W. Covalent immobilization of protein monolayers for biosensor applications. Biosens Bioelectron. 1994; 9:159-67.

Pierre S J, Thies J C, Dureault A, Cameron N R, van Hest J C M, Carette N, Michon T, Weberskirch R. Covalent enzyme immobilization onto photopolymerized highly porous monoliths. Adv Mater. 2006; 18:1822-6.

Dwevedi A, Kayastha A M. Optimal immobilization of beta-galactosidase from Pea (PsBGAL) onto Sephadex and chitosan beads using response surface methodology and its applications. Bioresour Technol. 2009; 100:2667-75.

Dwevedi A, Kayastha A M. Stabilization of beta-galactosidase (from peas) by immobilization onto amberlite MB-150 beads and its application in lactose hydrolysis. J Agric Food Chem. 2009; 57:682-8.

Mulagalapalli S, Kumar S, Kalathur R C, Kayastha A M. Immobilization of urease from pigeonpea (Caj anus cajan) on agar tablets and its application in urea assay. Appl Biochem Biotechnol. 2007; 142:291-7.

Das N, Kayastha A M, Malhotra O P. Immobilization of urease from pigeonpea (Cajanus cajan L.) in polyacrylamide gels and calcium alginate beads. Biotechnol Appl Biochem. 1998; 27:25-9.

Das N, Kayastha A M. Immobilization of urease from pigeonpea (Caj anus cajan L.) on flannel cloth using polyethylenimine. World J Microbiol Biotechnol. 1998; 14:927-9.

Kayastha A M, Srivastava P K. Pigeonpea (Caj anus cajan L.) urease immobilized on glutaraldehyde activated chitosan beads and its analytical applications. Appl Biochem Biotechnol. 2001; 96:41-53.

Tripathi P, Kumari A, Rath P, Kayastha A M. Immobilization of α-amylase from mung beans (*Vigna radiata*) on Amberlite MB 150 and chitosan beads: A comparative study. J Mol Catal B: Enzym. 2007; 49:69-74.

Kumar S, Dwevedi A, Kayastha A M. Immobilization of soybean (*Glycine max*) urease on alginate and chitosan beads showing improved stability: Analytical applications. J Mol Catal B: Enzym. 2009; 58:138-45.

Neto S A, Forti J C, Zucolotto V, Ciancaglini P, De Andrade A R. The kinetic behavior of dehydrogenase enzymes in solution and immobilized onto nanostructured carbon platforms. Process Biochem. 2011; 46:2347-52.

DeLouise L A, Miller B L. Enzyme Immobilization in porous silicon: Quantitative analysis of the kinetic parameters for glutathione-S-transferases. Anal Chem. 2005; 77:1950-6.

Reddy K R C, Turcu F, Schulte A, Kayastha A M, Schuhmann W. Fabrication of a potentiometric/amperometric bifunctional enzyme microbiosensor. Anal Chem. 2005; 77:5063-7.

Lin E-W, Boehnke N, Maynard H D. Protein-polymer conjugation via ligand affinity and photoactivation of glutathione S-transferase. Bioconjugate Chem. 2014; 25:1902-9.

Alconcel S N S, Baas A S, Maynard H D. FDA approved poly (ethylene glycol)-protein conjugate drugs. Polym Chem. 2011; 2:1442-8.

Canalle L A, Lowik D, van Hest J C M. Polypeptide-polymer bioconjugates. Chem Soc Rev. 2010; 39:329-53.

Self-assembly—Latest research and news I Nature. (n.d.). Retrieved from http://www.nature.com/subjects/self-assembly Silhavy, T. J., Benson, S. A., & Emr, S. D. (1983). Mechanisms of protein localization. *Microbiological Reviews,* 47(3), 313-344.

Mitra, S. D., Afonina, I., & Kline, K. A. (2016). Right Place, Right Time: Focalization of Membrane Proteins in Gram-Positive Bacteria. *Trends in Microbiology,* 24(8), 611-621.

Routledge, S. J., Mikaliunaite, L., Patel, A., Clare, M., Cartwright, S. P., Bawa, Z., . . . Bill, R. M. (2016). The synthesis of recombinant membrane proteins in yeast for structural studies. *Methods,* 95, 26-37.

H. I. Adler, W. D. Fisher, A. Cohen and Alice A. Hardigree, Miniature *Escherichia coli* Cells Deficient in DNA *Proceedings of the National Academy of Sciences of the United States of America Vol.* 57, No. 2 (Feb. 15, 1967), pp. 321-326

PIET A. J. DE BOER, ROBIN E. CROSSLEY, AND LAWRENCE I. ROTHFIELD, (1990) Central role for the *Escherichia coli* minC gene product in two different cell division-inhibition systems, Proc. Natl. Acad. Sci. USA Vol. 87, pp. 1129-1133, Xuan-Chuan Yu and William Margolin Deletion of the min Operon Results in Increased Thermosensitivity of anftsZ84 Mutant and Abnormal FtsZ Ring Assembly, Placement, and Disassembly, J Bacteriol. 2000 November; 182(21): 6203-6213.

Murphy K C. Targeted chromosomal gene knockout using PCR fragments. Methods Mol Biol. 2011; 765:27-42.

Maral Rahimzadeh, Majid Sadeghizadeh, Farhood Najafi, Seyed Arab, and Hamid Mobasheri Impact of heat shock step on bacterial transformation efficiency, Mol Biol Res Commun. 2016 December; 5(4): 257-261.

https://www.sigmaaldrich.com/content/dam/sigma-aldrich/docs/Sigma/General_Information/lipoproteinlipase.pdf Mitra, S. D., Afonina, I. and Kline, K. A. (2016) Right Place, Right Time: Focalization of Membrane Proteins in Gram-Positive Bacteria. Trends in Microbiology 24(8): 611-621.

Inselburg J, Segregation into and Replication of Plasmid Deoxyribonucleic Acid in Chromosomeless Segregants of *Escherichia coli* 1970 *J Bacteriol.* 102(3):642-647

Frazer A C, Curtiss R 3rd, Production, properties and utility of bacterial minicells 1975*, Curr. Topics Microbiol. Immunol.* 69:1-84

Reeve, J. N., and N. H. Mendelson. 1973. Pronase digestion of amino acid binding components on the surface of *Bacillus subtilis* cells and minicells. Biochem. Biophys. Res. Commun. 53:1325-1330

Tankersley W G, Woodward J M, Brown A. Induction and isolation of a minicell-producing strain of *Salmonella typhimurium*. Proc Soc Exp Biol Med. 1974 March; 145(3):802-805

Reeve J N, Mendelson N H, Coyne S I, Hallock L L, Cole R M, Minicells of *Bacillus subtilis,* 1973, J. Bacteriol. 114(2):860-873

Mendelson N H, Reeve J N, Cole R M, Physiological Studies of *Bacillus subtilis* Minicells 1974 J Bacteriol. 117(3):1312-1319.

Yang X, Sun S, Wang H F, Hang H Y 2013, Comparison of Autotransporter and Ice Nucleation Protein as Carrier Proteins for Antibody Displayon The Cell Surface of *Escherichia coli* Progress in Biochemistry and Biophysics 40(12): 1209-1219

Cid, M., Pedersen, H. L., Kaneko, S., Coutinho, P. M., Henrissat, B., Willats, W. G. T., & Boraston, A. B. (2010). Recognition of the Helical Structure of β-1,4-Galactan by a New Family of Carbohydrate-binding Modules. *Journal of Biological Chemistry,* 285(46), 35999-36009.

Datta, S., Christena, L. R., & Rajaram, Y. R. S. (2013). Enzyme immobilization: an overview on techniques and support materials. 3 *Biotech,* 3(1), 1-9.

Dimov, N., Kastner, E., Hussain, M., Perrie, Y., & Szita, N. (2017). Formation and purification of tailored liposomes for drug delivery using a module-based micro continuous-flow system. *Scientific Reports,* 7(1), 12045.

*Enzyme Immobilization—Advances in Industry, Agriculture,* |Alka Dwevedi|Springer. (2016). Retrieved from www.springer.com/us/book/9783319414164

Farley, M. M., Hu, B., Margolin, W., & Liu, J. (2016). Minicells, Back in Fashion. *Journal of Bacteriology,* 198(8), 1186-1195.

Gill, H. K., & Garg, H. (2014). Pesticides: Environmental Impacts and Management Strategies.

Jose, J., Maas, R. M., & Teese, M. G. (2012). Autodisplay of enzymes—molecular basis and perspectives. *Journal of Biotechnology,* 161(2), 92-103.

Linder, M., & Teeri, T. T. (1997). The roles and function of cellulose-binding domains. *Journal of Biotechnology,* 57(1), 15-28.

MacDiarmid, J. A., Mugridge, N. B., Weiss, J. C., Phillips, L., Burn, A. L., Paulin, R. P., . . . Brahmbhatt, H. (2007). Bacterially derived 400 nm particles for encapsulation and cancer cell targeting of chemotherapeutics. Cancer Cell, 11(5), 431-445.

Mahmood, T., & Yang, P.-C. (2012). Western Blot: Technique, Theory, and Trouble Shooting.

*North American Journal of Medical Sciences,* 4(9), 429-434.

Nuruzzaman, M., Rahman, M. M., Liu, Y., & Naidu, R. (2016). Nanoencapsulation, Nano-guard for Pesticides: A New Window for Safe Application. *Journal of Agricultural and Food Chemistry,* 64(7), 1447-1483.

Pimentel, D. (2005). 'Environmental and Economic Costs of the Application of Pesticides Primarily in the United States.' *Environment, Development and Sustainability,* 7(2), 229-252.

Shoseyov, O., Shani, Z., & Levy, I. (2006). Carbohydrate Binding Modules: Biochemical Properties and Novel Applications. *Microbiology and Molecular Biology Reviews,* 70(2), 283-295.

Singh, R., Kumar, M., Mittal, A., & Mehta, P. K. (2016). Microbial enzymes: industrial progress in 21st century. 3 *Biotech,* 6(2).

Sührer, I., Langemann, T., Lubitz, W., Weuster-Botz, D., & Castiglione, K. (2015). A novel one-step expression and immobilization method for the production of biocatalytic preparations. *Microbial Cell Factories,* 14, 180.

Sun, F., Pang, X., Xie, T., Zhai, Y., Wang, G., & Sun, F. (2015). BrkAutoDisplay: functional display of multiple exogenous proteins on the surface of *Escherichia coli* by using BrkA autotransporter. *Microbial Cell Factories,* 14.

Swords, W. E. (2003). Chemical transformation of *E. coli. Methods in Molecular Biology* (Clifton, NJ), 235, 49-53.

Wendel, S., Fischer, E. C., Martinez, V., Seppala, S., & Norholm, M. H. H. (2016). A nanobody:GFP bacterial platform that enables functional enzyme display and easy quantification of display capacity. *Microbial Cell Factories,* 15.

Zhang, S., & Cahalan, M. D. (2007). Purifying Plasmid DNA from Bacterial Colonies Using the Qiagen Miniprep Kit. *Journal of Visualized Experiments: JoVE,* (6).

Zhang, Y., Chen, S., Xu, M., Cavoco-Paulo, A., Wu, J., & Chen, J. (2010). Characterization of *Thermobifida fusca* Cutinase-Carbohydrate-Binding Module Fusion Proteins and Their Potential Application in Bioscouring. *Applied and Environmental Microbiology,* 76(20), 6870-6876.

What is claimed is:

1. An anucleated cell composition comprising: (a) an intact anucleated cell having encapsulated within said cell at least one non-expressed agricultural compound, and wherein said at least one non-expressed agricultural compound is a pesticide.

2. The anucleated cell composition according to claim 1, further comprising: (b) at least one agriculturally acceptable carrier.

3. The anucleated cell composition according to claim 1, wherein said intact anucleated cell is derived from a prokaryotic cell.

4. The anucleated cell composition according to claim 1, wherein said intact anucleated cell is a bacterially derived minicell.

5. The anucleated cell composition according to claim 1, wherein said intact anucleated cell is produced from a gram negative bacterial genus.

6. The anucleated cell composition according to claim 1, wherein said intact anucleated cell is produced from a bacterial genus selected from the group consisting of: *Escherichia, Salmonella, Shigella, Pseudomonas*, and *Agrobacterium.*

7. The anucleated cell composition according to claim 1, wherein said intact anucleated cell is produced from a bacterial species selected from the group consisting of: *Escherichia coli, Salmonella typhimurium, Shigella flexneri*, and *Pseudomonas aeruginosa.*

8. The anucleated cell composition according to claim 1, wherein said intact anucleated cell is produced from a P678-54 *E. coli* parental bacterial cell.

9. The anucleated cell composition according to claim 1, wherein said intact anucleated cell is produced from a gram positive bacterial genus.

10. The anucleated cell composition according to claim 1, wherein said intact anucleated cell is produced from a bacterial genus selected from the group consisting of: *Bacillus, Corynebacterium*, and *Lactobacillus.*

11. The anucleated cell composition according to claim 1, wherein said intact anucleated cell is produced from a bacterial species selected from the group consisting of: *Bacillus subtilis, Corynebacterium glutamicum*, and *Lactobacillus acidophilus.*

12. The anucleated cell composition according to claim 1, wherein said intact anucleated cell is a bacterially derived minicell that is produced from a parental bacterial cell deficient in WprA protease.

13. The anucleated cell composition according to claim 1, wherein said intact anucleated cell is a bacterially derived minicell that is produced from a protease deficient *B. subtilis* parental bacterial cell.

14. The anucleated cell composition according to claim 1, wherein said intact anucleated cell is a bacterially derived minicell that is produced from a protease deficient KO7 *B. subtilis* parental bacterial cell.

15. The anucleated cell composition according to claim 1, wherein said intact anucleated cell is a bacterially derived minicell that is produced from a protease deficient *B. subtilis* parental bacterial cell selected from the group consisting of: (1) CU403,DIVIVA; (2) CU403,DIVIVB,SPO-; (3) CU403, DIVIVB; and (4) CU403,DIVIVB1, wherein at least one protease encoding gene has been repressed, deleted, or silenced.

16. The anucleated cell composition according to claim 1, wherein said intact anucleated cell is a bacterially derived minicell that is produced from a protease deficient parental bacterial cell.

17. The anucleated cell composition according to claim 1, wherein said intact anucleated cell is a bacterially derived minicell that is produced from a parental bacterial cell deficient in Lon and OmpT proteases.

18. The anucleated cell composition according to claim 1, wherein said intact anucleated cell is a bacterially derived minicell that is produced from a protease deficient *E. coli* parental bacterial cell.

19. The anucleated cell composition according to claim 1, wherein said intact anucleated cell is a bacterially derived minicell that is produced from a protease deficient *E. coli* parental bacterial cell selected from the group consisting of: BL21, BL21(DE3), BL21-AI, LPS-modified BL21 (DE3) and B8.

20. The anucleated cell composition according to claim 1, wherein said intact anucleated cell is derived from an eukaryotic cell.

21. The anucleated cell composition according to claim 1, wherein the at least one non-expressed agricultural compound is an herbicide.

22. The anucleated cell composition according to claim 1, wherein the at least one non-expressed agricultural compound is a sulfonylurea herbicide.

23. The anucleated cell composition according to claim 1, wherein the at least one non-expressed agricultural compound is foramsulfuron.

24. The anucleated cell composition according to claim 1, wherein the at least one non-expressed agricultural compound is an insecticide.

25. The anucleated cell composition according to claim 1, wherein the at least one non-expressed agricultural compound is a neonicotinoid insecticide.

26. The anucleated cell composition according to claim 1, wherein the at least one non-expressed agricultural compound is clothianidin.

27. The anucleated cell composition according to claim 1, wherein the at least one non-expressed agricultural compound is a keto-enol insecticide.

28. The anucleated cell composition according to claim 1, wherein the at least one non-expressed agricultural compound is spirotetramat.

29. The anucleated cell composition according to claim 1, wherein the at least one non-expressed agricultural compound is a fungicide.

30. The anucleated cell composition according to claim 1, wherein the at least one non-expressed agricultural compound is a strobilurin fungicide.

31. The anucleated cell composition according to claim 1, wherein the at least one non-expressed agricultural compound is pyraclostrobin.

32. The anucleated cell composition according to claim 1, wherein the at least one non-expressed agricultural compound is a nematicide.

33. The anucleated cell composition according to claim 1, formulated as a liquid, dry composition, powder, granule, seed coating, drench, in-furrow composition, or foliar spray.

34. A method of delivering at least one non-expressed agricultural compound to a locus, comprising: applying the anucleated cell composition according to claim 1 to a desired locus.

35. A method of delivering at least one non-expressed agricultural compound to a plant, comprising: applying the anucleated cell composition according to claim 1 to a plant.

36. A method of delivering at least one non-expressed agricultural compound to a plant, comprising: applying the anucleated cell composition according to claim 1 to a plant, wherein the plant comprises the seed, stalk, flower, fruit, leaves, roots, or rhizome.

37. A method of delivering at least one non-expressed agricultural compound to a crop, comprising: applying the anucleated cell composition according to claim 1 to a crop or a locus in proximity to said crop.

38. The anucleated cell composition according to claim 1, wherein the anucleated cell is treated with a solvent.

39. The anucleated cell composition according to claim 38, wherein said solvent is ethanol, DMSO, polyethylene glycol, or glycerol.

40. The anucleated cell composition according to claim 38, wherein the anucleated cell is treated with an agent, in addition to said solvent.

41. The anucleated cell composition according to claim 40, wherein said agent is a fixative, a preservative or a cross-linking agent.

42. The anucleated cell composition according to claim 41, wherein said cross-linking agent is glutaraldehyde, formaldehyde, genipin, or epigallocatechin gallat.

43. The anucleated cell composition according to claim 38, wherein said solvent increases solubility of the at least one non-expressed agricultural compound into the anucleated cell.

44. The anucleated cell composition according to claim 38, wherein said solvent increases solubility of the at least one non-expressed agricultural compound into the anucleated cell, and wherein said solvent increases diffusion of the at least one non-expressed agricultural compound into the anucleated cell.

45. The anucleated cell composition according to claim 40, wherein said agent captures the at least one non-expressed agricultural compound within a membrane of the anucleated cell.

46. The anucleated cell composition according to claim 40, wherein said agent captures the at least one non-expressed agricultural compound within a membrane of the anucleated cell, and wherein said agent cross-links the at least one non-expressed agricultural compound to the anucleated cell, which improves stability of the anucleated cell.

47. The anucleated cell composition according to claim 40, wherein said agent enhances loading capacity of the at least one non-expressed agricultural compound into the anucleated cell.

48. The anucleated cell composition according to claim 40, wherein said agent enhances loading capacity of the at least one non-expressed agricultural compound into the anucleated cell, and wherein said agent controls a release rate of the at least one non-expressed agricultural compound from the anucleated cell.

49. The anucleated cell composition according to claim 1, wherein the anucleated cell exhibits a controlled release rate of the at least one non-expressed agricultural compound.

50. The anucleated cell composition according to claim 49, wherein the anucleated cell exhibits the controlled release rate of the at least one non-expressed agricultural compound, and wherein said at least one non-expressed agricultural compound is released at a steady rate.

51. The anucleated cell composition according to claim 1, wherein the anucleated cell exhibits an initial burst release of the at least one non-expressed agricultural compound.

52. The anucleated cell composition according to claim 51, wherein the anucleated cell exhibits the initial burst release of the at least one non-expressed agricultural compound, and wherein said burst release comprises a release of at least about 40% of the at least one non-expressed agricultural compound.

53. The anucleated cell composition according to claim 49, wherein the anucleated cell exhibits the controlled release rate of the at least one non-expressed agricultural compound, and wherein the controlled release rate is less than 40%, less than 30%, less than 20%, less than 15%, less than 10%, or less than 5% of the at least one non-expressed agricultural compound being released from the anucleated cell per day.

54. The anucleated cell composition according to claim 53, wherein the controlled release rate is less than 15% of the at least one non-expressed agricultural compound released from the anucleated cell per day.

55. The anucleated cell composition according to claim 53, wherein the controlled release rate is less than 10% of the at least one non-expressed agricultural compound released from the anucleated cell per day.

56. The anucleated cell composition according to claim 53, wherein the controlled release rate is about 10% of the at least one non-expressed agricultural compound released from the anucleated cell per day.

* * * * *